(12) United States Patent
Röder et al.

(10) Patent No.: US 10,950,348 B2
(45) Date of Patent: Mar. 16, 2021

(54) PREDICTIVE TEST FOR PATIENT BENEFIT FROM ANTIBODY DRUG BLOCKING LIGAND ACTIVATION OF THE T-CELL PROGRAMMED CELL DEATH 1 (PD-1) CHECKPOINT PROTEIN AND CLASSIFIER DEVELOPMENT METHODS

(71) Applicant: Biodesix, Inc., Boulder, CO (US)

(72) Inventors: Joanna Röder, Steamboat Springs, CO (US); Krista Meyer, Steamboat Springs, CO (US); Julia Grigorieva, Steamboat Springs, CO (US); Maxim Tsypin, Steamboat Springs, CO (US); Carlos Oliveira, Steamboat Springs, CO (US); Arni Steingrimsson, Steamboat Springs, CO (US); Heinrich Röder, Steamboat Springs, CO (US); Senait Asmellash, Denver, CO (US); Kevin Sayers, Denver, CO (US); Caroline Maher, Denver, CO (US)

(73) Assignee: BIODESIX, INC., Boulder, CO (US)

( * ) Notice: Subject to any disclaimer, the term of this patent is extended or adjusted under 35 U.S.C. 154(b) by 176 days.

(21) Appl. No.: 15/991,601

(22) Filed: May 29, 2018

(65) Prior Publication Data
US 2018/0277249 A1 Sep. 27, 2018

Related U.S. Application Data

(63) Continuation of application No. 15/207,825, filed on Jul. 12, 2016, now Pat. No. 10,007,766.

(60) Provisional application No. 62/340,727, filed on May 24, 2016, provisional application No. 62/319,958, filed on Apr. 8, 2016, provisional application No. 62/289,587, filed on Feb. 1, 2016, provisional application No. 62/191,895, filed on Jul. 13, 2015.

(51) Int. Cl.
| | |
|---|---|
| *G16H 50/20* | (2018.01) |
| *G16B 40/00* | (2019.01) |
| *G01N 33/574* | (2006.01) |
| *G01N 33/68* | (2006.01) |
| *G16B 40/10* | (2019.01) |
| *G16B 40/20* | (2019.01) |
| *G06F 19/00* | (2018.01) |
| *G16H 20/30* | (2018.01) |
| *G16H 20/10* | (2018.01) |
| *G16H 10/40* | (2018.01) |

(52) U.S. Cl.
CPC ......... *G16H 50/20* (2018.01); *G01N 33/5743* (2013.01); *G01N 33/6851* (2013.01); *G06F 19/00* (2013.01); *G06F 19/3456* (2013.01); *G06F 19/3481* (2013.01); *G16B 40/00* (2019.02); *G16B 40/10* (2019.02); *G16B 40/20* (2019.02); *G16H 10/40* (2018.01); *G16H 20/10* (2018.01); *G16H 20/30* (2018.01); *G01N 2333/70532* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,736,905 B2 | 6/2010 | Röder et al. | |
| 7,858,389 B2 | 12/2010 | Röder et al. | |
| 7,858,390 B2 | 12/2010 | Röder et al. | |
| 8,718,996 B2 | 5/2014 | Brauns et al. | |
| 8,914,238 B2 | 12/2014 | Röder et al. | |
| 9,279,798 B2 | 3/2016 | Röder et al. | |
| 9,724,413 B2 | 8/2017 | Maecker et al. | |
| 2003/0225526 A1 | 12/2003 | Golub et al. | |
| 2005/0149269 A1 | 7/2005 | Thomas et al. | |
| 2008/0032299 A1 | 2/2008 | Burczynski et al. | |
| 2011/0208433 A1 | 8/2011 | Grigorieva et al. | |

(Continued)

FOREIGN PATENT DOCUMENTS

| | | |
|---|---|---|
| CN | 103842030 A | 6/2014 |
| CN | 104470949 A | 3/2015 |

(Continued)

OTHER PUBLICATIONS

Taneja et al., World J. Surg. Oncol. 2(10):1-5 (2004) (Year: 2004).*
Qi et al., J. Can. Res. Ther., 10(2): C95-C101 (2014) (Year: 2014).*
Weber et al., "Safety, Efficacy, Biomarkers of Nivolumab With Vaccine in Ipilimumab-Refractory or—Naive Melanoma", J. Clin. Oncol., 31:4311-4318 (2013).
Mootha et al., "PGC-1α-responsive genes involved in oxidative phosphorylation are coordinately downregulated in human diabetes", Nat Genet. 34(3):267-73, (2003).

(Continued)

*Primary Examiner* — Thomas J. Visone
(74) *Attorney, Agent, or Firm* — DLA Piper LLP US

(57) ABSTRACT

A method is disclosed of predicting cancer patient response to immune checkpoint inhibitors, e.g., an antibody drug blocking ligand activation of programmed cell death 1 (PD-1) or CTLA4. The method includes obtaining mass spectrometry data from a blood-based sample of the patient, obtaining integrated intensity values in the mass spectrometry data of a multitude of pre-determined mass-spectral features; and operating on the mass spectral data with a programmed computer implementing a classifier. The classifier compares the integrated intensity values with feature values of a training set of class-labeled mass spectral data obtained from a multitude of melanoma patients with a classification algorithm and generates a class label for the sample. A class label "early" or the equivalent predicts the patient is likely to obtain relatively less benefit from the antibody drug and the class label "late" or the equivalent indicates the patient is likely to obtain relatively greater benefit from the antibody drug.

11 Claims, 103 Drawing Sheets

(56) References Cited

U.S. PATENT DOCUMENTS

| | | |
|---|---|---|
| 2011/0271358 A1 | 11/2011 | Freeman et al. |
| 2013/0344111 A1 | 12/2013 | Röder et al. |
| 2014/0341902 A1 | 11/2014 | Maecker et al. |
| 2015/0071910 A1 | 3/2015 | Kowanetz et al. |
| 2015/0102216 A1 | 4/2015 | Röder et al. |
| 2015/0125463 A1 | 5/2015 | Cogswell et al. |
| 2015/0285817 A1 | 10/2015 | Röder et al. |
| 2016/0018410 A1 | 1/2016 | Röder et al. |
| 2016/0019342 A1 | 1/2016 | Röder et al. |
| 2016/0098514 A1 | 4/2016 | Röder et al. |
| 2016/0163522 A1 | 6/2016 | Röder et al. |
| 2016/0299146 A1 | 10/2016 | Garraway et al. |
| 2018/0021431 A1 | 1/2018 | Maecker et al. |

FOREIGN PATENT DOCUMENTS

| | | |
|---|---|---|
| WO | 2014003853 A1 | 1/2014 |
| WO | 2014055543 A2 | 4/2014 |
| WO | 2015039021 A2 | 3/2015 |
| WO | 2016049385 A1 | 3/2016 |

OTHER PUBLICATIONS

Subramanian et al., "Gene set enrichment analysis: A knowledge-based approach for interpreting genome-wide expression profiles", Proc Natl Acad Sci USA 102(43): 15545-50, (2005).
Pio et al., "The role of complement in tumor growth", Adv Exp Med Biol, 772:229-62 (2014).
Janelle et al., "Role of the complement system in NK cell-mediated antitumor T-cell responses", Oncoimmunology 3, e27897 (2014).
Mathem et al., "Molecules Great and Small: The Complement System", Clin J Am Soc Nephrol, 10:1636-50 (2015).
Janelle et al., "Transient complement inhibition promotes a tumor-specific immune response through the implication of natural killer cells", Cancer Immunol Res, 2:200-6 (2014).
Markiewski et al., "Modulation of the antitumor immune response by complement", Nat Immunol, 9:1225-35 (2008).
Vadrevu et al., "Complement c5a receptor facilitates cancer metastasis by altering T-cell responses in the metastatic niche", Cancer Res, 74:3454-65 (2014).
Gunn et al., "Opposing roles for complement component C5a in tumor progression and the tumor microenvironment", J Immunol, 189:2985-94 (2012).
Zhang et al., "A Protective Role for C5a in the Development of Allergic Asthma Associated with Altered Levels of B7-H1 and B7-DC on Plasmacytoid Dendritic Cells", J. Immunol., 182:5123-5130 (2009).
Mantovani et al., "Cancer-related inflammation", Nature, 454:436-44 (2008).
Porta et al., "Cellular and molecular pathways linking inflammation and cancer", Immunobiology, 214:761-77 (2009).
Grivennikov et al., "Immunity, inflammation, and cancer", Cell, 140:883-99 (2010).
Tikhonov, "О"Об устойчивости обратных задач"" [On the stability of inverse problems]. Doklady Akademii Nauk SSSR, 39(5):195-198 (1943).
Tibshirani "Regression shrinkage and selection via the lasso", J. Royal. Statist. Soc B., 58(1):267-288 (1996).
Shrivastava, "Improving Neural Networks with Dropout", Master's Thesis, Graduate Department of Computer Science, University of Toronto).
Girosi et al., "Regularization Theory and Neural Networks Architectures", Neural Computation, 7:219-269 (1995).
International Search Report and Written Opinion for corresponding PCT Application No. PCT/US2016/041860 dated Oct. 6, 2016.
Karpievitch et al., "Liquid Chromatography Mass Spectrometry-Based Proteomics: Biological and Technological Aspects", Ann Appl Stat., 4(4):1797-1823 (2010).
Kennedy-Crispin et al., "Human keratinocytes' response to injury upregulates CCL20 and other genes linking innate and adaptive immunity", J Invest Dermatol., 132(1):105-113 (2012).
Kani et al., "Quantitiative Proteomic profiling identifies protein correlates to EGFR kinase inhibition", Mol Cancer Ther., 11(5):1071-1081 (2012).
Blanco et al., "Feature selection in Bayesian classifiers for the prognosis of survival of cirrhotic patients treated with TIPS", Journal of Biomedical Informatics, 38:376-388 (2005).
Carvajal-Hausdorf et al., "Quantitative Measurement of Cancer Tissue Biomarkers in the Lab and in the Clinic", Lab Invest, 95(4):385-396 (2015).
Romano et al., "The therapeutic promise of disrupting the PD-1/PD-L1 immunie checkpoint in cancer: unleashing the CD8 T cell mediated anti-tumor activity results in significant, unprecedented clinical efficacy in various solid tumors", J. ImmunoTher. Can. 3(15):1-5 (2015).
Vu et al., "RAC1 P29S regulates PD-L1 expression in melanoma", Pigment Cell Melanoma Res., 28(5):590-598 (2015).
Taguchi et al., "Mass Spectrometry to Classify Non-Small-Cell Lung Cancer Patients for Clinical Outcome after Treatment with Epidermal Growth Factor Receptor Tyrosine Kinase Inhibitors: A Multicohort Cross-Institutional Study" JNCI Journal of the National Cancer Institute, 99(11):838-846 (2007).
Redman et al., "Advances in immunotherapy for melanoma", BNC Medicine, 14(1):1-11 (2016).
Weber et al., "A Serum Protein Signature Associated with Outcome AFter Anti-PD-1 Therapy in Metastatic Melanoma", ACCR Special Conference on Tumor Immunology and Immunotherapy, Boston, MA, 6(1):79-86 (2016).
Larkin et al., "Combined Nivolumab and Ipilimumab or Monotherapy in Untreated Melanoma", The New England Journal of Medicine, 373(1):23-34 (2015).
Postow et al., "Peripheral and tumor immune correlates in patients with advanced melanoma treated with nivolumab (anti-PD-1, BMS-936558, ONO-4538) monotherapy or in combination with ipilimumab", Journal of Translational Medicine, 12(1):1-2 (2014).
Weber et al., "A test identifying advanced melanoma patients with long survival outcomes on nivolumab shows potential for selection for benefit from combination checkpoint blockade", 31st Annual Meeting and Associated Programs of the Society for Immunotherapy of Cancer, 4(82) (2016).
European Search Report for corresponding European application No. EP16825027, dated Feb. 8, 2019.
Zhang, "Simultaneous blocking of PD-1 and CTLA-4 increases in T cell infiltration in melanoma and reduces the number of Treg and bone-marrow derived suppressor cells", Progress in Physiological Sciences, vol. 43, No. 2, Dec. 31, 2012.
Zang et al., "Progress in immunotherpy of melanoma", Chinese Journal of Cancer Biotherapy, vol. 20, No. 3, Jun. 30, 2013.

* cited by examiner

TTP

OS

TTP

OS

Development OS

Development: TTP

Validation: OS

Validation: TTP

Development OS

Development: TTP

Approach 1: OS

Approach 1: TTP

PFS

OS

PFS

OS

Development (melanoma nivo): OS

Development (melanoma nivo): TTP

Development (NSCLC): OS

Development (NSCLC): PFS

Validation (NSCLC chemo): OS

Validation (NSCLC chemo): PFS

OS

PFS

OS

PFS

OS

PFS

OS

DFS

OS

DFS

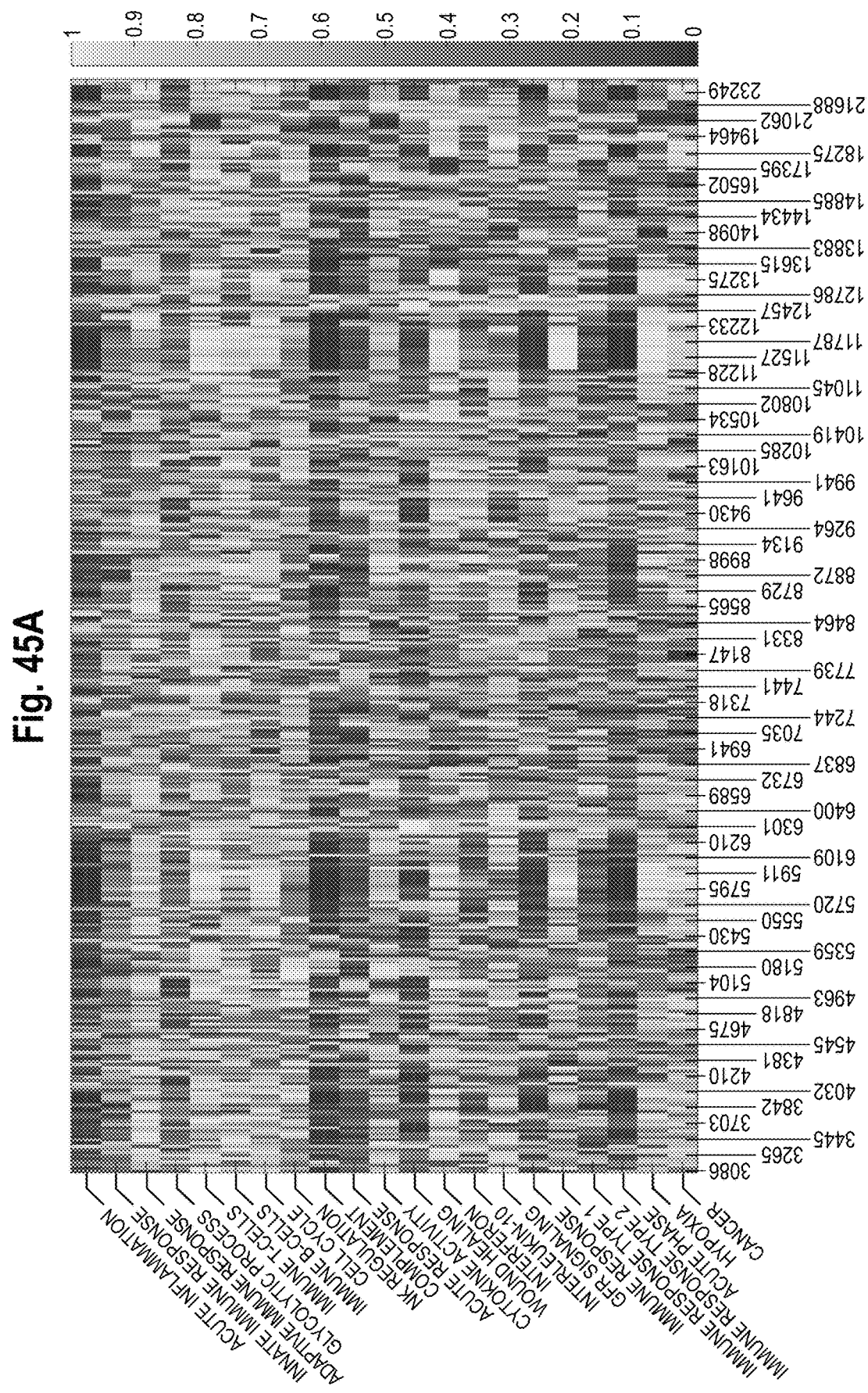

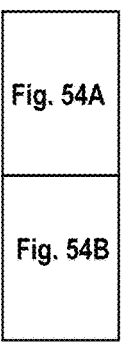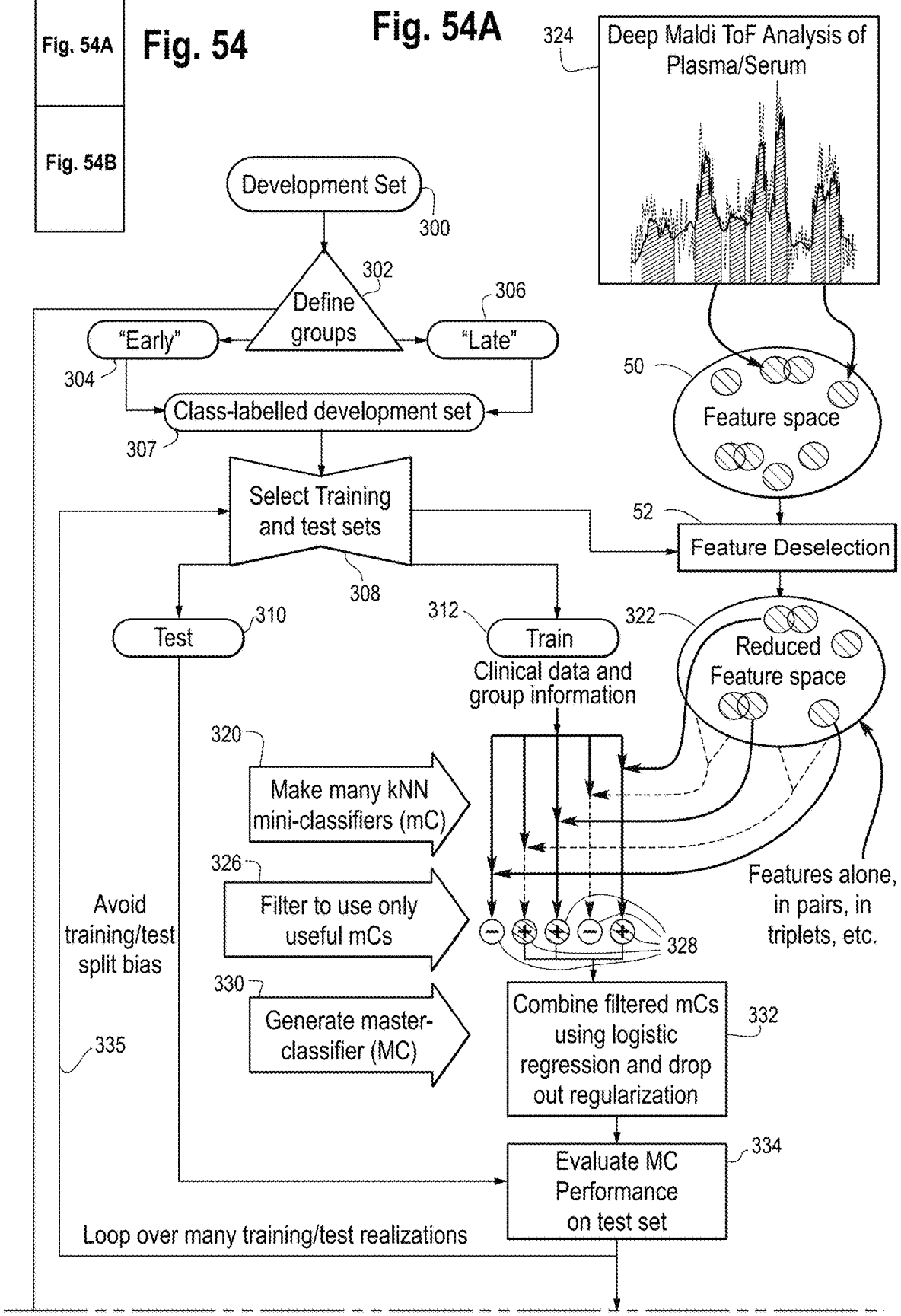

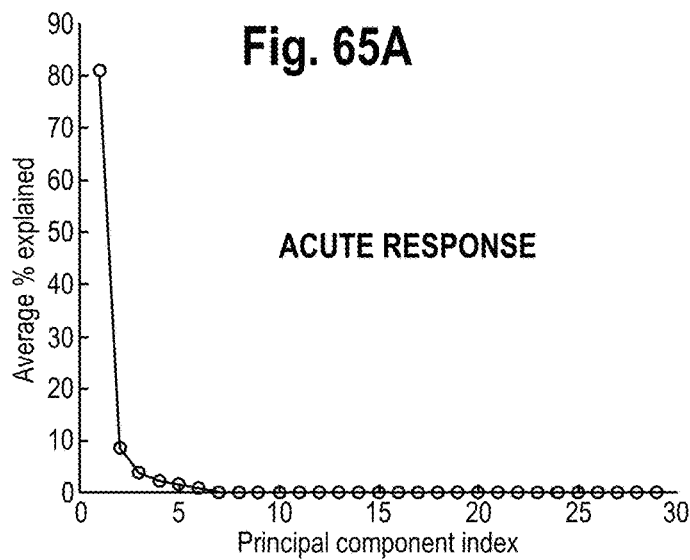
Fig. 65A ACUTE RESPONSE
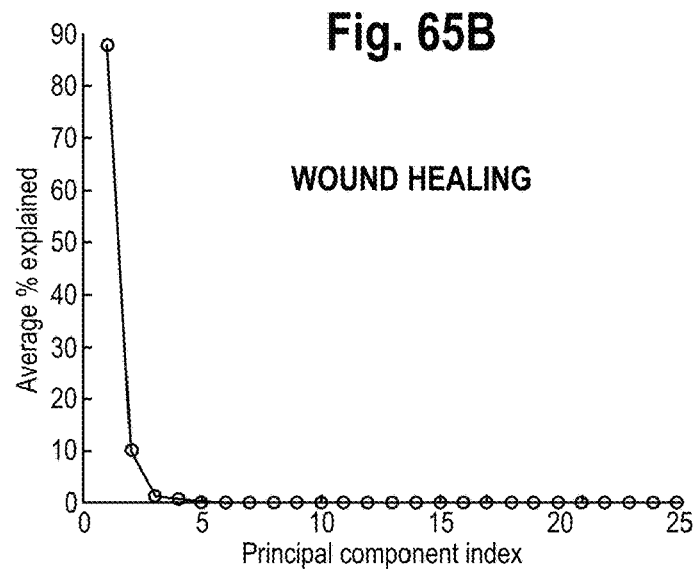
Fig. 65B WOUND HEALING
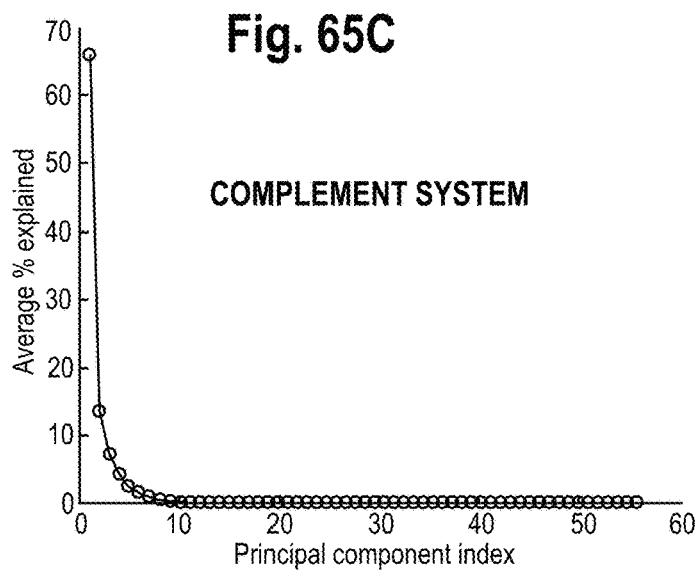
Fig. 65C COMPLEMENT SYSTEM "PROSE-chemo" OS "PROSE-chemo" PFS

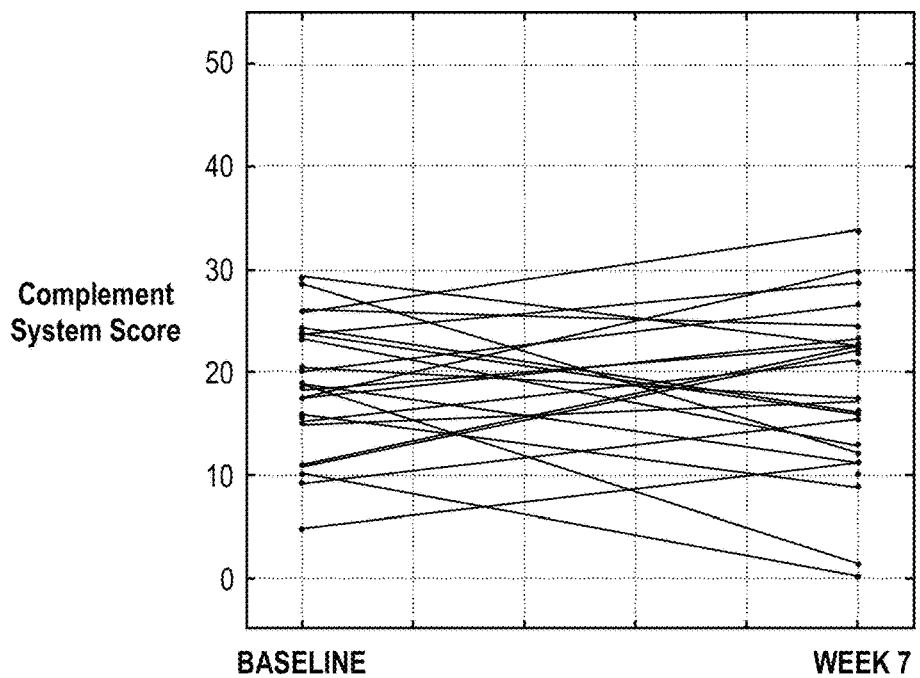
Fig. 76A EARLY - EARLY
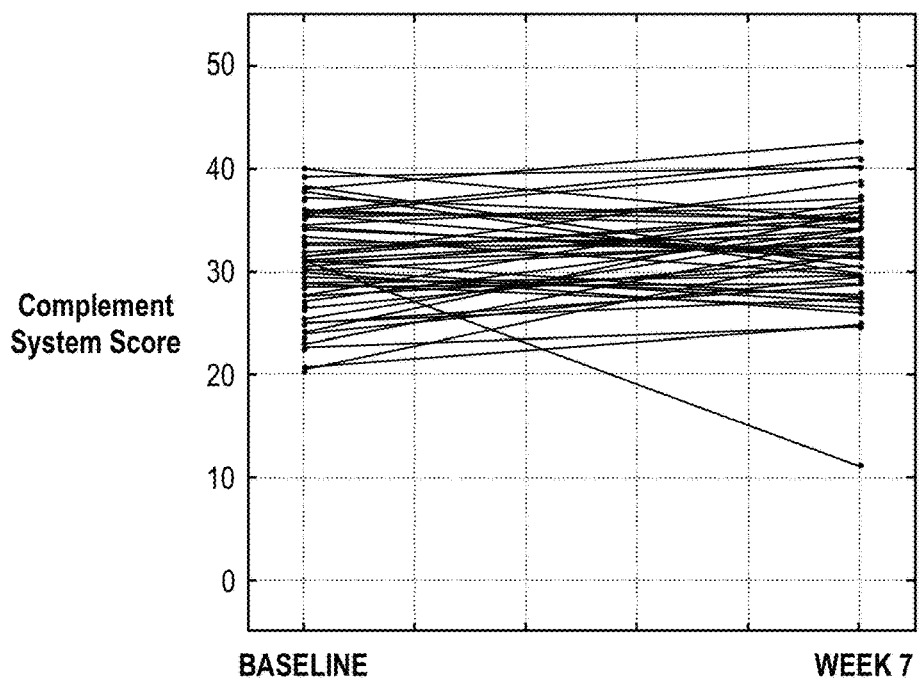
Fig. 76B LATE-LATE

Fig. 82

| | Feature 1 | Feature 2 | Feature 3 | ... | Feature $N_f$ |
|---|---|---|---|---|---|
| Sample 1 | $f_{1,1}$ | $f_{1,2}$ | $f_{1,3}$ | | $f_{1,Nf}$ |
| Sample 2 | $f_{2,1}$ | $f_{2,2}$ | $f_{2,3}$ | | $f_{2,Nf}$ |
| Sample 3 | $f_{3,1}$ | $f_{,3,2}$ | $f_{3,3}$ | | $f_{3,Nf}$ |
| . | . | . | . | | . |
| . | . | . | . | | . |
| . | . | . | . | | . |
| Sample $N_s$ | $f_{Ns,1}$ | $f_{Ns,2}$ | $f_{Ns,3}$ | | $f_{Ns,Nf}$ |

Feature intensities $f_{i,j}$ for feature j, significantly correlated with the particular biological function, and sample i from sample set ss

Fig. 83

Average first principal component vector, $\hat{u}_1$

| Component in direction of feature 1 | $(\hat{u}_1)_1$ |
|---|---|
| Component in direction of feature 2 | $(\hat{u}_1)_2$ |
| Component in direction of feature 3 | $(\hat{u}_1)_3$ |
| . | |
| . | |
| . | |
| Component in direction of feature $N_f$ | $(\hat{u}_1)_N$ |

PREDICTIVE TEST FOR PATIENT BENEFIT FROM ANTIBODY DRUG BLOCKING LIGAND ACTIVATION OF THE T-CELL PROGRAMMED CELL DEATH 1 (PD-1) CHECKPOINT PROTEIN AND CLASSIFIER DEVELOPMENT METHODS

PRIORITY

This application is a continuation of U.S. Ser. No. 15/207,825, filed on Jul. 12, 2016 (now allowed), which claims the benefit of U.S. Provisional Application Ser. No. 62/191,895 filed Jul. 13, 2015; 62/289,587 filed Feb. 1, 2016; 62/340,727 filed May 24, 2016, and 62/319,958 filed Apr. 8, 2016. The content of all of these applications, including appendices thereof, are incorporated by reference herein in their entirety.

FIELD

This invention relates to a method for predicting in advance of treatment whether a cancer patient is likely to benefit from administration of immune checkpoint inhibitors, including for example anti-PD-1 and/or anti-CTLA4 agents, allowing the immune system to attack the tumor. This application further relates to methods for developing. i.e., training, a computer-implemented classifier from a development set of samples.

BACKGROUND

Melanoma is a type of cancer primarily affecting the skin that develops from pigment-containing cells known as melanocytes. The primary cause of melanoma is ultraviolet light (UV) exposure in those with low levels of skin pigment, which causes damage to DNA in skin cells. The UV light may be from either the Sun or from tanning devices. About 25% of melanomas develop from moles. Individuals with many moles, a history of affected family members, or who have poor immune function are all at greater risk of developing a melanoma. A number of rare genetic defects also increase the risk of developing melanoma. Diagnosis of melanoma is typically done by visual inspection of any concerning lesion followed by biopsy.

Treatment of melanoma is typically removal by surgery. In those with slightly larger cancers nearby lymph nodes may be tested for spread. Most people are cured if spread has not occurred. In those in whom melanoma has spread, immunotherapy, biologic therapy, radiation therapy, or chemotherapy may improve survival. With treatment, the five-year survival rate in the United States is 98% among those with localized disease, but only 17% among those in whom spread has occurred. Melanoma is considered the most dangerous type of skin cancer. Globally, in 2012, it occurred in 232,000 people and resulted in 55,000 deaths.

Tumor mutations, including mutations associated with melanoma, create specific neoantigens that can be recognized by the immune system. Roughly 50% of melanomas are associated with an endogenous T-cell response. Cytotoxic T-cells (CT cells, or cytotoxic T lymphocytes (CTLs)) are leukocytes which destroy virus-infected cells and tumor cells, and are also implicated in transplant rejection. CTLs that express the CD8 glycoprotein at their surfaces are also known as CD8+ T-cells or CD8+ CTLs. Tumors develop a variety of mechanisms of immune evasion, including local immune suppression in the tumor microenvironment, induction of T-cell tolerance, and immunoediting. As a result, even when T-cells infiltrate the tumor they cannot kill the cancer cells. An example of this immunosuppression in cancer is mediated by a protein known as programmed cell death 1 (PD-1) which is expressed on the surface of activated T-cells. If another molecule, called programmed cell death 1 ligand 1 or programmed cell death 1 ligand 2 (PD-L1 or PD-L2), binds to PD-1, the T-cell becomes inactive. Production of PD-L1 and PD-L2 is one way that the body naturally regulates the immune system. Many cancer cells make PD-L1, hijacking this natural system and thereby allowing cancer cells to inhibit T-cells from attacking the tumor.

One approach to the treatment of cancer is to interfere with the inhibitory signals produced by cancer cells, such as PD-L1 and PD-L2, to effectively prevent the tumor cells from putting the brakes on the immune system. Recently, an anti-PD-1 monoclonal antibody, known as nivolumab, marketed as Opdivo®, was approved by the Food and Drug Administration for treatment of patients with unresectable or metastatic melanoma who no longer respond to other drugs. In addition, nivolumab was approved for the treatment of squamous and non-squamous non-small cell lung cancer and renal cell carcinoma. Nivolumab has also been approved in melanoma in combination with ipilimumab, an anti-cytotoxic T-lymphocyte-associated protein 4 (CTLA4) antibody. Nivolumab acts as an immunomodulator by blocking ligand activation of the PD-1 receptor on activated T-cells. In contrast to traditional chemotherapies and targeted anti-cancer therapies, which exert their effects by direct cytotoxic or tumor growth inhibition, nivolumab acts by blocking a negative regulator of T-cell activation and response, thus allowing the immune system to attack the tumor. PD-1 blockers appear to free up the immune system only around the tumor, rather than more generally, which could reduce side effects from these drugs.

The current clinical results of anti-PD-1 treatment in melanoma patients are encouraging and overall results lead to progression free and overall survival results that are superior to alternative therapies. However, the real promise of these therapies is related to durable responses and long-term clinical benefit seen in a subgroup of around 40% of melanoma patients. Some portion of the other ~60% of patients might do better on alternative therapies. Being able to select which patients derive little benefit from anti-PD-1 treatment from pre-treatment samples would enable better clinical understanding and enhance the development of alternative treatments for these patients. There is also considerable cost related to these therapies, e.g. the recently approved combination of ipilimumab and nivolumab in melanoma while showing spectacular results is only effective in about 55% of patients while costing around $295,000 per treatment course. (Leonard Saltz, M D, at ASCO 2015 plenary session: "The Opdivo+Yervoy combo is priced at approximately 4000× the price of gold ($158/mg)"). This results in a co-pay of around $60,000 for patients on a standard Medicare plan. Avoiding this cost by selecting these treatments only for those patients who are likely to benefit from them would result in substantial savings to the health care system and patients. It is also unclear whether the benefit of the combination of nivolumab and ipilimumab arises from a synergistic effect, or is just the sum of different patient populations responding to either nivolumab or ipilimumab. In any case having a test for nivolumab benefit would shed light on this question.

Much work has been performed to use the expression of PD-L1 measured by immunohistochemistry (IHC) as a biomarker for selection of anti-PD-1 treatments. Correlations between anti-PD-1 efficacy and outcome have been observed in some studies but not in others. Of particular issue is the current lack of standardization and universally accepted cut-offs in terms of IHC staining, which renders comparison of such data difficult. Of more fundamental issue is the observation that PD-L1 expression appears to be a dynamic marker, i.e. IHC expression changes during tumor evolution and during treatment. If one were to use PD-L1 expression via IHC in a rigorous manner one would require multiple repeat biopsies with a high corresponding risk and cost for patients. In contrast, a serum based test would not suffer from these effects.

The assignee Biodesix, Inc. has developed classifiers for predicting patient benefit or non-benefit of certain anticancer drugs using mass spectrometry of blood-based samples. Representative patents include U.S. Pat. Nos. 7,736,905; 8,914,238; 8,718,996; 7,858,389; 7,858,390; and U.S. patent application publications 2013/0344111 and 2011/0208433.

SUMMARY

In one aspect, and as will described in more detail in Examples 9 and 10, a practical method of guiding melanoma patient treatment with immunotherapy drugs is disclosed. The method includes the steps of a) conducting mass spectrometry on a blood-based sample of the patient and obtaining mass spectrometry data; (b) obtaining integrated intensity values in the mass spectrometry data of a multitude of mass-spectral features; and (c) operating on the mass spectral data with a programmed computer implementing a classifier. In the operating step the classifier compares the integrated intensity values with feature values of a reference set of class-labeled mass spectral data obtained from blood-based samples obtained from a multitude of other melanoma patients treated with an antibody drug blocking ligand activation of programmed cell death 1 (PD-1) with a classification algorithm and generates a class label for the sample. The class label "Good" or the equivalent (e.g., Late in the description of Example 10) predicts the patient is likely to obtain similar benefit from a combination therapy comprising an antibody drug blocking ligand activation of PD-1 and an antibody drug targeting CTLA4 and is therefore guided to a monotherapy of an antibody drug blocking ligand activation of PD-1 (e.g., nivolumab), whereas a class label of "Not Good" or the equivalent (e.g., Early in the description of Example 10) indicates the patient is likely to obtain greater benefit from the combination therapy as compared to the monotherapy of an antibody drug blocking ligand activation of programmed cell death 1 (PD-1) and is therefore guided to the combination therapy.

In still another embodiment, a method of treating a melanoma patient is disclosed. The method includes performing the method recited above and if the class label is Good or the equivalent the patient is administered a monotherapy of an antibody drug blocking ligand activation of PD-1 (e.g., nivolumab), whereas if the class label of "Not Good" or the equivalent is reported the patient is administered a combination therapy an antibody drug blocking ligand activation of PD-1 and an antibody drug targeting CTLA4, e.g., the combination of nivolumab and ipilimumab.

In one embodiment the mass spectral features include a multitude of features listed in Appendix A, Appendix B or Appendix C, or features associated with biological functions Acute Response and Wound Healing (see Examples 1, 6 and 10). In preferred embodiments the classifier is obtained from filtered mini-classifiers combined using a regularized combination method, e.g., using the procedure of FIG. 8 or FIG. 54. The regularized combination method can take the form of repeatedly conducting logistic regression with extreme dropout on the filtered mini-classifiers. In one example the mini-classifiers are filtered in accordance with criteria listed in Table 10. As disclosed in Example $_9$, the classifier may take the form of an ensemble of tumor classifiers (each having different proportions of patients with large and small tumors) combined in a hierarchical manner. In the illustrated embodiment of Example 9 if any one of the tumor classifiers returns an Early or the equivalent, the label the Not Good or equivalent class label is reported, whereas if all the tumor classifiers return a Late class label the Good or equivalent class label is reported.

In this method the relatively greater benefit from the combination therapy label means significantly greater (longer) overall survival as compared to monotherapy.

In another aspect, the reference set takes the form of a set of class-labeled mass spectral data of a development set of samples having either the class label Early or the equivalent or Late or the equivalent, wherein the samples having the class label Early are comprised of samples having relatively shorter overall survival on treatment with nivolumab as compared to samples having the class label Late.

In preferred embodiments the mass spectral data is acquired from at least 100,000 laser shots performed on the sample using MALDI-TOF mass spectrometry. This methodology is described in Example 1 and in prior patent documents cited in Example 1, In one embodiment, as indicated in Examples 6 and 10, the mass-spectral features are selected according to their association with at least one biological function, for example sets of features which are associated with biological functions Acute Response and Wound Healing.

In another aspect, a practical testing method is disclosed for predicting melanoma patient response to an antibody drug blocking ligand activation of PD-1. The method includes steps of a) conducting mass spectrometry on a blood-based sample of the melanoma patient and obtaining mass spectrometry data; (b) obtaining integrated intensity values in the mass spectral data of a multitude of pre-determined mass-spectral features; and (c) operating on the mass spectral data with a programmed computer implementing a classifier. In the operating step the classifier compares the integrated intensity values obtained in step (b) with feature values of a reference set of class-labeled mass spectral data obtained from a multitude of other melanoma patients treated with the drug with a classification algorithm and generates a class label for the sample. The class label "early" or the equivalent predicts the patient is likely to obtain relatively less benefit from the antibody drug and the class label "late" or the equivalent indicates the patient is likely to obtain relatively greater benefit from the antibody drug. The method of generating the classifier used in this test from a development set of sample data is described in detail in this disclosure.

In another aspect, a machine is described which is capable of predicting melanoma patient benefit from an antibody drug blocking ligand activation of the programmed cell death 1 (PD-1). The machine includes a memory storing a reference set in the form of feature values for a multitude of mass spectral features obtained from mass spectrometry of blood-based samples from a multitude of melanoma patients treated with the antibody drug. The memory further stores a set of code defining a set of master classifiers each generated from a plurality of filtered mini-classifiers combined using a regularized combination method. The machine further includes a central processing unit operating on the set of code and the reference set and mass spectral data obtained from a blood-based sample of a melanoma patient and responsively generates a class label for the blood-based sample, wherein the class label "early" or the equivalent predicts the patient is likely to obtain relatively less benefit from the antibody drug and the class label "late" or the equivalent indicates the patient is likely to obtain relatively greater benefit from the antibody drug.

In another aspect, a system is disclosed for predicting patient benefit from an anti-body drug blocking ligand activation of PD-1 in the form of a mass spectrometer for conducting mass spectrometry of the blood-based sample of the patient and the machine as recited in the previous paragraph.

In yet another aspect, a method of generating a classifier for predicting patient benefit from an antibody drug blocking ligand activation of programmed cell death 1 (PD-1) is disclosed. The method includes the steps of:

1) obtaining mass spectrometry data from a development set of blood-based samples obtained from melanoma patients treated with the antibody drug, in which a mass spectrum from at least 100,000 laser shots is acquired from each member of the set;

2) performing spectral pre-processing operations on the mass spectral data from the development sample set, including background estimation and subtraction, alignment, batch correction, and normalization;

3) performing the process of FIG. 8 steps 102-150 including generating a master classifier based on a regularized combination of a filtered set of mini-classifiers;

4) evaluating performance of the master classifiers generated in accordance with step 3); and 5) defining a final classifier based on the master classifiers generated in step 3).

In a preferred embodiment, the final classifier includes a training set including feature values for a set of features listed in Appendix A, Appendix B, or Appendix C. In one possible embodiment, the method may include the step of deselecting features from the list of features of Appendix A which are not contributing to classifier performance and performing steps 3), 4), and 5) using a reduced list of features. Such a reduced list of features may take the form of the list of features in one of the sets of Appendix B or the list of features in Appendix C.

In still another embodiment, a method of treating a melanoma patient is disclosed. The method includes performing the method recited of predicting whether the patient will benefit from the antibody drug blocking ligand activation of PD-1 as recited above, and if the patient has class label of Late or the equivalent for their blood-based sample then performing a step of administrating the antibody drug to the patient.

In still another aspect, an improved general purpose computer configured as a classifier for classifying a blood-based sample from a human cancer patient to make a prediction about the patient's survival or relative likelihood of obtaining benefit from a drug is disclosed. The improvement is in the form of a memory storing a reference set in the form of feature values for a multitude of mass spectral features obtained from mass spectrometry of blood-based samples from a multitude of melanoma patients treated with an immune checkpoint inhibitor and an associated class label for each of the blood-based samples in the reference set. The data of blood-based samples form a set used for developing the classifier. The memory further stores a set of computer-executable code defining a final classifier based on a multitude of master classifiers, each master classifier generated from a set of filtered mini-classifiers executing a classification algorithm and combined using a regularized combination method, such as extreme dropout and logistic regression. The multitude of master classifiers are obtained from many different realizations of a separation of the development set into classifier training and test sets. The improvement further includes a central processing unit operating on the set of code, the reference set, and mass spectral data obtained from the blood-based sample of the cancer patient to be tested and generating a class label for the blood-based sample.

In one embodiment, the memory stores feature values of at least 50 of the features listed in Appendix A. In another embodiment, the memory stores feature values for a reduced set of features, such as the features of one of the approaches listed in Appendix B or the list of features of Appendix C.

In one embodiment, the immune checkpoint inhibitor comprises an antibody blocking ligand activation of PD-1. In another embodiment, the immune checkpoint inhibitor comprises an antibody blocking ligand activation of CTLA4.

In still further aspects, a laboratory test center is described which includes a mass spectrometer for conducting mass spectrometry of a blood based sample from a cancer patient and a machine configured as a classifier and storing a reference set of mass spectral data as described herein.

We further describe in Example 9 below a general extension of classifier development to designing the development sets of an ensemble of classifiers to explore different clinical groups, for example different proportions of patients with large and small tumors. In one embodiment, a method of generating an ensemble of classifiers from a set of patient samples is disclosed, comprising the steps of:

a. defining a plurality of classifier development sample sets from the set of patient samples, each of which have different clinical characteristics (e.g., proportions of patients with large or small tumors, or other relevant clinical groupings);

b. conducting mass spectrometry on the set of patient samples and storing mass spectrometry data;

c. using a programmed computer, conducting a classifier development exercise using the mass spectral data for each of the development sets defined in step a. and storing in a memory associated with the computer the parameters of the classifiers thus generated, thereby generating an ensemble of classifiers;

and d. defining a rule or set of rules for generating a class label for a test sample subject to classification by the ensemble of classifiers generated in step c. A method of testing a sample using the ensemble of classifiers generated in accordance with this method is also disclosed in Examples 8 and 9. In this method, step b. can be performed before or after step a.

While we describe in the examples details of our discoveries in melanoma and anti-PD-1 and anti-CTLA4 antibody drugs, our studies of protein correlations with classification labels, set forth in great detail below, have allowed us to generalize our discoveries. In particular, we can expect that Example 1, Example 2 and Example 3 classifiers may be relevant/applicable for a broad variety of drugs affecting immunological status of the patient, such as various immune checkpoint inhibitors, high dose IL2, vaccines, and/or combinational therapy, e.g., anti-PD-1 and anti-CTLA4 combination therapy. Furthermore, since effects that are measured in serum reflect the organism status as a whole, and the complement system, found to be relevant in our discoveries, affects innate and adaptive immunity on the global level, not just in a tumor site, the classifiers are expected to have similar performance in different indications (e.g., lung, renal carcinoma), and are not restricted to melanoma.

In another aspect, a classifier generation method is described, including the steps of:

a) obtaining physical measurement data from a development set of samples and supplying the measurement data to a general purpose computer, each of the samples further associated with clinical data;

b) identifying a plurality of different clinical sub-groups 1 . . . N within the development set based on the clinical data;

c) for each of the different clinical sub-groups, conducting a classifier generation process from the measurement data for each of the members of the development set that is associated with such clinical sub-groups, thereby generating clinical sub-group classifiers C1 . . . CN; and d) storing in memory of a computer a classification procedure involving all of the classifiers C1 . . . CN developed in step c), each of the classifiers associated with a reference set comprising samples in the development set used to generate the classifier and associated measurement data.

In another aspect, a multi-stage classifier is disclosed which includes a programmed computer implementing a hierarchical classifier construction operating on mass spectral data of a test sample stored in memory and making use of a reference set of class-labeled mass spectral data stored in the memory. The classifier includes (a) a first stage classifier for stratifying the test mass spectral data into either an Early or Late group (or the equivalent, the moniker not being important); (b) a second stage classifier for further stratifying the Early group of the first stage classifier into Early and Late groups (or Earlier and Later groups, or the equivalent), the second stage implemented if the first stage classifier classifies the test mass spectral data into the Early group and the Early class label produced by the second stage classifier is associated with an exceptionally poor prognosis; and (c) a third stage classifier for further stratifying the Late group of the first stage classifier into Early and Late groups (or Earlier and Later groups, or the equivalent). The third stage classifier is implemented if the first stage classifier classifies the test mass spectral data into the Late group, wherein a Late class label (or Later or the equivalent) produced by the third stage classifier is associated with an exceptionally good prognosis.

In one embodiment the third stage classifier comprises one or more classifiers developed from one or more different clinical sub-groups of a classifier development set used to generate the first level classifier. In one example, the third stage classifier includes at least four different classifiers C1, C2, C3, and C4, each developed from different clinical sub-groups. In one specific embodiment, wherein the multi-stage classifier is configured to predict an ovarian cancer patient as being likely or not likely to benefit from platinum chemotherapy, and wherein the classifiers C1, C2, C3 and C4 are developed from the following clinical subgroups:

C1: developed from a subset of patients with non-serous histology or serous histology together with unknown FIGO score;

C2: developed from a subset of patients with serous histology not used to develop Classifier C1;

C3: developed from a subset of patients with residual tumor after surgery;

C4: developed from a subset of patients with no residual tumor after surgery.

In yet another aspect, we have discovered a method of generating a classifier for classifying a test sample from a development set of samples, each of the samples being associated with clinical data. The method includes the steps of:

(a) dividing the development set of samples into different clinical subgroups 1 . . . N based on the clinical data, where N is an integer of at least 2;

(b) performing a classifier development process (such as for example the process of FIG. 8) for each of the different clinical subgroups 1 . . . N, thereby generating different classifiers C1 . . . CN; and (c) defining a final classification process whereby a patient sample is classified by the classifiers C1 . . . CN.

In still another aspect, we have discovered a method of generating a classifier for classifying a test sample, comprising the steps of:

(a) generating a first classifier from measurement data of a development set of samples using a classifier development process;

(b) performing a classification of the measurement data of the development set of samples using the first classifier, thereby assigning each member of the development set of samples with a class label in a binary classification scheme (Early/Late, or the equivalent); and (c) generating a second classifier using the classifier development process with an input classifier development set being the members of the development set assigned one of the two class labels in the binary classification scheme by the first classifier (e.g., the Early group), the second classifier thereby stratifying the members of the set with the first class label into two further sub-groups. The method optionally includes the steps (d) dividing the development set of samples into different clinical subgroups 1 . . . N where N is an integer of at least 2; and (e) repeating the classifier development process for each of the different clinical sub-groups 1 . . . N, thereby generating different third classifiers C1 . . . CN; and (f) defining a hierarchical classification process whereby:

i. a patient sample is classified first by the first classifier generated in step a);

ii. if the class label assigned by the first classifier is the class label used to generate the second classifier, then classifying the patient sample with the second classifier; and iii. if the class label assigned by the first classifier is not the class label used to generate the second classifier, then classifying the patient sample with the third classifiers C1 . . . CN; and iv. assigning a final label as a result of classification steps ii or step iii.

Example 6 below describes our ability to correlate specific mass spectral features with protein functional groups circulating in serum and use such correlations to train a classifier, or to monitor changes in a biological process. In one embodiment, a method of training a classifier is disclosed, comprising the steps of:

a) obtaining a development set of samples from a population of subjects and optionally a second independent set of samples from a similar, but not necessarily identical population of subjects;

b) conducting mass spectrometry on the development set of samples, and optionally on the second set of samples, and identifying mass spectral features present in the mass spectra of the set(s) of samples;

c) obtaining protein expression data from a large panel of proteins spanning biological functions of interest for each of the samples in the development set of samples or optionally each of the samples in the second set of samples;

d) identifying statistically significant associations of one or more of the mass spectral features with sets of proteins grouped by their biological function using Gene Set Enrichment Analysis methods; and e) with the aid of a computer, training a classifier on the development set of samples using the one or more mass spectral features identified in step d), the classifier in the form of a set of parameters which assigns a class label to a sample of the same type as the development set of samples in accordance with programmed instructions.

In one embodiment the classifier is in the form of a combination of filtered mini-classifiers which have been subject to a regularization procedure. The samples in the development set, and optional second sample set, are blood-based samples, e.g., serum or plasma samples from human patients.

In another aspect, a classifier development system is disclosed which includes a mass spectrometer for conducting mass spectrometry on a development set of samples, and optionally a second independent set of samples, to generate mass spectral data, said data including a multitude of mass spectral features; a platform for conducting a gene set enrichment analysis on the development set of samples, or optionally the second independent set of samples, and identifying statistically significant associations of one or more of the mass spectral features with sets of proteins grouped by their biological function; and a computer programmed to train a classifier on the development set of samples using the one or more mass spectral features identified by the platform, the classifier in the form of a set of parameters which assigns a class label to a sample of the same type as the development set of samples in accordance with programmed instructions. In preferred embodiments the development set of samples, and optional second independent set of samples, are blood-based samples from humans. For example, the blood-based samples for the development sample set are obtained from melanoma patients obtained in advance of treatment with an immunotherapy drug, e.g., nivolumab.

BRIEF DESCRIPTION OF THE DRAWINGS

FIGS. 9-12 are Kaplan-Meier plots showing classifier performance for the classifiers we developed in Example 1 using the classifier development procedure of FIG. 8.

FIGS. 18A-18D are the plots of OS and TTP for the development and validation sets of the melanoma/nivolumab cohort. Note that FIGS. 18A-18D show the separation in the survival plots of the samples labeled Early and Late by the classifier of Example 2. FIGS. 18E-18H are the plots of OS and PFS for the development and validation sets of the ACORN NSCLC chemotherapy cohort. Note that the plots in the ACORN NSCLC cohort (FIGS. 18E-18G) show similar OS and PFS for samples labeled Early and Late by the classifier of Example 2.

FIG. 23 is similar to FIG. 20 in that both figures show that the classifiers of Example 1 and Example 2 of this disclosure are able to predict melanoma patients having relatively better or worse outcomes on anti-CTLA4 antibody treatment.

FIG. 36A shows the data for the large and small tumor classifiers classifying the members of the development sample set (after removal of the fast progressing patients) and fast progressing patients with available tumor size change data classified as Early ("Final"), whereas FIG. 36B shows the data for the full-set classifier of Example 1.

FIGS. 45A and 45B are "heat maps", namely plots of p values generated by GSEA associating all 351 defined mass spectral features (Appendix A) in our nivolumab study of Examples 1 and 6 with protein functional groups. FIG. 45A is the heat map for ES definition 1, and FIG. 45B is the heat map for ES definition 2. Only every $5^{th}$ spectral feature is labeled on the x axis.

FIGS. 54A and 54B are a flow chart showing a computer-implemented procedure for developing a classifier from a development sample set. In Example 9, the procedure of FIGS. 54A and 54B (up to and including step 350) was performed several different times for different configurations or subsets of the development sample set to result in the creation of a tiered or hierarchical series of classifiers (referred to as Classifiers A, B and C), as will be explained in more detail in the description of Example 9.

FIG. 55A shows the plot of DFS; FIG. 55B shows the plot for OS. Note that the plots for the development and validation sample sets are essentially the same.

FIG. 56A is a plot of OS for the development set; FIG. 56B is a plot of DFS for the development set; FIG. 56C is a plot of OS for the validation set; FIG. 56D is a plot of DFS for the validation set.

FIGS. 65A-65C are plots of the average of the percentage of the "PROSE-erlotinib" data set variances explained by each principal component (PC) as a function of the PC index (descending order of variance) from Example 10, for biological functions Acute Response (FIG. 65A), Wound Healing (FIG. 65B) and Complement system (FIG. 65C).

FIG. 69A is the plot for patients with class label Early at both baseline and week 7; FIG. 69B is the plot for the patients with class labels Late at both baseline and week 7; FIG. 69C is the plot for patients with class label Early at baseline and Late at week 7, and FIG. 69D is a plot for patients with class label Late at baseline and Early at week 7.

FIG. 70A is the plot for the PD: progressive disease treatment response; FIG. 70B is the plot for the PR: partial response to treatment, and FIG. 70C is the plot for SD: stable disease treatment response.

FIG. 73A is the plot for patients with class label Early at both baseline and week 7; FIG. 73B is the plot for the patients with class labels Late at both baseline and week 7; FIG. 73C is the plot for patients with class label Early at baseline and Late at week 7, and FIG. 73D is a plot for patients with class label Late at baseline and Early at week 7.

FIG. 74A is the plot for the PD: progressive disease treatment response; FIG. 74B is the plot for the PR: partial response to treatment, and FIG. 74C is the plot for SD: stable disease treatment response.

FIG. 76A-76D are illustrations of the evolution of the Complement System Score over time for 107 patients in both the Moffitt and Moffitt-Week7 sets, grouped by combination of IS2 label at baseline (before treatment) and week 7 (after treatment). Each line in the plots represents the score of an individual patient. FIG. 76A is the plot for patients with class label Early at both baseline and week 7; FIG. 76B is the plot for the patients with class labels Late at both baseline and week 7; FIG. 76C is the plot for patients with class label Early at baseline and Late at week 7, and FIG. 76D is a plot for patients with class label Late at baseline and Early at week 7.

FIG. 77A is the plot for the PD: progressive disease treatment response; FIG. 77B is the plot for the PR: partial response to treatment, and FIG. 77C is the plot for SD: stable disease treatment response.

FIG. 82 is an illustration of a partial feature table for sample set ss, $F^{ss}$ which is used in the calculation of a biological function score of Example 10.

FIG. 83 is an illustration of an average first principal component vector $\hat{u}_1$, which is used in the calculation of a biological function score of Example 10.

DETAILED DESCRIPTION

Figure 1A:
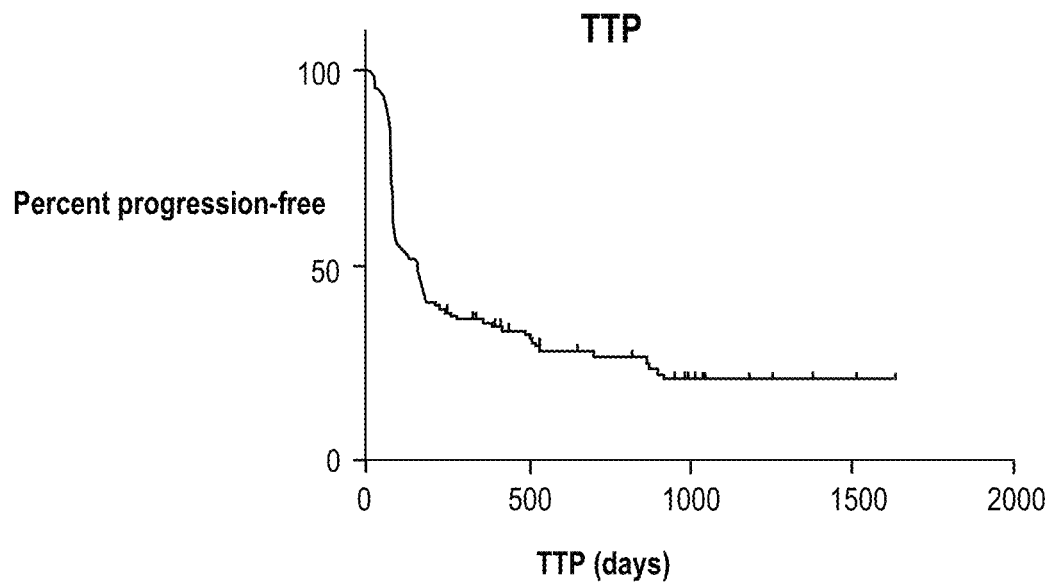
FIG. 1A illustrates Kaplan-Meier plot for time-to-progression (TTP) and FIG. 1B illustrates a Kaplan-Meir plot for overall survival (OS) for the cohort of 119 melanoma patients treated with nivolumab with available clinical data and spectra from pre-treatment samples.

A practical test (method) is disclosed in this document for predicting whether a cancer patient is likely to be benefit from administration of immune checkpoint inhibitors such as a monoclonal antibody drug blocking ligand activation of PD-1 on activated T cells, e.g., nivolumab. The method makes use of the mass spectrum of the patient's serum or plasma sample acquired pre-treatment, and a general purpose computer configured as a classifier which assigns a class label to the mass spectrum. The class label can take the form of "early" or the equivalent, or "late" or the equivalent, with the class label "late" indicating that the patient is a member of a class of patients that are likely to obtain relatively greater benefit from the drug than patients that are a member of the class of patients having the class label "early." The particular moniker used for the class label is not particularly important.

Overall survival is a primary indicator for assessing the benefit of antibody drugs blocking ligand activation of PD-1. Hence, when considering the meaning of the labels Early and Late, in one preferred embodiment the "relatively greater benefit" associated with the Late label means a patient whose sample is assigned the Late label is likely to have significantly greater (longer) overall survival than a patient with the Early class label.

The term "antibody drug blocking ligand activation of PD-1" is meant to include not only antibodies that bind that PD-1, but also those that bind to the ligands (PD-L1 and PD-L2). Anti-PD-L1 or anti-PD-L2 monoclonal antibodies (mAbs) would also block ligand activation of PD-1. The term "immune checkpoint inhibitors" is meant to include those that block PD-1 as well as those that block CLTA-4. The term immune checkpoints inhibitors or "checkpoint blockers" is defined as immunomodulatory mAbs that target CTLA4-like receptors and their ligands. See Galluzzi L, Kroemer G, Eggermont A. *Novel immune checkpoint blocker approved for the treatment of advanced melanoma.* Oncoimmunology 2014; 3:e967147. FDA-approved agents of this type include ipilimumab (anti-CTLA4), nivolumab (anti-PD-1), and pembrolizumab (anti-PD-1). Several publications/abstracts released during the last 13 months reported the results of clinical trials involving additional checkpoint blockers, such as the CTLA4-targeting mAb tremelimumab, the PD-1-targeting mAb pidilizumab, and the PD-L1-targeting mAbs MEDI4736 (durvalumab), MPDL3280A (atezolizumab), and MSB0010718C (avelumab). See Buqué A, Bloy N, Aranda F, Castoldi F, Eggermont A, Cremer I, Fridman W H, Fucikova J, Galon J, Marabelle A, Spisek R, Tartour E, Zitvogel L, Kroemer G, Galluzzi L. *Trial Watch: Immunomodulatory monoclonal antibodies for oncological indications* Oncoimmunology. 2015 Mar. 2; 4(4). The content of the above-cited scientific publications is incorporated by reference herein.

Example 1 explains the development of a classifier from a melanoma/nivolumab sample set and provides details of classifier performance.

Example 2 explains a redevelopment of the classifier of Example 1 that has been tuned to be more predictive and less prognostic for patient benefit from nivolumab.

Example 3 explains the development of a classifier that is predictive for melanoma patient benefit from anti-CTLA4 antibodies, another immune checkpoint inhibitor.

Example 4 explains how the classifier developed in accordance with Example 1 is also able to predict whether non-small cell lung cancer (NSCLC) and ovarian cancer patients are likely to have relatively higher or lower overall survival from chemotherapy.

Figure 15:
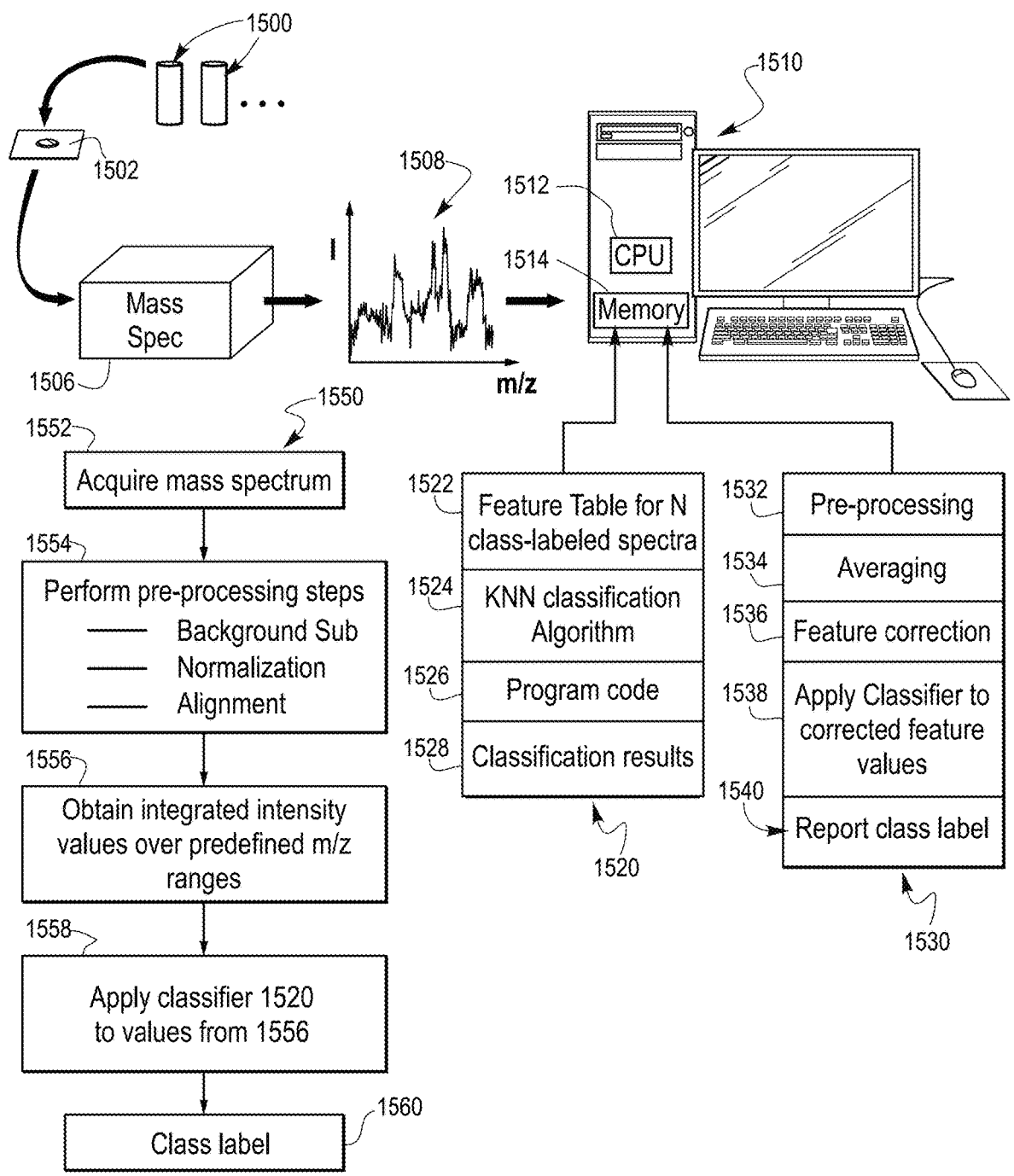
FIG. 15 is an illustration of a laboratory testing center including a mass spectrometer and a machine in the form of a general purpose computer for predicting melanoma patient benefit from antibody drugs blocking ligand activation of PD-1.

Example 5, and FIG. 15, describes a practical testing environment for conducting the tests of this disclosure on a blood-based sample from a patient in advance of treatment.

Example 6 describes our studies of proteins which are correlated to the Early and Late class labels in the Example 1 and Example 2 classifiers using Gene Set Enrichment Analysis, which allow us to generalize our discoveries to other immune checkpoint inhibitors and other types of cancers, as well as generate classifiers based on mass spectral features associated with particular protein functional groups.

Example 7 describes longitudinal studies from patient samples of Example 1 and how changes in class label produced by our classifiers can be used, inter alia, to monitor treatment efficacy and guide treatment.

Example 8 describes an ensemble of classifiers generated from different clinical subsets of the Example 1 development sample set population, in this example, melanoma patients with large and small tumors.

Example 9 provides further examples of development of an ensemble of classifiers from clinically different development sets, including a first example of an ensemble of classifiers from the nivolumab/melanoma set of Example 1 and a second example from study of ovarian cancer patients treated with chemotherapy.

Example 10 describes a methodology for measurement of a biological function score using mass spectrometry data. Example 10 further describes the measurement of biological functions scores in four different sample sets, each blood-based samples from humans with cancer. Example 10 describes how the scores can be used to guide treatment and to build a classifier using biological function scores as features for classifier training, e.g., using the procedure of FIG. 8. Example 10 also builds on the discoveries described in Example 6, including correlation of biological functions with mass spectrometry peaks.

Example 1

Classifier and Method for Predicting Melanoma Patient Benefit from Antibody Drug Blocking Ligand Activation of PD-1

We obtained samples to develop a classifier of Example 1 from a clinical trial of nivolumab in treatment of melanoma.

We describe briefly this trial below. We then describe the patient samples which we obtained, the mass spectrometry methods used to obtain spectra from the samples, including spectra processing steps. These mass spectral procedures are preferably in accordance with the so-called "Deep MALDI" method described in U.S. Pat. No. 9,279,798, the content of which is incorporated by reference herein. We then describe in detail a classifier generation process which was used to define a final classifier which can assign class labels to spectra in accordance with the test. We also describe below the results of the classifier generation process and demonstrate its ability to assign class labels to mass spectra from blood-based samples which predict whether the patient providing the sample is likely to obtain relatively greater or lesser benefit from the antibody drug.

The classifier generation method uses what we have called "combination of mini-classifiers with dropout regularization", or CMC/D, described in pending U.S. patent application Ser. No. 14/486,442 filed Sep. 15, 2014, published as U.S. patent application publication 2015/0102216, the content of which is incorporated by reference herein. This procedure for developing a classifier is also referred to herein as DIAGNOSTIC CORTEX, a trademark of Biodesix, Inc. See the discussion of FIG. 8 below. Applying this procedure to pre-treatment serum spectra from melanoma patients obtained using Deep MALDI spectral acquisition we have identified clinical groups "Early" and "Late." These groups are showing significant differences in outcome (both time to progression (TTP) and overall survival (OS)) following treatment with an anti-PD-1 treatment, nivolumab. See FIGS. 9-14 and the discussion below. We have presented a test procedure to identify these groups from pre-treatment samples, and validated the results in internal validation sets, and in an external validation set (see FIG. 14).

Patients whose serum classifies as "Early" exhibit significantly faster progression and shorter survival than patients whose serum classifies as "Late" making this test suitable as a biomarker for nivolumab therapy. The clinical groups "Early" and "Late" are not associated with PD-L1 expression, and our classification remains a significant predictor for outcome (both TTP and OS) even when other clinical attributes are included in a multivariate analysis.

While a correlative approach to test development does not easily lend itself to a deep understanding of the biology underlying the difference between the identified groups, we have done some initial work relating the two different groups to differences in acute phase reactants and the complement system. These studies are set forth in Example 1 and later in this document in Example 6. The success of this project exemplifies the power of the combination of Deep MALDI spectral acquisition and our inventive classifier development method in the construction of clinically useful, practical tests.

Clinical Trial

The trial from which samples were available for new classifier development was a study of nivolumab with or without a peptide vaccine in patients with unresectable stage III or stage IV melanoma. The trial is described in the paper of J. S. Weber, et al., *Safety, Efficacy, Biomarkers of Nivolumab With Vaccine in Ipilimumab-Refractory or -Naïve Melanoma*, J. Clin. Oncol. vol. 31 pp. 4311-4318 (2013), the content of which is incorporated by reference herein. Patients enrolled in the trial had experienced progression after at least one prior therapy, but no prior PD-1 or PD-L1 treatment. The trial consisted of 6 patient cohorts. Cohorts 1-3 enrolled patients who were ipilimumab-naïve, while patients in cohorts 4-6 had progressed after prior ipilimumab therapy. Cohorts 1-5 received the peptide vaccine in addition to nivolumab and cohort 6 received nivolumab alone. Cohort 5 enrolled only patients who had experienced grade 3 dose-limiting toxicities on ipilimumab therapy, while patients in cohorts 4 and 6 could only have experienced at most grade 2 dose-limiting ipilimumab toxicities. Cohorts 1-3 differed in the nivolumab dose (1 mg/kg, 3 mg/kg or 10 mg/kg). The number of prior treatment regimens was not restricted. All patients had ECOG performance status (PS) 0-1.

For the purpose of this new classifier development project, the dose of nivolumab and whether or not peptides were given in addition to nivolumab is not considered to be significant.

Samples

The samples available for this study were pretreatment serum samples. Clinical data and spectra were available from 119 patients. Available outcome data included time-to-progression (TTP), overall survival (OS), and response. The baseline clinical characteristics for patients with available spectra from pretreatment samples are listed in table 1. (Lactate dehydrogenase (LDH) is known to have prognostic significance across many cancer types and is used frequently as an important factor in assessing prognosis for patients with melanoma.)

TABLE 1

Baseline characteristics of patients with available spectra

| | | N (%) |
|---|---|---|
| Gender | Male | 72 (61) |
| | Female | 45 (38) |
| | NA | 2 (2) |
| Age | Median (Range) | 61 (16-87) |
| Response* | CR | 0 (0) |
| | PR | 31 (26) |
| | SD | 18 (15) |
| | PD | 70 (59) |
| TTP | Median (days) | 160 |
| OS | Median (weeks) | 94 |
| Prior Ipi | No | 31 (26) |
| | Yes | 88 (74) |
| Cohort | 1 | 9 (8) |
| | 2 | 11 (9) |
| | 3 | 11 (9) |
| | 4 | 10 (8) |
| | 5 | 21 (18) |
| | 6 | 57 (48) |
| PD-L1 expression (5% tumor) | Positive | 8 (7) |
| | Negative | 29 (24) |
| | NA | 82 (69) |
| PD-L1 expression (1% tumor) | Positive | 18 (15) |
| | Negative | 19 (16) |
| | NA | 82 (69) |
| PD-L1 expression (1% tumor + immune cells) | Positive | 28 (24) |
| | Negative | 7 (6) |
| | NA | 84 (71) |
| VeriStrat-like classification † | Good | 98 (82) |
| | Poor | 21 (18) |
| LDH level ˣ (IU/L) | Median (Range) | 486 (149-4914) |
| | >ULN ˣˣ | 100 (85) |
| | >2ULN | 31 (26) |

Figure 1B:
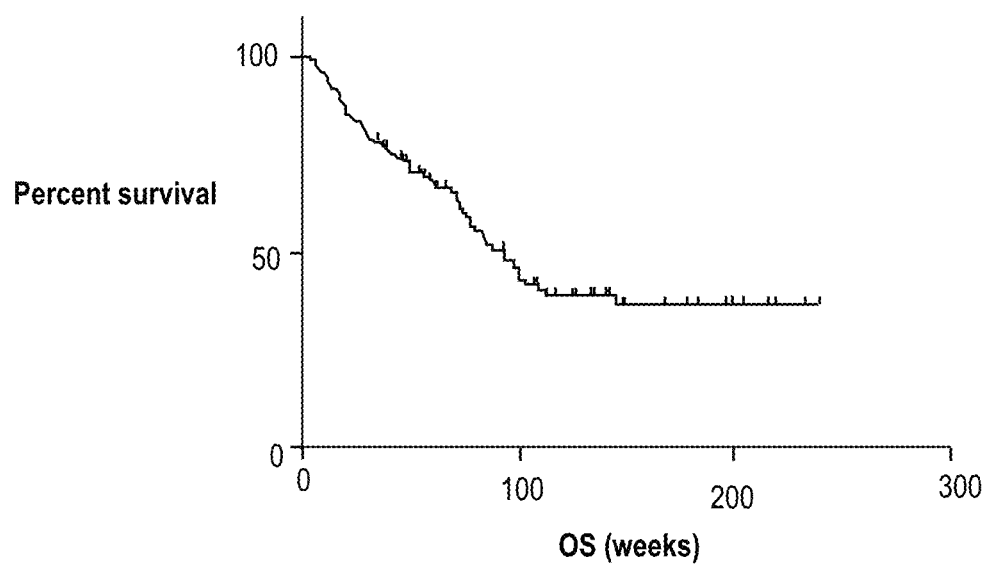

*subject to further data review; † see details in Appendix D of our prior provisional application,
ˣ Not available for one patient,
ˣˣ ULN = upper limit of normal range Kaplan-Meier plots for time-to-progression (TTP) and overall survival (OS) for the cohort of 119 patients with baseline samples and acquired spectra from pretreatment samples are shown in FIGS. 1A and 1B, respectively. Note: Of the 14 patients on the plateau of the TTP Kaplan-Meier plot, 3 (21%) had an objective response of SD rather than PR.

Figure 2A:
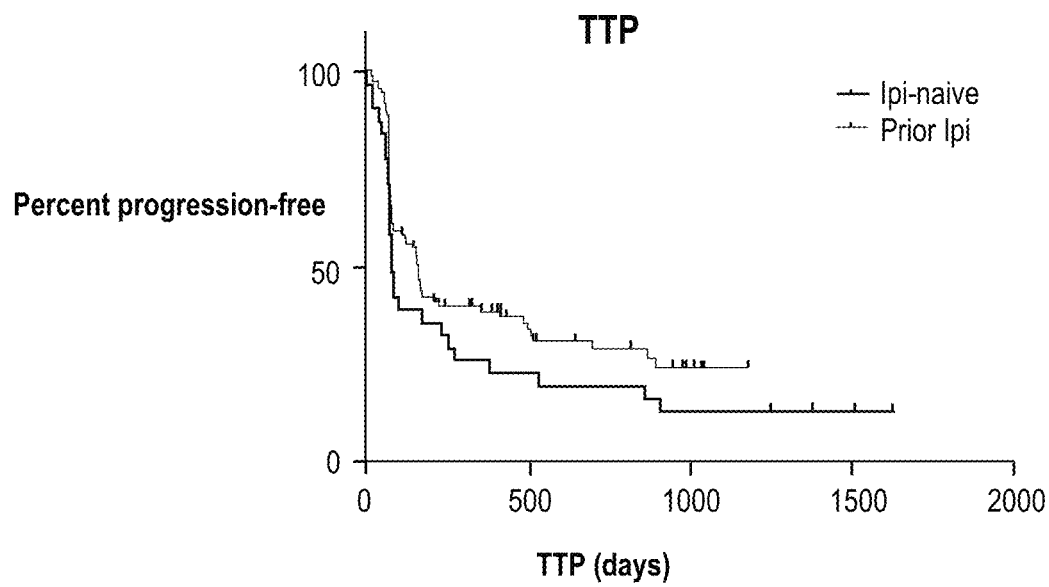
FIGS. 2A and 2B are Kaplan-Meier plots of time-to-event data (TTP and OS), respectively, for all 119 patients with available clinical data and spectra from pretreatment samples by prior treatment (no prior ipilimumab, prior ipilimumab). Differences in outcome were not statistically significant.
Figure 2B:
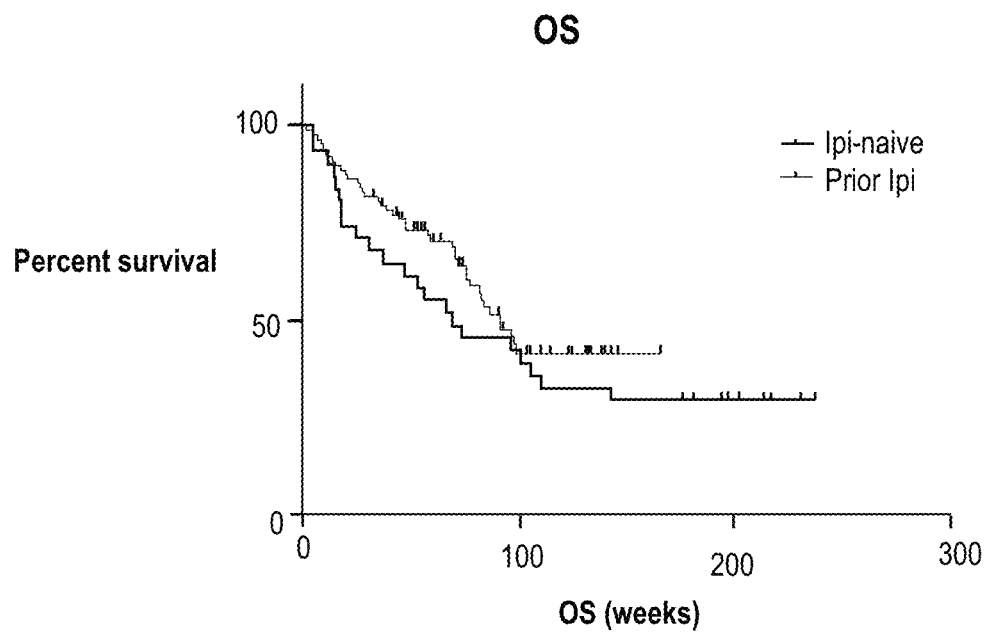

FIGS. 2A and 2B illustrate Kaplan-Meier plots of time-to-event data for all 119 patients with available clinical data and spectra from pretreatment samples by prior treatment (no prior ipilimumab, i.e., "Ipi-naïve"; prior ipilimumab). Differences in outcome were not statistically significant.

Figure 3A:
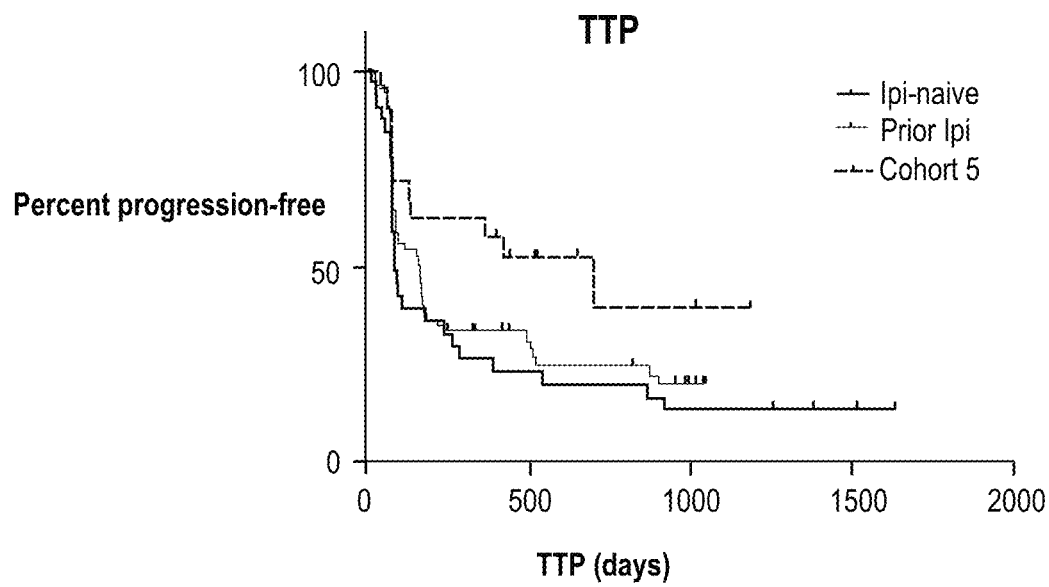
FIGS. 3A and 3B are Kaplan-Meier plots of time-to-event data (TTP and OS), respectively, for all 119 patients with available clinical data and spectra from pretreatment samples showing relatively good outcomes for patients in cohort 5.
Figure 3B:
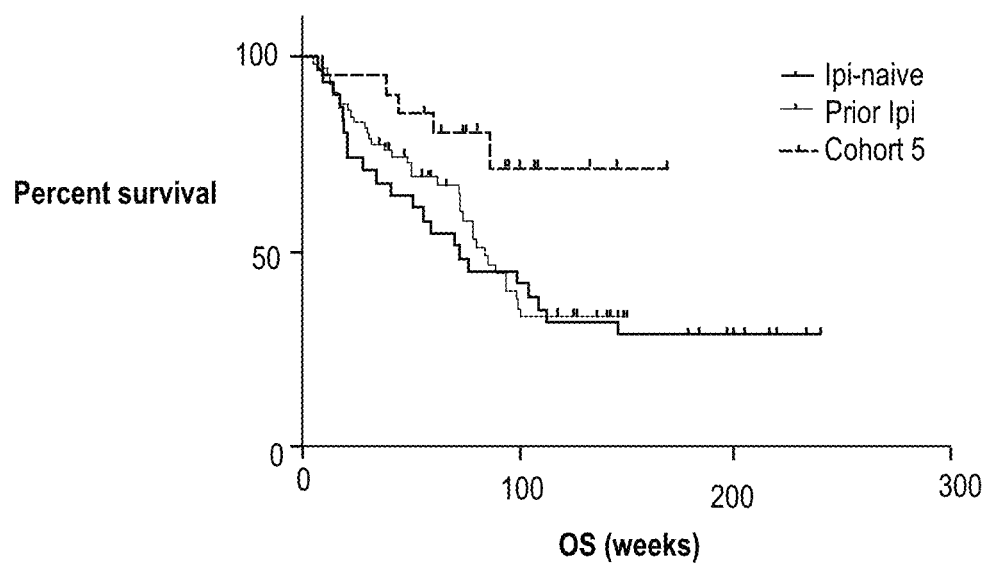

FIGS. 3A and 3B are Kaplan-Meier plots of time-to-event data (TTP and OS), respectively, for all 119 patients with available clinical data and spectra from pretreatment samples showing particularly good outcomes for patients in cohort 5, both in absolute terms and as compared to the ipilimumab-naïve patients and other patients with prior ipilimumab treatment. Recall that Cohort 5 in the nivolumab study involved patients that had progressed after or on prior ipilimumab therapy, and enrolled only patients who had experienced grade 3 dose-limiting toxicities on their prior ipilimumab therapy.

The relatively large number of samples (119) we obtained from the study allowed for a split of the samples into a development set and an internal validation set for classifier development. Two different splits were studied. The first (referred to in the following discussion as "DEV1") was stratified by VeriStrat-like classification, response, censoring of TTP and TTP. The second (referred in to the following discussion as "DEV2"), was stratified by cohort, VeriStrat-like classification, response, censoring of TTP and TTP. (By "VeriStrat-like classification" we mean assignment of a "Good" or "Poor" class label for the mass spectra using the classification algorithm and training set for the VeriStrat test described in U.S. Pat. No. 7,736,905). The assignment of individual samples to either the validation set or the development set is listed in Appendix E of our prior provisional application Ser. No. 62/289,587. Clinical characteristics are listed for the development and validation split in Tables 2A and 2B and comparison of the time-to-event data between development and validation sets is shown in FIGS. 4A-4D.

TABLE 2A

Baseline characteristics of patients with available spectra split into development and internal validation sets ("DEV1")

| | | Development Set (N = 60) n(%) | Validation Set (N = 59) n(%) |
|---|---|---|---|
| Gender | Male | 35 (58) | 37 (63) |
| | Female | 25 (42) | 20 (34) |
| | NA | 0 (0) | 2 (3) |
| Age | Median (Range) | 61 (23-86) | 61 (16-87) |
| Response | CR | 0 (0) | 0 (0) |
| | PR | 16 (27) | 16 (27) |
| | SD | 9 (15) | 8 (14) |
| | PD | 35 (58) | 35 (59) |
| TTP | Median (days) | 162 | 154 |
| OS | Median (weeks) | 94 | 86 |
| Cohort | 1 | 6 (10) | 3 (5) |
| | 2 | 5 (8) | 6 (10) |
| | 3 | 8 (13) | 3 (5) |
| | 4 | 6 (10) | 4 (7) |
| | 5 | 10 (17) | 11 (19) |
| | 6 | 25 (42) | 32 (54) |
| Prior ipi | yes | 41 (68) | 47 (80) |
| | no | 19 (32) | 12 (20) |
| VS-like classification | good | 10 (17) | 11 (19) |
| | poor | 50 (83) | 48 (81) |

TABLE 2B

Baseline characteristics of patients with available spectra split into development and internal validation sets ("DEV2")

| | | Development Set (N = 60) n(%) | Validation Set (N = 59) n(%) |
|---|---|---|---|
| Gender | Male | 36 (60) | 36 (61) |
| | Female | 23 (38) | 22 (37) |
| | NA | 1 (2) | 1 (2) |
| Age | Median (Range) | 60 (16-87) | 62 (34-85) |
| Response | CR | 0 (0) | 0 (0) |
| | PR | 16 (27) | 15 (25) |
| | SD | 9 (15) | 9 (15) |
| | PD | 35 (58) | 35 (59) |
| TTP | Median (days) | 162 | 132 |
| OS | Median (weeks) | 94 | 89 |
| Cohort | 1 | 4 (7) | 5 (8) |
| | 2 | 6 (10) | 5 (8) |
| | 3 | 6 (10) | 5 (8) |
| | 4 | 4 (7) | 6 (10) |
| | 5 | 11 (18) | 10 (17) |
| | 6 | 29 (48) | 28 (47) |
| Prior ipi | yes | 44 (73) | 44 (75) |
| | no | 16 (27) | 15 (25) |
| VS-like classification | good | 11 (18) | 10 (17) |
| | poor | 49 (82) | 49 (83) |

Figure 4A:
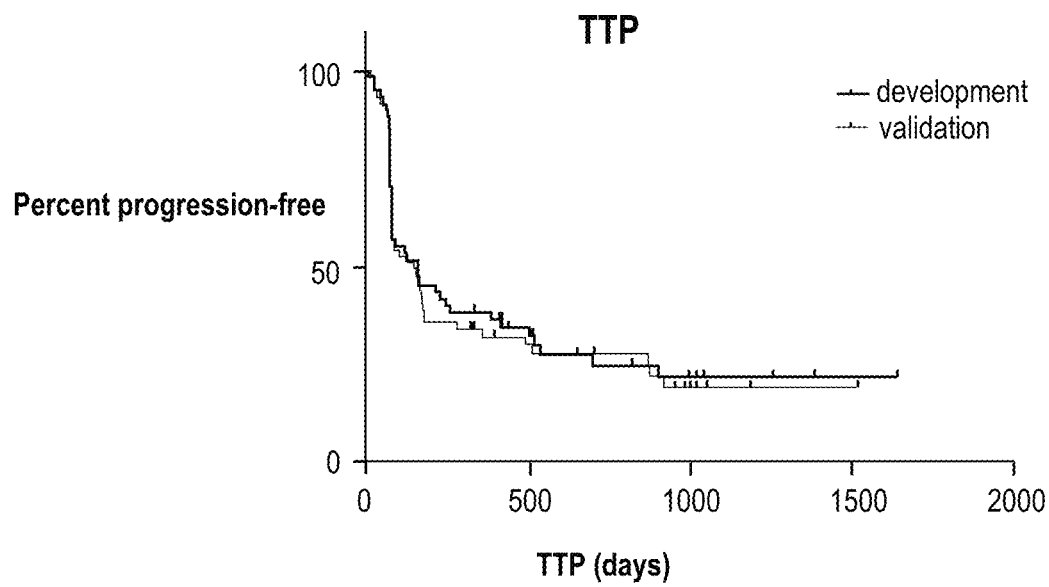
FIG. 4A and FIG. 4B are Kaplan-Meier plots showing time-to-event data for all 119 patients with available clinical data and spectra from pretreatment samples split into development (N=60) and validation (N=59) sets ("DEV1")
Figure 4B:
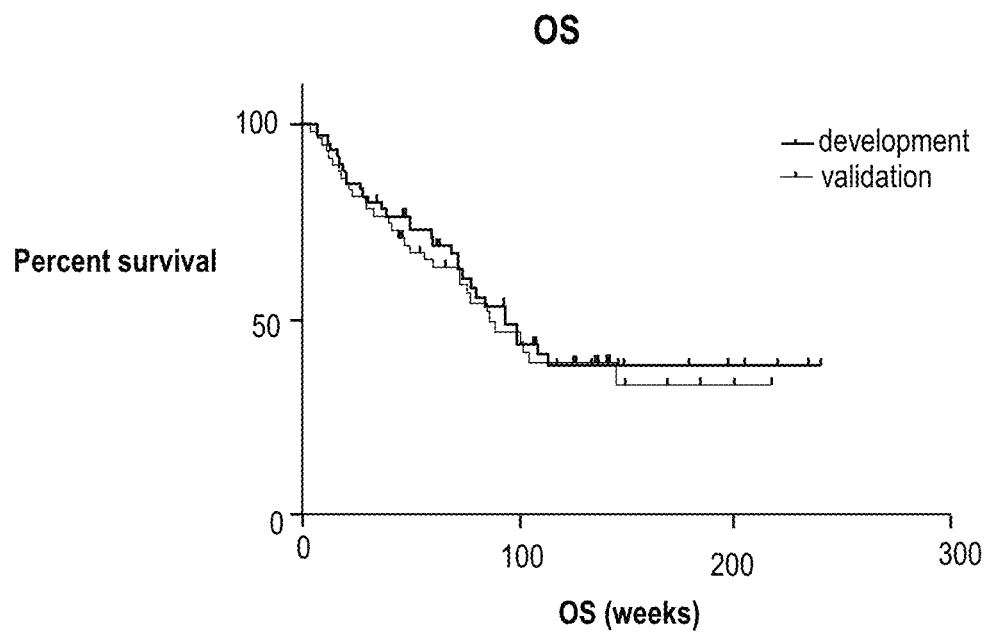
Figure 4C:
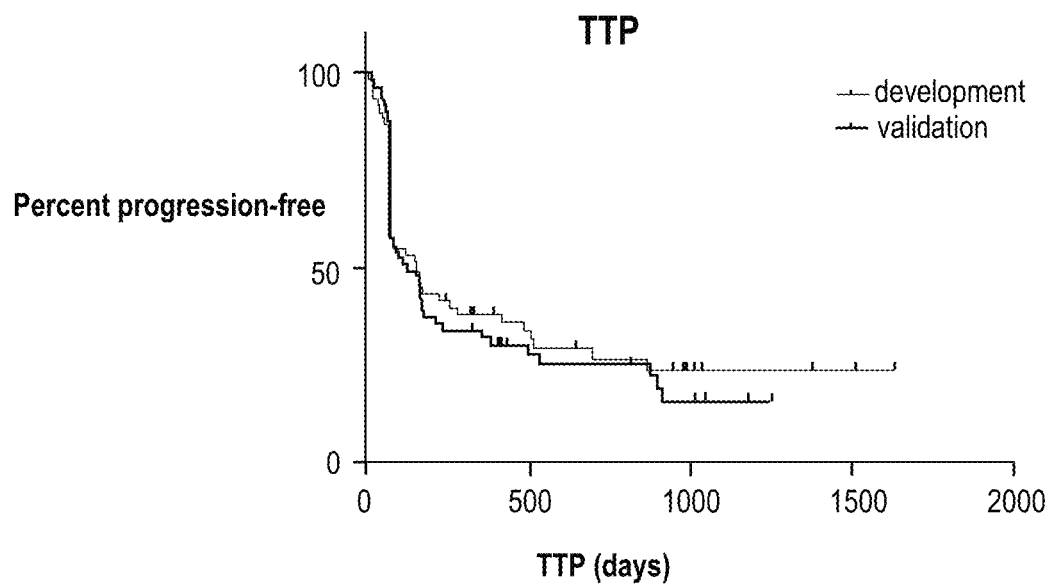
FIGS. 4C and 4D are Kaplan-Meier plots of time-to-event data for all 119 patients with available clinical data and spectra from pretreatment samples split into development (N=60) and validation (N=59) sets for a second split of samples into development and validation sets ("DEV2").
Figure 4D:
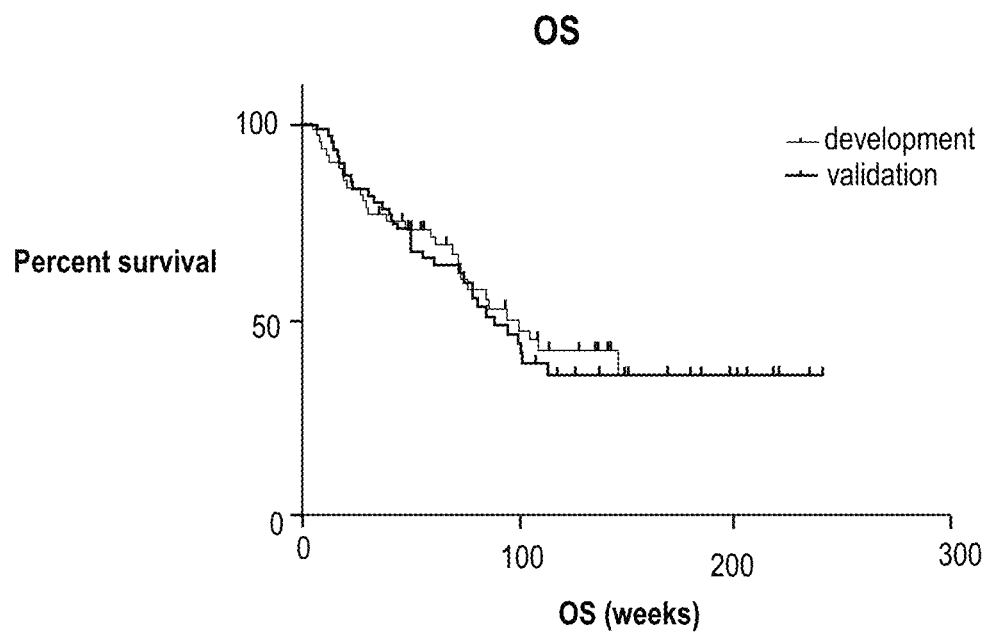

Kaplan-Meier plots for time-to-progression (TTP) and overall survival (OS) for development and validation sets are shown in FIGS. 4A, 4B, 4C and 4D. In particular, FIGS. 4A and 4B show the time-to-event data for all 119 patients with available clinical data and spectra from pretreatment samples split into development (N=60) and validation (N=59) sets for the first split ("DEV1"); FIGS. 4C and 4D shows the time-to-event data for all 119 patients with available clinical data and spectra from pretreatment samples split into development (N=60) and validation (N=59) sets for the second split ("DEV2").

Sample Preparation

Serum samples were thawed and 3 µl aliquots of each test sample (from patients treated with nivolumab) and quality control serum (a pooled sample obtained from serum of five healthy patients, purchased from ProMedDx, "SerumP3") were spotted onto VeriStrat TM cellulose serum cards (Therapak). The cards were allowed to dry for 1 hour at ambient temperature after which the whole serum spot was punched out with a 6 mm skin biopsy punch (Acuderm). Each punch was placed in a centrifugal filter with 0.45 µm nylon membrane (VWR). One hundred µl of HPLC grade water (JT Baker) was added to the centrifugal filter containing the punch. The punches were vortexed gently for 10 minutes then spun down at 14,000 rcf for two minutes. The flow-through was removed and transferred back on to the punch for a second round of extraction. For the second round of extraction, the punches were vortexed gently for three minutes then spun down at 14,000 rcf for two minutes. Twenty microliters of the filtrate from each sample was then transferred to a 0.5 ml eppendorf tube for MALDI analysis.

All subsequent sample preparation steps were carried out in a custom designed humidity and temperature control chamber (Coy Laboratory). The temperature was set to 30° C. and the relative humidity at 10%.

An equal volume of freshly prepared matrix (25 mg of sinapinic acid per 1 ml of 50% acetonitrile:50% water plus 0.1% TFA) was added to each 20 µl serum extract and the mix vortexed for 30 sec. The first three aliquots (2×2 µl) of sample:matrix mix were discarded into the tube cap. Eight aliquots of 2 µl sample:matrix mix were then spotted onto a stainless steel MALDI target plate (SimulTOF). The MALDI target was allowed to dry in the chamber before placement in the MALDI mass spectrometer.

This set of samples was processed for MALDI analysis in three batches. QC samples were added to the beginning (two preparations) and end (two preparations) of each batch run.

Spectral Acquisition

MALDI spectra were obtained using a MALDI-TOF mass spectrometer (SimulTOF 100 s/n: LinearBipolar 11.1024.01 from Virgin Instruments, Sudbury, Mass., USA). The instrument was set to operate in positive ion mode, with ions generated using a 349 nm, diode-pumped, frequency-tripled Nd:YLF laser operated at a laser repetition rate of 0.5 kHz. External calibration was performed using a mixture of standard proteins (Bruker Daltonics, Germany) consisting of insulin (m/z 5734.51 Da), ubiquitin (m/z, 8565.76 Da), cytochrome C (m/z 12360.97 Da), and myoglobin (m/z 16952.30 Da).

Spectra from each MALDI spot (8 spots per sample) were collected as 800 shot spectra that were 'hardware averaged' as the laser fires continuously across the spot while the stage is moving at a speed of 0.25 mm/sec. A minimum intensity threshold of 0.01 V was used to discard any 'flat line' spectra. All 800 shot spectra with intensity above this threshold were acquired without any further processing.

MALDI-TOF mass spectral data acquisition and processing (both for purposes of acquiring a set of data for classifier development and to perform a test on a sample for patient benefit) is optionally performed in accordance with the so-called "Deep MALDI" method described in U.S. Pat. No. 9,279,798 of H. Röder et al., the content of which is incorporated by reference herein. This ''798 patent describes the surprising discovery that collecting and averaging large numbers of laser shots (typically 100,000 to 500,000 or more) from the same MALDI spot or from the combination of accumulated spectra from multiple spots of the same sample, leads to a reduction in the relative level of noise vs. signal and that a significant amount of additional spectral information from mass spectrometry of complex biological samples is revealed. The document also demonstrates that it is possible to run hundreds of thousands of shots on a single spot before the protein content on the spot is completely depleted. Second, the reduction of noise via averaging many shots leads to the appearance of previously invisible peaks (i.e., peaks not apparent at spectra resulting from typical 1,000 laser shots). Even previously visible peaks become better defined and this allows for more reliable measurements of peak intensity and comparisons between samples when the sample is subject to a very large number of shots. The classifier of this disclosure takes advantage of the deep MALDI method to look deep into the proteome of serum samples and uses relatively large numbers of peaks (hundreds) for classification which would not be otherwise observable in conventional "dilute and shoot" spectra obtained from the typical ~1000 shot mass spectrum. See e.g. the definition of classification feature values listed in Appendix A.

The following section of this document describes the spectral processing we used on the raw spectra from the mass spectrometer in order to construct a feature table for use in classifier generation. The following procedures are executed in software in a general purpose computer which receives the spectra from the mass spectrometer. Some of the steps, such as for example defining the features used for classification, may be performed in part or in whole by a human operator by inspection of plots of the mass spectral data.

Spectral Processing

Raster Spectra Preprocessing

Rescaling

Instrument calibration can introduce dramatic drifts in the location of peaks (mass (m)/charge (z)=m/z), most apparent in the high mass region, by batch. This results in an inability to consistently use predefined workflows to process the data that rely on the position of peaks and a set tolerance for alignment. To overcome the problem, rescaling of the m/z data can be performed requiring a standard reference spectrum. The standard is compared to spectra from the current batch to identify if there is a shift in the position of common serum peaks. The m/z position is borrowed from the reference and any 'shift' applied to rescale the spectra. The results are rescaled spectra with comparable m/z across batches. In a sense, this is a batch correction procedure for gross alignment issues.

Alignment and Filtering

This workflow performs the ripple filter as it was observed that the resulting averages were improved in terms of noise. The spectra are then background subtracted and peaks are found in order to perform alignment. The spectra that are used in averaging are the aligned ripple filtered spectra without any other preprocessing. The calibration step uses a set of 43 alignment points listed below in table 3. Additional filtering parameters required that the spectra have at least 20 peaks and used at least 5 of the alignment points.

TABLE 3

Alignment points used to align the raster spectra m/z 3168
4153
4183
4792
5773
5802
6433
6631
7202
7563
7614
7934
8034
8206
8684
8812
8919
8994
9133
9310
9427
10739
10938
11527
12173
12572
12864
13555
13763
13882
14040
14405
15127
15263
15869
17253
18630
21066
23024
28090

TABLE 3-continued

Alignment points used to align the raster spectra

| m/z |
| --- |
| 28298 |
| 33500 |
| 67150 |

Raster Averaging

Averages were created from the pool of rescaled, aligned, and filtered raster spectra. A random selection of 500 spectra was averaged to create a final sample spectrum of 400,000 shots. We collected multiple 800 shot spectra per spot, so that we end up with a pool in excess of 500 in number of 800 shot raster spectra from the 8 spots from each sample. We randomly select 500 from this pool, which we average together to a final 400,000 shot average deep MALDI spectrum.

Deep MALDI Average Spectra Preprocessing

Background Estimation and Subtraction

Estimation of background was performed with additional consideration for the high mass region. The two window method of background estimation and subtraction was used (table 4).

TABLE 4

Background estimation windows

|  | m/Z | width |
| --- | --- | --- |
| Wide windows | 3000 | 80000 |
|  | 30000 | 80000 |
|  | 31000 | 160000 |
| Medium windows | 3000 | 5000 |
|  | 30000 | 5000 |
|  | 31000 | 10000 |

Details on background subtraction of mass spectra are known in the art and described in prior U.S. Pat. No. 7,736,905, such description is hereby incorporated by reference.

Normalization by Bin Method

A bin method was used to compare clinical groups of interest to ensure that normalization windows are not selected that are useful for classification. The feature definitions used in this analysis are included in Appendix C of our prior provisional application Ser. No. 62/289,587. This method compares feature values by clinical group and calculates the coefficient of variance (CV) of the feature for all samples. A threshold is set for p value and for the CV to remove any region that significantly distinguishes the groups of interest or has intrinsic instability (high CV). We used the clinical group comparisons Progressive Disease (PD) vs Stable Disease (SD) and Partial Response (PR), i.e., disease control (DC) no or yes, to calculate univariate p values. A second comparison was added that used PR vs PD and SD. For both, the p value cutoff was set to 0.22. Feature bins with p values less than 0.22 were not included to calculate the normalization scalars. The CV cutoff that was used was 1.0. Features that had CVs above 1.0 were also excluded. By hand, features above 25 kDa were removed and features known to be intrinsically unstable (17 kDa region) were also removed. A total of 16 bins were identified to include as normalization windows (see table 5).

TABLE 5

Iteration # 1 normalization bins

| Left | Center | Right |
| --- | --- | --- |
| 3530.679 | 3657.668 | 3784.658 |
| 3785.029 | 3931.884 | 4078.739 |
| 4220.21 | 4271.637 | 4323.065 |
| 4875.581 | 4909.742 | 4943.903 |
| 5260.635 | 5348.079 | 5435.524 |
| 5436.47 | 5559.451 | 5682.433 |
| 6050.421 | 6213.614 | 6376.807 |
| 6510.852 | 6555.966 | 6601.081 |
| 7751.414 | 7825.12 | 7898.826 |
| 10606.12 | 10751.66 | 10897.2 |
| 10908.61 | 11132.56 | 11356.51 |
| 12425.27 | 12476.27 | 12527.26 |
| 17710.35 | 18107.52 | 18504.69 |
| 19212.92 | 19978.37 | 20743.82 |
| 22108.95 | 22534.05 | 22959.15 |
| 23738.5 | 24238.77 | 24739.04 |

A second iteration of normalization by bin was performed on the spectra normalized using iteration #1 bins. The CVs following the first iteration were in general lower. This allowed a new threshold for CV of 0.68 to be set. The p value cutoff was increased to add stringency to the requirements. The same clinical groups were used in the evaluation. The second iteration resulted in 9 windows for inclusion as normalization bins (see table 6).

TABLE 6

Iteration # 2 normalization bins

| Left | Center | Right |
| --- | --- | --- |
| 4168.226 | 4194.033 | 4219.839 |
| 4875.581 | 4909.742 | 4943.903 |
| 4946.131 | 5011.854 | 5077.576 |
| 5080.918 | 5170.405 | 5259.892 |
| 5260.635 | 5348.079 | 5435.524 |
| 6510.852 | 6555.966 | 6601.081 |
| 7751.414 | 7825.12 | 7898.826 |
| 10606.12 | 10751.66 | 10897.2 |
| 10908.61 | 11132.56 | 11356.51 |

Figure 5:
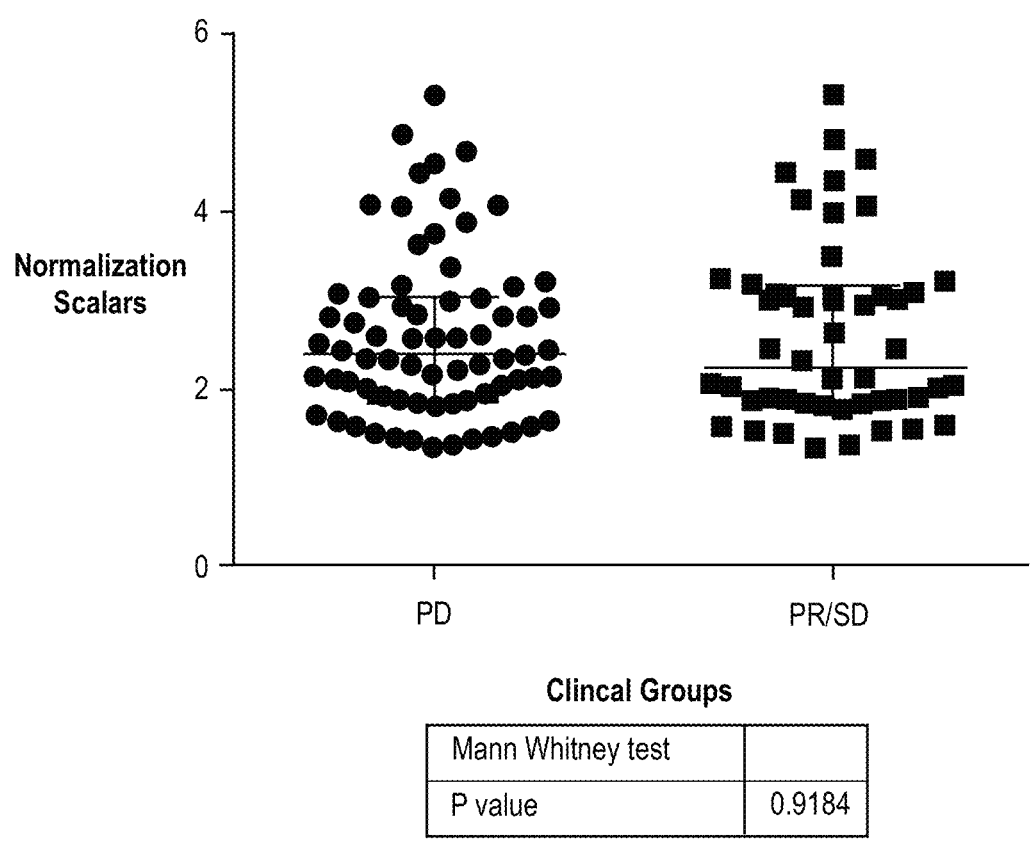
FIG. 5 is a plot of bin normalization scalars as a function of disease control (DC); the bin method is used to compare normalization scalars between clinical groups of interest to ensure that windows useful for classification are not used for partial ion current normalization.

The resulting scalars using these windows were found for each spectrum and were compared by disease control groups, i.e., scalars for spectra from patients with disease control were compared with spectra for patients with no disease control to ensure that there were no significant differences in scalars depending on clinical group. The plot of normalization scalars shown in FIG. 5 reveals that the distribution of the resulting scalars was not significantly different between the clinical groups, and thus the normalization bins were not useful for classification. The spectra were normalized using partial ion current (PIC) over these windows.

Average Spectra Alignment

The peak alignment of the average spectra is typically very good; however, a fine-tune alignment step was performed to address minor differences in peak positions in the spectra. A set of alignment points was identified and applied to the analysis spectra (Table 7).

TABLE 7

Alignment points used to align the spectral averages

| m/Z |
| --- |
| 3315 |
| 4153 |

TABLE 7-continued

Alignment points used to align the spectral averages

| m/Z |
|---|
| 4457 |
| 4710 |
| 5066 |
| 6433 |
| 6631 |
| 7934 |
| 8916 |
| 9423 |
| 9714 |
| 12868 |
| 13766 |
| 14045 |
| 14093 |
| 15131 |
| 15872 |
| 16078 |
| 17256 |
| 17383 |
| 18631 |
| 21069 |
| 21168 |
| 28084 |
| 28293 |
| 67150 |

Feature Definitions

Figure 6:
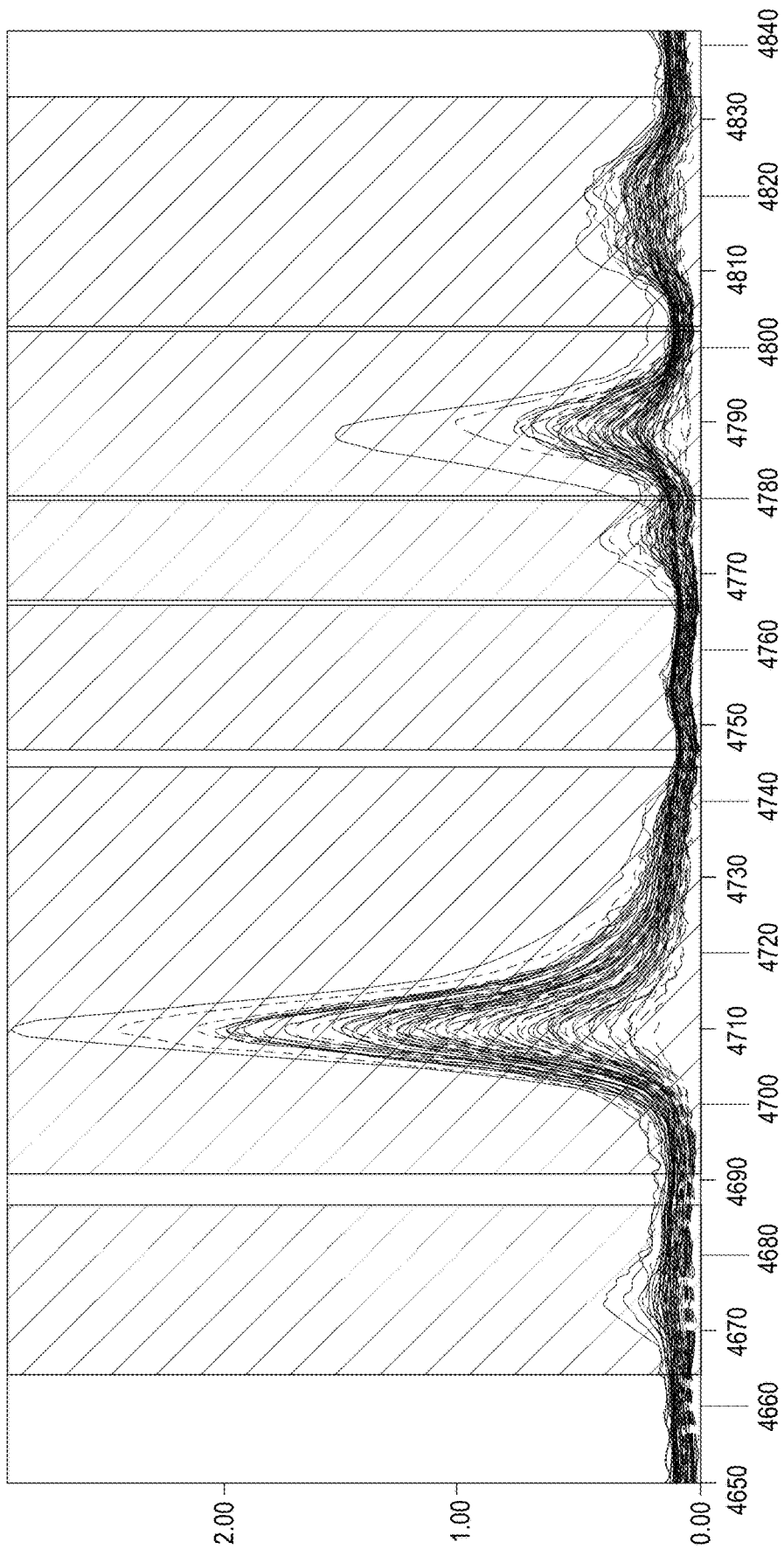
FIG. 6 is a plot of mass spectra from a multitude of samples showing several feature definitions defined within an m/z range of interest; different clinical performance groups are shown in contrasting line conventions.

After performing all of the above pre-processing steps, the process of classifier development proceeded with the identification and definition of features (m/z regions) that are useful for classification. All 119 average spectra were viewed simultaneously by clinical groups PD, SD, and PR to select features for classification. This method protects that features found only in a subset of the spectra are not missed and that feature definitions are broad enough to cover variations of peak width or position. A total of 351 features were defined for the dataset. See Appendix A. These feature definitions were applied to all spectra to create a feature table of feature values (integrated intensity values over each feature) for each of the 119 spectra. An example of selected features is shown in FIG. 6, with the shaded regions representing the m/z region defined for each feature.

Batch Correction of Analysis Spectra

Reference Sample "SerumP3" Analysis

Two preparations of the reference sample, SerumP3, were plated at the beginning (1,2) and end (3,4) of each run of samples through the MALDI-TOF mass spectrometer. The purpose of these samples is to ensure that variations by batch due to slight changes in instrument performance (for example, aging of the detector) can be corrected for. To perform batch correction, one spectrum, which is an average of one of the preparations from the beginning and one from the end of the batch, must serve as the reference for the batch. The procedure used for selecting the pair is described first.

The reference samples were preprocessed as described above. All 351 features (Appendix A) were used to evaluate the possible combinations (1-3, 1-4, 2-3, 2-4). We compared each possible combination of replicates using the function:

$$A=\min(\text{abs}(1-\text{ftrval1}/\text{ftrval2}), \text{abs}(1-\text{ftrval2}/\text{ftrval1}))$$

where ftrval1 (ftrval2) is the value of a feature for the first (second) replicate of the replicate pair. This quantity A gives a measure of how similar the replicates of the pair are. For each feature, A is reported. If the value is >0.5, then the feature is determined to be discordant, or 'Bad'. A tally of the bad features is reported for each possible combination. If the value of A is <0.1, then the feature is determined to be concordant and reported as 'Good'. A tally of the Good features is reported for each possible combination. Using the tallies of Bad and Good features from each possible combination, we computed the ratio of Bad/Good. The combination with the lowest ratio was reported as the most similar combination, unlikely to contain any systematic or localized outlier behavior in either of the reference spectra. If no ratio can be found that is less than 0.12, then the batch is declared a failure. Table 8 reports the combinations that were found most similar for each batch.

TABLE 8

SerumP3 preparations found to be most similar by batch

| Batch | Combination |
|---|---|
| 1 | 2_4 |
| 2 | 1_4 |
| 3 | 2_4 |

Batch Correction

Batch 1 was used as the baseline batch to correct all other batches. The reference sample was used to find the correction coefficients for each of the batches 2 and 3 by the following procedure.

Within each batch j ($2 \leq j \leq 3$), the ratio $$\hat{r}_i^j = \frac{A_i^j}{A_i^1}$$

and the average amplitude $$\bar{A}_i^j = \frac{1}{2}(A_i^j + A_i^1)$$

are defined for each $i^{th}$ feature centered at $(m/z)_i$, where $A_i^j$ is the average reference spectra amplitude of feature i in the batch being corrected and $A_i^1$ is the reference spectra amplitude of feature i in batch 1 (the reference standard). It is assumed that the ratio of amplitudes between two batches follows the dependence:

$$r(\bar{A},(m/z))=(a_0+a_1 \ln(\bar{A}))+(b_0+b_1 \ln(\bar{A}))(m/z)+c_0(m/z)^2.$$

On a batch to batch basis, a continuous fit is constructed by minimizing the sum of the square residuals, $\Delta^j=\Sigma_i(\hat{r}_i^j-r^j(a_0, a_1, b_0, b_1, c_0))^2$, and using the experimental data of the reference sample. The SerumP3 reference samples are used to calculate the correction function. Steps were taken to not include outlier points in order to avoid bias in the parameter estimates. The values of the coefficients $a_0$, $a_1$, $b_0$, $b_1$ and $c_0$, obtained for the different batches are listed in Appendix B (table B.1) of our prior provisional application Ser. No. 62/289,587. The projection in the $\hat{r}_i^j$ versus $(m/z)_i$ plane of the points used to construct the fit for each batch of reference spectra, together with the surface defined by the fit itself, is shown in Figure B.1 of Appendix B of our prior provisional application Ser. No. 62/289,587.

Once the final fit, $r_j(\bar{A},(m/z))$, is determined for each batch, the next step is to correct, for all the samples, all the features (with amplitude A at (m/z)) according to $$A_{corr} = \frac{A}{r^j(\overline{A}, (m/z))}.$$

After this correction, the corrected $(\overline{A}_i^j, (m/z)_i, \hat{r}_i^j)$ feature values calculated for reference spectra lie around the horizontal line defined by r=1, as shown in Figure B.1 of Appendix B of our prior provisional application Ser. No. 62/289,587. Post-correction coefficients are calculated to compare to quality control thresholds. These coefficients can be found in Appendix B table B.2 and the corresponding plots in Figure B.2 of our prior provisional application Ser. No. 62/289,587.

Using the 351 features and all SerumP3 samples from all batches, a reproducibility assessment was performed on the feature values before and after batch correction. In summary, the median and average CVs were 14.8% and 18.3% before batch correction. Following batch correction, the median and average CVs were 15.0% and 18.2%. As seen in the plots found in Appendix B of our prior provisional application Ser. No. 62/289,587, the batches were very similar requiring little in correction. This is reflected in the lack of improvement in the CVs by feature over all SerumP3 samples.

Partial Ion Current (PIC) Normalization

We have found it advantageous to perform a normalization of spectra before batch correction (see above). However, we have found that after batch correction we can improve the coefficient of variances (CVs) of features and obtain better results if we do another normalization. This second PIC normalization is based on smaller windows around individual peaks that are identified above.

The spectra were normalized using a partial ion current (PIC) normalization method. Background information on partial ion current normalization is described in the prior U.S. Pat. No. 7,736,905, such description is incorporated by reference here. The full feature table was examined to find regions of intrinsic stability to use as the final normalization windows. First, the univariate p values were found by comparing the DC groups by feature. Features with p values less than 0.15 were excluded from the PIC analysis as these features may contribute meaningful information to the test to be developed. A set of 221 features were used in the PIC analysis, of which 30 features were used for the final normalization (table 9).

TABLE 9

| Features used for PIC normalization m/Z |
|---|
| 3243 |
| 3265 |
| 3420 |
| 3554 |
| 3679 |
| 3953 |
| 4009 |
| 4409 |
| 4891 |
| 5068 |
| 5104 |
| 5403 |
| 6193 |
| 6438 |
| 6589 |
| 6612 |
| 6657 |
| 6681 |

TABLE 9-continued

| Features used for PIC normalization m/Z |
|---|
| 6732 |
| 7074 |
| 8902 |
| 9020 |
| 9038 |
| 10637 |
| 12738 |
| 12786 |
| 13943 |
| 14098 |
| 14199 |
| 14255 |

Figure 7:
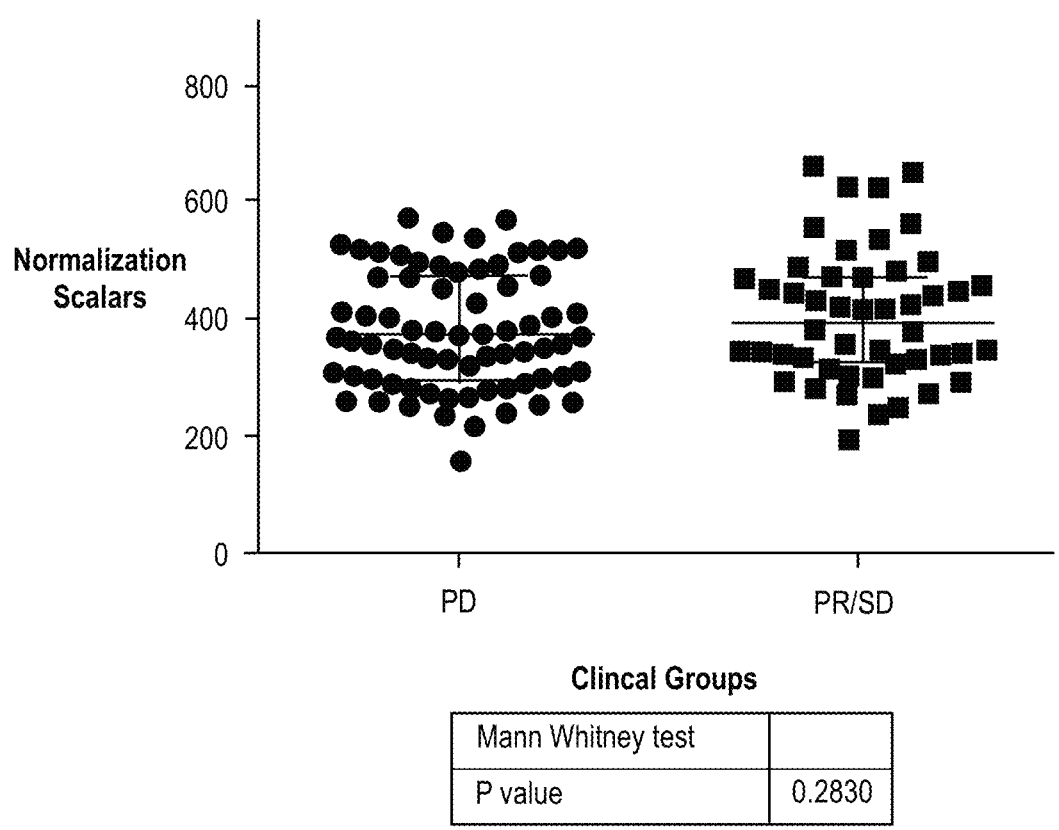
FIG. 7 is a plot of bin normalization scalars as a function of DC for a partial ion current normalization performed on the features in the final feature table used for classifier generation.

To normalize, the listed features were summed to find the normalization factor for each sample. All feature values were then divided by the normalization factor to arrive at the final feature table used in the subsequent classifier generation method of FIG. 8. The normalization factors were examined by DC groups to test that the calculated factors were not significantly correlated. The plot of FIG. 7 illustrates the distribution of the factors. The plots for the two groups are very similar, indicating that the normalization scalars are appropriate to use.

Classifier Development Using Diagnostic Cortex TM

Figures 8, 8A:
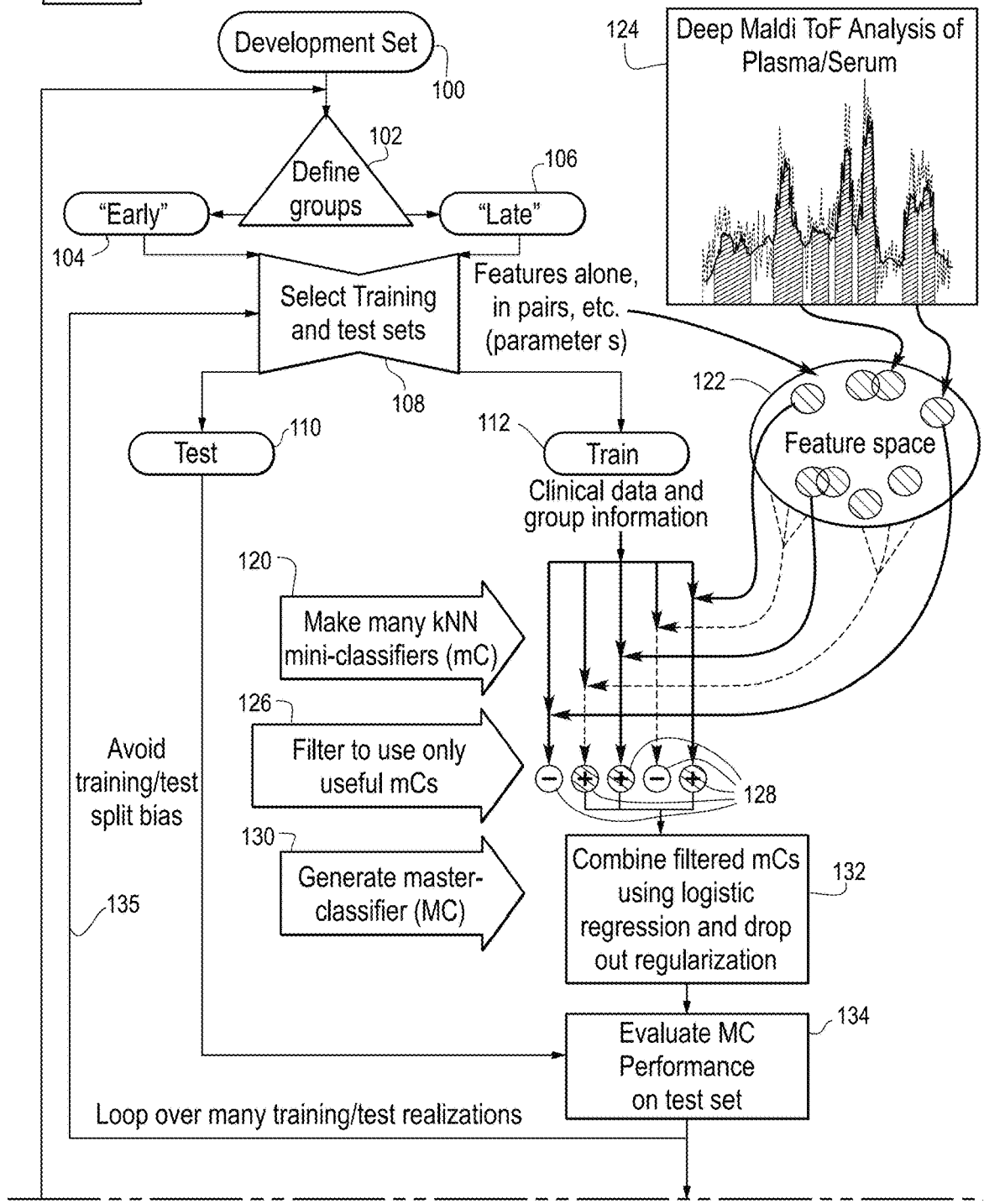
FIGS. 8A-8B are a flow chart of a classifier development process we used to develop the melanoma/nivolumab classifiers of this disclosure from the sample set of 119 serum samples from melanoma patients in the trial of nivolumab.

After the feature table for features in the mass spectra for the 119 samples was created (as explained above) we proceeded to develop a classifier using the classifier generation method shown in flow-chart form in FIG. 8. This method, known as "combination of mini-classifiers with drop-out regularization" or "CMC/D", or DIAGNOSTIC CORTEX TM, is described at length in the pending U.S. patent application publication no. 2015/0102216 of H. Röder et al., the entire content of which is incorporated by reference herein. An overview of the methodology will be provided here first, and then illustrated in detail in conjunction with FIG. 8 for the generation of the melanoma/nivolumab classifier.

In contrast to standard applications of machine learning focusing on developing classifiers when large training data sets are available, the big data challenge, in bio-life-sciences the problem setting is different. Here we have the problem that the number (n) of available samples, arising typically from clinical studies, is often limited, and the number of attributes (measurements) (p) per sample usually exceeds the number of samples. Rather than obtaining information from many instances, in these deep data problems one attempts to gain information from a deep description of individual instances. The present methods take advantage of this insight, and are particularly useful, as here, in problems where p>>n.

The method includes a first step a) of obtaining measurement data for classification from a multitude of samples, i.e., measurement data reflecting some physical property or characteristic of the samples. The data for each of the samples consists of a multitude of feature values, and a class label. In this example, the data takes the form of mass spectrometry data, in the form of feature values (integrated peak intensity values at a multitude of m/z ranges or peaks, see Appendix A) as well as a label indicating some attribute of the sample (for example, patient Early or Late death or disease progression). In this example, the class labels were assigned by a human operator to each of the samples after investigation of the clinical data associated with the sample.

The development sample set is then split into a training set and a test set and the training set is used in the following steps b), c) and d).

The method continues with a step b) of constructing a multitude of individual mini-classifiers using sets of feature values from the samples up to a pre-selected feature set sizes (s=integer 1 . . . n). For example a multiple of individual mini- or atomic classifiers could be constructed using a single feature (s=1), or pairs of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measurement data values (p) in the data set, and where p is in the hundreds, thousands or even tens of thousands, s will typically be 1, or 2 or possibly 3, depending on the computing resources available. The mini-classifiers execute a supervised learning classification algorithm, such as k-nearest neighbors (kNN), in which the values for a features, pairs or triplets of features of a sample instance are compared to the values of the same feature or features in a training set and the nearest neighbors (e.g., k=9) in an s-dimensional feature space are identified and by majority vote a class label is assigned to the sample instance for each mini-classifier. In practice, there may be thousands of such mini-classifiers depending on the number of features which are used for classification.

The method continues with a filtering step c), namely testing the performance, for example the accuracy, of each of the individual mini-classifiers to correctly classify the sample, or measuring the individual mini-classifier performance by some other metric (e.g. the difference between the Hazard Ratios (HRs) obtained between groups defined by the classifications of the individual mini-classifier for the training set samples) and retaining only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible kNN classifiers using feature sets up to a pre-selected size (parameter s). This gives us many "mini-classifiers": e.g. if we start with 100 features for each sample (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step c) we only use those "mini-classifiers" that pass predefined criteria. These filtering criteria are chosen dependent on the particular problem: If one has a two-class classification problem, one would select only those mini-classifiers whose classification accuracy exceeds a pre-defined threshold, i.e., are predictive to some reasonable degree. Even with this filtering of "mini-classifiers" we end up with many thousands of "mini-classifier" candidates with performance spanning the whole range from borderline to decent to excellent performance.

The method continues with step d) of generating a master classifier (MC) by combining the filtered mini-classifiers using a regularized combination method. In one embodiment, this regularized combination method takes the form of repeatedly conducting a logistic training of the filtered set of mini-classifiers to the class labels for the samples. This is done by randomly selecting a small fraction of the filtered mini-classifiers as a result of carrying out an extreme dropout from the filtered set of mini-classifiers (a technique referred to as drop-out regularization herein), and conducting logistical training on such selected mini-classifiers. While similar in spirit to standard classifier combination methods (see e.g. S. Tulyakov et al., Review of Classifier Combination Methods, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of filtered mini-classifiers are dropped out in each iteration.

In more detail, the result of each mini-classifier is one of two values, either "Early" or "Late" in this example. We can then use logistic regression to combine the results of the mini-classifiers in the spirit of a logistic regression by defining the probability of obtaining an "Early" label via standard logistic regression (see e.g. http://en.wikipedia.org/wiki/Logistic_regression)

$$P(\text{``Early''} | \text{feature for a spectrum}) = \frac{\exp\left(\sum_{mini\ classifiers} w_{mc} I(mc(\text{feature values}))\right)}{\text{Normalization}} \quad \text{Eq. (1)}$$

where I(mc(feature values))=1, if the mini-classifier mc applied to the feature values of a sample returns "Early", and 0 if the mini-classifier returns "Late". The weights $w_{mc}$ for the mini-classifiers are unknown and need to be determined from a regression fit of the above formula for all samples in the training set using +1 for the left hand side of the formula for the Late-labeled samples in the training set, and 0 for the Early-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same time, we use only a few of the mini-classifiers for a regression, but repeat this process many times in generating the master classifier. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

Other methods for performing the regularized combination method in step (d) that could be used include:

Logistic regression with a penalty function like ridge regression (based on Tikhonov regularization, Tikhonov, Andrey Nikolayevich (1943). "Об устойчивости обратных задач" [On the stability of inverse problems]. Doklady Akademii Nauk SSSR 39 (5): 195-198.)

The Lasso method (Tibshirani, R. (1996). Regression shrinkage and selection via the lasso. J. Royal. Statist. Soc B., Vol. 58, No. 1, pages 267-288).

Neural networks regularized by drop-out (Nitish Shrivastava, "Improving Neural Networks with Dropout", Master's Thesis, Graduate Department of Computer Science, University of Toronto), available from the website of the University of Toronto Computer Science department.

General regularized neural networks (Girosi F. et al, Neural Computation, (7), 219 (1995)).

The above-cited publications are incorporated by reference herein. Our approach of using drop-out regularization has shown promise in avoiding over-fitting, and increasing the likelihood of generating generalizable tests, i.e. tests that can be validated in independent sample sets. The performance of the master classifier is then evaluated by how well it classifies the subset of samples forming the test set.

In step e), steps b)-d) are repeated in the programmed computer for different realizations of the separation of the set of samples into test and training sets, thereby generating a plurality of master classifiers, one for each realization of the separation of the set of samples into training and test sets. The performance of the classifier is evaluated for all the realizations of the separation of the development set of samples into training and test sets. If there are some samples which persistently misclassify when in the test set, the process optionally loops back and steps b), c) and d) and e) are repeated with flipped class labels for such misclassified samples.

The method continues with step f) of defining a final classifier from one or a combination of more than one of the plurality of master classifiers. In the present example, the final classifier is defined as a majority vote of all the master classifiers resulting from each separation of the sample set into training and test sets, or alternatively by an average probability cutoff.

Turning now to FIG. 8, the classifier development process will be described in further detail in the context of the melanoma/nivolumab classifier.

The set of 119 samples we had available was initially randomly divided into two subsets, a set of 59 samples to be used for validation of the classifier we generated, and a development set (100) of the remaining 60 samples. This split was performed twice (see the discussion of DEV1 and DEV2 above) with stratification as described previously.

At step 102, a definition of the two class labels (or groups) for the samples in the development set 100 was performed. While some preliminary approaches used for classifier development employed well-defined class labels, such as response categories, these proved to be unsuccessful. All approaches discussed in this application make use of time-to-event data for classifier training. In this situation, the initial class label definition (Early, Late) is not obvious and, as shown in FIG. 8, the process uses an iterative method to refine class labels at the same time as creating the classifier (see loop 146 discussed below). At the beginning, an initial guess is made for the class labels. Typically, the samples are sorted on either TTP or OS and half of the samples with the lowest time-to-event outcome are assigned the "Early" class label (early death or progression, i.e. poor outcome) while the other half are assigned the "Late" class label (late death or progression, i.e. good outcome). A classifier is then constructed using the outcome data and these class labels. This classifier can then be used to generate classifications for all of the development set samples and these are then used as the new class labels for a second iteration of the classifier construction step. This process is iterated until convergence.

While one could define "Early" and Late" by setting a cutoff based on clinical data, we started with an initial assignment on training labels using TTP (time to progression) data, with 30 patients with lowest TTP assigned the class label "Early", and the 30 patients with highest TTP assigned the class label "Late". It will be noted that later in the process we have a procedure for flipping class labels for samples which persistently misclassify, so these initial class label assignments are not necessarily fixed. After this initial class label definition is arrived at the samples are then assigned to the Early and Late classes based on outcome data as indicated by the two groups 104 and 106 in FIG. 8.

At step 108, the Early and Late samples of the development set (100) are then divided randomly into training (112) and test sets (110), 30 patients each. This division is performed in a stratified manner. Twenty samples from each class were generally assigned to the training set and the remainder to the test set. Occasionally, during the class label flip refinement process, the number of samples in the Early group dropped too low to allow 20 samples to be assigned to the training set and still have a reasonable number of samples (e.g. more than 7 or 8) in the test set. In these cases, a smaller number of samples, for example 17 or 18, were assigned to the training set from each class. In all cases the number of samples assigned to training from each class was the same. The training set (112) is then subject to steps 120, 126 and 130. In step 120, many k-nearest neighbor (kNN) mini-classifiers (mCs) that use the training set as their reference set are constructed (defined) using subsets of features from the 351 mass spectral features identified (see Appendix A). For many of the investigations we performed, all possible single features and pairs of features were examined (s=2); however, when fewer features were used, triplets were also sometimes considered (s=3). Although different values of k in the kNN algorithm were tried in preliminary investigations, the approaches described in Example 1 all use k=9. To be able to consider subsets of single, two, or three features and improve classifier performance, it was necessary to deselect features that were not useful for classification from the set of 351 features. This was done using the bagged feature selection approach outlined in Appendix F of our prior provisional application Ser. No. 62/289,587. Further details on this methodology, its rationale and benefits, are described in the pending U.S. patent application of J. Roder et al., Ser. No. 15/091,417 filed Apr. 5, 2016 and in U.S. provisional application Ser. No. 62/319, 958 filed Apr. 8, 2016, the content of which is incorporated by reference herein. A reduced, selected list of features for different approaches for classification is listed in Appendix B.

In step 126 a filtering process was used to select only those mini-classifiers (mC) that had useful or good performance characteristics. This can be understood in FIG. 8 by the spectra 124 containing many individual features (shown by the hatched regions) and the features alone and in pairs are indicated in the feature space 122. For some of the kNN mini-classifiers, the features (singly or in pairs) perform well for classification of the samples and such mini-classifiers are retained (indicated by the "+" sign in FIG. 8 at 128) whereas others indicated by the "−" sign are not retained.

To target a final classifier that has certain performance characteristics, these mCs were filtered as follows. Each mC is applied to its training set and performance metrics are calculated from the resulting classifications of the training set. Only mCs that satisfy thresholds on these performance metrics pass filtering to be used further in the process. The mCs that fail filtering are discarded. For this project, accuracy filtering and hazard ratio filtering were used. Sometimes, a simple single filter was used, and sometimes a compound filter was constructed by combining multiple single filters with a logical "AND" operation. For accuracy filtering, the classifier was applied to the training set of samples, or a subset of the training set of samples, and the accuracy of the resulting classification had to lie within a preset range for the mC to pass filtering. For hazard ratio filtering, the classifier was applied to the training set, or a subset thereof. The hazard ratio for a specified outcome (TTP or OS) was then calculated between the group classified as Early and the rest classified as Late. The hazard ratio had to lie within specified bounds for the mC to pass filtering. In this particular classifier exercise, we filtered the mini-classifiers by Hazard ratio (HR) between early/late, and by accuracy for early class label (with TTP defined as <100 days) and late (with TTP defined as >365 days).

TABLE 10

Parameters used in mini-classifiers and filtering

| Approach | Depth s (max # features per mC) | Development/ Validation Split | Filter |
|---|---|---|---|
| 1 | 3 | DEV1 | HR on TTP and classification accuracy on TTP < 100 days and TTP > 365 days |
| 2 | 2 | DEV1 | HR on OS |
| 3 | 2 | DEV2 | HR on TTP and classification accuracy on TTP < 100 days and TTP > 365 days |
| 4 | 2 | DEV2 | HR on OS |

Here, "approach" means different classifier development exercises. In essence, the process of FIG. 8 was repeated a number of different times, with each iteration a different value of the depth parameter s was used and different mini-classifier filtering criteria were used in step 126 of FIG. 8 as indicated by Table 10. Note that this exercise was done twice for each of the two separations of the entire set of 119 samples into development and validation sets (DEV1 and DEV 2).

At step 130, we generated a master classifier (MC) for each realization of the separation of the development set into training and test sets at step 108. Once the filtering of the mCs was complete, at step 132 the mCs were combined in one master classifier (MC) using a logistic regression trained using the training set class labels, step 132. See the previous discussion of drop-out regularization. To help avoid overfitting the regression is regularized using extreme drop out with only a small number of the mCs chosen randomly for inclusion in each of the logistic regression iterations. The number of dropout iterations was selected based on the typical number of mCs passing filtering to ensure that each mC was likely to be included within the drop out process multiple times. All approaches outlined in Example 1 left in 10 randomly selected mCs per drop out iteration. Approaches using only single and pairs of features used 10,000 drop out iterations; approaches using single, pairs and triplets of features used 100,000 drop out iterations.

At step 134, we evaluated the performance of the MC arrived at in step 132 and its ability to classify the test set of samples (110). With each iteration of step 120, 126, 130, 134 we evaluate the performance of the resulting MC on its ability to classify the members of the test set 110.

After the evaluation step 134, the process looped back via loop 135 to step 108 and the generation of a different realization of the separation of the development set into training and test sets. The process of steps 108, 120, 126, 130, 132, 134 and looping back at 135 to a new separation of the development set into training and test sets (step 108) was performed many times, and in this project six hundred and twenty five different realizations (loops) were used. The methodology of FIG. 8 works best when the training set classes have the same number of samples. Hence, if classes had different numbers of members, they were split in different ratios into test and training. The use of multiple training/test splits (loop 135 and the subsequent performance of steps 120, 126, 130, 132 and 134) avoids selection of a single, particularly advantageous or difficult, training set split for classifier creation and avoids bias in performance assessment from testing on a test set that could be especially easy or difficult to classify.

At step 136, there is an optional procedure of analyzing the data from the training and test splits, and as shown by block 138 obtaining the performance characteristics of the MCs from each training/test set split and their classification results. Optional steps 136 and 138 were not performed in this project.

At step 144, we determine if there are samples which are persistently misclassified when they are present in the test set 110 during the many iterations of loop 135. If so, we flip the class label of such misclassified samples and loop back in loop 146 to the beginning of the process at step 102 and repeat the methodology shown in FIG. 8.

If at step 144 we do not have samples that persistently misclassify, we then proceed to step 150 and define a final classifier in one of several ways, including (i) a majority vote of each master classifier (MC) for each of the realizations of the separation of the development set into training and test sets, or (ii) an average probability cutoff. The output of the logistic regression that defines each MC (step 132) is a probability of being in one of the two training classes (Early or Late). These MC probabilities can be averaged to yield one average probability for a sample. When working with the development set (100), this approach is adjusted to average over MCs for which a given sample is not included in the training set ("out-of-bag" estimate). These average probabilities can be converted into a binary classification by applying a threshold (cutoff). During the iterative classifier construction and label refinement process, classifications were assigned by majority vote of the individual MC labels obtained with a cutoff of 0.5. This process was modified to incorporate only MCs where the sample was not in the training set for samples in the development set (modified, or "out-of-bag" majority vote). This procedure gives very similar classifications to using a cutoff of 0.5 on the average probabilities across MCs.

defined at step 150 is also validated on an independent sample set. We describe the validation on an independent set of samples later in this Example 1.

Results of Example 1 Classifier

The goal of this exercise was to determine if the final classifier defined in accordance with FIG. 8 could demonstrate a separation between the Early and Late class labels, in other words, predict from a mass spectrum of a pre-treatment serum sample whether the patient providing the sample was likely to obtain benefit from administration of nivolumab in treatment of cancer. We achieved this goal, as demonstrated by the classifier performance data in this section of the document. The performance of the classifiers was assessed using Kaplan-Meier plots of TTP and OS between samples classified as Early and Late, together with corresponding hazard ratios (HRs) and log-rank p values. The results for the four approaches of table 10 are summarized in table 11. The table lists the classifier performance for both the Development Set (100 in FIG. 8), and the other half of the set of 119 samples, i.e., the Validation Set. Note in table 11 the substantial difference in median OS and TTP between the Early and Late groups as identified by the classifier developed in FIG. 8, indicating the ability of the classifier to identify clinically useful groups.

TABLE 11

| Final Classifier performance summary for the four approaches of table 10 | | | | | | | |
|---|---|---|---|---|---|---|---|
| approach | #Early/#Late | OS HR (95% CI) | OS log-rank p | OS Median (Early, Late) | TTP HR (95% CI) | TTP log-rank p | TTP Median (Early, Late) |
| Development Set | | | | | | | |
| 1 | 26/34 | 0.38 (0.17-0.73) | 0.006 | 67, not reached (weeks) | 0.55 (0.28-0.96) | 0.040 | 83, 254 (days) |
| 2 | 26/34 | 0.30 (0.13-0.57) | 0.001 | 65, not reached (weeks) | 0.53 (0.27-0.94) | 0.032 | 83, 317 (days) |
| 3 | 25/35 | 0.32 (0.13-0.58) | 0.001 | 61, not reached (weeks) | 0.43 (0.19-0.71) | 0.003 | 82, 490 (days) |
| 4 | 28/32 | 0.36 (0.16-0.71) | 0.005 | 73, not reached (weeks) | 0.48 (0.24-0.84) | 0.013 | 83, 490 (days) |
| Validation Set | | | | | | | |
| 1 | 23/36 | 0.47 (0.20-0.91) | 0.029 | 60, 101 (weeks) | 0.51 (0.25-0.88) | 0.021 | 132, 181 (days) |
| 2 | 25/34 | 0.51 (0.23-1.01) | 0.053 | 73, 101 (weeks) | 0.46 (0.22-0.76) | 0.006 | 90, 273 (days) |
| 3 | 16/43 | 0.49 (0.18-0.95) | 0.040 | 55, 99 (weeks) | 0.50 (0.20-0.86) | 0.021 | 86, 179 (days) |
| 4 | 18/41 | 0.43 (0.16-0.80) | 0.013 | 55, 101 (weeks) | 0.48 (0.20-0.80) | 0.012 | 87, 183 (days) |

After the final classifier is defined at step 150, the process optionally continues with a validation step 152 in which the final classifier defined at step 150 is tested on an internal validation set of samples, if it is available. In the present example, the initial set of 119 samples was divided into development set (100) and a separate internal validation set, and so this validation set existed and was subject to the validation step 152. Ideally, in step 154 this final classifier as Kaplan-Meier plots corresponding to the data in table 11 are shown in FIGS. 9-12 for the four approaches. The classifications per sample for each approach are listed in Appendix G of our prior provisional application Ser. No. 62/289,587. Baseline clinical characteristics are summarized by classification group for each of the four approaches in table 12.

TABLE 12

Clinical characteristic by classification group

|  |  | Approach 1 | | Approach 2 | | Approach 3 | | Approach 4 | |
| --- | --- | --- | --- | --- | --- | --- | --- | --- | --- |
|  |  | Early (N = 49) | Late (N = 70) | Early (N = 51) | Late (N = 68) | Early (N = 41) | Late (N = 78) | Early (N = 46) | Late (N = 73) |
| Gender | Male | 30 | 42 | 31 | 41 | 23 | 49 | 27 | 45 |
|  | Female | 17 | 28 | 18 | 27 | 16 | 29 | 17 | 28 |
| Age | Median | 63 | 60 | 61 | 61 | 63 | 60 | 62 | 60 |
|  | (Range) | (23-86) | (16-87) | (23-86) | (16-87) | (23-86) | (16-87) | (23-86) | (16-87) |
| Response | PR | 9 | 22 | 8 | 23 | 6 | 25 | 7 | 24 |
|  | SD | 4 | 14 | 4 | 14 | 3 | 15 | 4 | 14 |
|  | PD | 36 | 34 | 39 | 31 | 32 | 38 | 35 | 35 |
| Cohort | 1 | 3 | 6 | 3 | 6 | 2 | 7 | 2 | 7 |
|  | 2 | 5 | 6 | 5 | 6 | 5 | 6 | 5 | 6 |
|  | 3 | 2 | 9 | 3 | 8 | 2 | 9 | 3 | 8 |
|  | 4 | 7 | 3 | 7 | 3 | 6 | 4 | 7 | 3 |
|  | 5 | 6 | 15 | 6 | 15 | 5 | 16 | 6 | 15 |
|  | 6 | 26 | 31 | 27 | 30 | 21 | 36 | 23 | 34 |
| Prior Ipi | Yes | 10 | 21 | 11 | 20 | 9 | 22 | 10 | 21 |
|  | No | 39 | 49 | 40 | 48 | 32 | 56 | 36 | 52 |
| VS-like classification | good | 28 | 70 | 30 | 68 | 20 | 78 | 25 | 73 |
|  | poor | 21 | 0 | 21 | 0 | 21 | 0 | 21 | 0 |
| PD-L1 expression (5% tumor) | Positive | 3 | 5 |  |  |  |  |  |  |
|  | Negative | 14 | 15 |  |  |  |  |  |  |
|  | NA | 32 | 50 |  |  |  |  |  |  |
| PD-L1 expression (1% tumor) | Positive | 8 | 10 |  |  |  |  |  |  |
|  | Negative | 9 | 10 |  |  |  |  |  |  |
|  | NA | 32 | 50 |  |  |  |  |  |  |
| PD-L1 expression (1% tumor/ immune cells) | Positive | 12 | 16 |  |  |  |  |  |  |
|  | Negative | 4 | 3 |  |  |  |  |  |  |
|  | NA | 33 | 51 |  |  |  |  |  |  |

The data in tables 11-12 and FIGS. 9-12 demonstrate that it is possible to build classifiers able to identify patients with better and worse outcomes on nivolumab therapy from mass spectra generated from pre-treatment serum samples. Patients classified as Late have better OS and TTP than patients classified as Early. In addition, patients classified as Late are more likely than patients classified as Early to have a partial response to or stable disease on nivolumab therapy. Table 12 illustrates that the proportions of patients PD-L1 positive is similar in Early and Late classification groups, so the two quantities are not significantly correlated and the serum classifier of Example 1 would provide additional information to any provided by PD-L1 expression levels.

These results shows a consistency in the ability to identify patients with better and worse outcomes on nivolumab therapy across development/validation set splits, with good generalization between validation and development set performance. Having demonstrated that there is an appreciable, validating performance, to create the most robust classifier, the two mini-classifier filtering methods used were applied to the whole set of 119 samples as the development set 100 of FIG. 8. The results are summarized in Table 13 and the Kaplan-Meier plots are shown in FIG. 13. (A classifier constructed in accordance with FIG. 8 using all 119 samples in the development set as explained here and in Table 13 is referred to as "the full-set classifier of Example 1" later in this document.)

TABLE 13

Performance of the two classifiers built on the whole set of 119 samples as development set

| Approach | #Early/#Late | OS HR (95% CI) | OS log-rank p | OS Median (Early, Late) | TTP HR (95% CI) | TTP log-rank p | TTP Median (Early, Late) |
| --- | --- | --- | --- | --- | --- | --- | --- |
| 2 (compound TTP filtering) | 47/72 | 0.42 (0.22-0.63) | <0.001 | 61, 113 (weeks) | 0.55 (0.33-0.80) | 0.004 | 85, 200 (days) |
| 1 (simple OS filtering) | 47/72 | 0.38 (0.19-0.55) | <0.001 | 61, not reached (weeks) | 0.50 (0.29-0.71) | 0.001 | 84, 230 (days) |

These two approaches show very similar performance, both being very consistent with the classifiers built on a development/validation split of the 119 samples. This is a further indication that the procedure of FIG. 8 produces reliable classifiers with good generalization.

Clinical characteristics are summarized by the classification groups given by approach 1 (simple OS filtering) in Table 14. There is no hint of association of Early and Late classification with PD-L1 expression with any cutoff or with gender or age. More than 70% of patients in cohort 5 are classified as Late, while patients in cohorts 4 and 6 are split roughly evenly between the two classification groups. LDH is significantly higher in the Early group than in the Late group (Mann-Whitney p value=0.003).

TABLE 14

Baseline characteristics by classification group for the full-set classifier approach 1

|  |  | Early (N = 47) | Late (N = 72) |
|---|---|---|---|
| Gender | Male | 28 (60) | 44 (61) |
|  | Female | 17 (36) | 28 (39) |
| Age | Median (Range) | 61 (23-86) | 60 (16-87) |
| Response | PR | 7 (15) | 24 (33) |
|  | SD | 4 (9) | 14 (19) |
|  | PD | 36 (77) | 34 (47) |
| Cohort | 1 | 2 (4) | 7 (10) |
|  | 2 | 5 (11) | 6 (8) |
|  | 3 | 3 (6) | 8 (11) |
|  | 4 | 7 (15) | 3 (4) |
|  | 5 | 6 (13) | 15 (21) |
|  | 6 | 24 (51) | 33 (46) |
| Prior Ipi | Yes | 10 (21) | 21 (29) |
|  | No | 37 (79) | 51 (71) |
| VS-like classification | good | 26 (55) | 72 (100) |
|  | poor | 21 (45) | 0 (0) |
| PD-L1 expression (5% tumor) | Positive | 3 (6) | 5 (7) |
|  | Negative | 15 (32) | 14 (19) |
|  | NA | 29 (62) | 53 (74) |
| PD-L1 expression (1% tumor) | Positive | 9 (19) | 9 (13) |
|  | Negative | 9 (19) | 10 (14) |
|  | NA | 29 (62) | 53 (74) |
| PD-L1 expression (1% tumor/ immune cells) | Positive | 13 (28) | 15 (21) |
|  | Negative | 4 (9) | 3 (4) |
|  | NA | 30 (64) | 54 (75) |
| LDH level [x] (IU/L) | Median (Range) | 655 (417-1130) | 469 (351-583) |
|  | >ULN [xx] | 43 (91) | 57 (80) |
|  | >2ULN | 23 (49) | 8 (11) |

[x] Missing for one patient,
[xx] ULN = upper limit of normal range

Multivariate analysis shows that Early/Late classification remains independently significant when adjusted for other clinical factors.

TABLE 15

Multivariate analysis of OS and TTP

|  | OS | | TTP | |
|---|---|---|---|---|
| Covariate | HR (95% CI) | P value | HR (95% CI) | P value |
| Late vs Early | 2.86 (1.69-5.00) | <0.001 | 2.22 (1.41-3.45) | <0.001 |
| Male vs Female | 1.66 (0.96-2.88) | 0.069 | 1.73 (1.09-2.75) | 0.020 |
| Prior Ipi (no vs yes) | 0.63 (0.35-1.12) | 0.112 | 0.70 (0.42-1.16) | 0.168 |
| PD-L1 (5%) −ve/NA vs +ve | 0.81 (0.27-2.41) | 0.704 | 1.25 (0.53-2.98) | 0.613 |
| PD-L1 (5%) −ve/+ve vs NA | 1.00 (0.55-1.81) | 0.987 | 1.18 (0.69-2.03) | 0.546 |
| LDH (IU/L)/ 1000 | 1.77 (1.26-2.48) | <0.001 | 1.59 (1.16-2.17) | 0.004 |

This table shows that the serum test adds information additional to the other available clinical characteristics and that the serum classification label remains a significant predictor of both TTP and OS even when adjusting for other available characteristics, including PD-L1 expression level and LDH level. In particular, it is of note that even though LDH level and test classification are associated with each other, they are both simultaneously independently significant predictors of OS and TTP. In addition, we have examined the dependence of the Early/Late classification on tumor size. Classification was significantly associated with tumor size (Mann-Whitney p<0.001), with the median tumor size in the Early classification group being 53 cm, compared with 16 cm in the Late classification group. However, while tumor size only showed a trend to significance as a predictor of OS and TTP (p=0.065 and p=0.07, respectively) in univariate analysis, Early and Late classification retained its highly significant predictive power of OS and TTP when adjusted for tumor size (p<0.001 for OS and p=0.004 for TTP).

Given the magnitude of the difference in outcomes between the classification groups Early and Late and its independence from other clinical information, the classifiers developed can provide additional information to physicians and patients to inform the decision whether nivolumab (or another anti-PD-1 antibody), or an alternative therapy is an appropriate treatment for the patient. A final classifier which would be considered preferred would be one generated from all the 119 patient samples in the development set with OS filtering (approach 1 in Table 13, Kaplan-Meier plots of FIGS. 13C and 13D). This classifier is referred to as the full-set classifier or Example 1 or "IS2" later in this document.

Independent Validation of the Classifier Generated Using FIG. 8 with a Second Set of Samples A set of 30 pretreatment samples from patients treated with anti-PD-1 antibodies at Yale University were available as an independent validation cohort.

Figure 14:
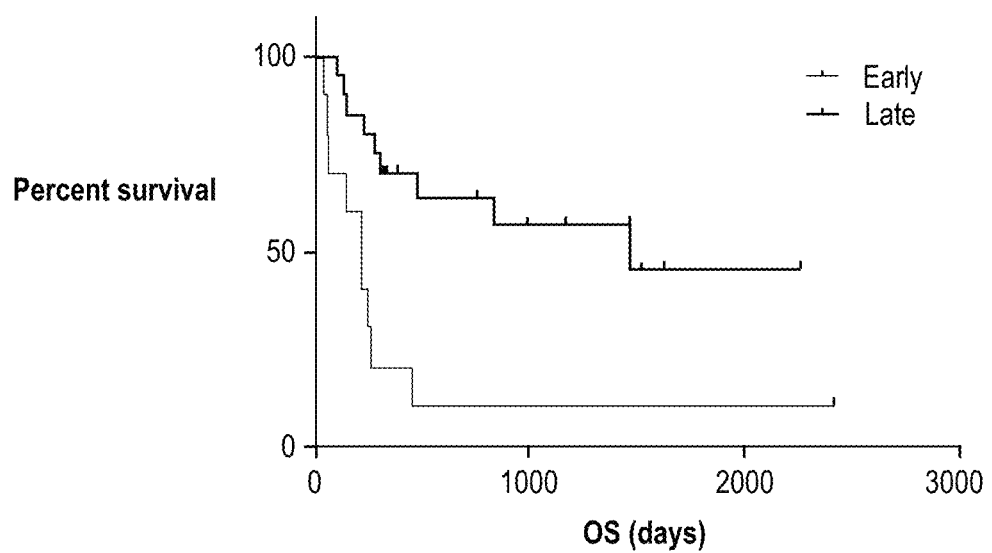
FIG. 14 is a Kaplan-Meier plot for the analysis of the Yale cohort of patients treated with anti-PD-1 antibodies, an independent sample set used for validation of the classifiers of Example 1 developed using FIG. 8.

Deep MALDI spectra were generated from these samples and processed using identical procedures to those used in classifier development of FIG. 8 and described previously. The classifier of "approach 1" for the whole set (table 13 approach 1) was applied to the resulting feature table, yielding a classification of "Early" or "Late" for each sample. Ten samples were classified as "Early" and the remaining 20 as "Late". The Kaplan-Meier plot of overall survival for the cohort is shown in FIG. 14 and a summary of the analysis of OS is given in Table 16. As was the case with FIG. 13, note the clear separation between the Early and Late groups in FIG. 14, indicating the ability of the final classifier of Table 13 and FIG. 13 to correctly classify the samples in the independent validation cohort.

TABLE 16

Summary of the performance of the classifier on the Yale anti-PD-1 antibody-treated cohort

| #Early/#Late | OS HR (95% CI) | OS log-rank p | OS Median (Early, Late) |
|---|---|---|---|
| 10/20 | 0.27 (0.05-0.52) | 0.0024 | 221, 1471 (days) |

The classifier of Example 1 also validated well on an independent cohort of 48 melanoma patients treated with the anti-CTLA4 antibody ipilimumab. See the Example 3 section below.

Protein Identification

Our approach to generating a classifier is based on a correlational analysis relating peak intensities to clinical outcome using the CMC/D process described above in conjunction with FIG. 8. As such, the proteins underlying the feature definitions used in the classifications may not be causally related to the outcome to treatment. It is also not trivial to relate peaks measured in a MALDI-TOF experiment to previously identified proteins and their functions. However, by studying the literature of observed serum proteins in MALDI-TOF studies it is still possible to give names to some of the peaks used in our classification. A tentative list is listed in Table 17:

TABLE 17

Tentative assignment of a subset of features used for classification to proteins/protein fragments

| Mass [Da] | Tentative protein identification |
|---|---|
| 4133 | c1 inhibitor |
| 4264 | ITIH4, C1 fragment |
| 4381 | Beta-defensin 4A |
| 5867 | Leukocyte-specific transcript 1 protein |
| 5889 | Leukocyte-specific transcript 1 protein |
| 5911 | Gamma sectretase C-terminal fragment 50 of Amyloid beta A4 protein |
| 5997 | Granulin-3 (Granulin-B) |
| 7318 | C-C motif chemokine 20 |
| 8413 | complement C3a |
| 9109 | Apolipoprotein C3 |
| 9226 | CDC42 small effector protein 2 |
| 10285 | B melanoma antigen 3 |
| 11686 | Serum Amyloid A (SAA) |
| 23469 | C-reactive protein (CRP) |

While the appearance of acute phase reactants like SAA and CRP was expected, we were surprised to find some evidence of proteins related to the complement system (complement C3a, c1 inhibitor, C1 fragment). The complement system is involved in the immune response and cancer immunotherapy (Markiewski et al., *Is complement good or bad for cancer patients? A new perspective on an old dilemma.* Trends Immunol. 30: 286-292 (2009)), and has recently been suggested to have a role in PD-1 inhibition (Seng-Ryong Woo, et al., *Innate Immune Recognition of Cancer* Annual Review of Immunology, Vol. 33: 445-474 (2015).

It appears that at least some part of the classification of patients into Early and Late groups is related to an interplay between acute phase reactants and the activation of the complement system. A more detailed explanation of the relationship between the features for classification, and the biological functions of the Early and Late class labels is set forth later in this document in Example 6.

Conclusions on the Classifiers we Developed in Example 1

Applying the DIAGNOSTIC CORTEX TM procedure (FIG. 8) to pre-treatment serum spectra from melanoma patients obtained using Deep MALDI spectral acquisition we have identified clinical groups "Early" and "Late". These groups are showing significant differences in outcome (both TTP and OS) following treatment with an anti-PD-1 treatment, nivolumab. We have presented a test procedure to identify these groups from pre-treatment samples, and validated the results in internal validation sets, and in an external validation set.

Patients whose serum classifies as "Early" exhibit significantly faster progression and shorter survival than patients whose serum classifies as "Late" making this test suitable as a biomarker for nivolumab therapy. The clinical groups "Early" and "Late" are not associated with PD-L1 expression, and our classification remains a significant predictor for outcome (both TTP and OS) even when other clinical attributes are included in a multivariate analysis.

While a correlative approach to test development does not easily lend itself to a deep understanding of the biology underlying the difference between the identified groups, we have done some initial work relating the two different groups to differences in acute phase reactants and the complement system. The success of this project exemplifies the power of the combination of Deep MALDI spectral acquisition and our classifier development methods in the construction of clinically useful tests.

The following clauses are offered as further descriptions of the inventions disclosed in Example 1.

1. A method of predicting melanoma patient benefit to an antibody drug blocking ligand activation of programmed cell death 1 (PD-1), comprising a) conducting mass spectrometry on a blood-based sample of the patient and obtaining mass spectrometry data;

(b) obtaining integrated intensity values in the mass spectrometry data of a multitude of mass-spectral features; and (c) operating on the mass spectral data with a programmed computer implementing a classifier;

wherein in the operating step the classifier compares the integrated intensity values with feature values of a reference set of class-labeled mass spectral data obtained from blood-based samples obtained from a multitude of other melanoma patients treated with the drug with a classification algorithm and generates a class label for the sample, wherein the class label "early" or the equivalent predicts the patient is likely to obtain relatively less benefit from the antibody drug and the class label "late" or the equivalent indicates the patient is likely to obtain relatively greater benefit from the antibody drug.

2. The method of clause 1, wherein the melanoma patient providing the blood-based sample has been treated previously with ipilimumab.

3. The method of clause 2, wherein the patient had high grade toxicity to ipilimumab.

4. The method of any of clauses 1-3, wherein the mass spectral features include a multitude of features listed in Appendix A, Appendix B, or Appendix C.

5. The method of any of clauses 1-4, wherein the classifier is generated from a combination of filtered mini-classifiers using a regularized combination method.

6. The method of any of clauses 1-5, wherein the mass spectral data is acquired from at least 100,000 laser shots performed on the sample using MALDI-TOF mass spectrometry.

7. The method of clause 6, wherein the mini-classifiers are filtered in accordance with any one of the criteria listed in Table 10.

8. The method of clause 5, wherein the classifier is defined from a multitude of master classifiers generated from a multitude of separations of a development set of samples into a training set and a test set.

9. The method of clause 5, wherein the classifier is developed from a sample set including patients with and without prior treatment from ipilimumab.

10. The method of clause 5, wherein the regularized combination method comprises repeatedly conducting logistic regression with extreme dropout.

11. The method of any of clauses 1-10 wherein the antibody drug comprises nivolumab.

12. The method of any of clauses 1-11, wherein the relatively greater benefit associated with the Late label means significantly greater (longer) overall survival as compared to the Early class label.

13. The method of any of clauses 1-12, wherein the reference set is derived from class-labeled blood-based samples from melanoma patients treated with nivolumab, wherein the class-labeled blood-based samples in the reference set have class labels of Early or Late, or the equivalent, and wherein the Late samples had greater overall survival on nivolumab as compared to the Early samples.

14. A machine (see FIG. 15) predicting melanoma patient benefit from an antibody drug blocking ligand activation of programmed cell death 1 (PD-1), comprising:

a memory storing a reference set in the form of feature values for a multitude of mass spectral features obtained from mass spectra of blood-based samples from a multitude of melanoma patients treated with the antibody drug;

the memory further storing a set of code defining a final classifier based on a multitude of master classifiers, each master classifier generated from filtered mini-classifiers combined using a regularized combination method;

a central processing unit operating on the set of code and the reference set and mass spectral data obtained from a blood-based sample of a melanoma patient to be tested and responsively generating a class label for the blood-based sample, wherein the class label "Early" or the equivalent predicts the patient is likely to obtain relatively less benefit from the antibody drug and the class label "Late" or the equivalent indicates the patient is likely to obtain relatively greater benefit from the antibody drug.

15. The machine of clause 14, wherein the mass spectral data for the development set and the sample are acquired from at least 100,000 laser shots performed on the samples forming the development set and the sample to be tested using MALDI-TOF mass spectrometry.

16. The machine of clause 14, wherein the mini-classifiers are filtered in accordance with any one of the criteria listed in Table 10.

17. The machine of clause 14, wherein the final classifier is defined from a multitude of master classifiers each generated from a separation of a classifier development set of samples into a training set and a test set.

18. The machine of clause 14, wherein the reference set includes mass spectral data from patients with and without prior treatment from ipilimumab.

19. The machine of clause 14, wherein the regularized combination method comprises logistic regression with extreme dropout.

20. The machine of any of clauses 14-19, wherein the drug comprises nivolumab.

21. The machine of any of clauses 14-20, wherein the mass spectral features include a multitude of features listed in Appendix A, Appendix B, or Appendix C.

22. The machine of any of clauses 14-21, wherein the relatively greater benefit associated with the Late label means significantly greater (longer) overall survival as compared to the Early class label.

23. A system for predicting patient benefit from an antibody drug blocking ligand activation of programmed cell death 1 (PD-1), a mass spectrometer and the machine of any one of clauses 14-22.

24. A method of generating a classifier for predicting patient benefit from an antibody drug blocking ligand activation of programmed cell death 1 (PD-1), comprising:

1) obtaining mass spectrometry data from a development set of blood-based samples obtained from melanoma patients treated with the antibody drug, in which a mass spectrum from at least 100,000 laser shots is acquired from each member of the set;

2) performing spectral pre-processing operations on the mass spectral data from the development sample set, including background estimation and subtraction, alignment, batch correction, and normalization;

3) performing the process of FIG. 8 steps 102-150 including generating a master classifier based on regularized combination of a filtered set of mini-classifiers for each separation of the development set of samples into training and test sets;

4) evaluating master classifier performance of the classifiers generated in accordance with step 3); and 5) defining a final classifier based on the master classifiers generated in step 3).

25. The method of clause 24, wherein the final classifier includes a reference set including feature values for a set of features listed in Appendix A, Appendix B, or Appendix C.

26. The method of clause 24, wherein integrated intensity values are obtained for each of the features listed in Appendix A, and wherein the method further comprises the step of deselecting features from the list of features of Appendix A which are not contributing to classifier performance and performing steps 3), 4), and 5) using a reduced list the features.

27. The method of clause 26, wherein the reduced list of features comprises the list of features in one of the sets of Appendix B or the list of features in Appendix C.

28. The method of clause 24, wherein the filtering criteria comprise the filtering criteria of Table 10.

29. A method for treating a melanoma patient, comprising administrating an antibody drug blocking ligand activation of PD-1 to the patient, wherein a blood-based sample of the patient has been previously assigned the class label of Late or the equivalent from performing the method of any one of clauses 1-13 on the blood-based sample.

30. An improved general purpose computer configured as a classifier for classifying a blood-based sample from a human cancer patient to make a prediction about the patient's survival or relative likelihood of obtaining benefit from a drug, comprising:

a memory storing a reference set in the form of feature values for a multitude of mass spectral features obtained from mass spectrometry of blood-based samples from a multitude of melanoma patients treated with an immune checkpoint inhibitor and an associated class label for each of the blood-based samples in the training set, the blood based samples forming a classifier development set;

the memory further storing a set of computer-executable code defining a final classifier based on a multitude of master classifiers, each master classifier generated from a set of filtered mini-classifiers executing a classification algorithm and combined using a regularized combination method; wherein the multitude of master classifiers are obtained from many different realizations of a separation of the development set into classifier training and test sets; and a central processing unit operating on the set of code, the reference set, and mass spectral data obtained from the blood-based sample of the cancer patient to be tested and generating a class label for the blood-based sample.

31. The improved computer of clause 30, wherein the memory stores feature values for at least 50 of the features listed in Appendix A.

Example 2

Predictive Classifier for Melanoma Patient Benefit from Immune Checkpoint Inhibitors The classifier of Example 1, including the classifiers built from one half of the sample set and the classifier built using the whole set of samples, showed similar performance and validated well on two independent sample sets. It was discovered that the classifiers of Example 1 also split a cohort of 173 first line, advanced non-small cell lung cancer (NSCLC) patients treated with platinum-doublet+cetuximab, and yet another cohort of 138 ovarian cancer patients treated with platinum-doublet after surgery into groups with better and worse OS and progression-free survival (PFS). For further details on this discovery, see Example 4 below.

It is possible to argue that the classifiers of Example 1 above have a strong prognostic component, since they seem to stratify patients according to their outcomes regardless of whether treatment was immunotherapy or chemotherapy. While clinically this might or might not matter, Example 2 describes the development of a classifier and test capable of splitting patients treated with immune checkpoint inhibitors according to their outcome, while not stratifying outcomes of patients treated with chemotherapy—i.e., a predictive test between immune checkpoint inhibitors and chemotherapy with less prognostic component.

Patient Samples

The samples we used to develop the classifier of Example 2 were pretreatment serum samples from two different cohorts. The first cohort was the 119 samples from melanoma patients treated with nivolumab, and discussed at length in Example 1, see Table 1 above for the baseline clinical characteristics, FIGS. 1A and 1B, etc. The set was split into development and validation sets as explained above in Example 1.

A second cohort, referred to as the ACORN NSCLC cohort, was a set of 173 pre-treatment serum samples, clinical data and associated mass spectra from non-small cell lung cancer (NSCLC) patients treated with platinum-doublet plus cetuximab. The purpose of the second cohort was to tune the development of a classifier such that it was (a) predictive for patient benefit on nivolumab but also (b) not outcome predictive in NSCLC patients treated with chemotherapy. Available outcome data included progression-free-survival (PFS) and overall survival (OS). Selected clinical characteristics for patients with available spectra from pre-treatment samples are listed in table 18.

TABLE 18

Selected baseline characteristics of NSCLC patients with available spectra

|  |  | N (%) |
|---|---|---|
| Gender | Male | 108 (62) |
|  | Female | 65 (38) |
| Age | Median (Range) | 66.4 (35.4-86.3) |
| PFS | Median (months) | 4.3 |
| OS | Median (months) | 9.5 |

Figure 16A:
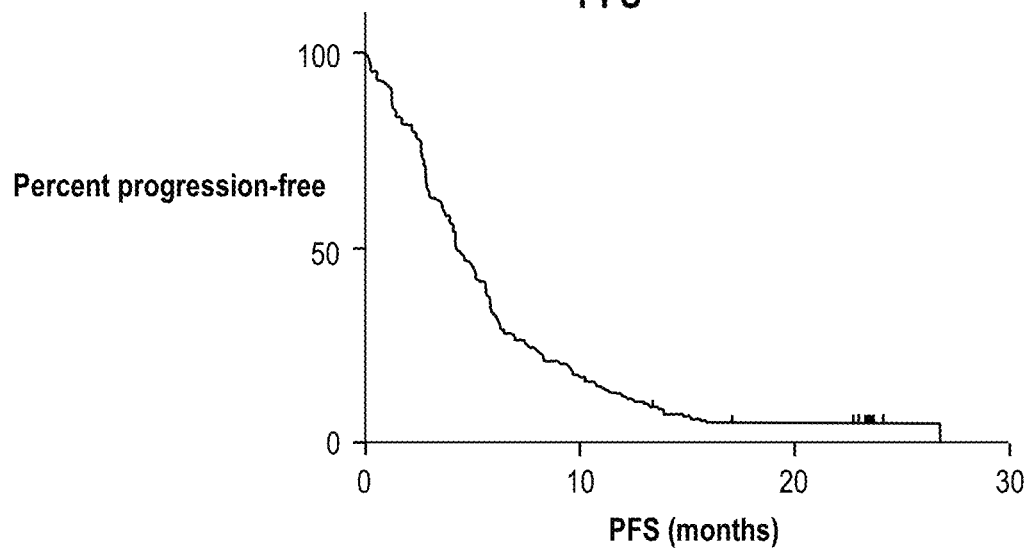
FIGS. 16A and 16B are Kaplan-Meier plots of progression free survival (PFS) and overall survival (OS), respectively, for all 173 non-small cell lung cancer (NSCLC) patients of the ACORN NSCLC cohort with available clinical data and spectra from pretreatment samples. The ACORN NSCLC cohort was used to develop and tune the classifier of Example 2 to be predictive of melanoma patient benefit of nivolumab.
Figure 16B:
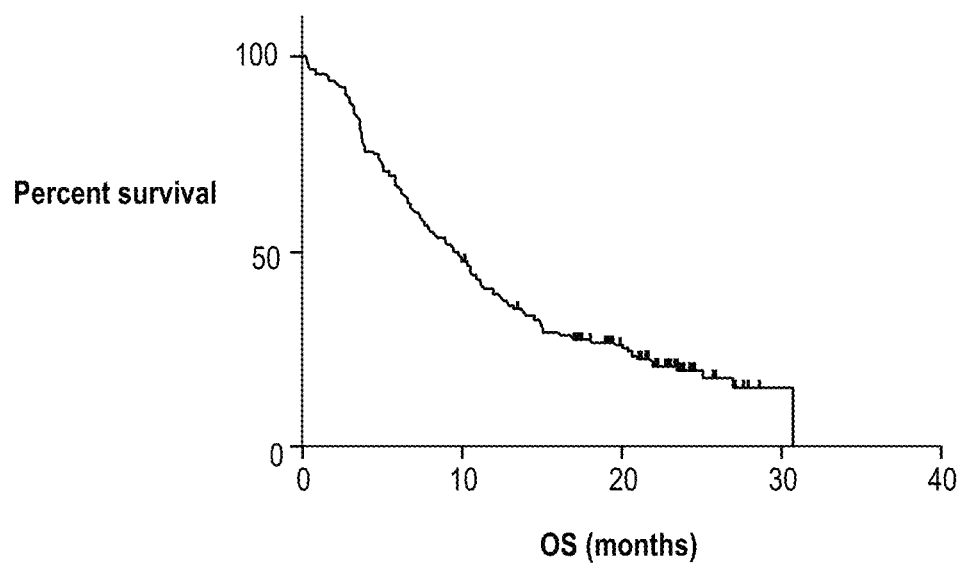

Kaplan-Meier plots for progression-free-survival (PFS) and overall survival (OS) for the second cohort of 173 NSCLC patients with baseline samples and acquired spectra are shown in FIGS. 16A and 16B.

Figure 17A:
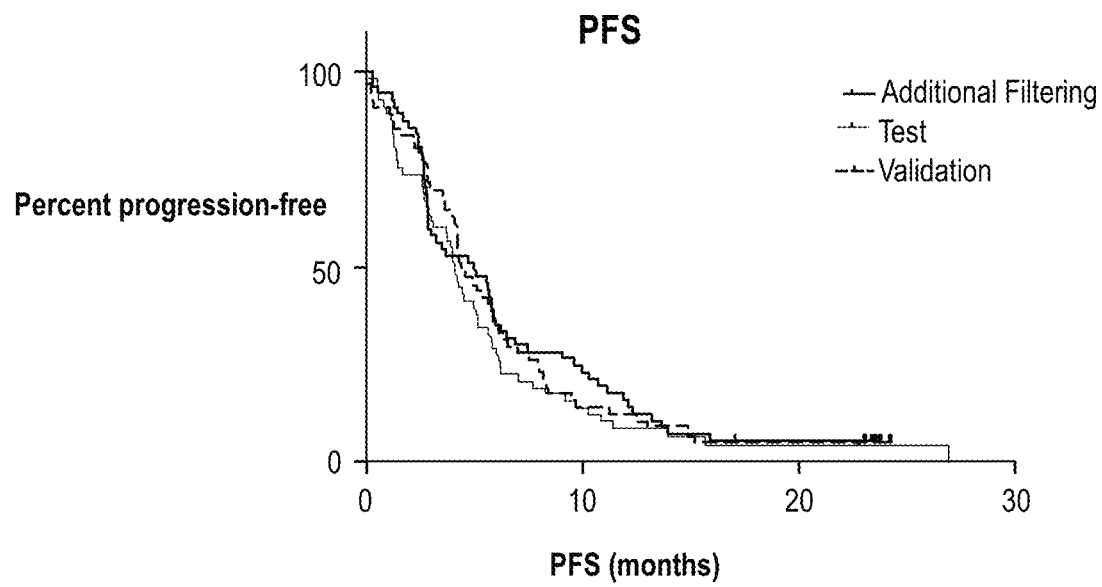
FIGS. 17A and 17B are plots of progression free survival PFS and overall survival OS for the three different subsets of the ACORN NSCLC cohort. One subset ("additional filtering" in the figures) was used to filter mini-classifiers in generation of the classifier of Example 2. One subset ("test" in the figures) was used for testing classifier performance together with the melanoma development set samples. The other subset ("validation" in the figures) was used as an internal validation set, in addition to a melanoma subset already held for that purpose. The similarity in the plots of FIGS. 17A and 17B indicate that the survival data for the "additional filtering" subset was representative of the other subsets.
Figure 17B:
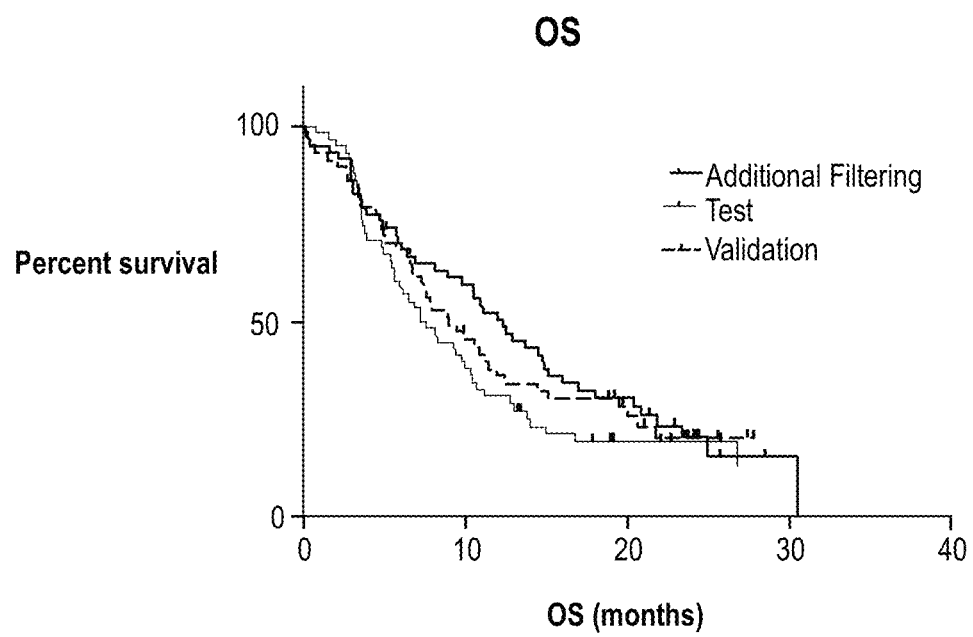
Figure 18A:
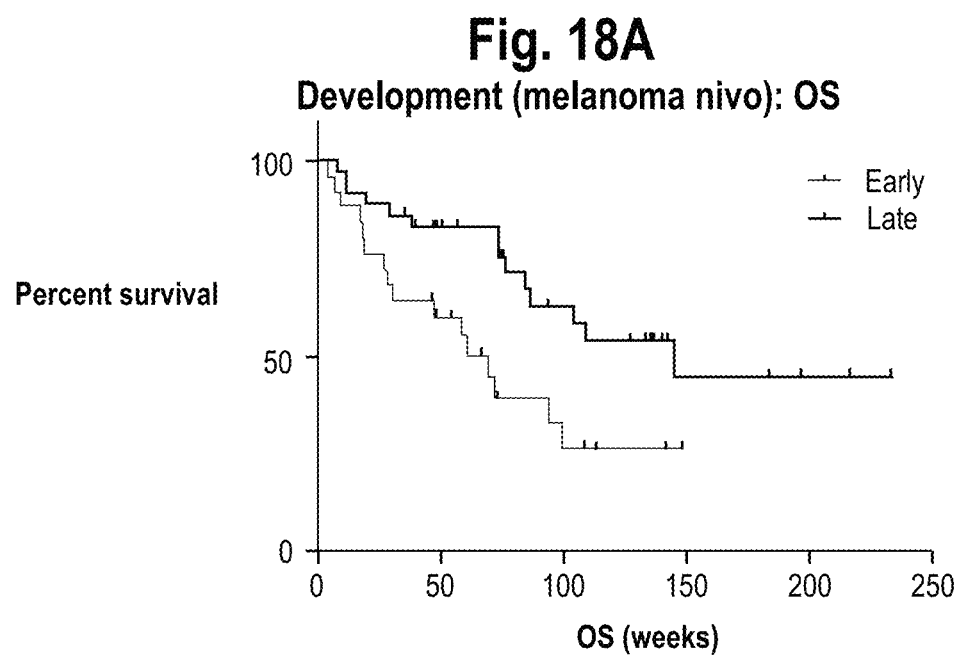
FIGS. 18A-18H are Kaplan-Meier plots of OS and TTP or PFS for the development and internal validation sets of samples. In particular.
Figure 18B:
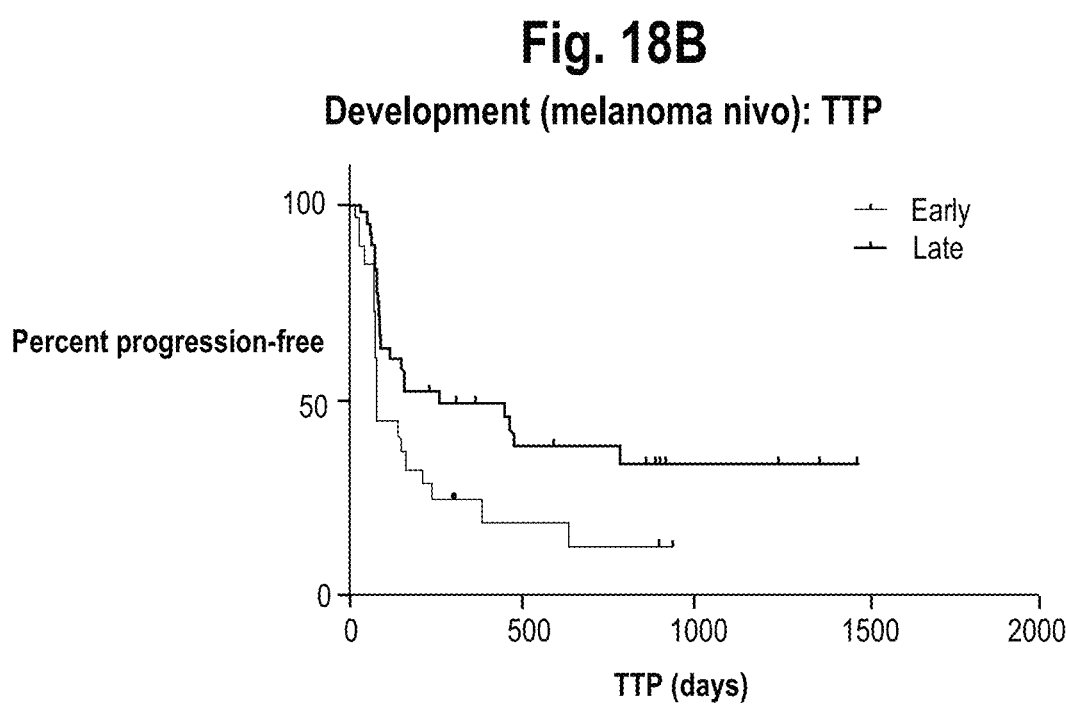
Figure 18C:
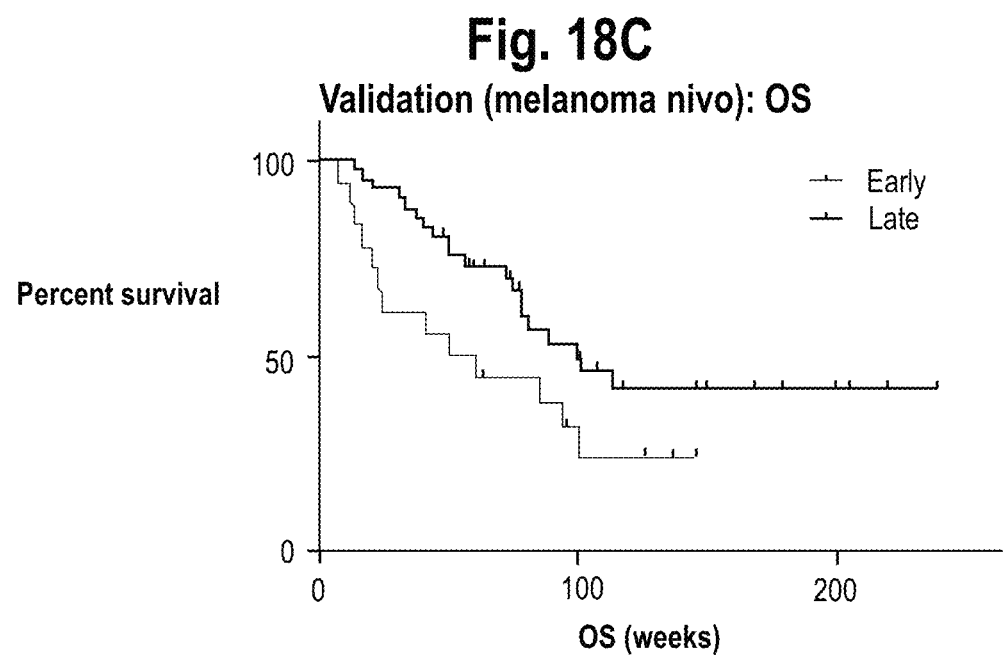
Figure 18D:
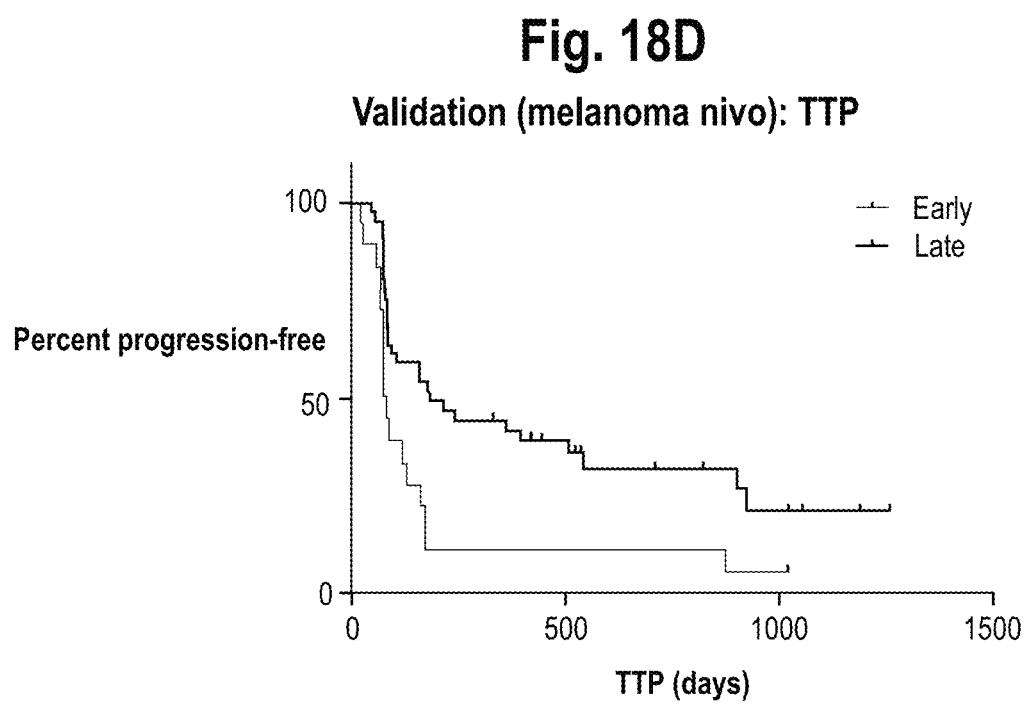
Figure 18E:
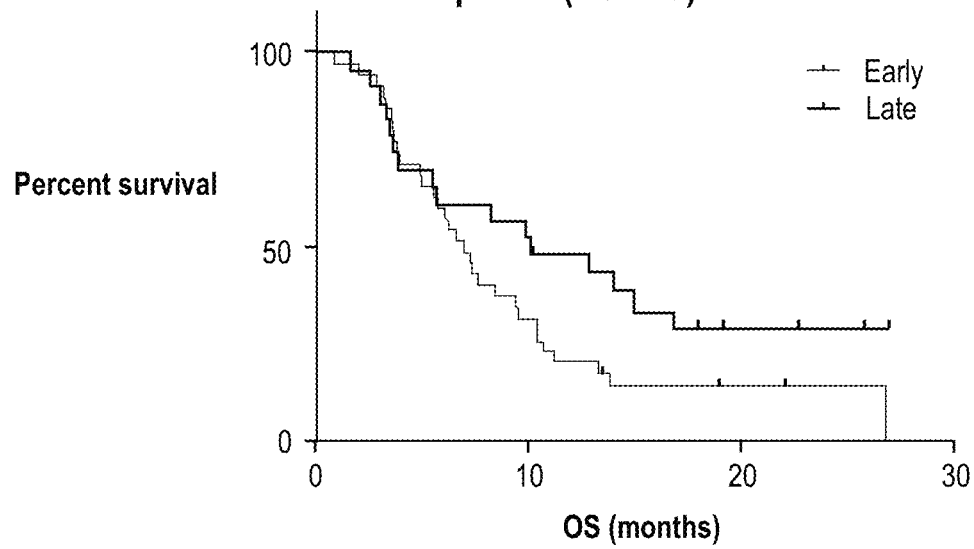
Figure 18F:
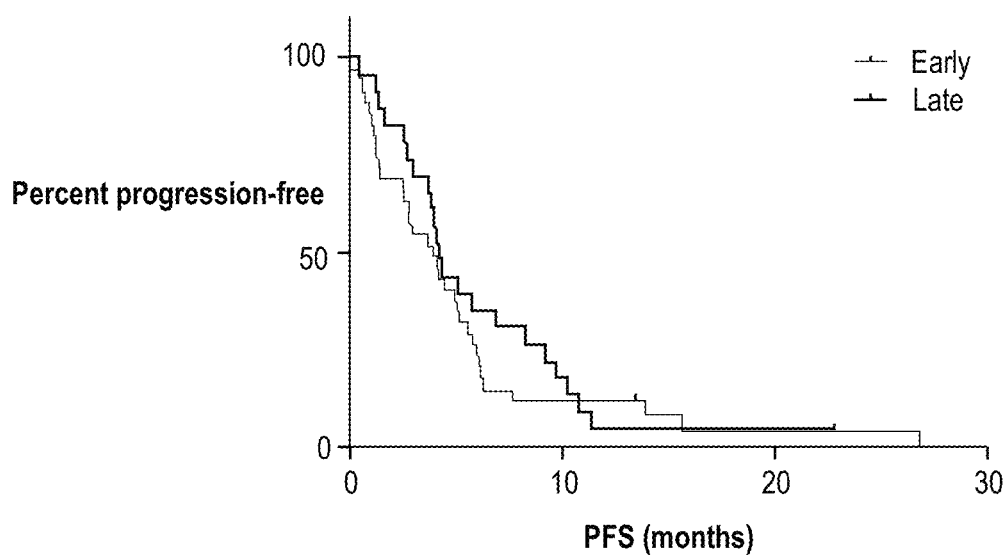
Figure 18G:
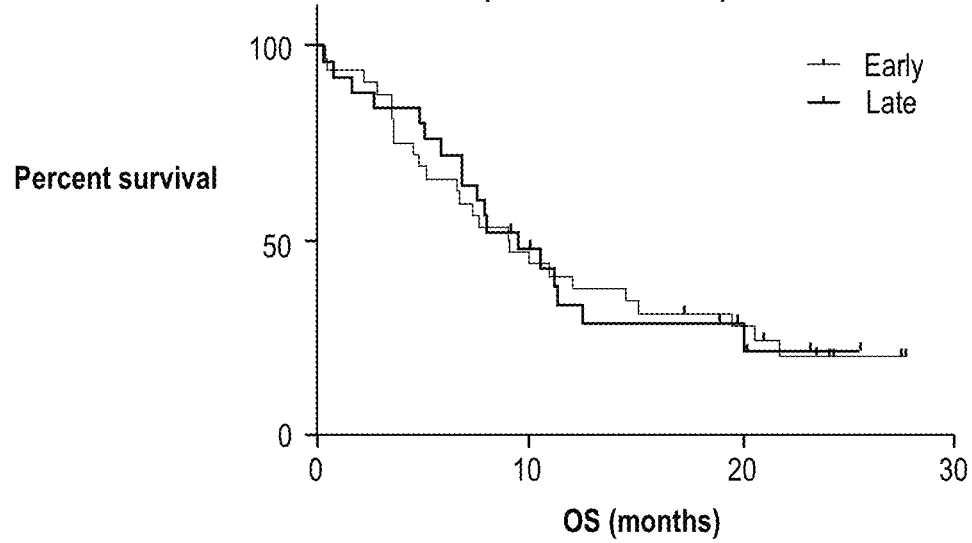
Figure 18H:
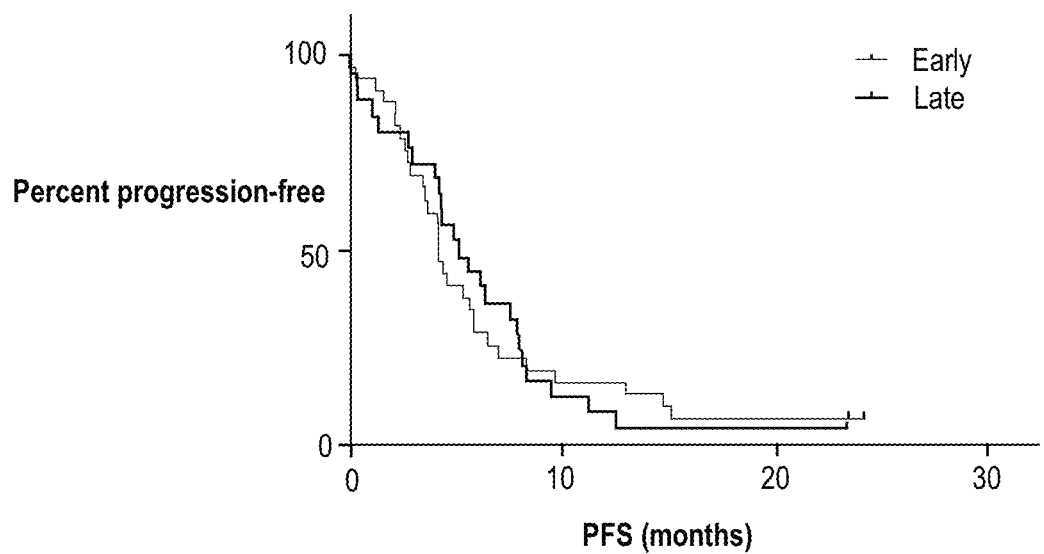

The ACORN NSCLC cohort was split into 3 subsets: 58 samples (referred to as "AddFilt" subset herein) were assigned for additional filtering of mini-classifiers as explained in detail below; 58 samples (the "Test" subset herein) were used for testing the classifier performance together with the melanoma development set samples; and 57 samples (the "Validation" subset herein) were used as part of the internal validation set, in addition to the melanoma validation subset already held for that purpose. A method was implemented in order to choose this split while ensuring the 3 subsets were balanced. The details of how we generated these splits are not particularly important. Suffice it to say that we analyzed mass spectral features which were correlated with overall survival, and chose the subsets such that it minimized the difference in such features across the three subsets. The clinical characteristics are listed for each of the subsets in table 19 and comparison of the time-to-event data is shown in FIGS. 17A and 17B.

TABLE 19

Baseline characteristics of NSCLC patients with available spectra for each of the 3 created subsets

|  |  | "AddFilt" subset (N = 58) n (%) | "Test" subset (N = 58) n (%) | "Validation" subset (N = 57) n (%) |
|---|---|---|---|---|
| Gender | Male | 19 (33) | 22 (38) | 24 (42) |
|  | Female | 39 (67) | 36 (62) | 33 (58) |
| Age | Median (Range) | 68.3 (35.4-86.3) | 66.8 (42.3-85.0) | 62.0 (44.9-76.7) |
| PFS | Median (months) | 5.0 | 4.1 | 4.4 |
| OS | Median (months) | 12.4 | 7.5 | 9.1 |

Sample Preparation

The sample preparation for the serum samples of both the ACORN NSCLC cohort was the same as the nivolumab cohort and described in detail in Example 1.

Spectral Acquisition

The acquisition of mass spectral data for the ACORN NSCLC cohort was the same as the nivolumab cohort and described in detail in Example 1.

Spectral Processing

The mass spectral data processing, including raster spectra preprocessing, Deep MALDI average spectra preprocessing (background subtraction, normalization, alignment) and batch correction, was the same as described in Example 1. In the project of Example 2 we did not use feature 9109 in the development of the classifier; however, we used all other 350 features listed in Appendix A.

Classifier Development

We used the classifier development process of FIG. 8 (described at length in Example 1) in developing the classifier of Example 2.

Definition of Class Labels (Step 102, FIG. 8A)

The classifier development of Example 2 makes use of OS data from the melanoma/nivolumab development set for initial assignment of classification group labels to the samples in the development set. In this situation, class labels are not obvious and, as shown in FIG. 8, the classifier development process uses an iterative method to refine class labels at the same time as creating the classifier. See FIG. 8B, step 144 and loop 146. An initial guess is made for the class labels in the initial iteration of the method, at step 102. The samples were sorted on OS and half of the samples with the lowest time-to-event outcome were assigned the "Early" class label (early death, i.e. poor outcome) while the other half were assigned the "Late" class label (late death, i.e. good outcome). A classifier was then constructed in accordance with FIG. 8 using the outcome data and these class labels. This classifier was used to generate classifications for all of the development set samples. The labels of samples that persistently misclassified across the ensemble of master classifiers created for the many splits into training and test sets (loop 146) were flipped. This refined set of class labels were then used as the new class labels for a second iteration of the method at step 102. This process was iterated until convergence, in exactly the same way as for Example 1.

Select Training and Test Sets (108, FIG. 8A)

The development set samples were split into training and test sets (step 108) in multiple different random realizations. Six hundred and twenty five realizations were used (i.e. iterations through loop 135). The methodology of FIG. 8 works best when the training classes Early and Late have the same number of samples in each realization or iteration through loop 135. Hence, if the training classes had different numbers of members, they were split in different ratios into test and training.

Creation and Filtering of Mini-Classifiers (120, 126, FIG. 8A)

Many k-nearest neighbor (kNN) mini-classifiers (mCs) that use the training set as their reference set were constructed in step 120 using subsets of features. In this project we used k=9. To be able to consider subsets of single and two features and improve classifier performance, we deselected features that were not useful for classification from the set of 350. This was done using a bagged feature selection approach as outlined in Appendix F of our prior provisional application Ser. No. 62/289,587 and in U.S. patent application of J. Roder et al. Ser. No. 15/091,417.

To target a final classifier that has certain performance characteristics, these mCs were filtered in step 126 of FIG. 8A as follows. Each mC is applied to its training set and to the "AddFilt" NSCLC subset, and performance metrics are calculated from the resulting classification. Only mCs that satisfy thresholds on these performance metrics pass filtering to be used further in the process. The mCs that fail filtering are discarded. For this project hazard ratio based on OS filtering was used. Table 20 shows the filtering criteria at step 126 used for deselecting mini-classifiers in each label-flip iteration (step 146) of the classifier development. In every iteration a compound filter was constructed by combining two single filters with an "AND" operation, see Table 21. Such filtering criteria were designed so that patients treated with immunotherapy would split according to their OS outcomes but patients treated with chemotherapy would not.

TABLE 20

Criteria used in the filtering step

| Iteration | HR range (melanoma samples, training subset) | HR range (NSCLC samples, "AddFilt" subset) |
|---|---|---|
| 0 | 2.0-10.0 | 0.9-1.111 |
| 1 | 2.0-10.0 | 0.8-1.25 |
| 2 | 2.0-10.0 | 0.8-1.25 |
| 3 | 2.0-10.0 | 0.8-1.25 |
| 4 | 2.0-10.0 | 0.8-1.25 |

TABLE 21

Parameters used in mini-classifiers and filtering

| Depth (parameter s, max # features per mC) | Filter |
|---|---|
| 2 | HR on OS (melanoma samples) .and. HR on OS (NSCLC samples), see Table 20 for HR values |

Combination of Mini-Classifiers Using Logistic Regression with Dropout (Steps 130, 132)

Once the filtering of the mCs was complete, the mCs were combined in one master classifier (MC) using a logistic regression trained using the training set class labels. To help avoid overfitting the regression is regularized using extreme drop out with only a small number of the mCs chosen randomly for inclusion in each of the logistic regression iterations. The number of dropout iterations was selected based on the typical number of mCs passing filtering to ensure that each mC was likely to be included within the drop out process multiple times. In all label-flip iterations, ten randomly selected mCs were taken in each of the 10,000 drop out iterations.

Although the ACORN NSCLC "AddFilt" subset of samples has been used in the filtering step as described above, such samples were not included in the training of the logistic regression that combines the mCs (or the reference sets of the kNN mini-classifiers). Only the training subset drawn from the development set (melanoma samples) was used for that purpose.

Training/Test Splits (Loop 135 of FIG. 8A)

The use of multiple training/test splits in loop 135, and in this Example 625 different training/test set realizations, avoids selection of a single, particularly advantageous or difficult, training set for classifier creation and avoids bias in performance assessment from testing on a test set that could be especially easy or difficult to classify.

Definition of Final Test in Step 150

The output of the logistic regression that defines each MC is a probability of being in one of the two training classes (Early or Late). These MC probabilities over all the 625 training and test set splits can be averaged to yield one average probability for a sample. When working with the development set, this approach is adjusted to average over MCs for which a given sample is not included in the training set ("out-of-bag" estimate). These average probabilities can be converted into a binary classification by applying a threshold (cutoff). During the iterative classifier construction and label refinement process, classifications were assigned by majority vote of the individual MC labels obtained with a cutoff of 0.5. This process was modified to incorporate only MCs where the sample was not in the training set for samples in the development set (modified, or "out-of-bag"

majority vote). This procedure gives very similar classifications to using a cutoff of 0.5 on the average probabilities across MCs.

Results

The performance of the classifiers developed in Example 2 was assessed using Kaplan-Meier plots of OS between samples classified as Early and Late, together with corresponding hazard ratios (HRs) and log-rank p values. This performance estimation was performed separately for melanoma patients treated with nivolumab and for NSCLC samples treated with chemotherapy. The results are summarized in table 22 for the time endpoints available for each sample set. Kaplan-Meier plots corresponding to the data in table 22 are shown in FIGS. 18A-18H. The plots of FIG. 18A-H and the corresponding results of table 22, in the case of the ACORN NSCLC set, did not consider any of the "AddFilt" subset samples since they were directly used in the mC filtering step in all of the 625 training/test realizations. The classifications of all 119 samples in the melanoma cohort are listed in Appendix I of our prior provisional application Ser. No. 62/289,587, together with their classifications obtained from Example 1 for comparison. The features used in the final label flip iteration of this classifier development are given in Appendix C.

TABLE 22

Performance summary

| | #Early/#Late | OS HR (95% CI) | OS log-rank p | OS Median (Early, Late) | TTP HR (95% CI) | TTP log-rank p | TTP Median (Early, Late) |
|---|---|---|---|---|---|---|---|
| Development (melanoma nivo) | 25/35 | 0.42 (0.18-0.81) | 0.014 | 61, 145 (weeks) | 0.53 (0.27-0.94) | 0.034 | 84, 285 (days) |
| Validation (melanoma nivo) | 18/41 | 0.52 (0.21-1.02) | 0.058 | 55, 99 (weeks) | 0.43 (0.17-0.70) | 0.004 | 80, 183 (days) |

| | | | | | PFS HR (95% CI) | PFS log-rank p | PFS Median (Early, Late) |
|---|---|---|---|---|---|---|---|
| Development (NSCLC chemo) | 35/23 | 0.60 (0.34-1.07) | 0.089 | 7.0, 10.1 (months) | 0.81 (0.48-1.37) | 0.434 | 3.9, 4.2 (months) |
| Validation (NSCLC chemo) | 32/25 | 0.99 (0.54-1.81) | 0.962 | 9.0, 9.5 (months) | 0.98 (0.58-1.68) | 0.952 | 4.2, 5.1 (months) |

Note that in FIGS. 18A-18D, for the melanoma/nivolumab cohort there is a clear separation in the OS and TTP curves between the classes Early and Late in both the development and validation sets, whereas in the NSCLC/chemotherapy cohort there is a little or no separation between the Early and Late classes in the development and validation sets. This demonstrates that our use of the NSCLC cohort for filtering mini-classifiers in the development of the Master Classifiers and in the definition of the final classifier was useful in creating a classifier that is predictive of benefit of nivolumab in melanoma but does not stratify outcomes of NSCLC patients treated with chemotherapy.

Baseline clinical characteristics of the melanoma/nivolumab sample set (development+validation) are summarized by classification group in table 23. Clinical characteristics of the ACORN NSCLC sample set ("Test"+ "Validation") are also summarized by classification group in table 24.

TABLE 23

Clinical characteristic by classification group (melanoma sample set)

| | | Early (N = 43) n (%) | Late (N = 76) n (%) |
|---|---|---|---|
| Gender | Male | 28 (65) | 44 (58) |
| | Female | 14 (33) | 31 (41) |
| | NA | 1 (2) | 1 (1) |
| Age | Median (Range) | 63 (23-87) | 60.5 (16-79) |
| Response | PR | 7 (16) | 24 (32) |
| | SD | 3 (7) | 15 (20) |
| | PD | 33 (77) | 37 (49) |
| Cohort | 1 | 1 (2) | 8 (11) |
| | 2 | 4 (9) | 7 (9) |
| | 3 | 3 (7) | 8 (11) |
| | 4 | 5 (12) | 5 (7) |
| | 5 | 5 (12) | 16 (21) |
| | 6 | 25 (58) | 32 (42) |
| Prior Ipi | No | 8 (19) | 23 (30) |
| | Yes | 35 (81) | 53 (70) |
| VS-like classification | good | 24 (56) | 74 (97) |
| | poor | 19 (44) | 2 (3) |
| PD-L1 expression (5% tumor) | Positive | 3 (7) | 5 (7) |
| | Negative | 11 (26) | 18 (24) |
| | NA | 29 (67) | 53 (70) |
| PD-L1 expression (1% tumor) | Positive | 7 (16) | 11 (14) |
| | Negative | 7 (16) | 12 (16) |
| | NA | 29 (67) | 53 (70) |

TABLE 23-continued

Clinical characteristic by classification group (melanoma sample set)

| | | Early (N = 43) n (%) | Late (N = 76) n (%) |
|---|---|---|---|
| PD-L1 expression (1% tumor/ immune cells) | Positive | 10 (23) | 18 (24) |
| | Negative | 3 (7) | 4 (5) |
| | NA | 30 (70) | 54 (71) |
| LDH level [x] (IU/L) | Median (Range) | 655 (414-1292) | 469 (353-583) |
| | >ULN[xx] | 40 (93) | 60 (80) |
| | >2ULN | 21 (49) | 10 (13) |

[x] Missing for one patient,

[xx] ULN = upper limit of normal range

TABLE 24

Clinical characteristic by classification group (ACORN NSCLC sample set)

|  |  | Early (N = 67) n (%) | Late (N = 48) n (%) |
|---|---|---|---|
| Gender | Male | 37 (55) | 32 (67) |
|  | Female | 30 (45) | 16 (33) |
| Age | Median (Range) | 66.5 (42.3-85.0) | 63.4 (46.3-80.7) |

The reader will note that the data in Table 14 differs slightly from the data in Table 23. In particular, the classifications we obtain from the classifier of Example 2 are not exactly the same as the classifications we get from the Example 1 classifier; although not surprisingly a sizeable proportion of samples get the same label for both classifiers. See Appendix I of our prior provisional application Ser. No. 62/289,587 for the labels produced from the Example 1 and Example 2 classifiers for all 119 samples. The reader will also note that Appendix C lists the subset of the 350 features that we used for the final classifier of Example 2.

The idea behind the reduced features set of Appendix C for the classifier of Example 2 is that instead of just taking all of the mCs (and associated features) that give a prognostic behavior for treatment with nivolumab, in the Example 2 classifier we only use the subset of mCs that, in addition to being useful to predict benefit/nonbenefit from nivolumab treatment, show no separation on the ACORN NSCLC cohort. So, we use a smaller subset of all mCs as we have an additional constraint on their behavior. Then, when we combine these mC, we obtain a different classifier with different sample classifications and different behavior (at least on the ACORN NSCLC set). To get the different behavior on the ACORN set, we have to get some different labels on the melanoma set—but not enough to destroy the nice separation between the Early and Late populations that we had with the Example 1 classifier. A priori it is not clear that it is possible to do this, but the results of Example 2 demonstrate that it is possible to generate such a classifier.

The results of a multivariate analysis of the melanoma sample set (development+validation) are shown in table 25. Two samples, for which gender was not available, and one sample without LDH level were not considered in such analysis.

TABLE 25

Multivariate analysis of OS and TTP for the melanoma set (Development + Validation)

|  | OS | | TTP | |
|---|---|---|---|---|
| Covariate | HR (95% CI) | P value | HR (95% CI) | P value |
| Late vs Early | 2.38 (1.37-4.17) | 0.002 | 2.22 (1.41-3.57) | <0.001 |
| Male vs Female | 1.73 (1.00-3.01) | 0.052 | 1.76 (1.11-2.79) | 0.017 |
| Prior Ipi (no vs yes) | 0.63 (0.35-1.13) | 0.122 | 0.66 (0.40-1.11) | 0.115 |
| PD-L1 (5%) −ve vs +ve | 0.69 (0.23-2.06) | 0.506 | 1.10 (0.46-2.64) | 0.825 |
| PD-L1 (5%) −ve vs NA | 0.81 (0.44-1.48) | 0.491 | 1.04 (0.61-1.79) | 0.848 |
| LDH (IU/L)/1000 | 1.74 (1.25-2.44) | 0.001 | 1.54 (1.12-2.11) | 0.009 |

Even though the classification of Example 2 is significantly associated with LDH level (table 23), both quantities are independently significant predictors of TTP and OS in multivariate analysis. In addition, analysis of tumor size showed that although strongly associated with Early and Late classification (Mann-Whitney p<0.001), with the median tumor size being 48 cm in the Early group and 16 cm in the Late group, Early/Late classification retained its significance as a predictor of OS and TTP when adjusted for tumor size (p=0.014 for OS and p=0.005 for TTP). Thus the classification has independent predictive power in addition to other prognostic factors such as LDH and tumor size.

Independent Validation of Example 2 Classifier

The developed classifier was applied to several sample sets from two different cancer types (melanoma and ovarian) and therapies (immune checkpoint inhibitors and chemotherapies). For all samples Deep MALDI spectra were generated and processed using identical procedures to those used in development. For each sample a classification of "Early" or "Late" was obtained. For each cohort, Kaplan-Meier plots of the available time endpoints are shown and a summary of the analysis of time-to-event is given.

A. Yale Anti-PD-1 Cohort

Figure 19:
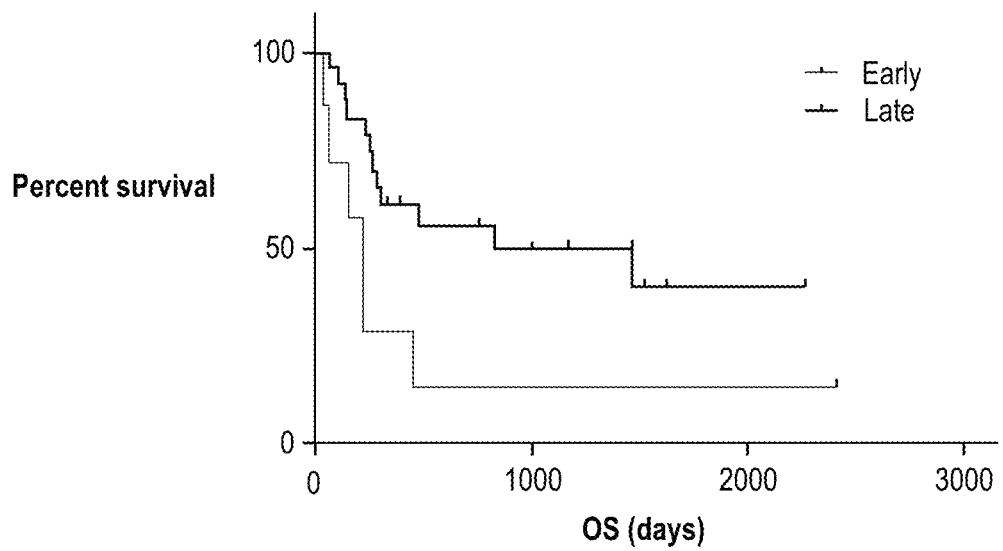
FIG. 19 is a Kaplan-Meier plot for an independent validation cohort of patients treated with anti-PD-1 antibodies (the Yale anti-PD-1 cohort), showing the separation of OS plots for patient samples labeled Early and Late by the classifier of Example 2.

The following results refer to a set of 30 pretreatment samples from patients with advanced unresectable melanoma treated with anti-PD-1 antibodies at Yale University. FIG. 19 is a Kaplan-Meier plot of overall survival for the Yale cohort of patients. It shows a clear separation of the survival curves between the two classes Early and Late. The statistics for the results are shown in Table 26.

TABLE 26

Summary of the performance of the classifier on the Yale anti-PD-1 antibody-treated cohort

| #Early/#Late | OS HR (95% CI) | OS log-rank p | OS Median (Early, Late) |
|---|---|---|---|
| 7/23 | 0.37 (0.07-0.89) | 0.034 | 221, 832 (days) |

These results show that the classifier of Example 2 generalized well to an independent sample set.

The baseline clinical data available for this cohort of patients is summarized in table 27.

TABLE 27

Baseline characteristics of the cohort

|  |  | n (%) |
|---|---|---|
| Gender | Male | 19 (63) |
|  | Female | 11 (37) |
| Age | Median (Range) | 55.5 (26-83) |
| Race | White | 29 (97) |
|  | Black | 1 (3) |
| VeriStrat Label | Good | 24 (80) |
|  | Poor | 6 (20) |

We obtained qualitatively similar results for this cohort of anti-PD-1 antibody treated patients for the full-set classifier developed in accordance with Example 1, Table 13, OS filtering.

B. Yale Anti-CTLA4 Cohort

The following results refer to a set of 48 pretreatment samples from advanced, unresectable melanoma patients treated with anti-CTLA-4 antibodies (ipilimumab or other similar antibodies) at Yale University. The small amount of baseline clinical data available for this cohort of patients is summarized in table 28.

TABLE 28

Baseline characteristics of the Yale anti-CTLA4 cohort

|  |  | n (%) |
|---|---|---|
| Gender | Male | 31 (65) |
|  | Female | 17 (35) |
| Race | White | 48 (100) |
| VeriStrat Label | Good | 40 (83) |
|  | Poor | 8 (17) |

Figure 20:
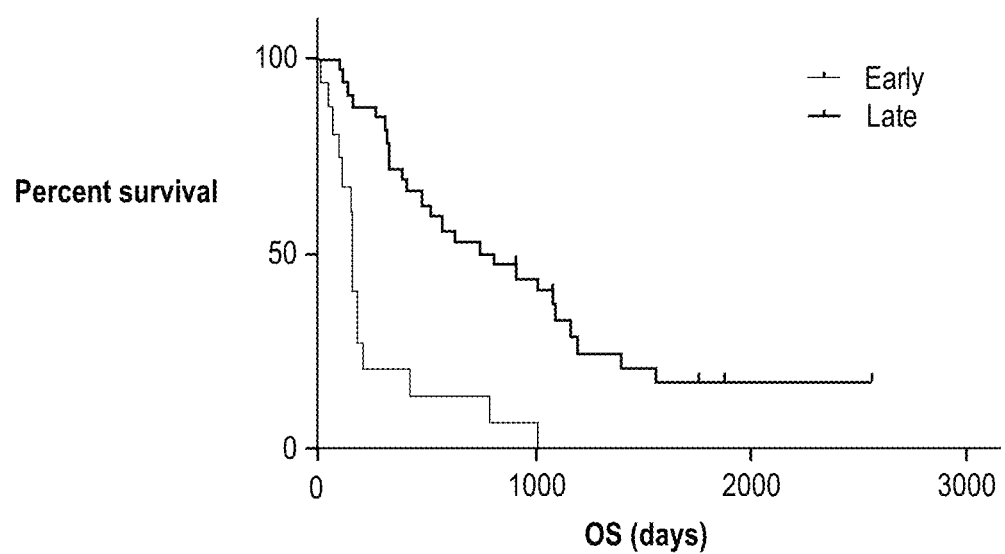
FIG. 20 is a Kaplan-Meier plot for an independent Yale validation cohort of melanoma patients treated with anti-CTLA4 antibodies, showing the separation of OS plots for patient samples labeled Early and Late by the classifier of Example 2.

FIG. 20 is a Kaplan-Meier plot of overall survival for the Yale anti-CTLA4 cohort by classification produced by the classifier of Example 2. Note the clear separation of the Early and Late classes produced by the classifier of Example 2 on this cohort, indicating the classifier's ability to predict melanoma patient benefit from administration of anti-CTLA4 antibodies. The statistics for the performance of the classifier on this cohort are set forth in table 29.

TABLE 29

Summary of the performance of the classifier on the Yale cohort treated with ipilimumab

| #Early/#Late | OS HR (95% CI) | OS log-rank p | OS Median (Early, Late) |
|---|---|---|---|
| 16/32 | 0.27 (0.05-0.28) | <0.0001 | 156, 782 (days) |

B. Ovarian Chemotherapy

Figure 21A:
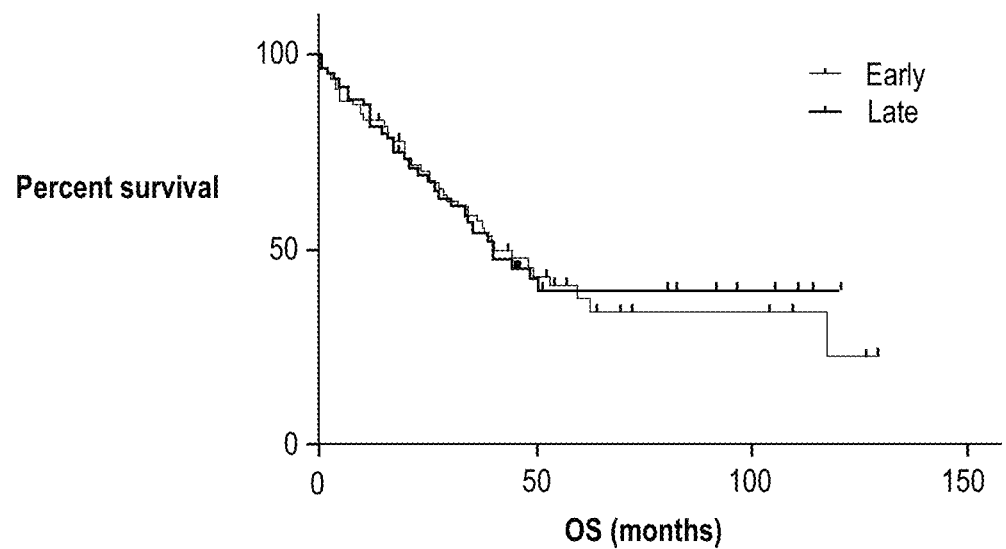
FIGS. 21A and 21B are Kaplan-Meier plots of OS (FIG. 21A) and disease free survival (DFS, FIG. 21B) for the independent validation cohort of patients with ovarian cancer treated with platinum-doublet chemotherapy after surgery. Like the plots of FIGS. 18E-18G, the plots of FIGS. 21A and 21B show a lack of separation in OS and DFS for the ovarian cancer patients whose samples are classified as Early or Late by the classifier of Example 2.
Figure 21B:
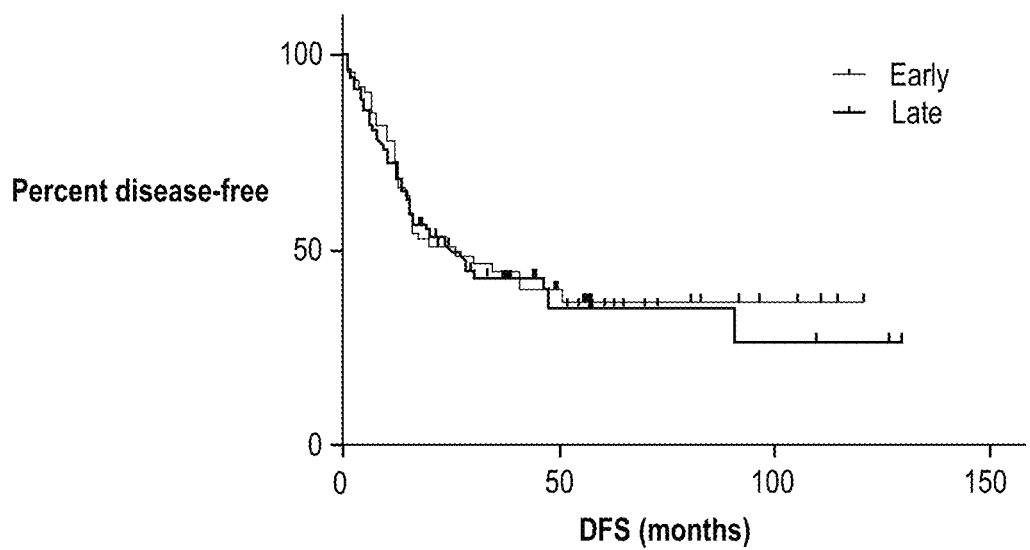
Figure 22:
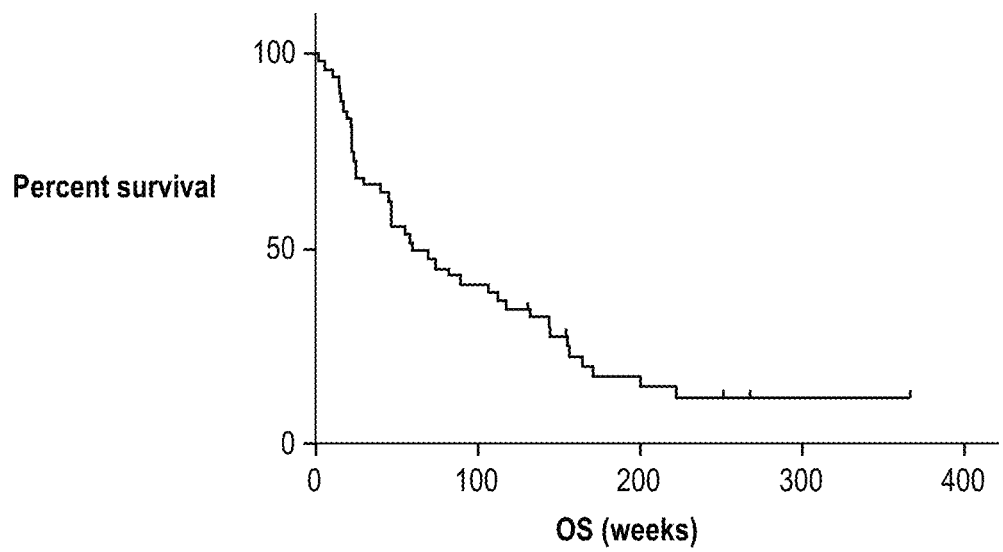
FIG. 22 is a Kaplan-Meier plot of overall survival for the Yale anti-CTLA4 cohort.

The following results refer to a set of 138 pretreatment samples from patients with ovarian cancer treated with platinum-doublet chemotherapy after surgery. Two of these patients have no disease-free survival (DFS) data. The Kaplan-Meier plots for the ovarian cancer cohort by classification produced by the classifier of Example 2 are shown in FIG. 21A (overall survival) and FIG. 21B (disease free survival). Note that the classifiers did not produce a stratification of the Early and Late classification groups in this cohort. This is consistent with the classifier not stratifying the NSCLC patients treated with chemotherapy. Statistics for the classifier performance shown in FIGS. 21A and 21B are set forth in Table 30.

TABLE 30

Summary of the performance of the classifier on the cohort of patients with ovarian cancer treated with platinum-doublet chemotherapy after surgery

| #Early/#Late | OS HR (95% CI) | OS log-rank p | OS Median (Early, Late) | DFS HR (95% CI) | DFS log-rank p | DFS Median (Early, Late) |
|---|---|---|---|---|---|---|
| 77/61 | 0.98 (0.61-1.56) | 0.922 | 41, 41 (months) | 0.94 (0.60-1.47) | 0.787 | 25, 27 (months) |

Reproducibility

Two sample sets (the melanoma/nivolumab and Yale anti-CTLA4 cohorts) were rerun to assess the reproducibility of the classifier of Example 2. Spectra were acquired in completely separate batches from the original runs. In all cases, the mass spectrometer used for the original mass spectral acquisition and the rerun mass spectral acquisition had been used on other projects of the assignee in the interim. Reproducibility of the classifier labels is summarized in table 31.

A. The Melanoma/Nivolumab Cohort

The classifier was concordant between the original run and rerun in 113 of the 119 samples, for an overall concordance of 95%. Of the 43 samples originally classified as Early, 38 were classified as Early and 5 as Late in the rerun. Of the 76 samples originally classified as Late, 75 were classified as Late and 1 classified as Early in the rerun.

B. Yale Anti-CTLA4 Cohort

The reproducibility of the classifier was evaluated only in a subset of 43 samples of the cohort. The classifier was concordant between the original run and rerun in 40 of those 43 samples, for an overall concordance of 93%. Within the subset of 43 samples, of the 13 originally classified as Early, 12 were classified as Early and 1 as Late in the rerun. Of the 30 samples originally classified as Late, 28 were classified as Late and 2 classified as Early in the rerun.

TABLE 31

Reproducibility of the classifications assigned by the predictive classifier across sample sets

| Sample Set | Label concordance |
|---|---|
| nivolumab | 113/119 (95%) |
| anti-CTLA4 | 40/43 (93%) |

Example 2 Conclusions

We were able to construct a classifier that could separate patients treated with immune checkpoint inhibitors into groups with better and worse outcomes (TTP, OS), while not separating patients treated with chemotherapies according to their outcome (OS and PFS or DFS). The classifier was constructed using deep MALDI mass spectra generated from pretreatment serum samples, and was trained using half of the available 119 melanoma samples treated with nivolumab. One third of the 173 available NSCLC samples treated with platinum-doublet plus cetuximab chemotherapy was used to tune the classifier to be predictive and not just prognostic.

The classifier generalized well by stratifying by outcome two independent cohorts of melanoma patients treated with immune checkpoint inhibitors and not stratifying by outcome a third cohort of ovarian cancer patients treated with post-surgery platinum-doublet chemotherapy.

The classifier demonstrated acceptable reproducibility on two separate cohorts, with concordance of 93% or higher.

The following clauses are offered as further descriptions of the inventions disclosed in Example 2:

1. An improved general purpose computer configured as a classifier for classifying a blood-based sample from a human cancer patient to make a prediction about the patient's survival or relative likelihood of obtaining benefit from a drug, comprising:

a memory storing a reference set in the form of feature values for a multitude of mass spectral features obtained from mass spectrometry of blood-based samples from a multitude of melanoma patients treated with an immune checkpoint inhibitor and an associated class label for each of the blood-based samples in the training set, the blood based samples forming a classifier development set;

the memory further storing a set of computer-executable code defining a final classifier based on a multitude of master classifiers, each master classifier generated from a set of filtered mini-classifiers executing a classification algorithm and combined using a regularized combination method; wherein the multitude of master classifiers are obtained from many different realizations of a separation of the development set into classifier training and test sets; and a central processing unit operating on the set of code, the reference set, and mass spectral data obtained from the blood-based sample of the cancer patient to be tested and generating a class label for the blood-based sample; and wherein the mini-classifiers are filtered, in part, by classifier performance of the mini-classifiers on feature values for a set of mass spectral data obtained from blood-based samples of non-small cell lung cancer (NSCLC) patients.

2. The improved computer of clause 1, wherein the set of code is programmed to generate a class label for the sample of the form of Early or the equivalent or Late of the equivalent, wherein the class label Early or the equivalent predicts the patient is likely to obtain relatively less benefit from an immune checkpoint inhibitor drug and the class label Late or the equivalent indicates the patient is likely to obtain relatively greater benefit from the immune checkpoint inhibitor.

3. The improved computer of clause 2, wherein the immune checkpoint inhibitor comprises a monoclonal antibody blocking ligand activation of programmed cell death 1(PD-1).

4. The improved computer of clause 2, wherein the cancer patient providing the blood-based sample to be tested has been diagnosed with lung cancer, ovarian cancer, or melanoma.

5. The improved computer of clause 2, wherein the relatively greater benefit associated with the Late label means significantly greater (longer) overall survival as compared to the Early class label.

Example 3

Classifier for Predicting Melanoma Patient Benefit from Anti-CTLA4 Antibodies

FIG. 20 and Table 29 above demonstrate that the classifier of Example 2 was able to predict melanoma patient benefit from administration of anti-CTLA4 antibodies. Ipilimumab is a specific example of such a drug. It is known that the majority of the patients in the Yale cohort received ipilimumab. We are not certain that they all received ipilimumab and not some other anti-CTLA4 antibody under development. These results demonstrate that it is possible to predict from a blood-based sample in advance of treatment whether a melanoma patient is likely to benefit from anti-CTLA4 antibody drugs. Note further that this classifier for predicting patient benefit for anti-CTLA4 antibody drugs was developed from a sample set of patients who were treated with nivolumab, which is an anti-PD-1 antibody.

Figure 23:
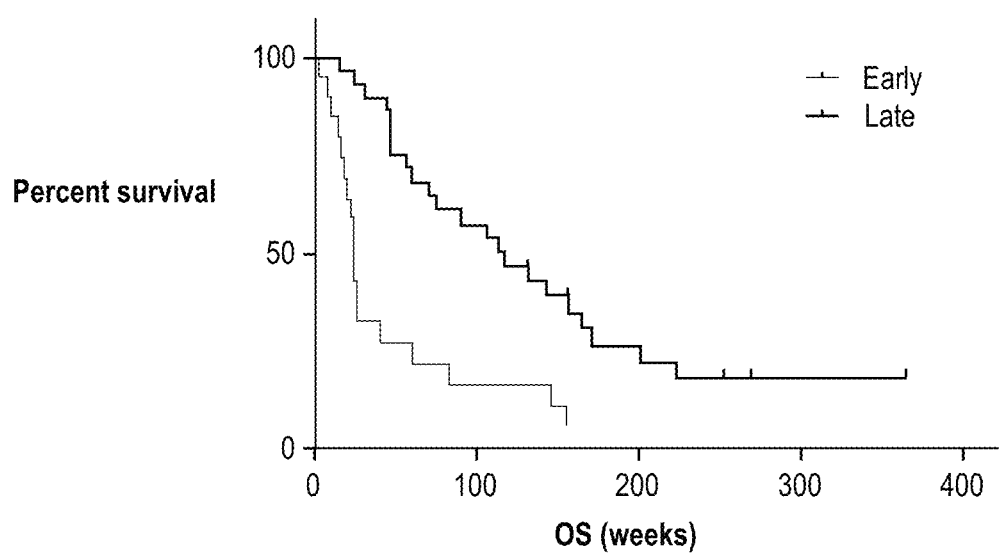
FIG. 23 is a Kaplan-Meier plot for the Yale cohort of melanoma patients treated with anti-CTLA4 antibodies for the "full-set" classifier of Example 1, see Table 13 below.

We further found that the full-set classifier of Example 1 also validated well on this cohort. (The term "full-set classifier of Example 1" means the classifier developed from all 119 patient samples in the nivolumab cohort in accordance with FIG. 8 as explained above in Example 1, see discussion of Table 13, Approach 2, with OS mini-classifier filtering.) FIG. 23 shows the Kaplan-Meier curves for the Early and Late groups from the full set classifier of Example 1 applied to this cohort. Table 32 is a summary of the performance of the classifier on the Yale anti-CTLA4 antibody-treated cohort for the full-set classifier of Example 1.

TABLE 32

Summary of the performance of the classifier

| #Early/#Late | OS HR (95% CI) | OS log-rank p | OS Median (Early, Late) |
|---|---|---|---|
| 20/28 | 0.33 (0.10-0.47) | 0.0002 | 156, 804 (days) 22, 115 (weeks) |

TABLE 33

Baseline characteristics of the cohort by classification group

| | | Early (N = 20) n (%) | Late (N = 28) n (%) |
|---|---|---|---|
| Gender | Male | 12 (60) | 19 (68) |
| | Female | 8 (40) | 9 (32) |
| VeriStrat Label | Good | 12 (60) | 28 (100) |
| | Poor | 8 (40) | 0 (0) |

A subset of 43 samples from this cohort (16 classified as Early and 27 classified as Late) was rerun with independent sample preparation and spectral acquisition. Of the 43 samples, 41 were assigned the same class label as in the original run (95% concordance). Two samples initially classified as Early were classified as Late on the rerun.

We also developed a classifier for identification of patients with better and worse outcomes on anti-CTLA4 therapy using pre-treatment serum samples from patients subsequently treated with anti-CTLA4 agents. We will now describe the pertinent aspects of this classifier development exercise and the performance of the classifier developed from this sample set.

In this classifier development exercise, we had 48 pre-treatment serum samples available from a cohort of patients, subsequently treated with anti-CTLA4 agents along with associated clinical data. Most patients are known to have received ipilimumab, but some may have received an alternative anti-CTLA4 antibody. These are the same 48 patients that we ran Example 1 and Example 2 validation tests on which are already described above in Example 3. Overall survival (OS) was the only outcome endpoint available.

For this classifier development, we used the same spectra and the same spectral processing and features, i.e. identical feature table, as we did for the Examples 1 and 2. The only difference was that feature 9109 was dropped from the feature table, as we are concerned that it has reproducibility issues and little value for classification.

We used the same Diagnostic Cortex method of FIG. 8 in classifier development, as detailed throughout the description of Examples 1 and 2, with label flip iterations. The initial class definitions were based on shorter or longer OS. We used mini-classifier filtering based on hazard ratio for OS between the classification groups of the training set.

Figure 23A:
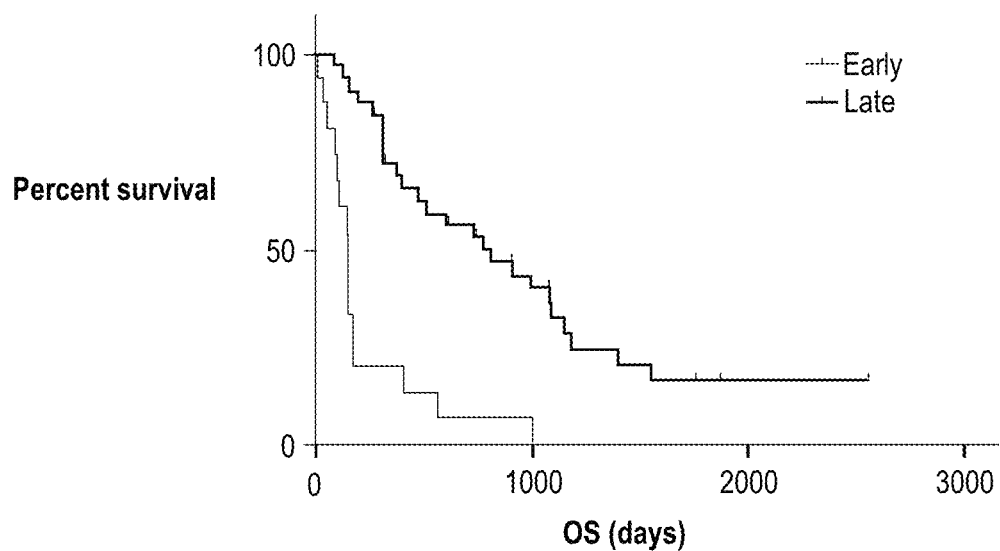
FIGS. 23A and 23B are Kaplan-Meier plots of classifier performance of a second anti-CTLA4 antibody classifier, which was developed from the Yale anti-CTLA4 cohort.

The resulting classifier assigned 16 patients to the Early group and 32 to the Late group. (This compares with 20 in the Early group and 28 in the Late group from the Example 1 full-set classifier.) The Kaplan-Meier plot of classifier performance is shown in FIG. 23A for the groups defined by the new classifier trained on the anti-CTLA4 cohort. Note the clear separation in the overall survival between the Early and Late groups in the plot of FIG. 23A. None of the patients in the Early group survived more than 3 years. The statistics for the classifier performance are as follows

| #Early/ #Late | HR (95% CI) | log rank p | Median OS |
|---|---|---|---|
| 16/32 | 0.24 (0.04-0.23) | <0.0001 | Early: 155 days, Late: 804 days |

Figure 23B:
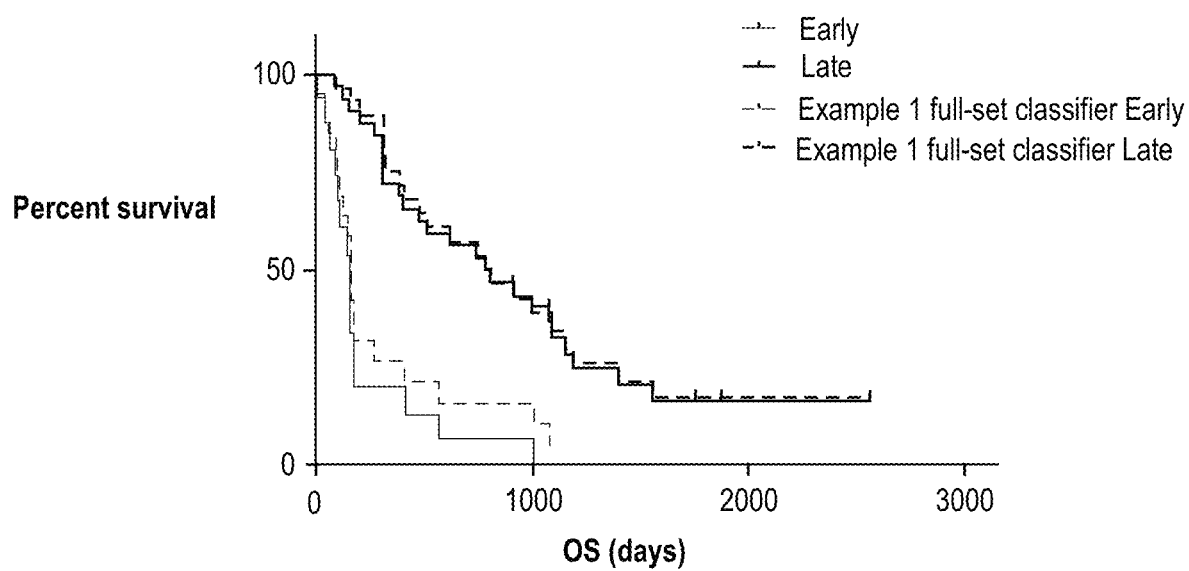

A comparison of this result with the classifier performance we obtained for the Example 1 full-set classifier operating on the Yale cohort is shown in FIG. 23B. Note in FIG. 23B the almost perfect overlap between the Early and Late groups in the classifiers developed from the melanoma/nivolumab sample set ("example 1 full-set classifier" and the classifiers developed from the Yale anti-CTLA4 cohort ("Early" and "Late").

So, comparing the Kaplan-Meier plots of FIG. 23 and the statistics of the two classifiers, the classifier performance results do not seem to be significantly better with the classifier developed on the anti-CTLA4 cohort than with the classifier developed on the nivolumab-treated cohort. The fact that the two classifiers produce quite similar results using completely different development sets supports our assertions that the Diagnostic Cortex method of FIG. 8 produces tests that do not overfit to development sample sets, but rather extract the information that will generalize to other sample sets.

In one embodiment, testing method of making a prediction of whether a melanoma patient is likely to benefit from anti-CTLA4 antibody drug involves the following steps:

(a) conducting mass spectrometry on a blood-based sample of the patient and obtaining mass spectrometry data;

(b) obtaining integrated intensity values in the mass spectrometry data of a multitude of pre-determined mass-spectral features (such as for example the features listed in Appendix A or some subset thereof, e.g., after a deselection of noisy features that do not significantly contribute to classifier performance such as the features of one of the sets of Appendix B or Appendix C); and (c) operating on the mass spectral data with a programmed computer implementing a classifier (e.g., a classifier generated in accordance with FIG. 8 as explained in Example 2 or the full-set classifier of Example 1).

In the operating step the classifier compares the integrated intensity values with feature values of a training set of class-labeled mass spectral data obtained from blood-based samples obtained from a multitude of other melanoma patients. This training set could be of one of two types, namely class labeled mass-spectral data from a set of samples from patients treated with an antibody drug blocking ligand activation of programmed cell death 1 (PD-1), e.g., nivolumab. Alternatively, this training set could be class-labeled mass spectral data from a set of samples from patients treated with an anti-CTLA4 antibody. The classifier performs this comparison with a classification algorithm. The classifier generates a class label for the sample, wherein the class label "early" or the equivalent predicts the patient is likely to obtain relatively less benefit from the anti-CTLA4 antibody drug and the class label "late" or the equivalent indicates the patient is likely to obtain relatively greater benefit from the anti-CTLA4 antibody drug.

Additionally, preferably the mass spectral data is acquired from at least 100,000 laser shots performed on the blood-based sample using MALDI-TOF mass spectrometry.

The classifier is preferably obtained from a combination of filtered mini-classifiers using a regularized combination method. The mini-classifiers may be filtered as explained in Example 2 by retaining mini-classifiers defined during classifier generation so that mass spectra from patients treated with immunotherapy would split according to their OS outcomes, but when such mini-classifiers are applied to mass spectra from patients treated with chemotherapy they would not split. This is considered optional, as the "full-set" classifier of Example 1, which can be used in this test, was developed without using any filtering of mini-classifiers on a set of samples from a chemotherapy cohort.

A testing environment for conducting the test of Example 3 on a blood-based sample of a melanoma patient can take the form of the system shown in FIG. 15 and described in detail below in Example 5.

The following clauses are offered as further descriptions of the disclosed inventions of Example 3.

1. A method of predicting melanoma patient response to an antibody drug targeting CTLA-4, comprising:

a) conducting mass spectrometry on a blood-based sample of the patient and obtaining mass spectrometry data;

(b) obtaining integrated intensity values of a multitude of pre-determined mass-spectral features in the mass spectrometry data; and (c) operating on the mass spectral data with a programmed computer implementing a classifier;

wherein in the operating step the classifier compares the integrated intensity values with feature values of a reference set of class-labeled mass spectral data obtained from blood-based samples obtained from a multitude of other melanoma patients treated with either (1) an antibody drug targeting programmed cell death 1 (PD-1) or (2) an antibody drug targeting CTLA4 with a classification algorithm and generates a class label for the sample, wherein the class label "early" or the equivalent predicts the patient is likely to obtain relatively less benefit from the antibody drug targeting CTLA-4, and the class label "late" or the equivalent indicates the patient is likely to obtain relatively greater benefit from the antibody drug targeting CTLA4.

2. The method of clause 1, wherein the pre-determined mass spectral features include a multitude of features listed in Appendix A, Appendix B, or Appendix C.

3. The method of clause 1, wherein the classifier is configured as a combination of filtered mini-classifiers using a regularized combination method.

4. The method of clause 1, wherein the mass spectral data is acquired from at least 100,000 laser shots performed on the sample using MALDI-TOF mass spectrometry.

5. The method of clause 1, wherein the mini-classifiers are filtered in accordance with any one of the criteria listed in Table 10.

6. The method of clause 1, wherein the classifier is defined from a multitude of master classifiers generated from a multitude of separations of a development set of samples into a training set and a test set.

7. The method of clause 1, wherein the reference set is in the form of class-labeled mass spectral data obtained from blood-based samples obtained from a multitude of melanoma patients treated with an antibody drug targeting programmed cell death 1 (PD-1).

8. A machine predicting melanoma patient benefit of an antibody drug targeting CTLA-4, comprising:

a memory storing a reference set in the form of feature values for a multitude of mass spectral features obtained from mass spectra of blood-based samples from a multitude of melanoma patients either (1) treated with an antibody drug blocking ligand activation of programmed cell death 1 (PD-1) or (2) treated with an antibody drug targeting CTLA4;

the memory further storing a set of code defining a final classifier based on a multitude of master classifiers, each master classifier generated from filtered mini-classifiers combined using a regularized combination method;

a central processing unit operating on the set of code and the reference set and mass spectral data obtained from a blood-based sample of a melanoma patient to be tested and responsively generating a class label for the blood-based sample, wherein the class label "early" or the equivalent predicts the patient is likely to obtain relatively less benefit from the antibody drug targeting CTLA4 and the class label "late" or the equivalent indicates the patient is likely to obtain relatively greater benefit from the antibody drug targeting CTLA4.

9. The machine of clause 8, wherein the memory stores integrated intensity values for a multitude of features listed in Appendix A, or Appendix B, or Appendix C.

10. A method of treating a melanoma patient, comprising the step of administrating an antibody drug targeting CTLA-4 to the patient, wherein the patient has been previously selected for such administration by the performance of the method of any of clauses 1-7 on a blood-based sample of the patient and the patient was assigned the class label of Late or the equivalent.

Example 4

Classifier for Predicting Better or Worse Survival in Ovarian and NSCLC Patients Treated with Chemotherapy We discovered that the classifier of Example 1 split a cohort of 173 first line, advanced non-small cell lung cancer (NSCLC) patients treated with platinum-doublet+cetuximab, and yet another cohort of 138 ovarian cancer patients treated with platinum-doublet after surgery into groups with better and worse OS and progression-free (or disease-free) survival (PFS or DFS). Practical tests for predicting better or worse survival in ovarian and NSCLC patients will be described in this section. Further details on the ACORN NSCLC and ovarian cancer cohorts will also be described in this Example 4. Note that the classifier of Example 2 (with the use of the ACORN NSCLC cohort for mini-classifier filtering) does not identify those ovarian and NSCLC patients which are likely to benefit from chemotherapy, hence the classifier and test for predicting better or worse survival in ovarian and NSCLC on platinum chemotherapy is constructed in accordance with Example 1.

ACORN NSCLC Cohort

Figure 24A:
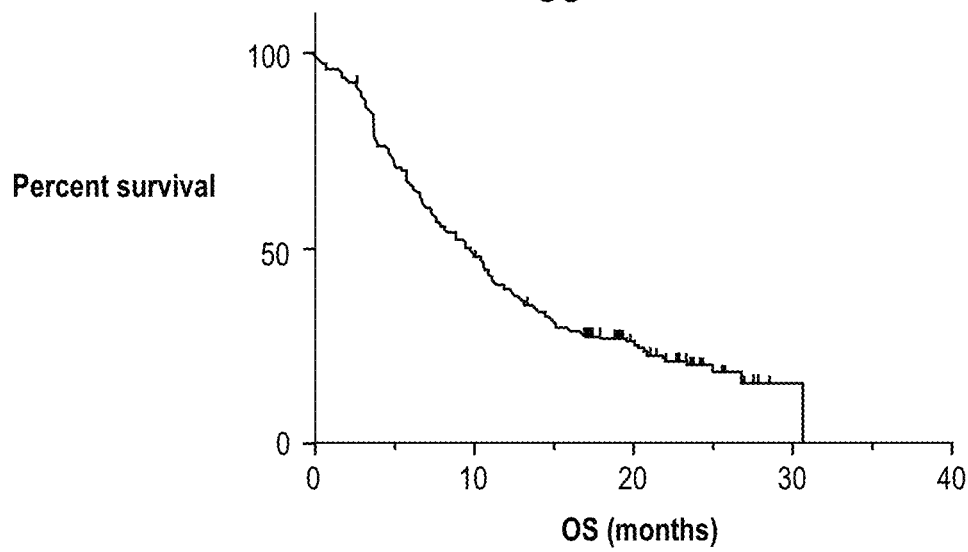
FIGS. 24A and 24B are Kaplan-Meier plots of OS and PFS, respectively, for the ACORN NSCLC cohort used in the development of the classifier of Example 2.
Figure 24B:
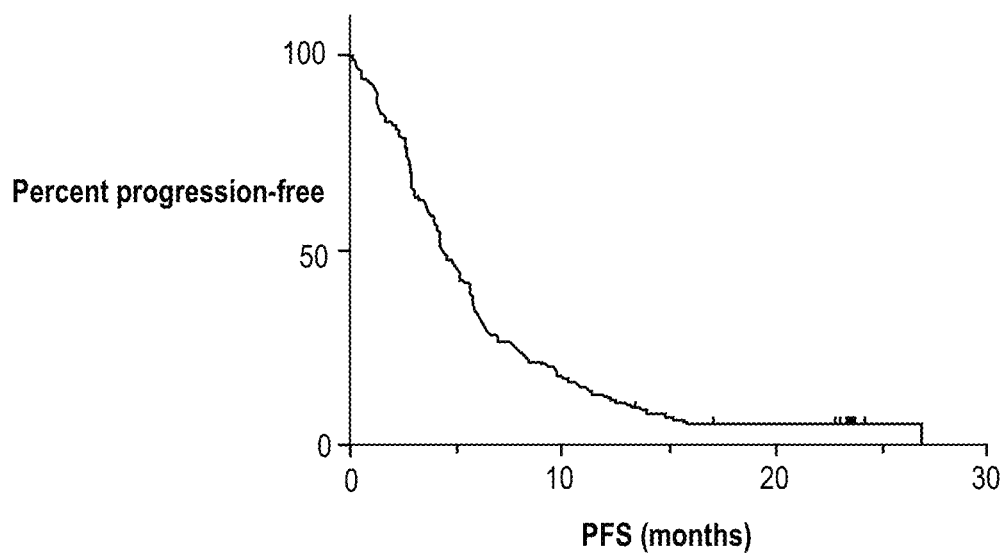

A set of 173 pretreatment blood-based samples from patients with previously untreated advanced non-small cell lung cancer (NSCLC) were available. Patients received platinum-based chemotherapy with cetuximab as part of a clinical trial. The most important baseline clinical data available for this cohort of patients are summarized in table 34 and OS and progression-free survival (PFS) for the whole cohort is shown in FIGS. 24A and 24B, respectively.

TABLE 34

Baseline characteristics of the ACORN NSCLC cohort

|   |   | n (%) |
|---|---|---|
| Gender | Male | 108 (62) |
|  | Female | 65 (38) |
| Race | White | 133 (77) |
|  | Black | 23 (13) |
|  | Other | 17 (10) |
| Histology | squamous | 63 (36) |
|  | non-squamous | 110 (64) |
| VeriStrat Label | Good | 122 (71) |
|  | Poor | 51 (29) |
| Performance Status | 0 | 61 (35) |
|  | 1 | 112 (65) |
| Disease Stage | IIIB | 8 (5) |
|  | IV | 165 (95) |
| Treatment | Carboplatin/Paclitaxel/Cetuximab | 68 (39) |
|  | Carbo- or Cisplatin/Gemcitabine/Cetuximab | 69 (40) |
|  | Carbo- or Cisplatin/Pemetrexed/Cetuximab | 36 (21) |
| Age | Median (range) | 66 (35-86) |

Figure 25A:
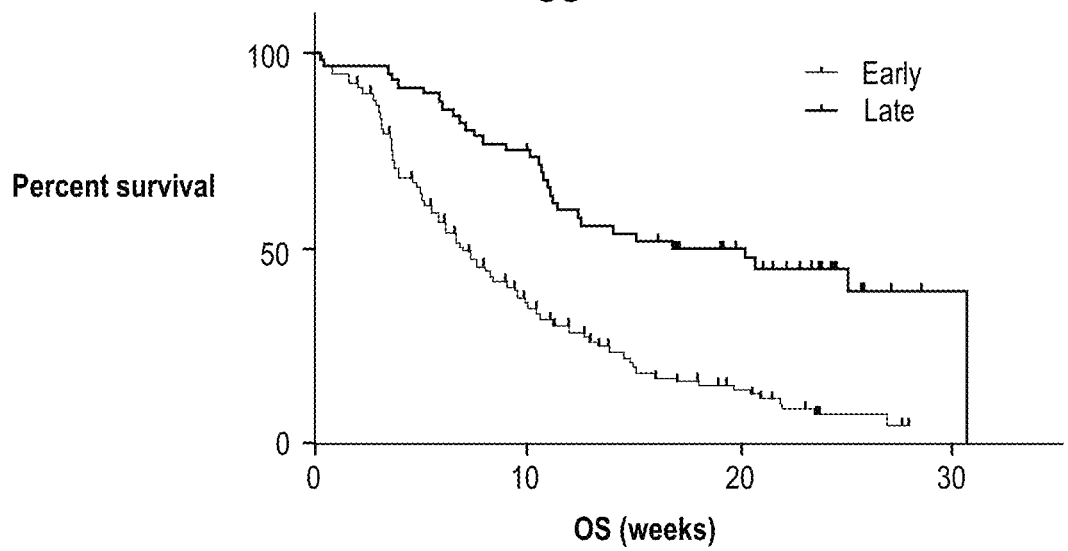
FIGS. 25A and 25B are Kaplan-Meier plots of OS and PFS, respectively, for the ACORN NSCLC cohort, by classification produced by the "full-set" classifier of Example 1. Note the clear separation in the overall survival plot of FIG. 25A between the samples classified as Early and Late by the full-set classifier of Example 1. A separation in PFS between the Early and Late classified samples is also shown in FIG. 25B.
Figure 25B:
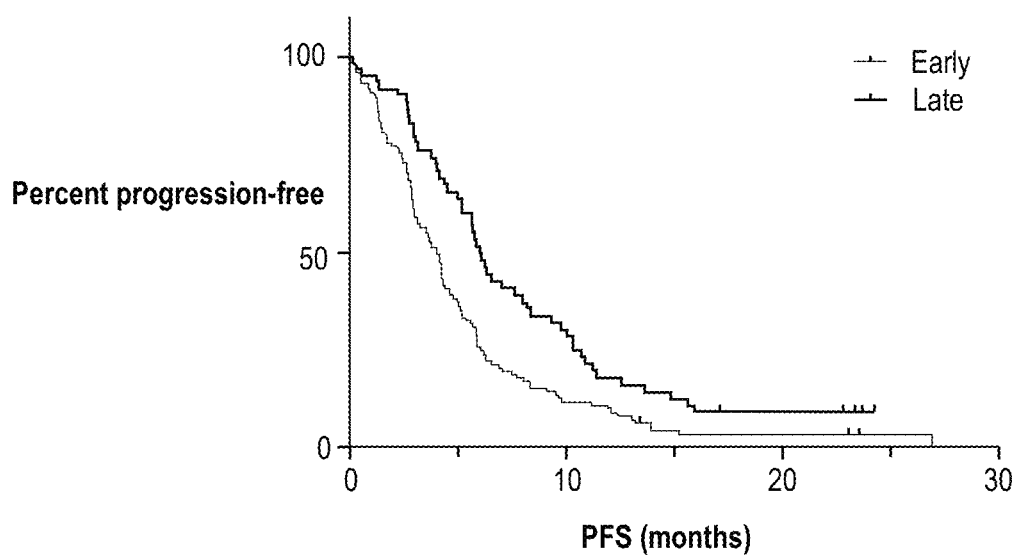

Deep MALDI spectra had been generated from these samples for a prior project, but in an identical way to that described in Example 1, and these were processed using identical procedures to those used in development of the classifiers of Example 1. The full-set classifier of Example 1 was applied to the resulting feature table, yielding a classification of "Early" or "Late" for each sample. One hundred sixteen samples were classified as Early and the remaining 57 as Late. The Kaplan-Meier plot of overall survival for the cohort by classification group is shown in FIGS. 25A and 25B and a summary of the analysis of OS and PPFS is given in table 35. Patient baseline characteristics are summarized by classification group in table 36.

TABLE 35

Summary of the performance of the classifier on the ACORN NSCLC cohort

| #Early/#Late | Endpoint | HR (95% CI) | log-rank p | Median (Early, Late) |
|---|---|---|---|---|
| 116/57 | OS | 0.36 (0.28-0.55) | <0.0001 | 7.0, 20.1 (months) |
| 116/57 | PFS | 0.60 (0.44-0.82) | 0.0017 | 3.9, 5.9 (months) |

TABLE 36

Baseline characteristics by classification of full-set classifier of Example 1

|   |   | Early n (%) | Late n (%) |
|---|---|---|---|
| Gender | Male | 74 (64) | 34 (60) |
|  | Female | 42 (36) | 23 (40) |
| Race | White | 86 (74) | 47 (82) |
|  | Black | 19 (16) | 4 (7) |
|  | Other | 11 (9) | 6 (11) |
| Histology | squamous | 45 (39) | 18 (32) |
|  | non-squamous | 71 (61) | 39 (68) |
| VeriStrat Label | Good | 65 (56) | 57 (100) |
|  | Poor | 51 (44) | 0 (0) |
| Performance Status | 0 | 34 (29) | 27 (47) |
|  | 1 | 82 (71) | 30 (53) |
| Disease Stage | IIIB | 5 (4) | 3 (5) |
|  | IV | 111 (96) | 54 (95) |
| Treatment | Carboplatin/Paclitaxel/Cetuximab | 46 (40) | 22 (39) |

TABLE 36-continued

Baseline characteristics by classification of full-set classifier of Example 1

|   |   | Early n (%) | Late n (%) |
|---|---|---|---|
|   | Carbo- or Cisplatin/Gemcitabine/Cetuximab | 46 (40) | 23 (40) |
|   | Carbo- orCisplatin/Pemetrexed/Cetuximab | 24 (21) | 12 (21) |
| Age | Median (range) | 66.5 (35-85) | 64 (46-86) |

Figure 26A:
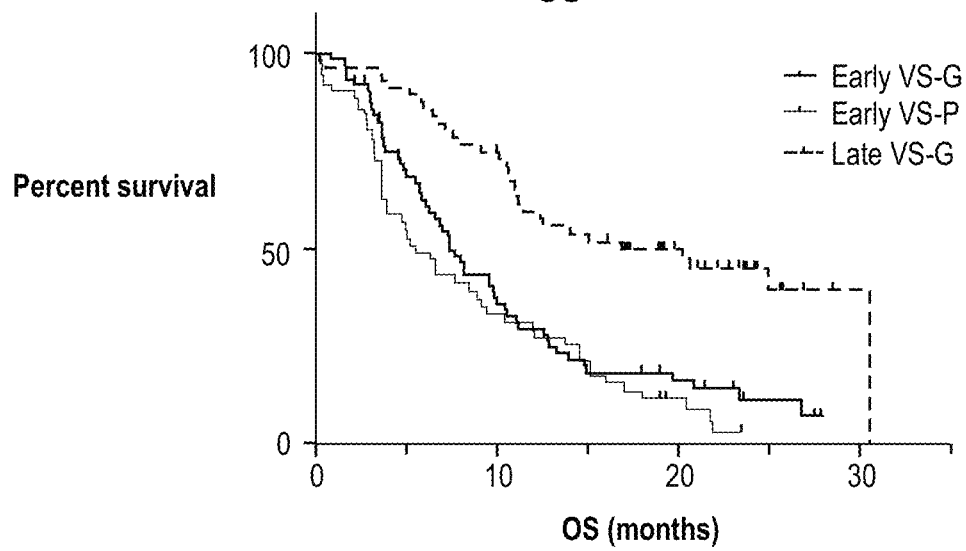
FIGS. 26A and 26B are Kaplan-Meier plots for the ACORN NSCLC cohort by classification and VeriStrat label (assigned in accordance with the classifier and training set of U.S. Pat. No. 7,736,905). Note that there is essentially no separation between the VeriStrat Good (VS-G) and Poor (VS-P) samples classified Early by the full-set classifier of Example 1, and the clear separation in the survival plots between those classified Late and those classified Early by the full-set classifier of Example 1.
Figure 26B:
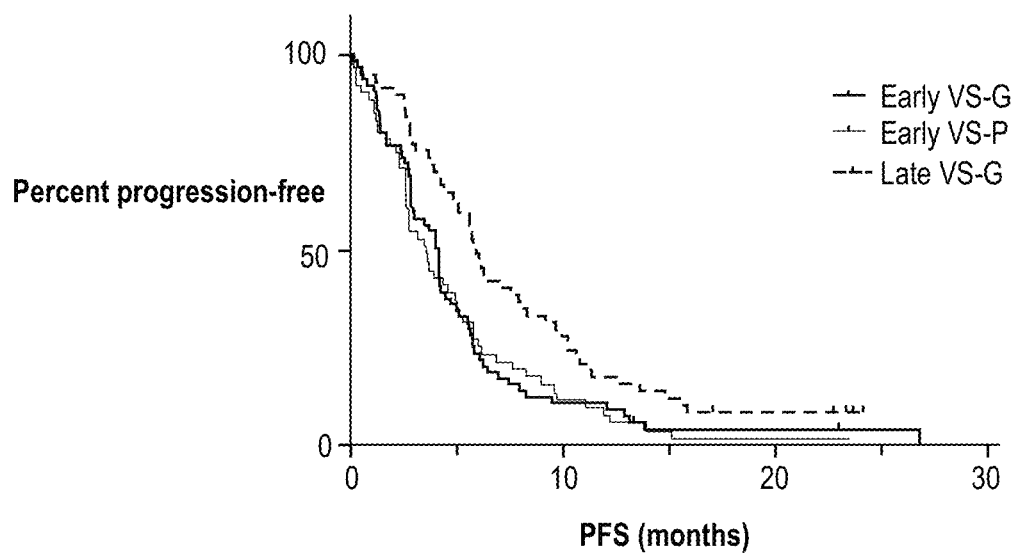

FIGS. 26A and 26B shows the time-to-event outcomes broken down by classification and VeriStrat label (using the classification algorithm, feature definitions, and NSCLC training set described in U.S. Pat. No. 7,736,905). It is apparent that both VeriStrat groups within the Early classification group have similarly poor outcomes.

Ovarian Cancer Cohort

Figure 27A:
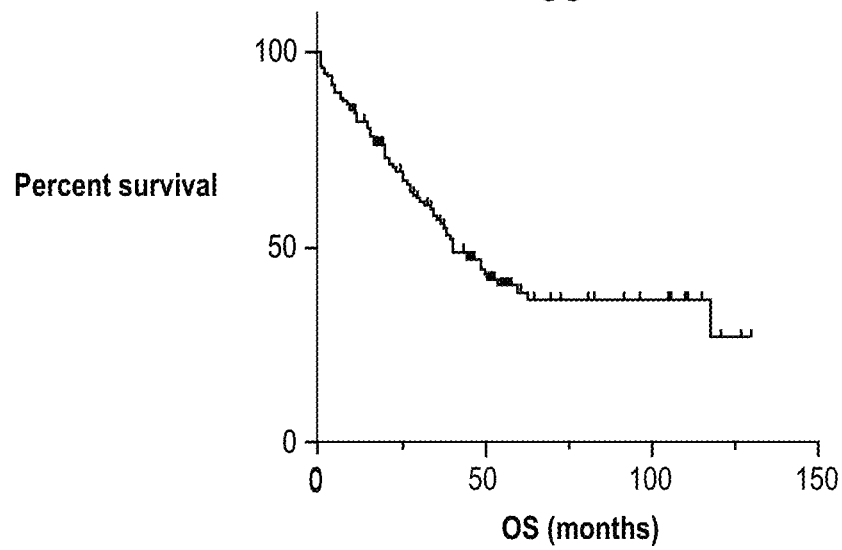
FIGS. 27A and 27B are Kaplan-Meier plots of OS and DFS for the ovarian cancer chemotherapy cohort of 138 patients used for internal validation of the classifier of Example 2.
Figure 27B:
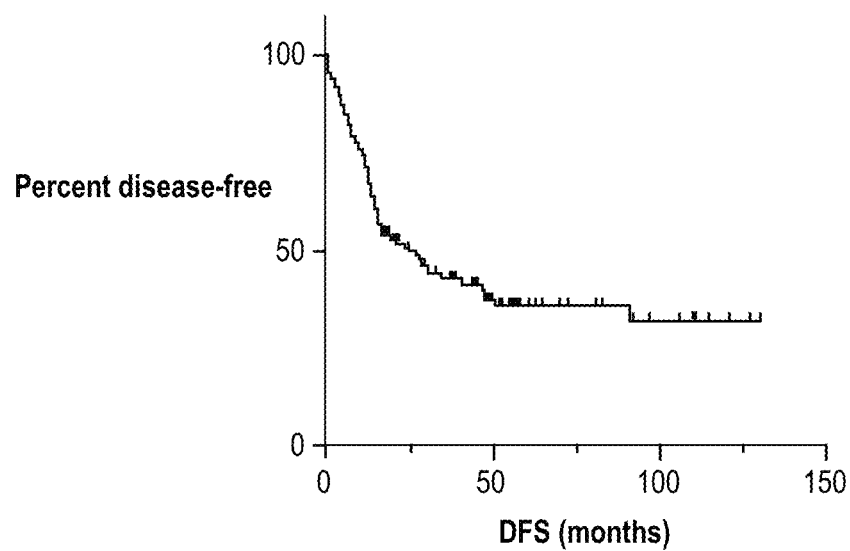

A set of 165 samples from an observation trial of patients with ovarian cancer were available. Patients underwent surgery followed by platinum-based chemotherapy. Samples were taken at the time of surgery. Of the 165 patients, 23 did actually not start chemotherapy, were not newly diagnosed, or had received prior therapy for ovarian cancer. Outcome data was not available for an additional four patients. Data are presented here for the remaining 138 patients. The most important baseline clinical data available for these patients are summarized in table 37 and OS and disease-free survival (DFS) are shown in FIGS. 27A and 27B. Note, two patients of the 138 did not have DFS available.

TABLE 37

Baseline characteristics of the ovarian cohort

|   |   | n (%) |
|---|---|---|
| Histology | serous | 100 (72) |
|   | non-serous | 38 (28) |
| VeriStrat Label | Good | 110 (80) |
|   | Poor | 27 (20) |
|   | Indeterminate | 1 (1) |
| FIGO | 1 | 13 (9) |
|   | 2 | 3 (2) |
|   | 3 | 54 (39) |
|   | 4 | 29 (21) |
|   | NA | 39 (28) |
| Histologic Grade | NA | 2 (1) |
|   | 1 | 7 (5) |
|   | 2 | 53 (38) |
|   | 3 | 76 (55) |
| Metastatic Disease | yes | 20 (14) |
|   | no | 118 (86) |
| Age | Median (range) | 59 (18-88) |

Figure 28A:
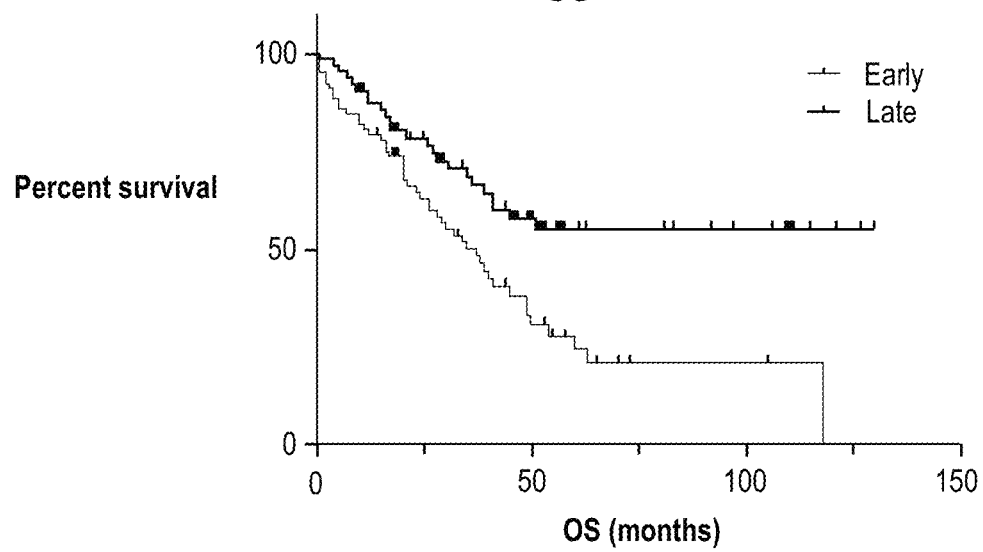
FIGS. 28A and 28B are Kaplan-Meier plots for OS and DFS, respectively, of the ovarian cancer chemotherapy cohort by classification produced by the "full-set" classifier of Example 1. Note the clear separation in the overall survival plot of FIG. 28A between the samples classified as Early and Late by the full-set classifier of Example 1. A clear separation in DFS between the Early and Late classified samples is also shown in FIG. 28B. Thus, the FIGS. demonstrate the ability of the full-set classifier of Example 1 to predict ovarian cancer survival on chemotherapy.
Figure 28B:
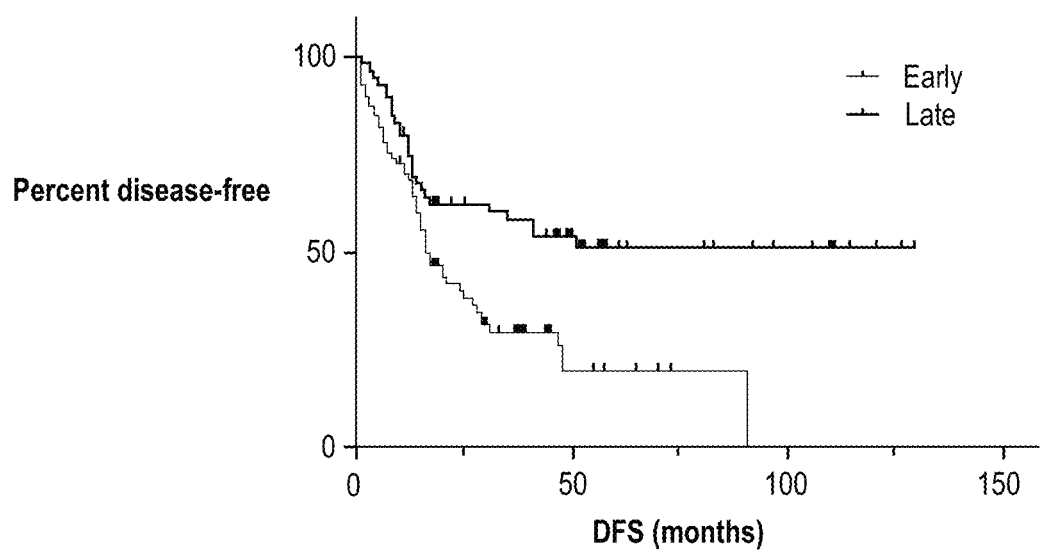

Deep MALDI spectra had been generated from these samples for a prior project, in an identical manner as outlined in Example 1, and these were processed using identical procedures to those used in development of the nivolumab test described in Example 1. The Example 1 full-set classifier was applied to the resulting feature table, yielding a classification of "Early" or "Late" for each sample. Seventy six samples were classified as Early and the remaining 62 as Late. The Kaplan-Meier plots of overall and disease-free survival by classification are shown in FIGS. 28A and 28B, and a summary of the analysis of OS and PFS is given in table 38. Patient baseline characteristics are summarized by classification group in table 39.

TABLE 38

Summary of the performance of the full-set classifier of Example 1 on the ovarian cancer cohort

| #Early/#Late | Endpoint | HR (95% CI) | log-rank p | Median (Early, Late) |
|---|---|---|---|---|
| 76/62 | OS | 0.48 (0.30-0.76) | 0.0021 | 35, not reached (months) |
| 74/62 | PFS | 0.48 (0.30-0.73) | 0.0011 | 17, not reached (months) |

TABLE 39

Baseline characteristics by classification produced from full-set classifier of Example 1

|   |   | Early n (%) | Late n (%) |
|---|---|---|---|
| Histology | serous | 61 (80) | 39 (63) |
|   | non-serous | 15 (20) | 23 (37) |
| VeriStrat Label | Good | 48 (63) | 62 (100) |
|   | Poor | 27 (36) | 0 (0) |
|   | Indeterminate | 1 (1) | 0 (0) |
| FIGO | 1 | 2 (3) | 11 (18) |
|   | 2 | 2 (3) | 1 (2) |
|   | 3 | 32 (42) | 22 (35) |
|   | 4 | 22 (29) | 7 (11) |
|   | NA | 18 (24) | 21 (34) |
| Histologic Grade | NA | 0 (0) | 2 (3) |
|   | 1 | 1 (1) | 6 (10) |
|   | 2 | 32 (42) | 21 (34) |
|   | 3 | 43 (57) | 33 (53) |
| Metastatic Disease | yes | 15 (20) | 5 (8) |
|   | no | 61 (80) | 57 (92) |
| Age | Median (range) | 60 (35-88) | 57.5 (18-83) |

Figure 29A:
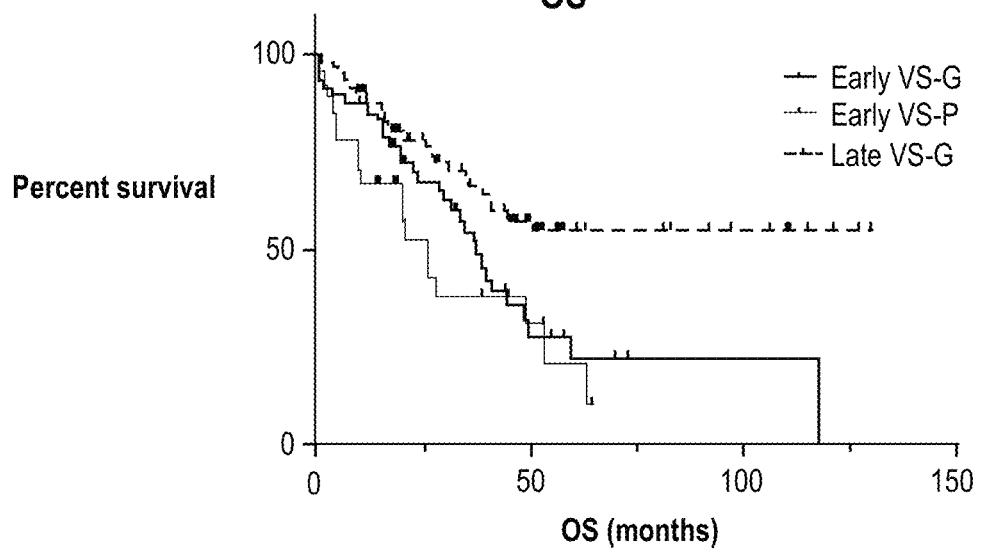
FIGS. 29A and 29B are Kaplan-Meier plots of the ovarian cancer chemotherapy cohort by classification and VeriStrat label. Note that there is essentially no separation between the samples classified Early and tested as VeriStrat Good (VS-G) and Poor (VS-P) by the full-set classifier of Example 1, and the clear separation in the survival plots between those classified Late and those classified Early by the full-set classifier of Example 1. As in the NSCLC cohort, it is apparent that outcomes are similar between VeriStrat subgroups within the group of patients classified as Early.
Figure 29B:
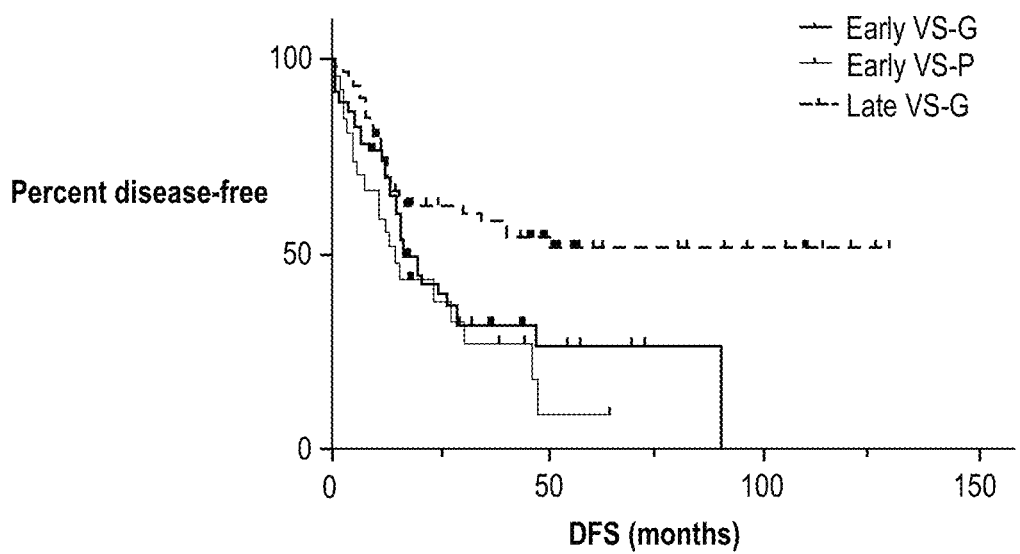

FIGS. 29A and 29B show the time-to-event outcomes broken down by classification and VeriStrat label (testing in accordance with U.S. Pat. No. 7,736,905). It is apparent that both VeriStrat groups Good and Poor within the Early classification produced by the full-set classifier of Example 1 have similarly poor outcomes.

In summary, a testing method of making a prediction of whether an ovarian or NSCLC patient is likely to benefit from chemotherapy, e.g., platinum doublet chemotherapy, involves the following steps:

a) conducting mass spectrometry on a blood-based sample of the patient and obtaining mass spectrometry data;

(b) obtaining integrated intensity values in the mass spectrometry data of a multitude of pre-determined mass-spectral features (such as for examples the features listed in Appendix A or some subset thereof, e.g., after a deselection of noisy features that do not significantly contribute to classifier performance such as the features of one of the sets of Appendix B); and (c) operating on the mass spectral data with a programmed computer implementing a classifier (e.g., a classifier generated in accordance with FIG. 8, the full-set classifier of Example 1).

In the operating step the classifier compares the integrated intensity values with feature values of a training set of class-labeled mass spectral data obtained from blood-based samples obtained from a multitude of melanoma patients treated with an antibody drug blocking ligand activation of programmed cell death 1 (PD-1), e.g., nivolumab, with a classification algorithm. The classifier generates a class label for the sample, wherein the class label "early" or the equivalent predicts the patient is likely to obtain relatively less benefit and/or have worse outcome from the chemotherapy and the class label "late" or the equivalent indicates the patient is likely to obtain relatively greater benefit and/or have better outcome from the chemotherapy. In one embodiment the chemotherapy is platinum-doublet chemotherapy.

Additionally, preferably the mass spectral data is acquired from at least 100,000 laser shots performed on the blood-based sample using MALDI-TOF mass spectrometry.

The classifier is preferably obtained from a combination of filtered mini-classifiers using a regularized combination method.

A practical testing environment for conducting the test on ovarian and NSCLC cancer patients is described in FIG. 15 and the following section.

The following clauses are offered as further examples of the inventions disclosed in Example 4.

1. A method of predicting overall survival of a non-small cell lung cancer (NSCLC) or ovarian cancer patient treated with chemotherapy, comprising:
a) conducting mass spectrometry on a blood-based sample of the patient and obtaining mass spectrometry data;
(b) obtaining integrated intensity values of a multitude of pre-determined mass-spectral features in the mass spectrometry data; and
(c) operating on the mass spectral data with a programmed computer implementing a classifier;
wherein in the operating step the classifier compares the integrated intensity values with feature values of a reference set of class-labeled mass spectral data obtained from blood-based samples obtained from a multitude of melanoma patients treated with an antibody drug targeting programmed cell death 1 (PD-1) with a classification algorithm and generates a class label for the sample, wherein the class label "early" or the equivalent predicts the patient is likely to have a relatively less benefit and/or worse outcome (survival) and the class label of "late" or the equivalent indicates the patient is likely to obtain relatively greater benefit and/or better outcome (survival) from the chemotherapy.

2. The method of clause 1, wherein the chemotherapy comprises platinum doublet chemotherapy.

3. The method of clause 1, wherein the chemotherapy comprises the combination of platinum doublet+cetuximab chemotherapy.

4. The method of clause 1, wherein the pre-determined mass spectral features include a multitude of features listed in Appendix A or Appendix B.

5. The method of any of clauses 1-4, wherein the mass spectral data is acquired from at least 100,000 laser shots performed on the sample using MALDI-TOF mass spectrometry.

6. The method of any of clauses 1-5, wherein classifier is obtained from a filtered combination of miniClassifiers which are combined using a regularization procedure.

7. The method of clause 6, wherein the mini-classifiers are filtered in accordance with any one of the criteria listed in Table 10.

8. The method of clause 6, wherein the classifier is obtained from a multitude of master classifiers generated from a multitude of separations of a development set of samples into a training set and a test set.

9. A machine predicting overall survival of a non-small cell lung cancer (NSCLC) or ovarian cancer patient treated with chemotherapy, comprising:
a memory storing a reference set in the form of feature values for a multitude of mass spectral features obtained from mass spectra of blood-based samples from a multitude of melanoma patients treated with an antibody drug blocking ligand activation of programmed cell death 1 (PD-1);
the memory further storing a set of code defining a final classifier based on a multitude of master classifiers, each master classifier generated from filtered mini-classifiers combined using a regularized combination method;
a central processing unit operating on the set of code and the reference set and mass spectral data obtained from a blood-based sample of a NSCLC or ovarian cancer patient to be tested and responsively generating a class label for the blood-based sample, wherein the class label "early" or the equivalent predicts the patient is likely to have a relatively less benefit and/or worse survival and the class label of "late" or the equivalent indicates the patient is likely to obtain relatively greater benefit and/or better survival from the chemotherapy.

10. A laboratory test center comprising the machine of clause 9 and a MALDI-TOF mass spectrometer configured for conducting mass spectrometry on the blood-based sample from the NSCLC or ovarian cancer patient.

11. A method of treatment of a NSCLC or ovarian cancer patient, comprising:
administering chemotherapy to the NSCLC or ovarian cancer patient,
wherein the patient has been previously selected for chemotherapy by performance of the method of any one of clauses 1-9 on a blood-based sample of the patient and the sample was assigned the class label of late or the equivalent.

12. The method of clause 11, wherein the chemotherapy comprises platinum doublet chemotherapy.

13. The method of clause 11, wherein the cancer patient is a NSCLC patient, and wherein the chemotherapy comprises platinum doublet plus cetuximab.

Example 5

Laboratory Test Center and Computer Configured as Classifier

Once the classifier as described in conjunction with Examples 1, 2, 3, 9 (or the other Examples) has been developed, its parameters and reference set can now be stored and implemented in a general purpose computer and used to generate a class label for a blood-based sample, e.g., in accordance with the tests described in Examples 1, 2, 3 and 4. Depending on the particular clinical question being asked (and the type of patient the sample is obtained from), the class label can predict in advance whether a melanoma or other cancer patient is likely to benefit from immune checkpoint inhibitors such as antibodies blocking ligand activation of PD-1, such as nivolumab, or for example predict melanoma or other cancer patient benefit from antibodies blocking CTLA4, or if developed in accordance with Example 1, predict whether an ovarian or NSCLC cancer patient is likely to have better or worse overall survival on chemotherapy.

FIG. 15 is an illustration of a laboratory testing center or system for processing a test sample (in this example, a blood-based sample from a melanoma, ovarian or NSCLC patient) using a classifier generated in accordance with FIG. 8. The system includes a mass spectrometer 1506 and a general purpose computer 1510 having CPU 1512 implementing a classifier 1520 coded as machine-readable instructions and a memory 1514 storing reference mass spectral data set including a feature table 1522 of class-labeled mass spectrometry data. This reference mass spectral data set forming the feature table 1522 will be understood to be the mass spectral data (integrated intensity values of predefined features, see Appendix A or Appendix B), associated with a development sample set to create the classifier of FIG. 8 and Examples 1-4. This data set could be from all the samples, e.g., for the full-set classifier of Example 1 or a subset of the samples (e.g., development set of one half the samples) plus a set of mass spectral data from NSCLC patients used to develop the classifier of Example 2. It will be appreciated that the mass spectrometer 1506 and computer 1510 of FIG. 15 could be used to generate the classifier 1520 in accordance with the process of FIG. 8.

The operation of the system of FIG. 15 will be described in the context of conducting a predictive test for predicting patient benefit or non-benefit from antibodies blocking ligand activation of PD-1 as explained above. The following discussion assumes that the classifier 1520 is already generated at the time of use of the classifier to generate a class label (Early or Late, or the equivalent) for a test sample. The method of operation of FIG. 15 for the other tests (benefit from anti-CTLA4 drugs, overall survival prediction on chemotherapy in ovarian and NSCLC, etc.) is the same.

The system of FIG. 15 obtains a multitude of samples 1500, e.g., blood-based samples (serum or plasma) from diverse cancer (e.g., melanoma) patients and generates a class label for the sample as a fee-for-service. The samples 1500 are used by the classifier 1520 (implemented in the computer 1510) to make predictions as to whether the patient providing a particular sample is likely or not likely to benefit from immune checkpoint inhibitor therapy. The outcome of the test is a binary class label such as Early or Late or the like which is assigned to the patient blood-based sample. The particular moniker for the class label is not particularly important and could be generic such as "class 1", "class 2" or the like, but as noted earlier the class label is associated with some clinical attribute relevant to the question being answered by the classifier. As noted earlier, in the present context the Early class label is associated with a prediction of relatively poor overall survival, and the Late class label is associated with a prediction of relatively better (longer) overall survival on the immune checkpoint inhibitor.

The samples may be obtained on serum cards or the like in which the blood-based sample is blotted onto a cellulose or other type card. Aliquots of the sample are spotted onto one or several spots of a MALDI-TOF sample "plate" 1502 and the plate inserted into a MALDI-TOF mass spectrometer 1506. The mass spectrometer 1506 acquires mass spectra 1508 from each of the spots of the sample. The mass spectra are represented in digital form and supplied to a programmed general purpose computer 1510. The computer 1510 includes a central processing unit 1512 executing programmed instructions. The memory 1514 stores the data representing the mass spectra 1508. Ideally, the sample preparation, spotting and mass spectrometry steps are the same as those used to generate the classifier in accordance with FIG. 8 and Examples 1 and 2.

The memory 1514 also stores a data set representing classifier 1520, which includes a) a reference mass spectral data set 1522 in the form of a feature table of N class-labeled spectra, where N is some integer number, in this example a development sample set of spectra used to develop the classifier as explained above or some sub-set of the development sample set (e.g., DEV1 or DEV2 above in Example 1, or all of the 119 samples). The classifier 1520 includes b) code 1524 representing a kNN classification algorithm (which is implemented in the mini-classifiers as explained above), including the features and depth of the kNN algorithm (parameter s) and identification of all the mini-classifiers passing filtering, c) program code 1526 for executing the final classifier generated in accordance with FIG. 8 on the mass spectra of patients, including logistic regression weights and data representing master classifier(s) forming the final classifier, including probability cutoff parameter, mini-classifier parameters for each mini-classifier that passed filtering, etc., and d) a data structure 1528 for storing classification results, including a final class label for the test sample. The memory 1514 also stores program code 1530 for implementing the processing shown at 1550, including code (not shown) for acquiring the mass spectral data from the mass spectrometer in step 1552; a pre-processing routine 1532 for implementing the background subtraction, normalization and alignment step 1554 (details explained above), filtering and averaging of the 800 shot spectra at multiple locations per spot and over multiple MALDI spots to make a single 100,000+shot average spectrum (as explained above) a module (not shown) for calculating integrated intensity values at predefined m/z positions in the background subtracted, normalized and aligned spectrum (step 1556), and a code routine 1538 for implementing the final classifier 1520 using the reference dataset feature table 1522 on the values obtained at step 1556. The process 1558 produces a class label at step 1560. The module 1540 reports the class label as indicated at 1560 (i.e., "Early" or "Late" or the equivalent).

The program code 1530 can include additional and optional modules, for example a feature correction function code 1536 (described in U.S. patent application publication 2015/0102216) for correcting fluctuations in performance of the mass spectrometer, a set of routines for processing the spectrum from a reference sample to define a feature correction function, a module storing feature dependent noise characteristics and generating noisy feature value realizations and classifying such noisy feature value realizations, modules storing statistical algorithms for obtaining statistical data on the performance of the classifier on the noisy feature value realizations, or modules to combine class labels defined from multiple individual replicate testing of a sample to produce a single class label for that sample. Still other optional software modules could be included as will be apparent to persons skilled in the art.

The system of FIG. 15 can be implemented as a laboratory test processing center obtaining a multitude of patient samples from oncologists, patients, clinics, etc., and generating a class label for the patient samples as a fee-for-service. The mass spectrometer 1506 need not be physically located at the laboratory test center but rather the computer 1510 could obtain the data representing the mass spectra of the test sample over a computer network.

Example 6

Correlation of Protein Functional Groups with Classification Groups and Mass Spectral Features When building tests using the procedure of FIG. 8, it is not essential to be able to identify which proteins correspond to which mass spectral features in the MALDI TOF spectrum or to understand the function of proteins correlated with these features. Whether the process produces a useful classifier depends entirely on classifier performance on the development set and how well the classifier performs when classifying new sample sets. However, once a classifier has been developed it may be of interest to investigate the proteins or function of proteins which directly contribute to, or are correlated with, the mass spectral features used in the classifier. In addition, it may be informative to explore protein expression or function of proteins, measured by other platforms, that are correlated with the test classification groups.

Appendix K to our prior provisional application Ser. No. 62/289,587 sets forth the results of an analysis aimed at associating protein function with classification groups of the Example 1 and Example 2 classifiers and the mass spectral features measured in Deep MALDI spectra. In Appendix K, the nomenclature "IS2" corresponds to the full-set approach 1 classifier of Example 1, and "IS4" corresponds to the classifier of Example 2. A summary of the pertinent details of the methods we used and the results we found are set forth in this Example. The discoveries we made lead to new examples of how the classifiers of this disclosure can be characterized and generalization of the classifiers to other immune checkpoint inhibitors and other cancer indications beyond melanoma.

The data we used for the study include the feature table created during the application of the Example 1 full-set approach 1 classifier on a set of 49 serum samples ("Analysis Set") composed of patients with cancer and some donors without cancer. This is a table of feature values for each of the 59 features used in the Example 1 whole set approach 1 classifier (see Appendix B) and 292 other features (see Appendix A) not used in the Example 1 full-set approach 1 classifier. The feature values were obtained from MALDI-TOF mass spectra obtained using the fully specified spectral acquisition and spectral processing processes defined in the Example 1 description for each of the 49 samples. We also used the list of classifications (Early/Late) obtained for the 49 samples in the Analysis Set produced by the Example 1 full-set approach 1 classifier. We also used the list of classifications (Early/Late) obtained for the 49 samples in the Analysis Set produced by the Example 2 classifier. We also used a table of 1129 protein/peptide expression measurements obtained from running a SomaLogic 1129 protein/peptide panel on the Analysis Set.

We used a method known as Gene Set Enrichment Analysis (GSEA) applied to protein expression data. Background information on this method is set forth in Mootha, et al., *PGC-1α-responsive genes involved in oxidative phosphorylation are coordinately downregulated in human diabetes.* Nat Genet. 2003; 34(3):267-73 and Subramanian, et al., *Gene set enrichment analysis: A knowledge-based approach for interpreting genome-wide expression profiles.* Proc Natl Acad Sci USA 2005; 102(43): 15545-50, the content of which are incorporated by reference herein. Specific protein sets were created based on the intersection of the list of SomaLogic 1129 panel targets and results of queries from GeneOntology/AmiGO2 and UniProt databases.

The implementation of the GSEA method was performed using Matlab. Basically, in our method we evaluated the correlation r between individual proteins and group labels (Early and Late). Once these correlations had been calculated for each protein, we ranked the proteins by value of r from largest to smallest, with larger values of r indicating greater correlation, and a value of r=0 meaning no correlation was found. We then calculated an enrichment score (ES) (as explained in the Subramanian et al. paper above), which is designed to reflect the degree to which elements of a particular protein set are over-represented at the top or bottom of the ranked list of proteins. We considered two possible definitions for the enrichment score, the details of which are set forth at page 5 of Appendix K of our prior provisional application Ser. No. 62/289,587. We also calculated the corresponding p value for the proteins, in order to assess the significance of the deviation of the calculated enrichment score from its average value for a random distribution. We also calculated a running sum (RS), as part of the calculation of the enrichment score, the details of which are explained in Appendix K of our prior provisional application Ser. No. 62/289,587.

The results for the correlation of the protein sets with the Example 1 full-set approach 1 classifier class labels (Early or Late) of the 49 samples are shown in table 40.

TABLE 40

Results of GSEA applied to protein sets and Example 1 class labels of the Analysis Set

|  | Definition 1 of enrichment score | | Definition 2 of enrichment score | |
| --- | --- | --- | --- | --- |
|  | ES definition 1 | p value | ES definition 2 | p value |
| Acute inflammatory response | 0.424 | 0.02 | 0.480 | 0.03 |
| Activation of innate immune response | 0.412 | 0.55 | 0.518 | 0.56 |
| Regulation of adaptive immune response | −0.234 | 0.90 | 0.338 | 0.95 |
| Positive regulation of glycolytic process | −0.495 | 0.29 | 0.673 | 0.21 |
| Immune T-cells | −0.156 | 0.97 | 0.274 | 0.96 |
| Immune B-cells | 0.213 | 0.91 | 0.312 | 0.95 |
| Cell cycle regulation | −0.207 | 0.81 | 0.371 | 0.50 |
| Natural killer regulation | −0.406 | 0.39 | 0.429 | 0.68 |
| Complement system | 0.552 | 0.01 | 0.565 | 0.02 |
| Acute response | 0.539 | 0.10 | 0.700 | 0.02 |
| Cytokine activity | −0.231 | 0.68 | 0.342 | 0.74 |
| Wound healing | −0.373 | 0.11 | 0.476 | 0.11 |
| Interferon | −0.178 | 0.94 | 0.330 | 0.84 |
| Interleukin-10 | 0.190 | 0.77 | 0.332 | 0.64 |
| Growth factor receptor signaling | −0.221 | 0.45 | 0.309 | 0.84 |
| Immune Response Type 1 | −0.402 | 0.56 | 0.506 | 0.71 |
| Immune Response Type 2 | 0.511 | 0.48 | 0.552 | 0.84 |
| Acute phase | 0.572 | 0.01 | 0.693 | <0.01 |
| Hypoxia | −0.247 | 0.65 | 0.363 | 0.71 |
| Cancer | 0.153 | 0.96 | 0.298 | 0.80 |

There are correlations at the p<0.05 level of the class labels with the protein sets corresponding to the following biological processes: acute inflammatory response, acute phase, and complement system. Correlations with p values around 0.1 were found for the wound healing protein set. The correlation for the acute response has a p value of 0.02. We then used statistical methods (see Appendix K of our prior provisional application Ser. No. 62/289,587) for identifying subsets of proteins of the complement system, acute phase, acute response, and acute inflammatory response protein sets that are most important for these correlations, the results of which are shown in Tables 41A, 41B, 41C and 41D, respectively.

TABLE 41A

Proteins included in the extended leading edge set for complement (Amigo9).

| UniProtID | Protein Name | Correlation | P value |
| --- | --- | --- | --- |
| P01024 | Complement C3b | 0.626 | <0.01 |
| P02741 | C-reactive protein | 0.582 | <0.01 |
| P02748 | Complement C9 | 0.559 | <0.01 |
| P01024 | Complement C3a anaphylatoxin | 0.556 | <0.01 |
| P01024 | Complement C3 | 0.525 | <0.01 |
| P11226 | Mannose-binding protein C | 0.461 | <0.01 |
| P06681 | Complement C2 | 0.418 | 0.01 |
| P12956 | ATP-dependent DNA helicase II 70 kDa subunit | 0.412 | 0.01 |

TABLE 41A-continued

Proteins included in the extended leading edge set for complement (Amigo9).

| UniProtID | Protein Name | Correlation | P value |
|---|---|---|---|
| P01031 | Complement C5a | 0.394 | 0.02 |
| P02743 | Serum amyloid P | 0.391 | 0.02 |
| P07357 P07358 P07360 | Complement C8 | 0.377 | 0.03 |
| P01031 P13671 | Complement C5b,6 Complex | 0.350 | 0.04 |
| P01031 | Complement C5 | 0.337 | 0.05 |
| P00751 | Complement factor B | 0.323 | 0.05 |
| P01024 | Complement C3b, inactivated | 0.323 | 0.05 |
| P05155 | C1-Esterase Inhibitor | 0.313 | 0.06 |
| P00736 | Complement C1r | 0.310 | 0.07 |
| P13671 | Complement C6 | 0.310 | 0.07 |
| P48740 | Mannan-binding lectin serine peptidase 1 | 0.283 | 0.09 |
| P16109 | P-Selectin | −0.475*† | <0.01 |
| Q6YHK3 | CD109 | −0.364† | 0.03 |

*indicates proteins to the right of the minimum of RS and †indicates proteins with anti-correlations of at least as great magnitude as that at the maximum of RS.

TABLE 41B

Proteins included in the extended leading edge set for acute phase (UniProt1).

| UniProtID | Protein Name | Correlation | P value |
|---|---|---|---|
| P01009 | alpha1-Antitrypsin | 0.801 | <0.01 |
| P0DJI8 | Serum amyloid A | 0.704 | <0.01 |
| P18428 | Lipopolysaccharide-binding protein | 0.640 | <0.01 |
| Q14624 | Inter-alpha-trypsin inhibitor heavy chain H4 | 0.603 | <0.01 |
| P02741 | C-reactive protein | 0.582 | <0.01 |
| P02671 P02675 P02679 | D-dimer | 0.529 | <0.01 |
| P11226 | Mannose-binding protein C | 0.461 | <0.01 |
| P00738 | Haptoglobin | 0.455 | <0.01 |
| P02743 | Serum amyloid P | 0.391 | 0.02 |
| P02765 | alpha2-HS-Glycoprotein | −0.593*† | <0.01 |
| P02787 | Transferrin | −0.502*† | <0.01 |
| P08697 | alpha2-Antiplasmin | −0.347*† | 0.04 |
| P08887 | Interleukin-6 receptor alpha chain | −0.347*† | 0.04 |

*indicates proteins to the right of the minimum of RS and †indicates proteins with anti-correlations of at least as great magnitude as that at the maximum of RS.

TABLE 41C

Proteins included in the extended leading edge set for acute response (Amigo11).

| UniProtID | Protein Name | Correlation | P value |
|---|---|---|---|
| P18428 | Lipopolysaccharide-binding protein | 0.640 | <0.01 |
| Q14624 | Inter-alpha-trypsin inhibitor heavy chain H4 | 0.603 | <0.01 |
| P05155 | C1-Esterase Inhibitor | 0.313 | 0.06 |
| P13726 | Tissue Factor | 0.306 | 0.07 |
| P48740 | Mannan-binding lectin serine peptidase 1 | 0.283 | 0.09 |
| P05231 | Interleukin-6 | 0.266 | 0.11 |
| P02765 | alpha2-HS-Glycoprotein | −0.593*† | <0.01 |

*indicates proteins to the right of the minimum of RS and †indicates proteins with anti-correlations of at least as great magnitude as that at the maximum of RS.

TABLE 41D

Proteins included in the extended leading edge set for acute inflammatory response (Amigo1).

| UniProtID | Protein Name | Correlation | P value |
|---|---|---|---|
| P01009 | alpha1-Antitrypsin | 0.801 | <0.01 |
| Q14624 | Inter-alpha-trypsin inhibitor heavy chain H4 | 0.603 | <0.01 |
| P02741 | C-reactive protein | 0.582 | <0.01 |
| P01024 | Complement C3a anaphylatoxin | 0.556 | <0.01 |
| P01024 | Complement C3 | 0.525 | <0.01 |
| P10600 | Transforming growth factor beta-3 | 0.498 | <0.01 |
| Q00535 Q15078 | Cyclin-dependent kinase 5: activator p35 complex | 0.492 | <0.01 |
| P07951 | Tropomyosin beta chain | 0.478 | <0.01 |
| P02679 | Fibrinogen gamma chain dimer | 0.475 | <0.01 |
| P11226 | Mannose-binding protein C | 0.461 | <0.01 |
| P00738 | Haptoglobin | 0.455 | <0.01 |
| P12956 | ATP-dependent DNA helicase II 70 kDa subunit | 0.412 | 0.01 |
| P02743 | Serum amyloid P | 0.391 | 0.02 |
| P07357 P07358 P07360 | Complement C8 | 0.377 | 0.03 |
| P06744 | Glucose phosphate isomerase | 0.364 | 0.03 |
| P06400 | Retinoblastoma 1 | 0.340 | 0.04 |
| P01031 | Complement C5 | 0.337 | 0.05 |
| P08107 | Hsp70 | 0.306 | 0.07 |
| Q9Y5S2 | Myotonic dystrophy protein kinase-like beta | 0.290 | 0.09 |
| Q8NEV9 Q14213 | Interleukin-27 | 0.290 | 0.09 |
| P05231 | Interleukin-6 | 0.266 | 0.11 |
| P01019 | Angiotensinogen | 0.263 | 0.12 |
| P02765 | alpha2-HS-Glycoprotein | −0.593*† | <0.01 |
| O00626 | Macrophage-derived chemokine | −0.535*† | <0.01 |
| P02649 | Apolipoprotein E | −0.421† | 0.01 |
| P08697 | alpha2-Antiplasmin | −0.347† | 0.04 |
| P08887 | Interleukin-6 receptor alpha chain | −0.347† | 0.04 |
| P08514 P05106 | Integrin alpha-IIb: beta-3 complex | −0.303† | 0.07 |
| Q9BZR6 | Nogo Receptor/reticulon 4 receptor | −0.300† | 0.08 |
| P00747 | Angiostatin | −0.276† | 0.10 |

*indicates proteins to the right of the minimum of RS and †indicates proteins with anti-correlations of at least as great magnitude as that at the maximum of RS.

We further investigated the interaction of the processes related to the ontologies common to the groups of proteins we identified from RS plots. We found that the processes are related to the complement activation, activation and regulation of the immune system, as well as innate immune response and inflammatory response. Charts showing these relationships are found in Appendix K of our prior provisional application Ser. No. 62/289,587. Appendix K, FIG. 8 also shows "heat maps" (i.e., plots of p values generated by GSEA analysis associating mass spectral features with protein expression values for all the m/z features used by the classifier of Example 1, Appendix B), which demonstrate the results of the correlation of the protein sets with the mass spectral features used for the Example 1 full-set approach 1 classifier. See also FIGS. 45A and 45B and the discussion thereof later in this document. We discovered that many of the mass spectral features used in the Example 1 classifier are related to the following biological processes: (1) acute phase, (2) acute response, (3) complement system, and (4) acute inflammatory response. Very few of the mass spectral features used are associated with the specific immune-related protein functions we investigated (i.e., "activation of innate immune response", "regulation of adaptive immune response", "immune T-cells", "immune B-cells", "interferon", "interleukin-10"). These relationships are demonstrated by the heat maps of FIG. 8 of Appendix K of our prior provisional application Ser. No. 62/289,587, with darker areas associated with lower p values and thus higher correlation between protein and class label. FIG. 8 shows the heat maps for two different definitions of the enrichment score, but the plots are similar. See also FIGS. 45A and 45B of this document and the associated discussion below.

We performed the same analysis of the correlation between the protein sets with the class labels produced by the classifier of Example 2. The results are shown in Table 42. Note that the proteins associated with the following biological processes are strongly correlated with the class labels: acute inflammatory response, complement system, acute response and acute phase. In addition, proteins associated with Immune Response Type 2 were also strongly correlated with the class labels.

TABLE 42

Results of GSEA applied to protein sets and Example 2 class labels of the Analysis Set

| | Definition 1 | | Definition 2 | |
| --- | --- | --- | --- | --- |
| | ES definition 1 | p value | ES definition 2 | p value |
| Acute inflammatory response | 0.451 | <0.01 | 0.487 | 0.03 |
| Activation of innate immune response | 0.511 | 0.33 | 0.511 | 0.58 |
| Regulation of adaptive immune response | 0.173 | 0.99 | 0.332 | 0.96 |
| Positive regulation of glycolytic process | −0.328 | 0.80 | 0.446 | 0.91 |
| Immune T-cells | −0.181 | 0.91 | 0.323 | 0.81 |
| Immune B-cells | 0.404 | 0.22 | 0.418 | 0.65 |
| Cell cycle regulation | −0.178 | 0.95 | 0.338 | 0.75 |
| Natural killer regulation | −0.241 | 0.87 | 0.255 | 0.10 |
| Complement system | 0.629 | <0.01 | 0.633 | <0.01 |
| Acute response | 0.535 | 0.12 | 0.688 | 0.03 |
| Cytokine activity | −0.224 | 0.71 | 0.401 | 0.35 |
| Wound healing | −0.324 | 0.23 | 0.499 | 0.06 |
| Interferon | 0.201 | 0.86 | 0.319 | 0.88 |
| Interleukin-10 | 0.306 | 0.05 | 0.369 | 0.31 |
| Growth factor receptor signaling | −0.199 | 0.66 | 0.345 | 0.55 |
| Immune Response Type 1 | −0.227 | 0.98 | 0.386 | 0.97 |
| Immune Response Type 2 | 0.852 | <0.01 | 0.871 | 0.04 |
| Acute phase | 0.659 | <0.01 | 0.752 | <0.01 |
| Hypoxia | 0.242 | 0.68 | 0.408 | 0.45 |
| Cancer | 0.154 | 0.95 | 0.273 | 0.96 |

There are correlations at the $p<0.05$ level of the class labels with the protein sets corresponding to acute inflammatory response, acute response, acute phase, complement system, interleukin-10 (with ES definition 1), and immune response type 2. Correlations with p values below 0.1 were also found for the wound healing protein set.

We further identified proteins from the complement system, acute phase, acute response, acute inflammatory response, and interleukin-10, and immune response type 2 processes important for the Example 2 classifier. The results are listed in Tables 11A-11F of Appendix K of our prior provisional application Ser. No. 62/289,587. Many of the proteins listed in Tables 11A-11D are found in the Tables 41A-41D. We also calculated the correlations of the protein sets with the mass spectral features used in Example 2 classifier and produced heat maps, see FIGS. 10 and 11 of Appendix K of our prior provisional application Ser. No. 62/289,587. Many mass spectral features used in the Example 2 classification are related to the complement system and acute inflammation/acute phase reaction. However, these biological processes are somewhat less dominant as compared to the mass spectral features used in the Example 1 full-set approach 1 classifier. Table 12 of Appendix K of our prior provisional application Ser. No. 62/289, 587 shows the number of mass spectral features (out of the 351 listed in Appendix A) which are associated with the protein sets at various significance levels (p values). In general, there are more mass spectral features associated with the proteins of the acute inflammation, complement system, acute response, acute phase, immune response type 2, and wound healing processes as compared to other processes.

The above discussion, and the report of Appendix K of our prior provisional application Ser. No. 62/289,587, demonstrates that the combination of Deep MALDI measurements with simple modifications of GSEA shows promise for extracting useful information on the biological functions related to our test labels of this disclosure. It also allows us to gain insight into the functions related to the mass spectral features (Deep MALDI peaks) that we measure from serum samples.

The protein functions associated with the mass spectral features used in the Example 1 full-set approach 1 classifier were consistent with the protein functions associated with the class labels, namely acute phase reactants and the complement system. These functions are also consistent with the functions of the available protein IDs of the features used in the same Example 1 classifier (Table 17, Example 1). Other plausible biological functions did not show any significant association with the class labels. This does not imply that these other functions are not relevant for the biology of immunotherapies; it just means that we have no evidence that they play a major role in the classifications produced by the full-set approach 1 classifier of Example 1. However, although we measured features (proteins) related to most of these other functions, they were not used in our tests, and the test classifications were not significantly associated with these protein functions.

In the case of the Example 2 classifier, we saw that the strength of association of classification with acute phase and complement functions increased quite significantly compared with Example 1, which may be an indication that the classifier of Example 2 is a "cleaner" test, less confounded by prognostic effects. We also observed that IL-10 related functions are associated with the Example 2 class groups at the $p=0.05$ significance level.

There are limitations with these data caused mainly by the limited size of the Analysis Set of samples, resulting in fairly wide null distributions, and hence limited statistical power. The simplest way to improve on this would be to have paired Deep MALDI/Somalogic data on more samples. This would also allow us to have an independent validation of these present results. While the number of proteins in the Somalogic panel is rather large, one could also consider using additional or extended panels.

Due to computer resource limitations we did not perform a false discovery rate analysis wrapped around the protein sets. Such an analysis would also require further theoretical work to assess the applicability of, and possibly work to improve on, the suggested set normalizations in the Subramanian paper. While this should in principle be done, the observed effects, especially for some of the mass spectral features, are so clear and large that we do not expect any substantial qualitative changes to the main conclusions of this analysis.

Because it is well-known that many proteins in circulation are related to acute phase reactants and the complement system, it may be not surprising that these two functions appear associated with many of the mass spectral features we measure with Deep MALDI. However, we did see other significant correlations, especially in the case of the Example 2 classifier, indicating that our results are not a trivial reflection of abundance of circulating proteins. In addition, within the subset of features used in the full-set approach 1 Example 1 classifier (see Appendix B), the proportion of features associated with acute phase and the complement system was substantially higher than that observed in the whole set of 351 Deep MALDI features listed in Appendix A.

The above discoveries can be used to build a classifier used in guiding immune checkpoint inhibitor treatment for a cancer patient. In particular, such a classifier includes a memory storing a reference set of class-labelled mass spectral data obtained from blood-based samples of melanoma patients treated with an immune checkpoint inhibitor agent. The mass spectral data is in the form of feature values for a multitude of mass spectral features, wherein the mass spectral features are identified with proteins circulating in serum associated with at least the following biological processes: (1) acute phase, (2) acute response, (3) complement system, and (4) acute inflammatory response. See the above discussion and the heat maps of FIGS. 8, 10 and 11 of Appendix K of our prior provisional application Ser. No. 62/289,587. The classifier further includes a programmed computer (see FIG. 15) implementing a classification algorithm on a set of mass spectral data including feature values for the multitude of mass spectral features obtained from a test blood-based sample and the reference set and generating a class label for the test blood-based sample. Alternatively, the mass spectral features may further include features associated with immune response type 2 and interleukin-10 processes. In one embodiment, the features include the features listed in Appendix A, Appendix B or Appendix C.

Furthermore, application of GSEA methods to the data obtained using the SomaLogic panel in combination with the results of full-set approach 1 classifier of Example 1 and further analysis allowed us to correlate up- and down-regulation of proteins with Early and Late classifications. In particular, proteins in Tables 41 A-D with positive correlation coefficient, are correlated with up-regulation in samples classified as Early.

Further analysis of the running sum of the Complement protein set allowed identifying proteins that have the biggest impact on the correlation of the corresponding proteins sets with the classification results (Table 5, Appendix K of our prior provisional application Ser. No. 62/289,587). Table 43 below lists proteins which have P-value for correlation with classification labels ≤0.05 and are included in Group1 (leading edge) of the Complement protein set.

TABLE 43

Proteins associated with gene ontology "Complement system" and correlated with full-set approach 1 classifier of Example 1.

| UniProt ID | Full Name | Correlated Expression in the "Early" group |
|---|---|---|
| P02741 | C-reactive protein | Up |
| P00736 | Complement C1r | Up |
| P01024 | Complement C3 | Up |
| P01024 | Complement C3a anaphylatoxin | Up |
| P01024 | Complement C3b | Up |
| P01031 | Complement C5 | Up |
| P01031 | Complement C5a | Up |
| P01031 | Complement C5b,6 Complex | Up |
| P07357 | Complement C8 | Up |

TABLE 43-continued

Proteins associated with gene ontology "Complement system" and correlated with full-set approach 1 classifier of Example 1.

| UniProt ID | Full Name | Correlated Expression in the "Early" group |
|---|---|---|
| P02748 | Complement C9 | Up |
| P00751 | Complement factor B | Up |
| P01024 | Complement C3b, inactivated | Up |
| P16109 | P-Selectin | Down |
| P02743 | Serum amyloid P | Up |
| P06681 | Complement C2 | Up |
| P12956 | ATP-dependent DNA helicase II 70 kDa subunit | Up |
| P11226 | Mannose-binding protein C | Up |
| Q6YHK3 | CD109 | Down |

One can see that the group classified as Early is characterized by up-regulation of most of the components of the complement system, which raises the question of possible biological relationship between this up-regulation and unfavorable prognosis of patients classified as Early, as well as their little benefit from PD-1 inhibitors and, possibly, other types of immunotherapy.

A growing body of evidence suggests a complex role for the complement system in tumorigenesis, which, depending on an intricate balance of multiple factors, can be pro- or anti-tumor. Neoplastic transformation is accompanied by an increased capacity to activate complement. Pio, R., Corrales, L. & Lambris, J. D. *The role of complement in tumor growth.* Adv Exp Med Biol 772, 229-62 (2014). Activated complement proteins have been shown to inhibit tumor growth by promoting complement-dependent cytotoxicity (Janelle, V. & Lamarre, A. *Role of the complement system in NK cell-mediated antitumor T-cell responses.* Oncoimmunology 3, e27897 (2014)) and inhibition of Treg function. Mathern, D. R. & Heeger, P. S. *Molecules Great and Small: The Complement System.* Clin J Am Soc Nephrol 10, 1636-50 (2015).

On the other hand, recent data have demonstrated that activated complement proteins, interacting with the components of the innate and adaptive immune systems, can promote carcinogenesis. For example, in mouse models of melanoma it was shown that "decomplementation" led to a robust antitumor CD8+ response and improved cytotoxic activity of NK cells, while activated complement system resulted in limited accumulation of tumor-specific cytotoxic T cells (CTLs), and, at the same time, promoted tumor infiltration with immunosuppressive myeloid-derived suppressor cells (MDSc), which suppress NK- and T-cell functions. Janelle, V. et al. *Transient complement inhibition promotes a tumor-specific immune response through the implication of natural killer cells.* Cancer Immunol Res 2, 200-6 (2014). Similarly, complement activation and C5a signaling were shown to be associated with recruitment of MDSCs into tumors, suppression of effector CD8+ and CD4+ T cells, generation of regulatory T cells (Tregs), Th2 predominant immune responses, and facilitation of lung and liver metastasis in models of breast and cervical cancer. Markiewski, M. M. et al. *Modulation of the antitumor immune response by complement.* Nat Immunol 9, 1225-35 (2008); Vadrevu, S. K. et al. *Complement c5a receptor facilitates cancer metastasis by altering T-cell responses in the metastatic niche.* Cancer Res 74, 3454-65 (2014). C5a was shown to promote differentiation of Tregs, causing inhibition on antitumor activity. Gunn, L. et al. *Opposing roles for complement component C5a in tumor progression*

*and the tumor microenvironment.* J Immunol 189, 2985-94 (2012). Complement can assist the escape of tumor cells from immunosurveillance, support chronic inflammation, promote angiogenesis, activate mitogenic signaling pathways, sustain cell proliferation and insensitivity to apoptosis, and participate in tumor invasion and migration. Pio et al., supra. In lung cancer models, blockade of C5a signaling led to the inhibition of key immunosuppressive molecules within the tumor. These molecules included IL-10, IL-6, CTLA4, LAF3, and PDL18.

The latter findings have direct implications for the activity of the immune checkpoint inhibitors in cancer patients, and, consequently, for the role of our Example 1 and Example 2 classifiers. In particular, the observed upregulation of the complement system proteins in the group classified as Early may indicate that these patients have higher levels of immunosuppression, and/or higher levels of pro-tumor inflammation, related to the activation of the corresponding immune checkpoints, and as a result are less responsive to such drugs as nivolumab, ipilimumab, pembrolizumab, or other agents targeting these pathways. Interestingly, it has been shown that the complement protein C5a promotes the expression of the PD-1 ligands, PD-L1 and PD-L2. Zhang, J. Immunol. 2009; 182: 5123-5130. In this scenario one could envision that excessive complement upregulation might compete with efforts to inhibit PD-1. On the other hand, the results of recent clinical trials suggest that patients with tumor microenvironment characterized by high expression of PDL1 and presence of Tregs are more likely to respond to anti-PD-1, anti-CTLA4, or high dose IL-2 therapy. Though we do not know how exactly upregulation of the complement system is correlated with Example 1 and Example 2 classifications, this connection is in line with the biological effects discussed above.

Consequently, we can expect that Example 1 and Example 2 classifiers may be relevant for the broad variety of drugs affecting the immunological status of the patient, such as various immune checkpoint inhibitors, high dose IL-2, vaccines, and/or combinational therapy. Furthermore, since effects that are measured in serum reflect the organism status as a whole, and the complement system affects innate and adaptive immunity on the global level, not just in a tumor site, the classifiers are expected to have similar performance in different indications in cancer (e.g., lung, renal carcinoma), and are not restricted to melanoma.

Another large gene ontology protein set correlated with Example 1 and Example 2 Early and Late classifications is "Acute inflammatory response". Proteins correlated with these classification groups from this set ($p \leq 0.05$) are presented in Table 44.

TABLE 44

Proteins associated with gene ontology "Acute Inflammatory response" and correlated with full set approach 1 Example 1 classification.

| UniProtID | Protein Name | Correlated Expression in the "Early" group |
| --- | --- | --- |
| P01009 | alpha1-Antitrypsin | Up |
| Q14624 | Inter-alpha-trypsin inhibitor heavy chain H4 | Up |
| P02741 | C-reactive protein | Up |
| P01024 | Complement C3a anaphylatoxin | Up |
| P01024 | Complement C3 | Up |
| P10600 | Transforming growth factor beta-3 | Up |
| Q0053, Q15078 | Cyclin-dependent kinase 5: activator p35 complex | Up |

TABLE 44-continued

Proteins associated with gene ontology "Acute Inflammatory response" and correlated with full set approach 1 Example 1 classification.

| UniProtID | Protein Name | Correlated Expression in the "Early" group |
| --- | --- | --- |
| P07951 | Tropomyosin beta chain | Up |
| P02679 | Fibrinogen gamma chain dimer | Up |
| P11226 | Mannose-binding protein C | Up |
| P00738 | Haptoglobin | Up |
| P12956 | ATP-dependent DNA helicase II 70 kDa subunit | Up |
| P02743 | Serum amyloid P | Up |
| P07357, P07358, P07360, P06744 | Complement C8 | Up |
| | Glucose phosphate isomerase | Up |
| P06400 | Retinoblastoma 1 | Up |
| P01031 | Complement C5 | Up |
| P01019 | Angiotensinogen | Down |
| P02765 | alpha2-HS-Glycoprotein | Down |
| O00626 | Macrophage-derived chemokine | Down |
| P02649 | Apolipoprotein E | Down |
| P08697 | alpha2-Antiplasmin | Down |
| P08887 | Interleukin-6 receptor alpha chain | Down |

It is generally accepted that cancer triggers an intrinsic inflammatory response that creates a pro-tumorigenic microenvironment (Mantovani, A., Allavena, P., Sica, A. & Balkwill, F. *Cancer-related inflammation.* Nature 454, 436-44 (2008)); "smouldering" inflammation is associated with most, if not all, tumors and supports their progression. Porta, C. et al. *Cellular and molecular pathways linking inflammation and cancer.* Immunobiology 214, 761-77 (2009). Inflammation is intrinsically associated with the complement system, and complement system promotes tumor growth in the context of inflammation. Hence, it seems logical that both systems came out as significantly correlated with Example 1 and Example 2 classifications.

Tumor associated inflammatory response can be initiated and/or modulated by cancer therapy. On one hand, it can have tumor-promoting functions, but on the other hand it can enhance presentation of tumor-antigens and subsequent induction of anti-tumor immune response. Grivennikov, S. I., Greten, F. R. & Karin, M. *Immunity, inflammation, and cancer.* Cell 140, 883-99 (2010). While a T-cell inflamed microenvironment, characterized by recruiting of CD8+ and CD4+ lymphocytes to the tumor, is considered a necessary condition for effective immunotherapeutic treatment, activation of the elements of the acute inflammatory pathway is likely correlated with the negative prognosis. The exact mechanisms of action remain poorly understood, but our data on upregulation of this system in the Early group seem to be consistent with the existing clinical data.

Figure 8B:
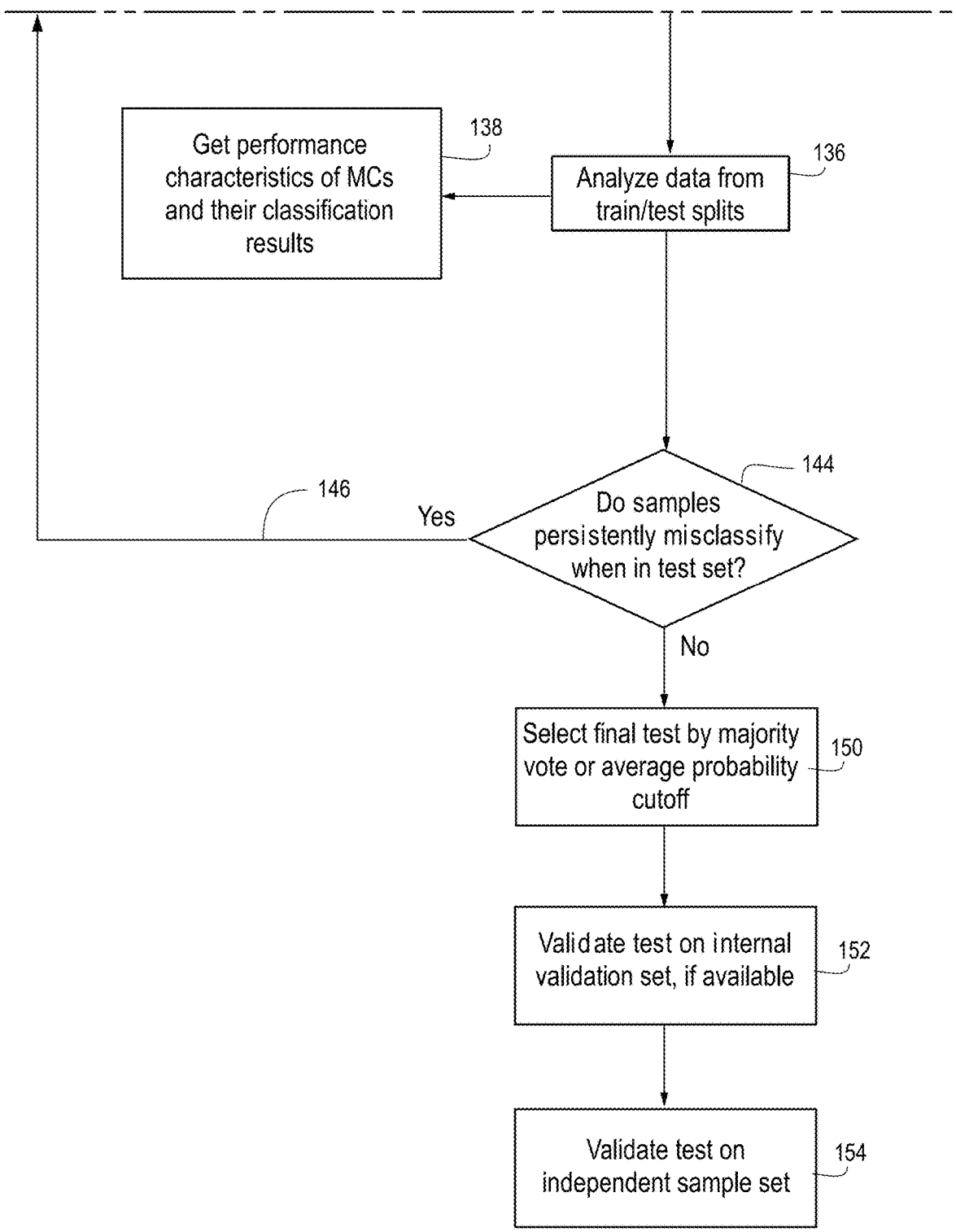
Figure 9A:
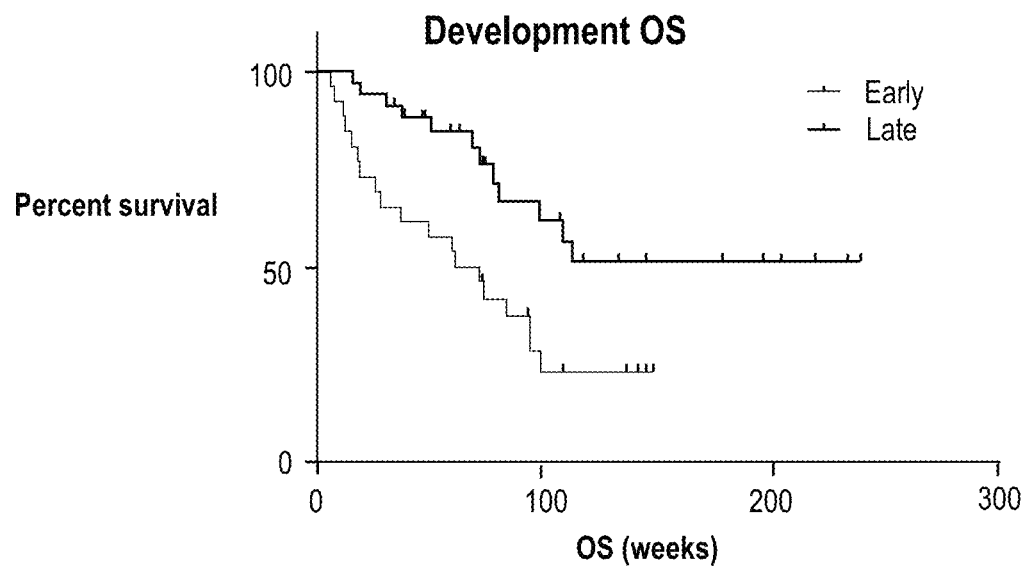
FIGS. 9A and 9B show Kaplan-Meier plots for OS and TTP, respectively, by Early and Late classification groups for "approach 1" (see table 10) for the development set
Figure 9B:
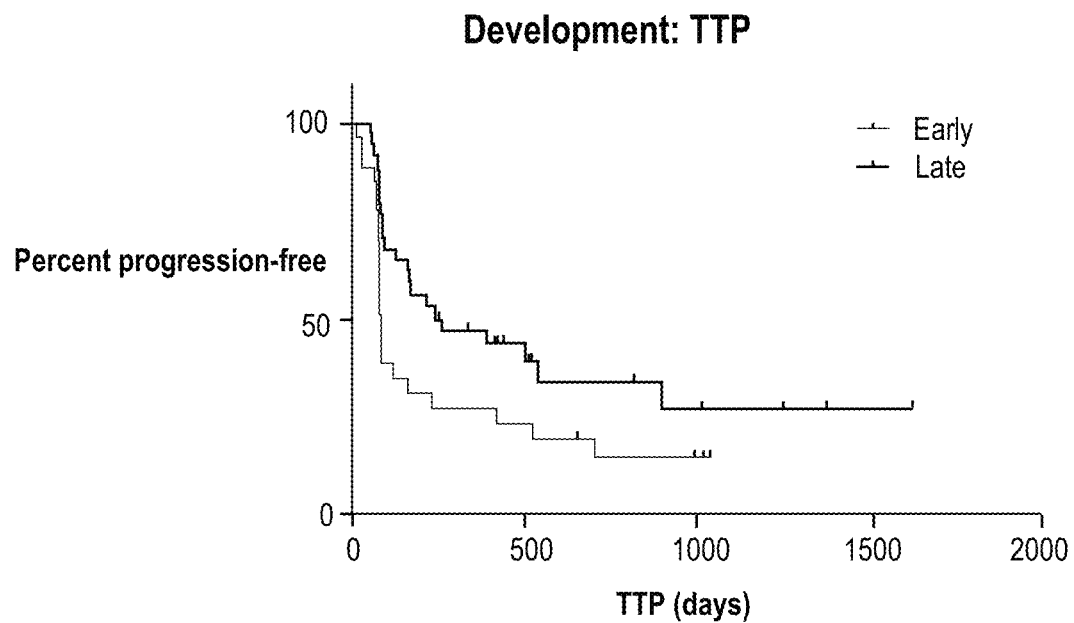
Figure 9C:
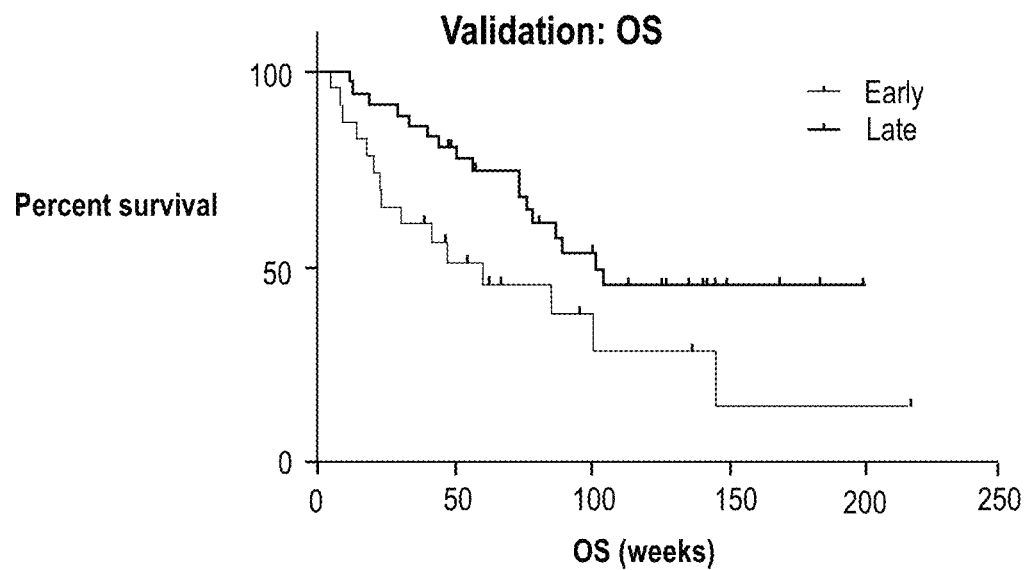
FIGS. 9C and 9D show the Kaplan-Meier plots for OS and TTP, respectively, by Early and Late classification groups for approach 1 (see table 10) for the validation set.
Figure 9D:
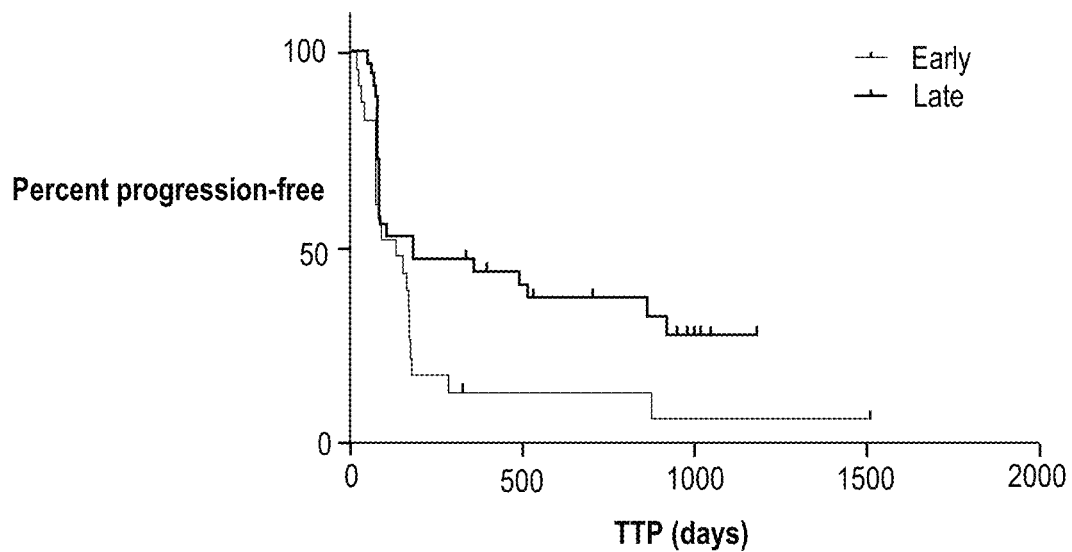
Figure 10A:
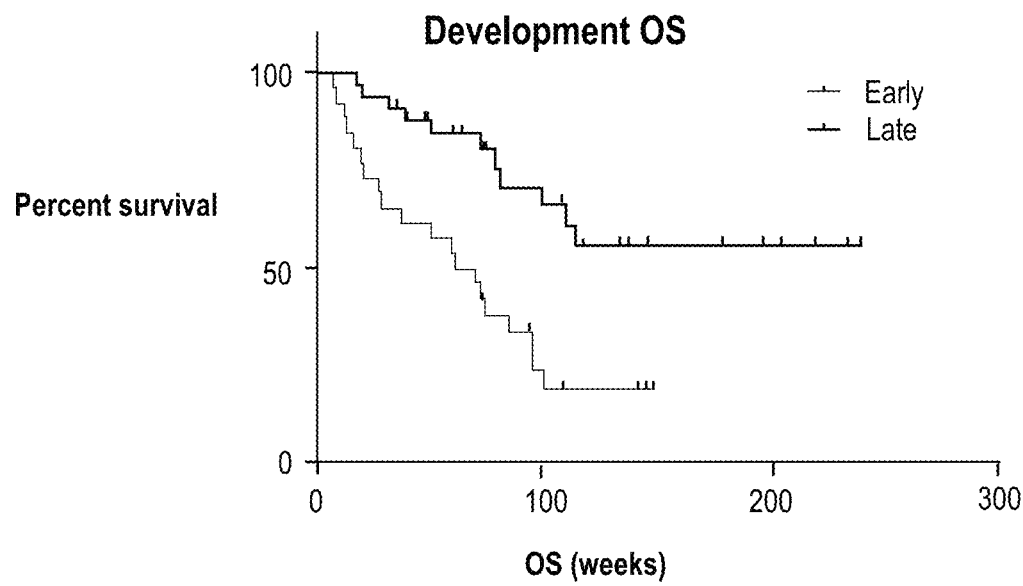
FIGS. 10A and 10B show Kaplan-Meier plots for OS and TTP, respectively, by Early and Late classification groups for "approach 2" (see table 10) for the development set.
Figure 10B:
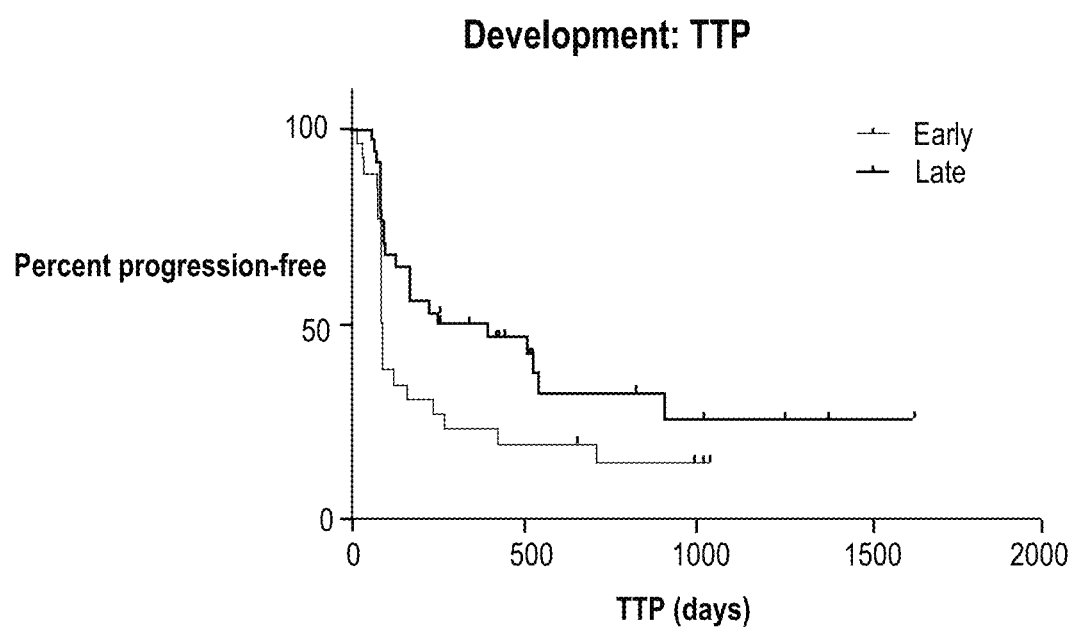
Figure 10C:
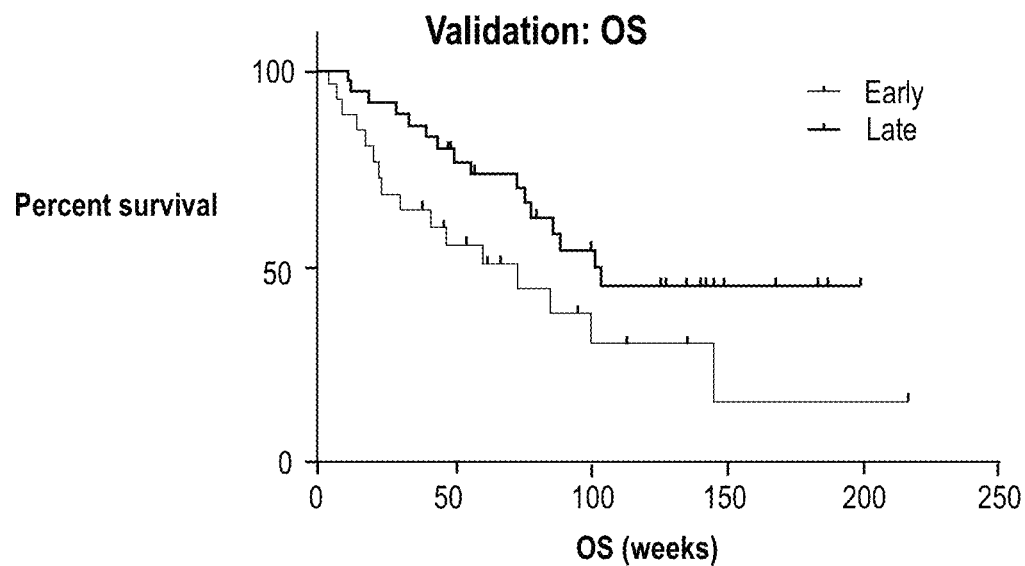
FIGS. 10C and 10D show the Kaplan-Meier plots for OS and TTP, respectively, by Early and Late classification groups for approach 2 (see table 10) for the validation set.
Figure 10D:
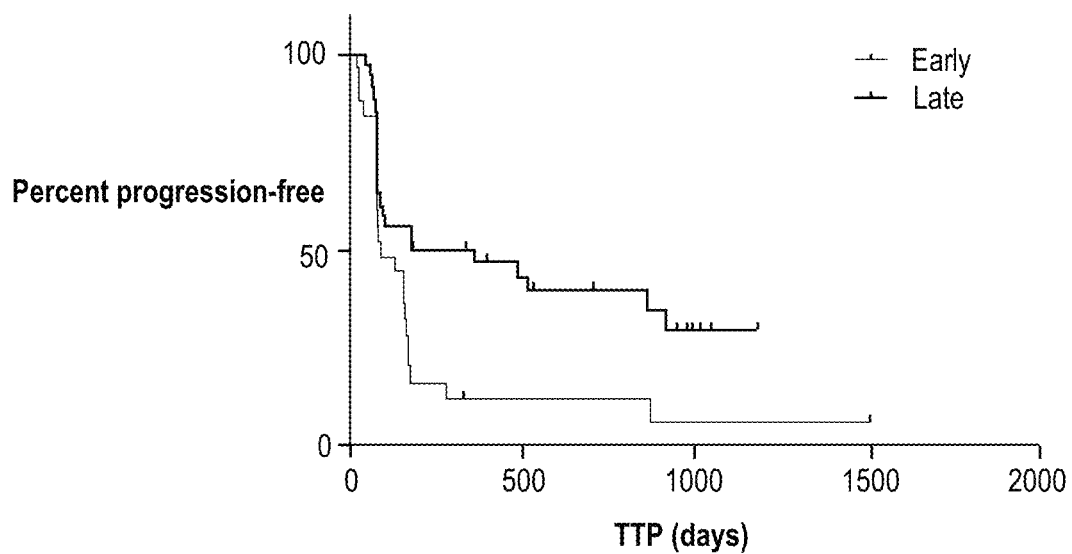
Figure 11A:
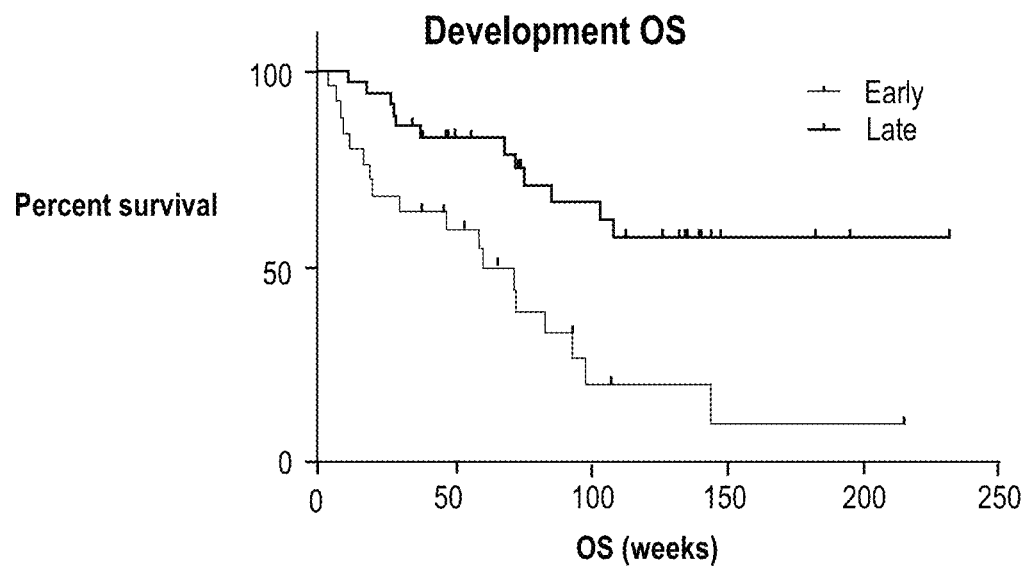
FIGS. 11A and 11B show Kaplan-Meier plots for OS and TTP, respectively, by Early and Late classification groups for "approach 3" (see table 10) for the development set
Figure 11B:
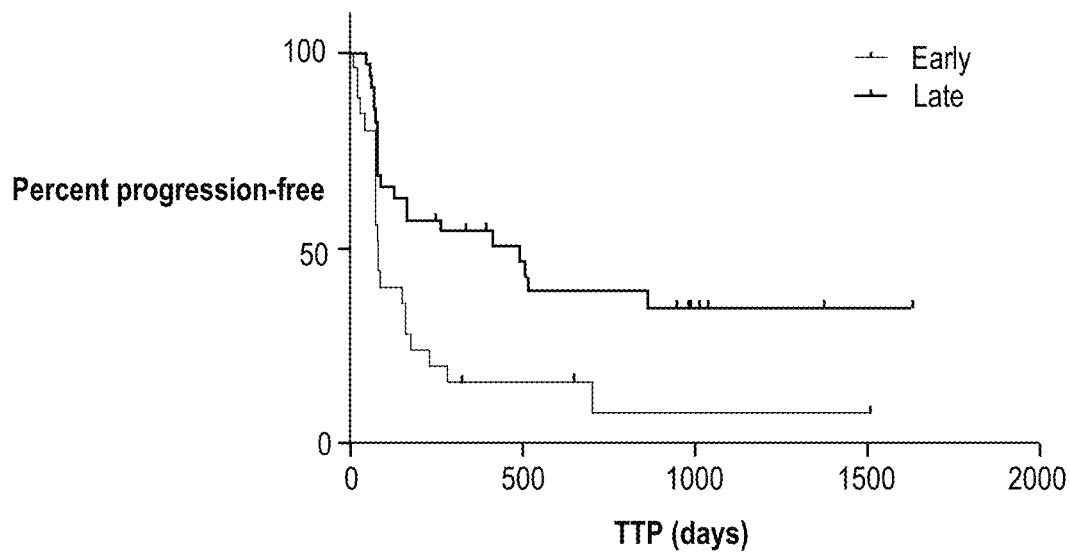
Figure 11C:
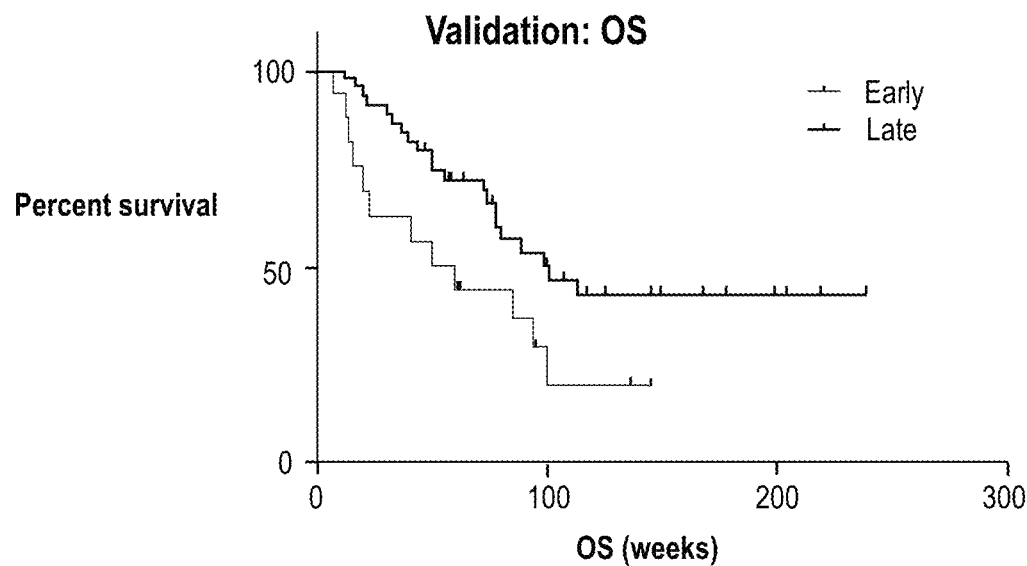
FIGS. 11C and 11D show Kaplan-Meier plots for OS and TTP, respectively, by Early and Late classification groups for approach 3 (see table 10) for the validation set.
Figure 11D:
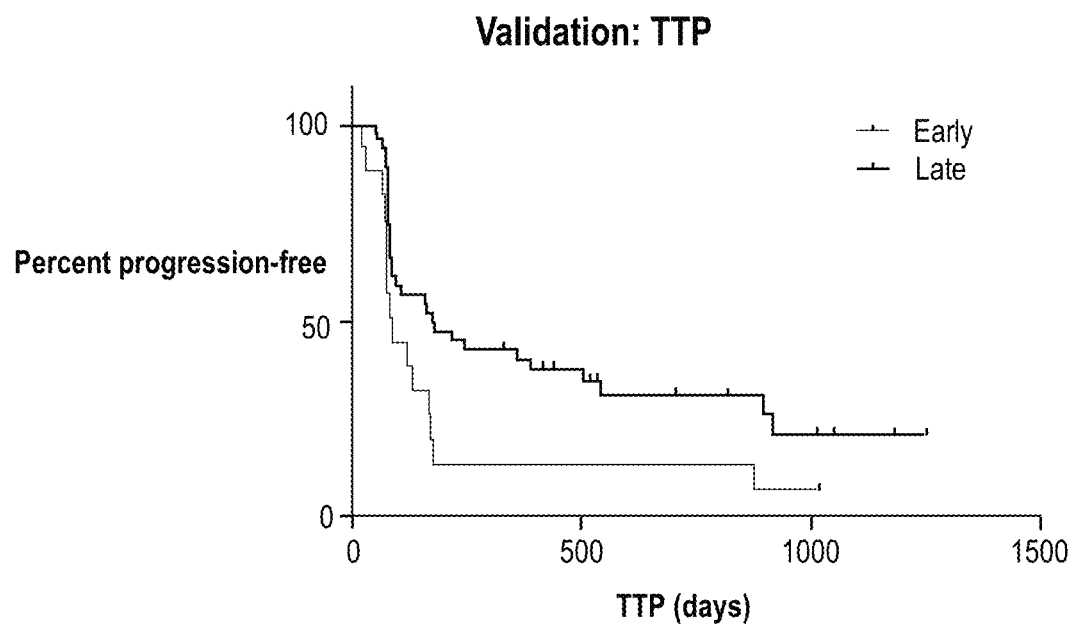
Figure 12A:
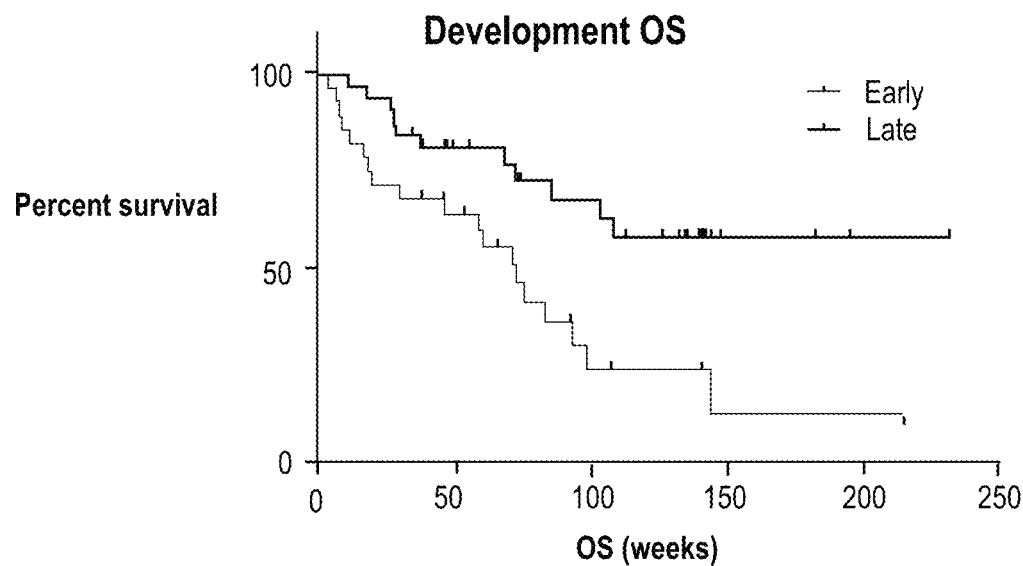
FIGS. 12A and 12B show Kaplan-Meier plots for OS and TTP by Early and Late classification groups for "approach 4" (see table 10) for the development set.
Figure 12B:
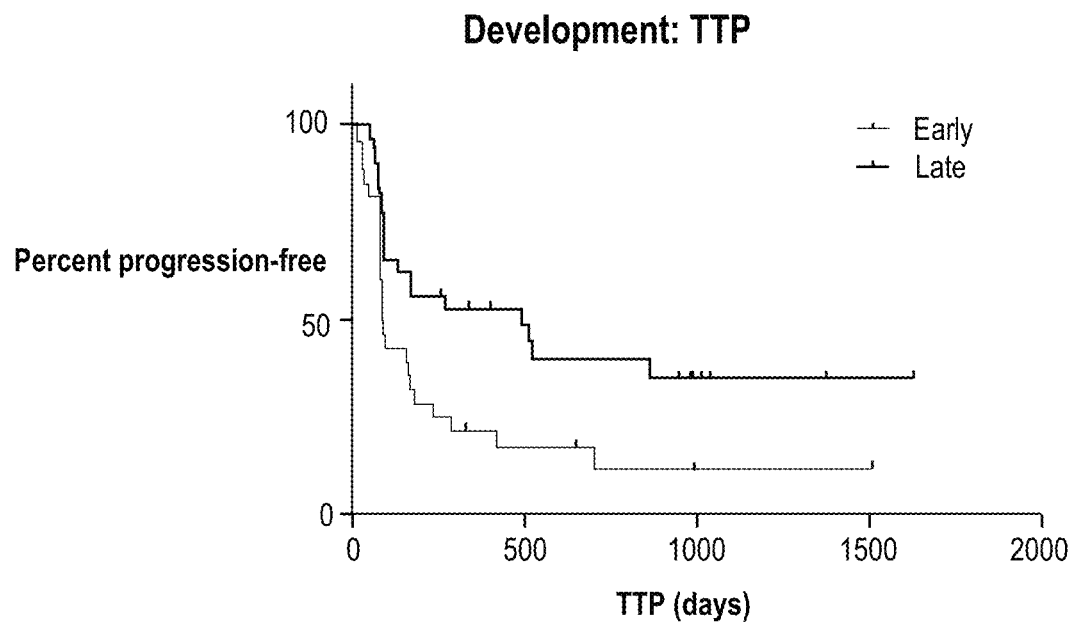
Figure 12C:
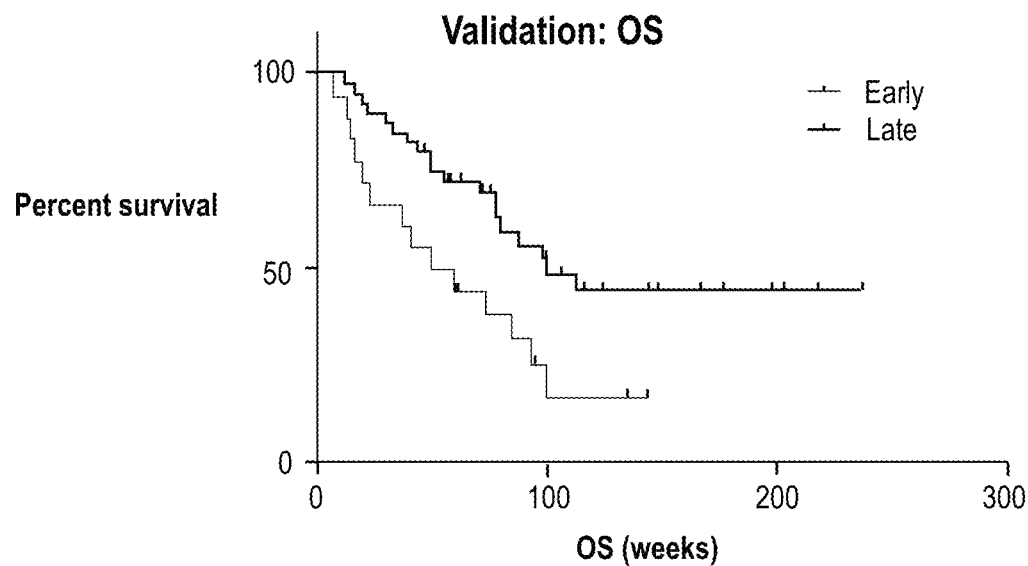
FIGS. 12C and 12D show the Kaplan-Meier plots for OS and TTP by Early and Late classification groups for approach 4 (see table 10) for the validation set.
Figure 12D:
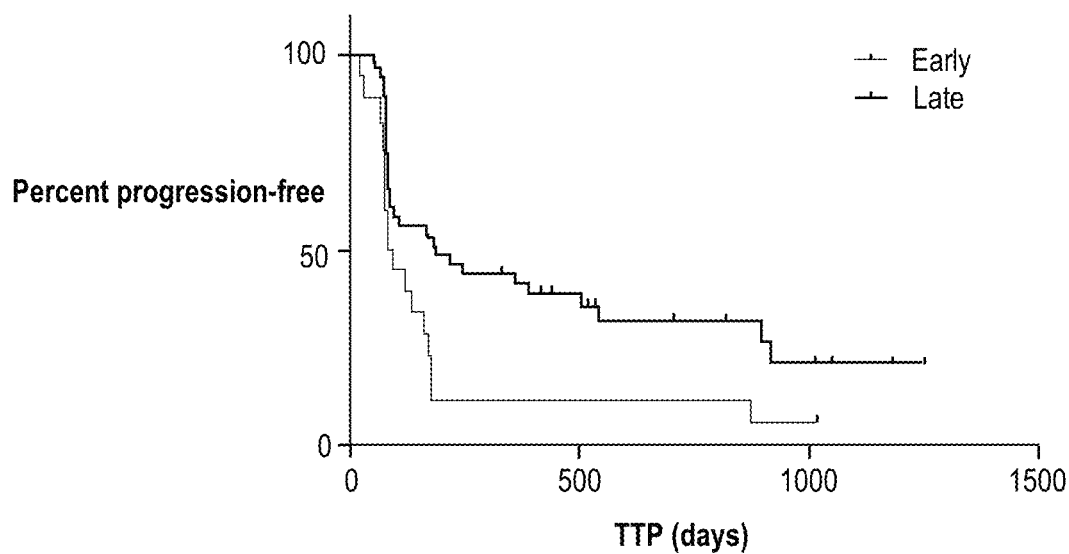
Figure 13A:
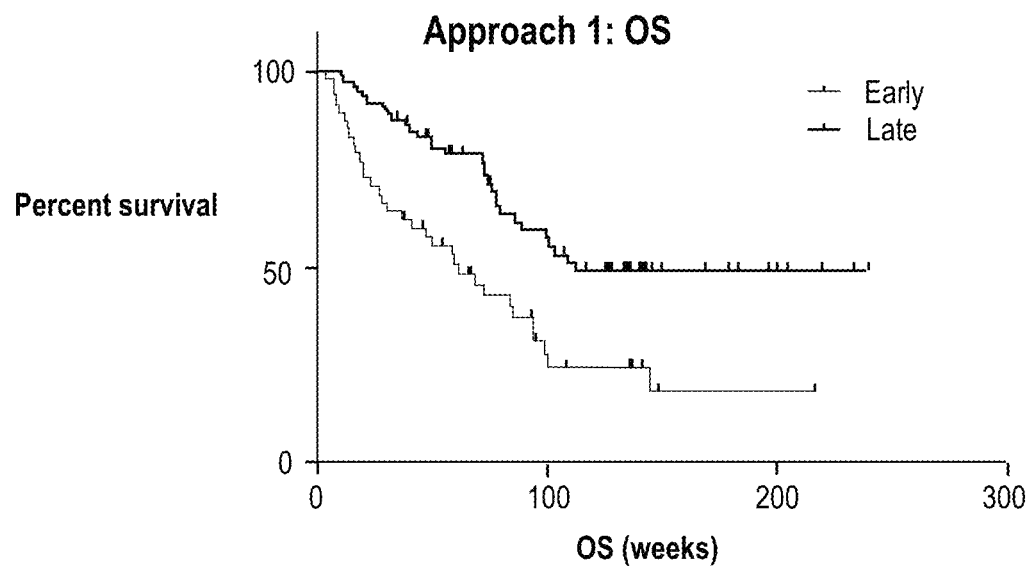
FIGS. 13A and 13B illustrate Kaplan-Meier plots for OS and TTP, respectively, by Early and Late classification groups for a first approach shown in Table 13 applied to the whole set of 119 samples as development set (100) for classifier generation in accordance with FIG. 8.
Figure 13B:
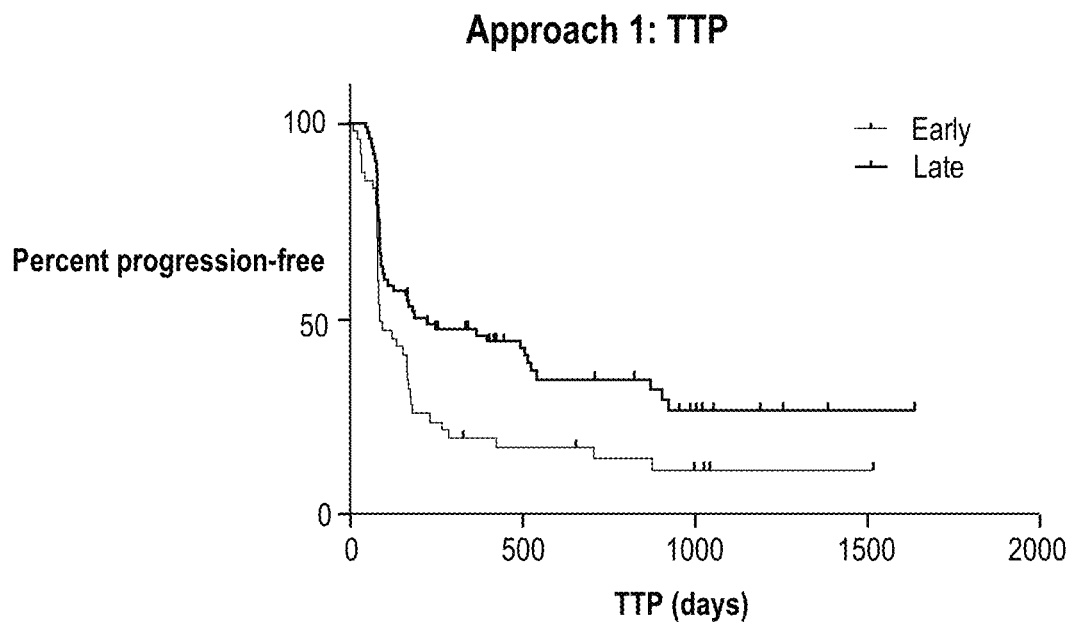
Figure 13C:
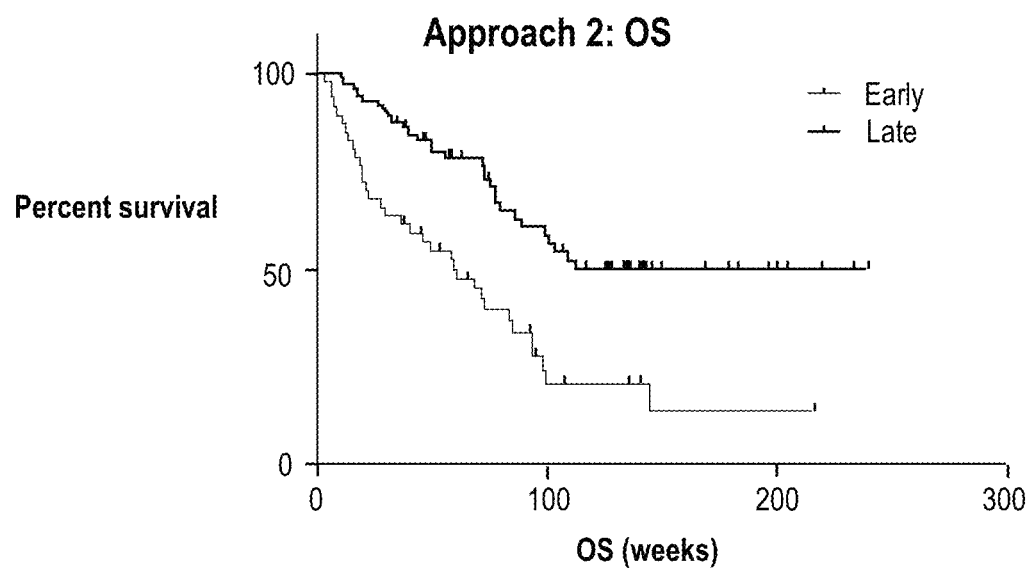
FIGS. 13C and 13D illustrate Kaplan-Meier plots for OS and TTP, respectively, by Early and Late classification groups for a second approach shown in Table 13 applied to the whole set of 119 samples as development set (100) for classifier generation in accordance with FIG. 8.
Figure 13D:
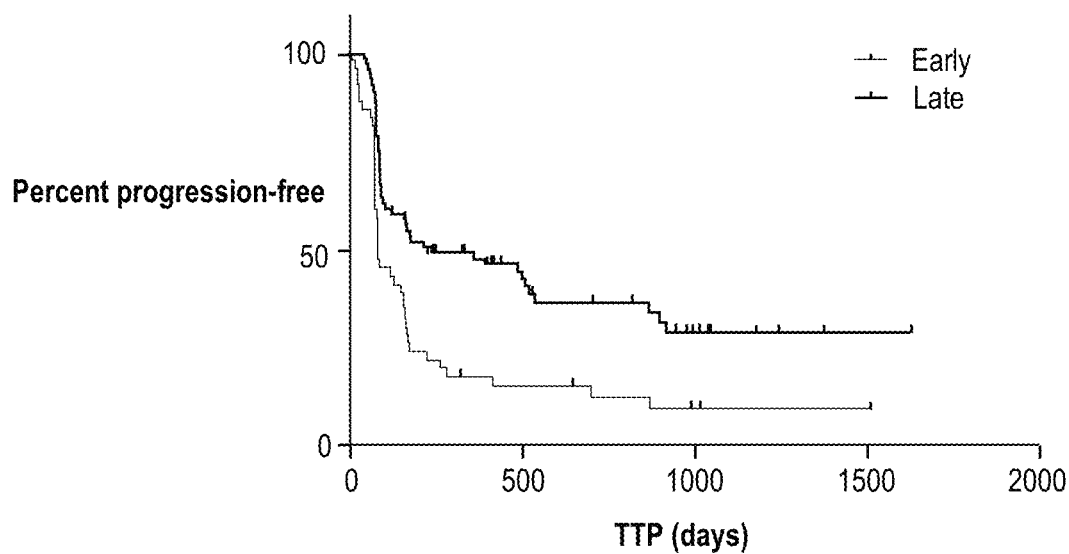

The present disclosure demonstrates how it is possible to incorporate biological insight into a classifier development exercise, such as for example the approach of FIGS. 8A and 8B, using mass spectrometry data. The present disclosure also demonstrates how it is possible to test biologically motivated hypotheses about the relevance of biological functions for certain disease states using mass spectral data. This is achieved by using gene set enrichment analysis to associate biological functions, via subsets of proteins related to these functions, with features (peaks) in mass spectra obtained from serum samples, and using such identified features to train a classifier with the aid of a computer.

In particular, classifier development and training methods are disclosed which make use of mass spectrometry of a development set of samples. Protein expression data are obtained from a large panel of proteins spanning biological functions of interest either for each of the samples in the development set of samples or, alternatively and more typically, for each of the samples in another sample cohort for which mass spectrometry data are also available. The latter case is preferred because the measurement of abundance of many proteins via a protein assay requires a large amount of sample and is expensive and time consuming. It is also not necessary to construct the relation between mass spectral peaks and biological function for every development project because we can infer the correlation of mass spectral features to function from any reference set that has sufficient protein coverage. In the following we exemplify our methods using these two options interchangeably.

In our method, we identify statistically significant associations of one or more of the mass spectral features with sets of proteins grouped by their biological function. With the aid of a computer, we then use these one or more mass spectral features that were identified (and typically 10-50 of such features) to train a classifier. This training may take the form of a classifier development exercise, one example of which is shown in FIG. 8 and described in detail previously. The classifier is in the form of a set of parameters and associated program instructions or code, which when executed by a computer assigns a class label to mass spectrometry data of a sample of the same type as the development set of samples in accordance with the programmed instructions.

As described in this Example, using Gene Set Enrichment Analysis (GSEA) methods, it is possible to look for statistically significant associations of mass spectral features with sets of proteins grouped by their biological function ("protein functional groups") avoiding direct protein identification, and taking advantage of the high-throughput aspect of mass spectrometry. A system or set of components that conducts GSEA and identifies such mass spectral features with a particular protein functional group or subset is referred to herein as a "platform" or "GSEA platform." Such a platform consists of both a known, conventional protein expression assay system (e.g., the SOMAscan assay provided by SomaLogic of Boulder Colo.) and a computer for implementing GSEA analytical procedures to identify the mass spectra features associated with functional groups of proteins as described in this document.

It is necessary to have matched mass spectral data (preferably from a high sensitivity method such as "Deep MALDI" see U.S. Pat. No. 9,279,798, the content of which is incorporated by reference herein) and protein expression data from a large panel of proteins spanning biological functions of interest on a single set of serum samples. Using well-known protein databases, such as UniProt or GeneOntology/AmiGO2, subsets of proteins from the universe of measured proteins can be defined based on their biological functions. The entire list of measured proteins is first ranked according to the correlation of each protein with the mass spectral feature of interest. The GSEA method then looks for over- or under-representation of the proteins included in a particular protein functional subset as a function of rank in this ranked list of all measured proteins and provides a way of assessing its statistical significance. Thus, the association of the mass spectral feature of interest with different protein functional groups can be assessed. This procedure can be repeated for as many spectral features and as many protein functional groups as desired. Setting a cutoff on the degree of association or the p value for significance of the association, all mass spectral features associated with a particular protein functional subset can be identified. This set of mass spectral features is then used to train a classifier, such as a k-Nearest Neighbor (kNN) classifier.

One method we prefer for classifier training and development is known as Diagnostic Cortex, which is described at length previously in the context of FIG. 8. It has been demonstrated that using the Diagnostic Cortex classifier development procedure, clinical data and Deep MALDI mass spectrometry data can be combined to produce clinically useful molecular diagnostic tests. One advantage of this method is that it allows for the design and tuning of tests to meet required standards of clinical utility. The use of subsets of functionally related mass spectral features (identified from the procedures mentioned in the previous paragraph) instead of all available mass spectral data provides an additional option for test design and optimization. The mass spectral features associated with one or more protein functional subsets can be selected and combined with the clinical data of a set of samples to create a new classifier and associated test, allowing for the investigation of the relevance of individual biological functions or groups of biological functions for the required classification task.

We also describe creation of a multitude of different classifiers using different feature subsets related to different protein functional groups and combine them, for example by simple majority vote, more complex ensemble averaging, or some rule-based system, to produce an overall classification that combines the information content across various biological functions. In one variation of this, we can look at the functional subsets becoming relevant on the groups defined by the classifier after taking out, or taking care of the main effects, by using the peaks related to the functional groups in the classifier, and using these newly relevant peaks for building a new classifier in terms of a hierarchy of biological functions. For example, we can use peaks associated with acute response function to train a first level classifier. We train a second classifier using a set of peaks associated with a wound healing protein function. A sample which tests Late (or the equivalent) on the first level classifier is then classified by the second level classifier. If one has a big enough set, it is possible to iterate this process further and define a third level classifier on a set of peaks associated with a third protein function and use that for a group classified by the second level classifiers, etc. As there are often multiple protein functional groups associated with a given peak this approach attempts to disentangle compound effects.

Thus, in one aspect of this disclosure a method of generating a classifier is described including the steps of: a) obtaining a development set of samples from a population of subjects; b) conducting mass spectrometry on the development set of samples and identifying mass spectral features present the mass spectra of the development set of samples; c) obtaining protein expression data from a large panel of proteins spanning biological functions of interest for each of the samples in the development set of samples, or, alternatively, for each of the samples in an additional cohort of samples with associated mass spectral data; d) identifying statistically significant associations of one or more of the mass spectral features with sets of proteins grouped by their biological function using the set of samples with matched mass spectral and protein expression data; and e) with the aid of a computer, using the one or more mass spectral features identified in step d) and clinical data from the development set of samples to train a classifier, the classifier in the form of a set of parameters which assigns a class label to a sample of the same type as the development set of samples in accordance with programmed instructions.

In another aspect, the invention can take the form of a programmed computer configured as a classifier generated in accordance with the method of the previous paragraph.

In another aspect, a method of testing a sample is disclosed, which includes the steps of a) training a classifier using a set of mass spectra features that have been determined to have statistically significant associations with sets of proteins grouped by their biological function; b) storing the parameters of the classifier including a feature table of the set of mass spectral features in a memory; c) conducting mass spectrometry on a test sample; and d) classifying the test sample with the trained classifier with the aid of the computer. In one variation, the steps include training two classifiers using different subsets of features associated with different functional groups of proteins, storing the parameters of the first and second classifiers including a feature table of the sets of mass spectral features in a memory, and logical instructions for combining the first and second classifiers into a final classifier; c) conducting mass spectrometry on a test sample; and d) classifying the test sample with the final classifier with the aid of the computer.

In another aspect, a computer configured as a classifier is disclosed including a memory storing a feature table in the form of intensity data for a set of mass spectral features obtained from a biological sample, wherein the set of mass spectra features have been determined to have statistically significant associations with sets of proteins grouped by their biological function, and a set of parameters defining a classifier including a classification algorithm operating on mass spectral data from a test sample and the feature table.

In another aspect, a classifier development system is disclosed, including a mass spectrometer for conducting mass spectrometry on a development set of samples to generate mass spectral data, said data including a multitude of mass spectral features; a platform for conducting a gene set enrichment analysis on the development set of samples or, more typically, another set of samples with associated mass spectral data, and identifying statistically significant associations of one or more of the mass spectral features with sets of proteins grouped by their biological function; and a computer programmed to train a classifier using the one or more mass spectral features identified by the platform, the classifier in the form of a set of parameters which assigns a class label to a sample of the same type as the development set of samples in accordance with programmed instructions.

In the above methods and systems, the development set of samples can take the form of blood-based samples (serum or plasma) from humans, for example humans enrolled in a clinical trial of a drug or combination of drugs. Such humans can be cancer patients. We describe the inventive methods and systems below in the context of a development set of blood-based samples obtained from melanoma patients treated with an immunotherapy drug, namely a programmed cell death 1 (PD-1) checkpoint inhibitor.

This document demonstrates that it is possible to associate features in mass spectra with biological functions without direct identification of the proteins or peptides producing the mass spectral feature, and incorporate biological insights into the choice of mass spectral features for use in reliable classifier training or development, e.g., using the Diagnostic Cortex platform.

Association of mass spectral features directly with biological processes is important as it is often difficult and time-consuming, and sometimes impossible, to identify the proteins or peptides producing individual peaks in mass spectra. This method circumvents the need for thousands of protein identification studies, which even when successful, do not always allow the matching of biological processes to mass spectral peaks (the specific functions of many peptides and protein fragments remain to be determined).

The ability to find mass spectral features generated from human serum reliably associated with biological processes provides a new way to monitor these processes in a longitudinal manner in a minimally-invasive, high throughput manner. Serum samples could be collected from patients at many time points during the course of a therapy or disease and changes in specific biological processes could potentially be inferred from the analysis of mass spectra generated from the serum samples. Such changes can be due to an intervention (e.g., treatment), or to the natural evolution of the disease. While the study considered an application in oncology, this could be of interest across many disease areas.

The incorporation of biological insights into classifier training for reliable molecular diagnostic test development provides another avenue for the design and tuning of the tests that can be created. Experience with the Diagnostic Cortex platform has shown that in some situations the ability to tune tests to meet clinical needs is reduced and similar tests are produced despite attempts to tune towards other performance goals. It was believed that this was due to the dominance of certain mass spectral features and correlations between features, but previous attempts to remove these dominating effects to allow investigation of other subsidiary, but potentially important, effects had proved quite unsuccessful. The ability to determine which features are associated with individual biological processes provides a new way to look at the universe of mass spectral features that can be used in classification, allowing us to attempt to separate out effects that might confound each other or to remove processes that dominate classification to reveal other processes that can improve test performance and test biological hypotheses.

The application of GSEA-based feature selection could be very broad and potentially could lead to the extension of our understanding of the role of specific biological processes and related treatment in any disease. As an example, type 2 diabetes is known to be a metabolic disorder. However, it is also known that inflammation plays an important role (see G L King et al., The role of inflammatory cytokines in diabetes and its complications. J Periodontol. 2008 August; 79(8 Suppl):1527-34. doi: 10.1902/jop.2008.080246 and A O Odegaard et al., Oxidative stress, inflammation, endothelial dysfunction and incidence of type 2 diabetes. Cardiovasc Diabetol. 2016 Mar. 24; 15(1):51. doi: 10.1186/s12933-016-0369-6). If we decide to build a prognostic test for diabetes, we might consider selecting separate feature sets: one associated with the insulin pathway, and another one with inflammation. Using the approach outlined in this report, we can attempt to separate out the effects of these two broad biological processes on prognosis, and even estimate the relative effect of each of them on the prognostic classification. Furthermore, if we try to find a predictive test for a novel drug, we might even be able to better understand the mechanism of action of the therapy, for example, if only one of the hypothetically relevant feature sets would work well.

Since almost no disease is defined just by a single process disruption, the application of the methods of this disclosure is very broad, and is limited only by the adequate measurement of the related proteins in the sample of choice and by (in)sufficient understanding of the roles of these proteins in particular biological processes. So, theoretically, this method could allow researchers to separate and test effects of multiple biological processes associated with practically any disorder, as well as to better understand the mechanism of action of treatments. While this study involves MALDI mass spectrometry of serum, and so is limited to processes that can be explored via circulatory proteins and peptides, the method per se does not depend on sample type and so can be extended even beyond this already wide regime of applicability.

Further details and an example of GSEA-based feature selection with an application in classifier development will now be described with particularity.

Two sample sets were used in this study:
1. A set of 49 serum samples ("the GSEA cohort", or "analysis" set or cohort) from 45 patients with non-small cell lung cancer and 4 subjects without cancer, for which mass spectral data were collected and protein expression data were generated using the 1129 protein SOMAscan® aptamer panel (SomaLogic, Boulder, Colo.). We used this set to determine peaks which were used for classifier training from a GSEA analysis.
2. A set of 119 pretreatment serum samples from 119 patients with advanced melanoma who were treated with the anti-programmed cell death-1 (PD-1) therapy, nivolumab, with or without the addition of a multi-peptide vaccine as part of a clinical trial ("the NCD cohort", also called "Moffitt" in this disclosure) (Details of the trial can be found in J. Weber et al., *Safety, Efficacy, and biomarkers with Vaccine in Ipilimumab-Refractory or -Naïve Melanoma*, J Clin Oncol 2013 Dec. 1; 31(34) 4311). Outcome data were available for patients in this cohort and mass spectral data were collected from these samples. Samples from this set were used in classifier training. This sample set is described in Example 1.

Generation of Protein Expression Data and GSEA Platform

Protein expression data were collected from the GSEA cohort using the 1129 protein SOMAscan aptamer panel by SomaLogic at their laboratory in Boulder, Colo. A list of the 1129 proteins contained in the assay is contained in Appendix A of our prior provisional application Ser. No. 62/340, 727 filed May 24, 2016. Further details on the identification of protein groups associated with mass spectral features are set forth later on in this document.

The generation and processing of mass spectral data from both the GSEA cohort and the NCD cohort was performed as explained in great detail previously in Example 1.

Application of Gene Set Enrichment Analysis (GSEA) Methods

GSEA (see the Mootha et al. and Subramanian et al. papers cited previously) was introduced as a method to help deal with or try to minimize some essential problems in gene expression analysis studies: identification of gene sets and resulting tests in development sample sets that cannot generalize to other sample sets (overfitting), the multiple testing problem, and the inability to identify smaller expression changes consistent across multiple related genes that might be swamped by larger randomly occurring expression changes in a dataset. These are problems inherent in dealing with "p>n" datasets, i.e. where the number of measured expression values greatly exceeds the number of samples for which the measurements are available. Instead of looking at expression differences feature by feature (gene by gene), the method looks for expression differences that are consistent across pre-specified groups or sets of features. The feature sets can be created based on biological insight or one can use feature sets that have been defined by prior hypothesis-free studies. Correlating with sets of features rather than single features provides some protection against identifying isolated features that are randomly correlated with study groups and would not generalize to other sample sets. Typically, the number of feature sets that are tested for correlation is smaller than the number of single features in a typical gene expression study, so this reduces somewhat the multiple testing problem. In addition, because the method looks for consistent correlations across a group of features, it is possible to identify a significant effect that is smaller in magnitude (per feature) than that which could be identified for a single feature.

Definition of Protein Sets

Specific protein sets were created based on the intersection of the list of SOMAscan 1129 panel proteins and results of queries from GeneOntology/AmiGO2 and UniProt databases.

The AmiGO2 queries were filtered by:
document category: annotation
taxon: *H sapiens*
evidence type: experimental
The individual filters used are listed in Table 45.

TABLE 45

Filters used in the AmiGO2 database

| Protein Set Name | Keyword |
|---|---|
| Amigo 1 | Acute inflammatory response |
| Amigo 2 | Activation of innate immune response |
| Amigo 3 | Regulation of adaptive immune response |
| Amigo 4 | Positive regulation of glycolytic process |
| Amigo 5 | Immune T-cells |
| Amigo 6 | Immune B-cells |
| Amigo 7 | Cell cycle regulation |
| Amigo 8 | Natural killer regulation |
| Amigo 9 | Complement system |
| Amigo 11 | Acute response |
| Amigo 14 | Cytokine activity |
| Amigo 16 | Wound healing |
| Amigo 17 | Interferon |
| Amigo 18 | Interleukin-10 |
| Amigo 20 | Growth factor receptor signaling |
| Amigo 21 | Immune Response |
| Amigo 22 | Immune Response Type 1 |
| Amigo 23 | Immune Response Type 2 |

The UniProt queries were filtered by:
Organism: *H. sapiens*
DB: reviewed (SwissProt)
The individual filters used in the UniProt database are listed in table 46.

TABLE 46

Filters used in the UniProt database

| Uniprot 1 | Acute phase |
|---|---|
| Uniprot 2 | Hypoxia |
| Uniprot 4 | Cancer |

The proteins included in each protein set are listed in the Appendix D of our prior provisional application Ser. No. 62/340,727. (Uniprot 4 Cancer is not included in the listing as it contains more than 400 proteins.)

Implementation of GSEA Method

The implementation of the GSEA method was done on a general purpose computer using Matlab (version R2015a). The process can be decomposed into several steps.

Let us assume that we have data from a set of $N_s$ samples and for each sample, i, we are given a continuous variable $Q_i$ and the expression values of $N_f$ proteins, $F_i^j$, where i runs over the samples ($1 \leq i \leq N_s$) and j runs over the proteins ($1 \leq j \leq N_f$). We have k predefined protein sets $S_l$ ($1 \leq l \leq k$) that we are interested in correlating with the mass spectral data. Each protein set $S_l$ consists of $N_h^l$ members ($1 \leq N_h^l \leq N_f$) and is a subset of the complete set of $N_f$ proteins.

1. Evaluation of the Correlation Between Individual Proteins and a Continuous Variable (the Mass Spectral Feature Value)

The strength of the correlation, $r_j$, between each individual protein j in the full protein set and the continuous variable associated with the samples is calculated. Spearman's rank correlation was used to assess the degree of correlation. Once a correlation, $r_j$, had been calculated for each protein, j, the $N_f$ proteins were ranked by $r_j$, from largest to smallest.

2. Calculation of an Enrichment Score

Figure 43:
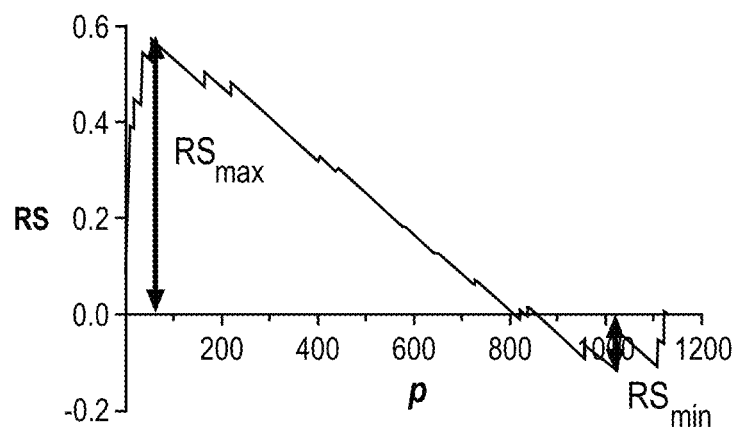
FIG. 43 is an example of a plot of running sum (RS) score ($RS(S_{l,p})$) calculated in a gene set enrichment analysis (GSEA) for one protein set $S_l$.

As explained in the Subramanian et al. paper cited previously, the enrichment score, $ES_l$, is designed to reflect the degree to which elements of a particular protein set, $S_l$, are over-represented at the top or bottom of the ranked list of proteins. We start at the top of the rank list and construct a running sum, $RS(S_l,p)$, at item p on the ranked list by starting at zero and adding a term $|r_j|/N_{norm}$ for the jth item in the ranked list if protein j is contained in $S_l$ and subtracting a term $1/(N-N_h^l)$ for the jth item in the ranked list if protein j is not contained in $S_l$ until one reaches item p. $N_{norm}$ is a normalization coefficient defined by $N_{norm} = \Sigma |r_j|$, where the sum runs over all proteins j contained in $S_l$. An example of a calculated $RS(S_l,p)$ is shown in FIG. 43.

We consider two possible definitions for ES. First, $ES_l$ is defined in terms of the largest positive value of $RS(S_l,p)$ as a function of p, $RS_{max}$, and the smallest value of $RS(S_l,p)$, $RS_{min}$. These are illustrated in FIG. 43. If $RS_{max} \geq |RS_{min}|$, $ES=RS_{max}$; if $RS_{max} < |RS_{min}|$, $ES=RS_{min}$ (This is the definition used in Subramanian et al. with their exponent p set to 1.) To be able to take account of protein sets containing mixtures of over- and under-expressed proteins by group or mixture or proteins meaningfully correlated and anti-correlated with the continuous variable, we also consider an alternative definition of ES as $RS_{max} + |RS_{min}|$. (If all proteins in the protein set are over-expressed (positively correlated), the two definitions are identical.)

3. Calculation of the Corresponding p Value

Figure 44A:
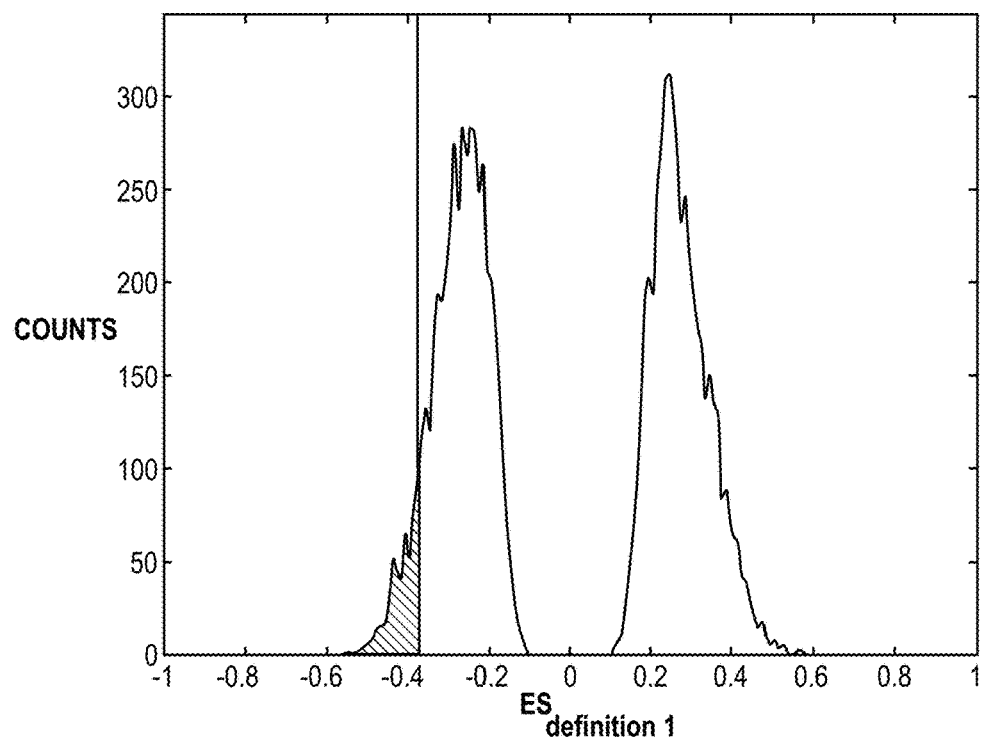
FIGS. 44A and 44B are examples of the null distributions for the two definitions of the enrichment scores (ES) used in a GSEA, showing the calculated ES and the regions assessed to determine the p value.
Figure 44B:
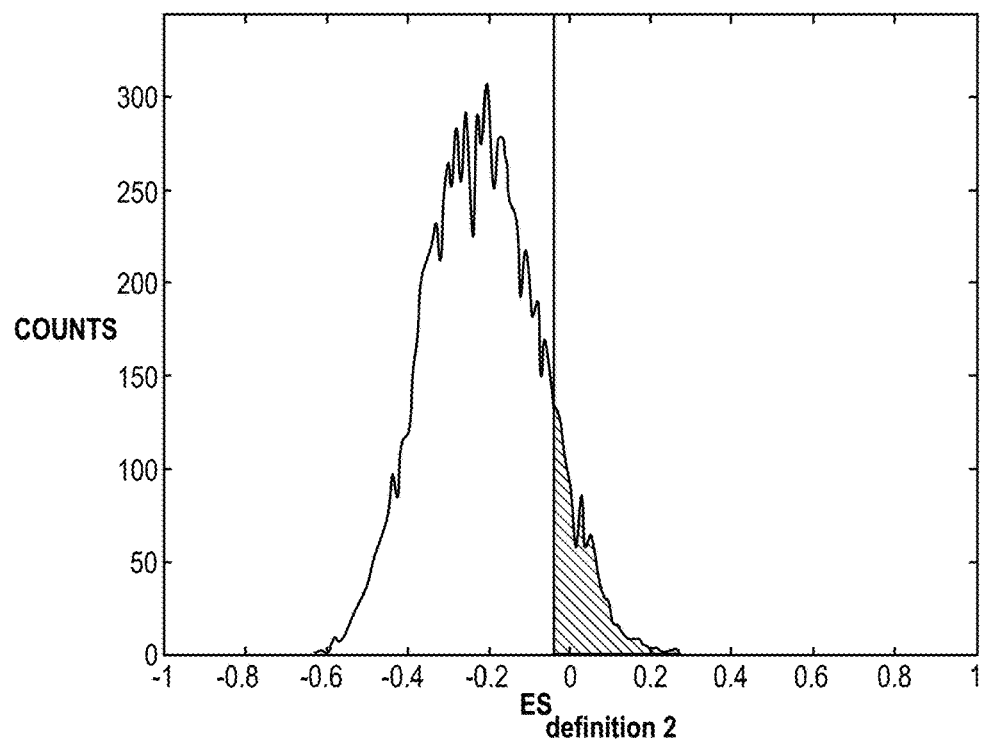

To assess the significance of the deviation of the calculated ES from its average value for a random distribution, the null distribution of ES is calculated by generating many realizations of a random association between the continuous variable and the protein expressions and evaluating ES for each. These realizations are created by permuting the values of the continuous variable assigned to each sample. Note that this maintains the correlation structure within the protein expression values for each sample. Once the null distribution has been generated, the p value for the calculated ES can be read off as the proportion of random permutations generating an ES further from random (more extreme) than the calculated ES. (Note that the first definition of ES requires an assessment of positive and negative ES separately). Examples of the null and calculated ES for one protein set are shown in FIGS. 44A and 44B. The null distribution has to be evaluated separately for each comparison (each individual continuous variable (i.e., each mass spectral feature) and protein set pair). For the correlation with mass spectral feature value, 2000 realizations were generated.

4. Corrections for Multiple Testing

The p values produced by the method outlined above do not take into account multiple testing. It is possible to extend the analysis to take account of multiple testing either by a very conservative Bonferroni correction or by generating many permutations of the random permutations over the continuous variable also over the ranked protein list for all protein sets and computing the ES for each realization. This latter method also requires a normalization of the ES to allow the combination of results across different protein sets. At present neither of these approaches has been implemented and the results in this report have not been corrected for multiple testing.

GSEA Results

Figure 45B:
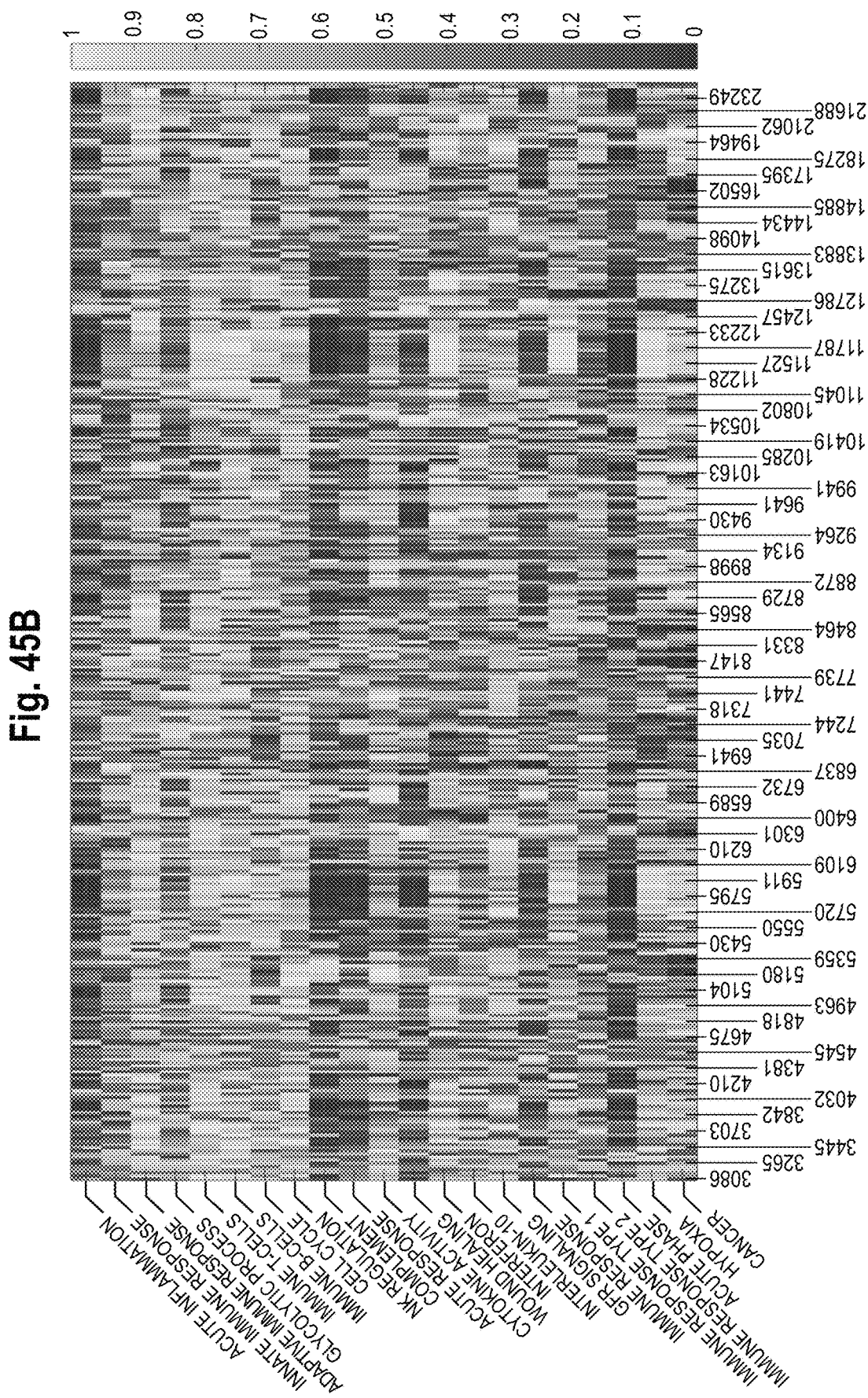

Using the methodology described above, a GSEA p value was obtained for each mass spectral feature for each protein functional group. The results for the correlation of the protein functional groups with the all 351 defined mass spectral features (Appendix A) for the 49 samples of the GSEA cohort are shown in the heat maps of FIGS. 45A and 45B. In particular, FIGS. 45A and 45B show the p values generated by the GSEA analysis associating all 351 defined mass spectral features with different protein functional groups (biological processes). FIG. 45(a) shows the p values for ES definition1 and FIG. 45(b) for ES definition 2. Note: Mass spectral features are ordered in increasing m/z and only every $5^{th}$ spectral feature is labeled on the x axis.

Table 47 shows the number of mass spectral features (out of the 351 defined) associated with the protein functional groups with p values below a variety of thresholds for each of the protein functional subsets for definition 1 and definition 2 of the enrichment score.

TABLE 47

Number of mass spectral features associated with protein functional groups for p values below a variety of thresholds

| Protein Set Function | ES Definition 1 p value | | | | | ES Definition 2 p value | | | | |
|---|---|---|---|---|---|---|---|---|---|---|
| | <0.001* | <0.01 | <0.03 | <0.05 | <0.1 | <0.0005* | <0.01 | <0.03 | <0.05 | <0.1 |
| Acute Inflammation | 1 | 33 | 65 | 93 | 129 | 5 | 28 | 57 | 79 | 112 |
| Innate Immune Response | 0 | 3 | 6 | 12 | 29 | 0 | 0 | 5 | 10 | 27 |
| Adaptive Immune Response | 0 | 1 | 1 | 2 | 5 | 0 | 1 | 4 | 10 | 12 |
| Glycolytic Process | 3 | 3 | 8 | 17 | 36 | 1 | 3 | 9 | 17 | 35 |
| Immune T-cells | 0 | 0 | 3 | 8 | 13 | 0 | 0 | 2 | 4 | 4 |
| Immune B-cells | 0 | 2 | 2 | 8 | 15 | 0 | 0 | 2 | 2 | 7 |
| Cell cycle | 0 | 1 | 4 | 6 | 10 | 1 | 3 | 8 | 15 | 20 |
| NK Regulation | 0 | 0 | 0 | 2 | 4 | 0 | 0 | 1 | 2 | 7 |
| Complement | 15 | 62 | 95 | 122 | 157 | 8 | 44 | 77 | 93 | 125 |
| Acute Response | 0 | 9 | 22 | 33 | 64 | 0 | 8 | 30 | 47 | 85 |
| Cytokine Activity | 0 | 1 | 5 | 12 | 18 | 0 | 0 | 2 | 2 | 13 |

TABLE 47-continued

Number of mass spectral features associated with protein functional
groups for p values below a variety of thresholds

| Protein Set Function | ES Definition 1 p value | | | | | ES Definition 2 p value | | | | |
| --- | --- | --- | --- | --- | --- | --- | --- | --- | --- | --- |
| | <0.001* | <0.01 | <0.03 | <0.05 | <0.1 | <0.0005* | <0.01 | <0.03 | <0.05 | <0.1 |
| Wound Healing | 2 | 15 | 32 | 46 | 78 | 1 | 16 | 40 | 60 | 77 |
| Interferon | 0 | 1 | 4 | 6 | 17 | 0 | 5 | 8 | 14 | 20 |
| Interleukin-10 | 0 | 2 | 5 | 10 | 25 | 0 | 1 | 7 | 13 | 25 |
| Growth Factor Receptor Signaling | 0 | 0 | 2 | 6 | 18 | 0 | 1 | 2 | 4 | 13 |
| Immune Response | 1 | 8 | 31 | 55 | 80 | 1 | 6 | 23 | 46 | 81 |
| Immune Response Type 1 | 1 | 2 | 5 | 9 | 16 | 2 | 2 | 3 | 14 | 23 |
| Immune Response Type 2 | 1 | 5 | 10 | 16 | 37 | 0 | 7 | 12 | 18 | 34 |
| Acute phase | 8 | 41 | 67 | 84 | 111 | 6 | 66 | 90 | 110 | 149 |
| Hypoxia | 0 | 0 | 2 | 10 | 26 | 0 | 3 | 14 | 24 | 40 |
| Cancer | 0 | 3 | 11 | 17 | 32 | 1 | 18 | 30 | 34 | 46 |

*Indicates that ES was greater (or smaller) than that obtained in any of the realizations generated to assess the null distribution It is clear that many of the 351 mass spectral features are associated with acute phase reactants (acute response, acute phase, acute inflammation), the complement system, or wound healing. However, there also exist mass spectral features that are associated with other quite distinct protein functional groups, such as glycolytic process, cell cycle, or cancer. Hence, it is potentially possible to use measurements of mass spectral features that have been determined to be associated with a particular biological function from serum samples from a patient in order to monitor the particular biological function in the patient.

A cutoff of p=0.05 was chosen for the first definition of enrichment score (ES definition 1) and for each protein functional subset, so that the mass spectral features with GSEA p<0.05 were taken to be associated with the biological function. The mass spectral features associated with several of the protein functional subsets (Acute Response, Wound Healing, Immune Response) investigated are tabulated in Appendix E of our prior provisional application 62/340,727.

We then proceeded to develop classifiers using the FIGS. 8A and 8B methodology and peaks associated with particular protein functional groups. First, classifier development using the procedure of FIG. 8, steps 102-150 was performed on all 119 samples in the new classifier development (NCD) cohort, with the subset of 33 mass spectral features associated with the acute response protein functional group. Using the procedure of FIG. 8, we created a classifier, referred to below as "Classifier 1" which was able to stratify melanoma/nivolumab patients into two groups with better and worse prognosis in terms of OS and TTP (Classifier 1). No feature deselection was used, i.e., all 33 mass spectral features associated with the acute response protein functional group were used at each step of refinement of the class labels. Fifty one samples were assigned to the poor performing group and these were given an "Early" classification label. The particular choice of moniker for the class label generated by the classifier is not particularly important.

The remaining 68 samples, assigned to the good performing group, were used as the development set for a second classifier generated in accordance with FIG. 8 steps 102-150, referred to as "Classifier 2". This classifier was trained on the subset of 26 mass spectral features which had been identified as being associated with wound healing, but not associated with acute response or immune response. The second classifier again used no feature deselection and stratified patients well into groups with better or worse TTP. Samples in the good TTP group were assigned a "Late" classification and samples in the poor TTP group were assigned an "Early" classification.

Figure 46:
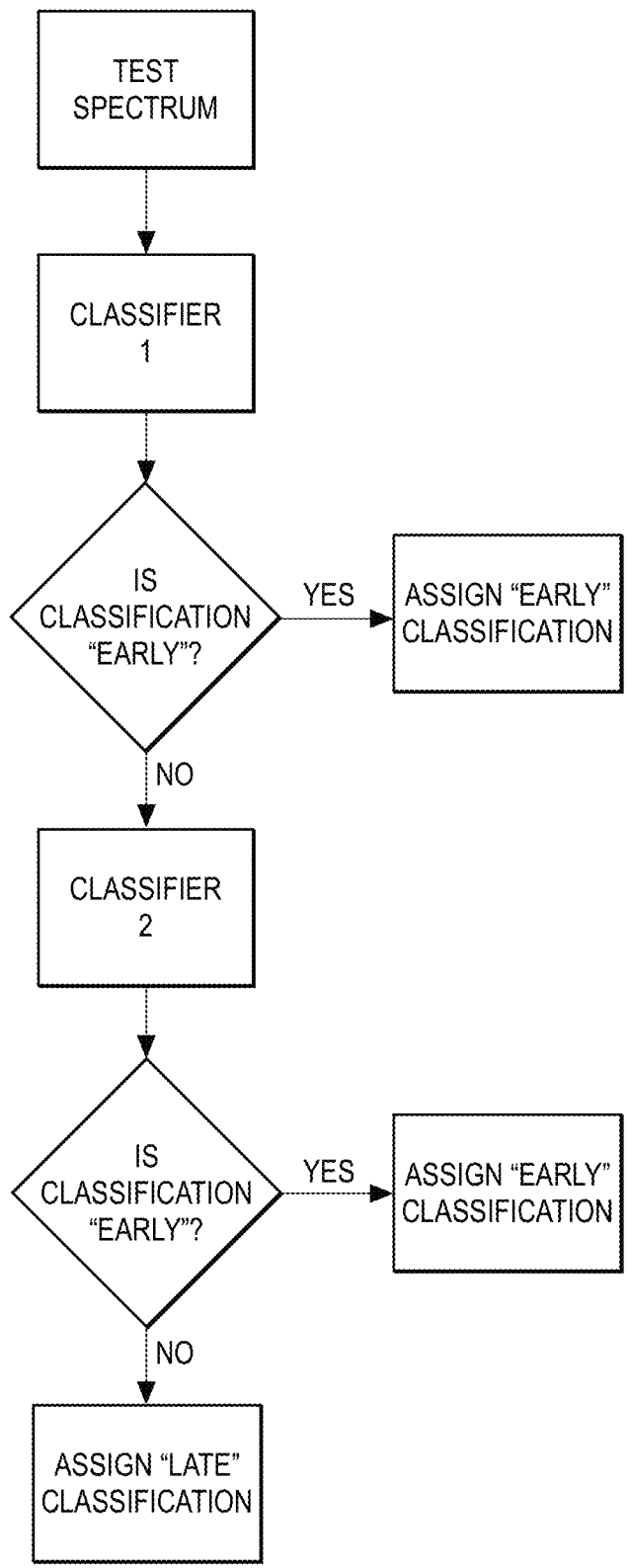
FIG. 46 is a schema of a final classification procedure of Example 6.

We then defined a final classifier as a hierarchical combination of classifiers 1 and 2. The resulting final classifier (i.e., a combination of two Diagnostic Cortex classifiers with logical instructions for use in a hierarchical manner) uses a total of 59 features, listed in Appendix D of this document. FIG. 46 illustrates schematically how a classification is assigned to a test sample by the combination of Classifier 1, based on mass spectral features associated with acute response, and Classifier 2, based on mass spectral features associated with wound healing but not with acute response or immune response. In particular, the mass spectrum is obtained for a test sample ("test spectrum" in FIG. 46) and in particular feature values for the 59 features of Appendix D are obtained. This data is supplied to Classifier 1 and Classifier 1 then produces a label for the sample. If the label reported is Early (or the equivalent) the sample is assigned the Early classification label. If Classifier 1 does not produce the Early label, the spectral data is supplied to Classifier 2. If Classifier 2 produces the Early label, then the sample is assigned the Early classification label. If Classifier 2 does not produce the Early label, then the sample is assigned the Late classification label. The Early and Late labels have the same clinical meaning as explained in Example 1 previously.

Note that this is an example of the creation of multiple different classifiers using different feature subsets related to different protein functional groups and the combination of them, by a rule-based system, to produce an overall classification that combines the information content across various biological functions. In this particular example we look at the functional groups becoming relevant on the groups defined by the classifier after taking out, or taking care of the main effects, by using the peaks related to the functional groups used in the first classifier, and using newly relevant peaks for building a new or second classifier in terms of a hierarchy of biological functions. If one has a big enough set, it is possible to iterate this process further and define a third level classifier on a set of peaks associated with a third protein function and use that for a group classified by the second level classifiers, etc. As there are often multiple protein functional groups associated with a given peak this approach attempts to disentangle compound effects.

Results

1. Classifier 1 Alone

Figure 47A:
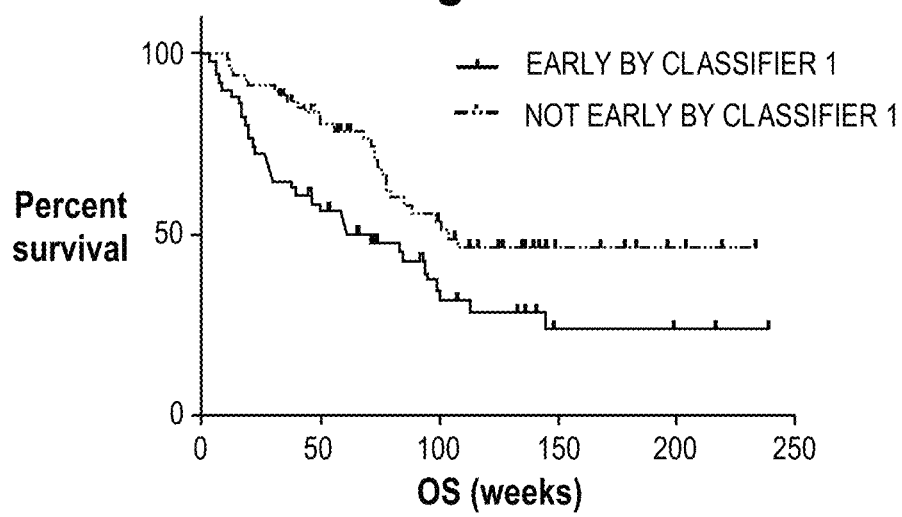
FIGS. 47A and 47B illustrate Kaplan-Meier plots of overall survival (OS) (FIG. 47A) and time to progression (TTP) (FIG. 47B) for the melanoma/immunotherapy new classifier development (NCD) cohort by classification group from Classifier 1 of Example 6.
Figure 47B:
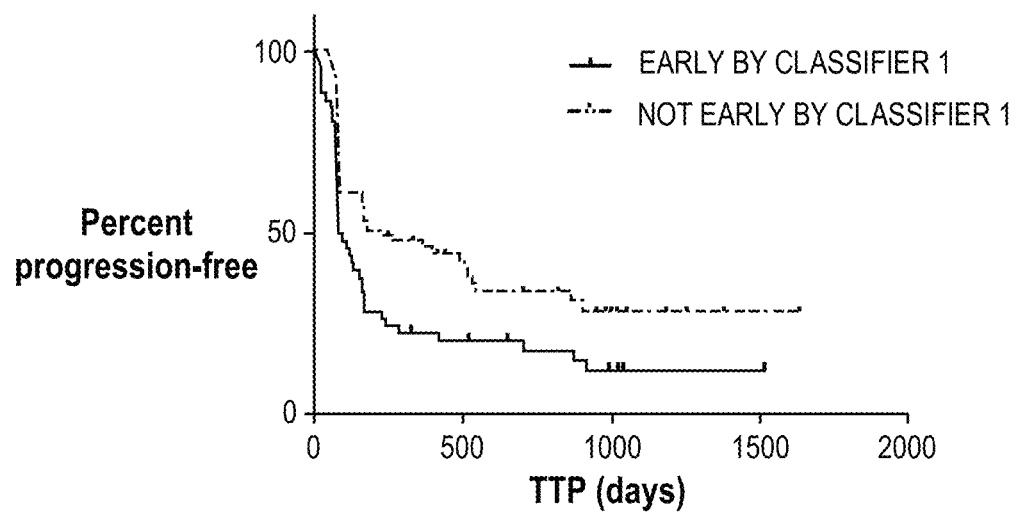

Classifier 1 assigned 51 of 119 samples an "Early" classification. FIGS. 47A and 47B show the Kaplan-Meier plots of OS and TTP for the classifications provided by Classifier 1 for the NCD cohort. The classifier based on acute response achieves a clear separation between the good and poor prognosis groups.

2. Classifier 2 Alone

Figure 48A:
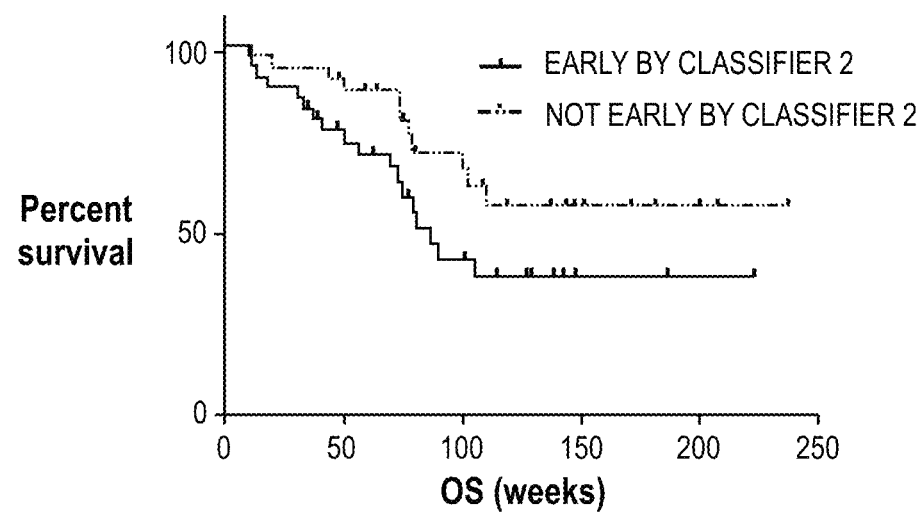
FIGS. 48A and 48B illustrate Kaplan-Meier plots of OS and TTP, respectively, for the 68 samples not classified as "Early" by Classifier 1, by classification group from Classifier 2 of Example 6.
Figure 48B:
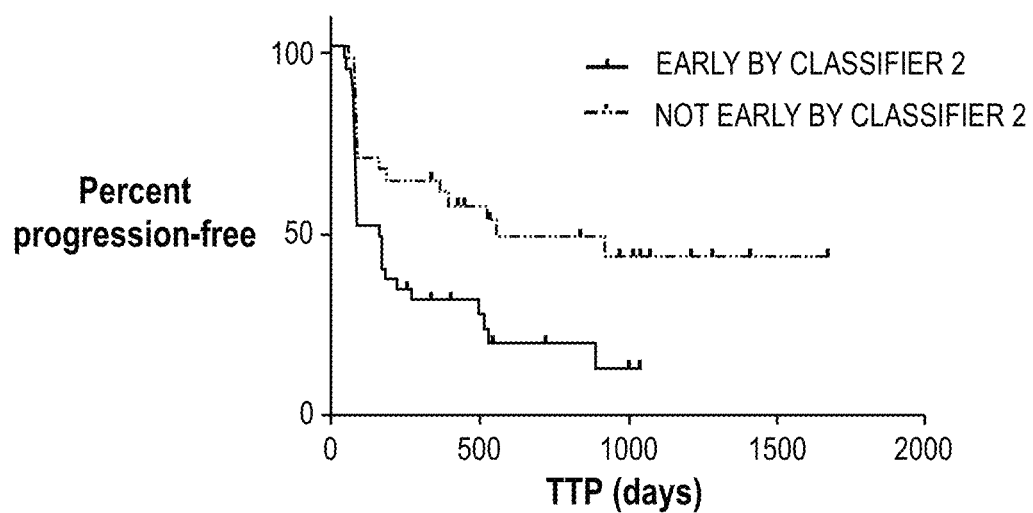

Classifier 2 assigned 35 of the 68 samples not classified as "Early" by Classifier 1 an "Early" classification and the remaining 33 a "Late" classification. Kaplan-Meier plots of OS and TTP for the classifications provided by Classifier 2 of these 68 samples are shown in FIGS. 48A and 48B.

Classifier 2, using features associated with wound healing, but not those associated with acute response or immune response, further stratifies the 68 samples not classified as "Early" by classifier 1.

2. Final Classifier Defined as a Combination of Classifiers 1 and 2

Combining the classifiers in a hierarchical manner as shown in FIG. 46, one obtains a superior binary stratification of the whole set of 119 samples. Thirty three (28%) samples were classified as "Late" and 88 (72%) as "Early". This is illustrated in the Kaplan-Meier plots of OS and TTP for the whole NCD cohort of 119 samples by overall classification in FIGS. 49A and 49B. Associated statistics characterizing the clear stratification of the cohort are given in table 48.

TABLE 48

Figure 49A:
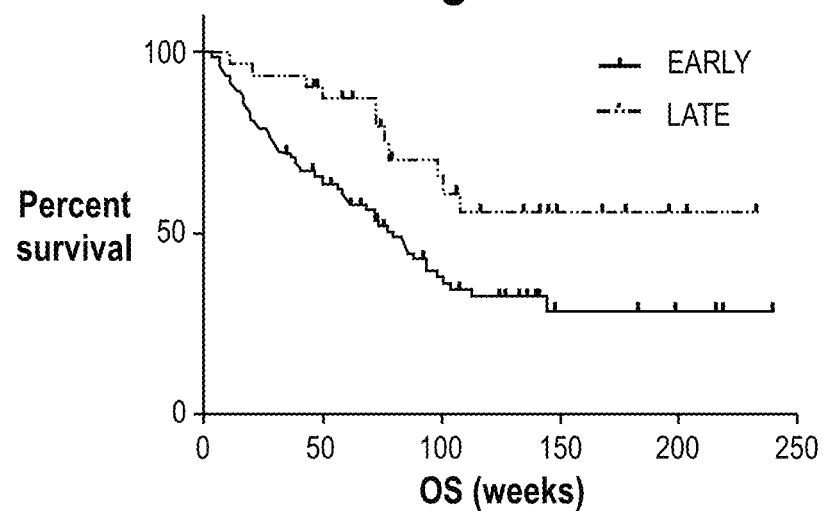
FIGS. 49A and 49B illustrate Kaplan-Meier plots of OS and TTP, respectively, for all 119 samples by overall classification produced by the classifier schema of FIG. 46.
Figure 49B:
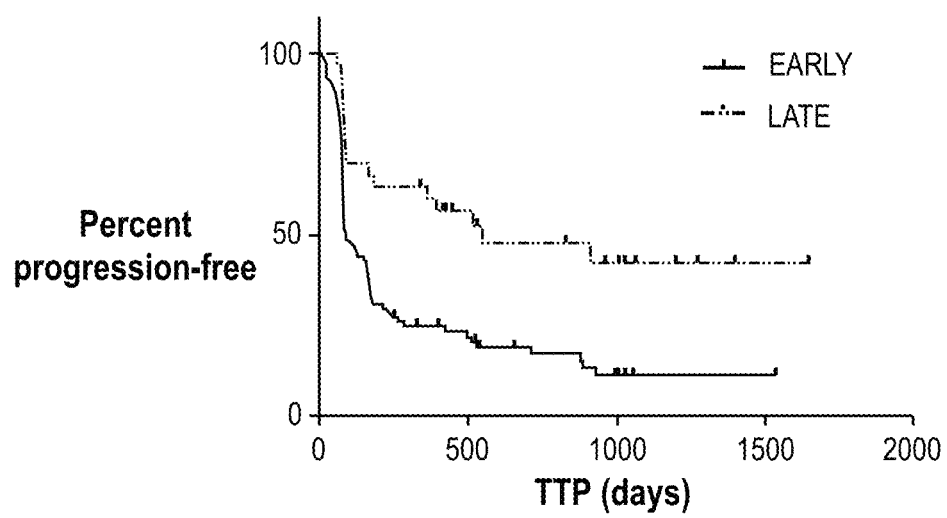

Statistics related to the Kaplan-Meier plots of FIGS. 49A and 49B (CPH = Cox Proportional Hazard)

|  | OS | | | TTP | | |
| --- | --- | --- | --- | --- | --- | --- |
|  | log-rank p | CPH p | HR (95% CI) | log-rank p | CPH p | HR (95% CI) |
| Late vs Early | 0.006 | 0.008 | 0.42 (0.22-0.80) | <0.001 | 0.001 | 0.40 (0.23-0.68) |
|  | Median (95% CI) in weeks | | | Median (95% CI) in days | | |
| Early | 80 (59-99) | | | 92 (82-162) | | |
| Late | Not reached (78-undefined) | | | 541 (163-undefined) | | |

Table 49 shows some landmark survival and progression-free statistics and table 50 summarizes the response data.

TABLE 49

Proportions still alive and progression-free at key time points

|  | Early | Late |
| --- | --- | --- |
| % alive at 1 year | 63 | 88 |
| % alive at 2 years | 34 | 61 |
| % progression-free at 6 months | 31 | 67 |
| % progression-free at 1 year | 25 | 60 |

TABLE 50

Response by test classification

|  | Early (n = 86) | Late (n = 33) |
| --- | --- | --- |
| PR | 19 (22%) | 12 (36%) |
| SD | 9 (10%) | 9 (27%) |
| PD | 58 (67%) | 12 (36%) |

Table 51 shows the baseline patient characteristic by classification group.

TABLE 51

Baseline patient characteristics by test classification

|  |  | Early (N = 86) n (%) | Late (N = 33) n (%) |
| --- | --- | --- | --- |
| Gender | Male | 52 (60) | 20 (61) |
|  | Female | 32 (37) | 13 (39) |
|  | NA | 2 (2) | 0 (0) |
| Age | Median (Range) | 62 (16-87) | 60 (27-76) |
| Cohort | 1 | 6 (7) | 3 (9) |
|  | 2 | 10 (12) | 1 (3) |
|  | 3 | 6 (7) | 5 (15) |
|  | 4 | 8 (9) | 2 (6) |
|  | 5 | 13 (15) | 8 (24) |
|  | 6 | 43 (50) | 14 (42) |
| Prior Ipi | No | 22 (26) | 9 (27) |
|  | Yes | 64 (74) | 24 (73) |
| PD-L1 expression (5% tumor) | Positive | 6 (7) | 2 (6) |
|  | Negative | 20 (23) | 9 (27) |
|  | NA | 60 (70) | 22 (67) |
| PD-L1 | Positive | 14 (16) | 4 (12) |

TABLE 51-continued

Baseline patient characteristics by test classification

|  |  | Early (N = 86) n (%) | Late (N = 33) n (%) |
| --- | --- | --- | --- |
| expression (1% tumor) | Negative | 12 (14) | 7 (21) |
|  | NA | 60 (70) | 22 (67) |
| PD-L1 expression (1% tumor/ immune cells) | Positive | 20 (23) | 8 (24) |
|  | Negative | 5 (6) | 2 (6) |
|  | NA | 61 (71) | 23 (70) |
| Serum LDH levels | <ULN | 12 (4) | 6 (18) |
|  | <2ULN | 55 (64) | 32 (97) |
|  | median | 496 (174-4914) | 472 (149-789) |
|  | range |  |  |
| Baseline tumor size | median range | 31.05 (1.50-259.03) | 11.43 (0.88-1.13) |

Fisher's exact test shows a significant correlation of serum LDH level <2ULN with classification (p<0.001) and Mann-Whitney p=0.070 for association of LDH level with classification. Baseline tumor size was greater in the Early group than in the Late group (Mann-Whitney p<0.001). Classification was not associated with PD-L1 expression at any available cutoff, however.

Multivariate analysis of the time-to-event outcomes allows the adjustment of the effect sizes (hazard ratios) for other known prognostic characteristics, such as serum LDH level. The results of this analysis are given in table 52. Classification remains a significant predictor of both OS and TTP, in addition to serum LDH level, indicating that the classification is providing supplementary information on outcome following nivolumab therapy.

TABLE 52

Multivariate Analysis of Time-to-Event Endpoints

|  | OS | | TTP | |
| --- | --- | --- | --- | --- |
|  | CPH p | HR (95% CI) | CPH p | HR (95% CI) |
| Late vs Early | 0.023 | 0.46 (0.23-0.90) | 0.002 | 0.43 (0.25-0.74) |
| Female vs Male | 0.079 | 1.63 (0.95-2.82) | 0.032 | 1.65 (1.04-2.61) |
| LDH/1000 | 0.004 | 1.66 (1.18-2.33) | 0.015 | 1.49 (1.08-2.06) |
| PD-L1 5% + vs − | 0.696 | 0.81 (0.29-2.30) | 0.750 | 1.14 (0.52-2.50) |
| PD-L1 5% NA vs − | 0.569 | 1.19 (0.65-2.20) | 0.864 | 0.95 (0.54-1.67) |
| Prior Ipilimumab Yes vs No | 0.383 | 0.77 (0.44-1.37) | 0.369 | 0.80 (0.48-1.31) |

It is interesting to note that the performance of the overall classification obtained using these feature subsets selected using biological hypotheses may be superior to that obtained previously on this sample cohort. FIGS. 50A-50D compare the Kaplan-Meier plots for the present classification with those obtained for two previously developed classifiers, one (IS2=full-set classifier of Example 1) developed using all mass spectral features simultaneously and the other (IS6) using an ensemble of classifiers with clinically different development subsets again using all mass spectral features. (These classifiers are described in Example 1, and Example 8, respectively).

Figure 51:
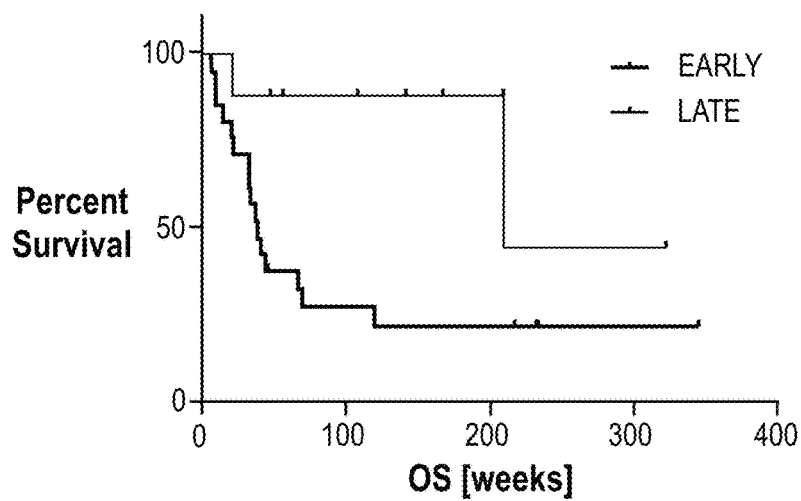
FIG. 51 is a Kaplan-Meier plot of OS for the validation cohort of Example 6 by classification group.

Samples from a cohort of 30 patients also treated with anti-PD 1 therapy were available for independent validation of the classifier. Twenty-one patients (70%) were classified as "Early" and 9 (30%) as "Late". The Kaplan-Meier plot for OS is shown in FIG. 51 and associated statistics in table 53. (TTP was not available for this observational cohort.)

TABLE 53

Statistics related to the Kaplan-Meier plots of FIG. 51

|  | OS | | |
| --- | --- | --- | --- |
|  | log-rank p | CPH p | HR (95% CI) |
| Late vs Early | 0.016 | 0.030 | 0.20 (0.05-0.86) |

|  | Median (95% CI) in weeks | 1 year survival | 2 year survival |
| --- | --- | --- | --- |
| Early | 37 (21-68) | 38% | 27% |
| Late | 210 (20-undefined) | 89% | 89% |

Example 6 Conclusions and Discussion

This study of Example 6 has demonstrated that it is possible to:
1) associate features in mass spectra with biological functions without direct identification of the proteins or peptides producing the mass spectral feature, and
2) incorporate biological insights into the choice of mass spectral features for use in reliable classifier development, e.g., using the Diagnostic Cortex platform of FIG. 8.

It will be further appreciated that once a classifier has been developed as explained above, it is then stored as a set parameters in memory of a computer (e.g., feature table of mass spectral features used for classifications, identification of mini-classifiers, logistic regression weights, kNN parameters, program code for executing one or more master classifiers and logic defining a final classifier, as per FIG. 8 step 150 or FIG. 46, etc.). A laboratory test center, for example as described in FIG. 15, includes such a computer as well as a mass spectrometer to conduct mass spectrometry on a blood-based sample. The resulting mass spectrum is subject to pre-processing steps (same as performed on the samples of the classifier development set) and then the classifier is applied to the mass spectral data of the sample. The classifier then generates a class label, e.g., Early or Late, and provides the class label to a requesting physician or clinic as a fee for service.

Figure 52:
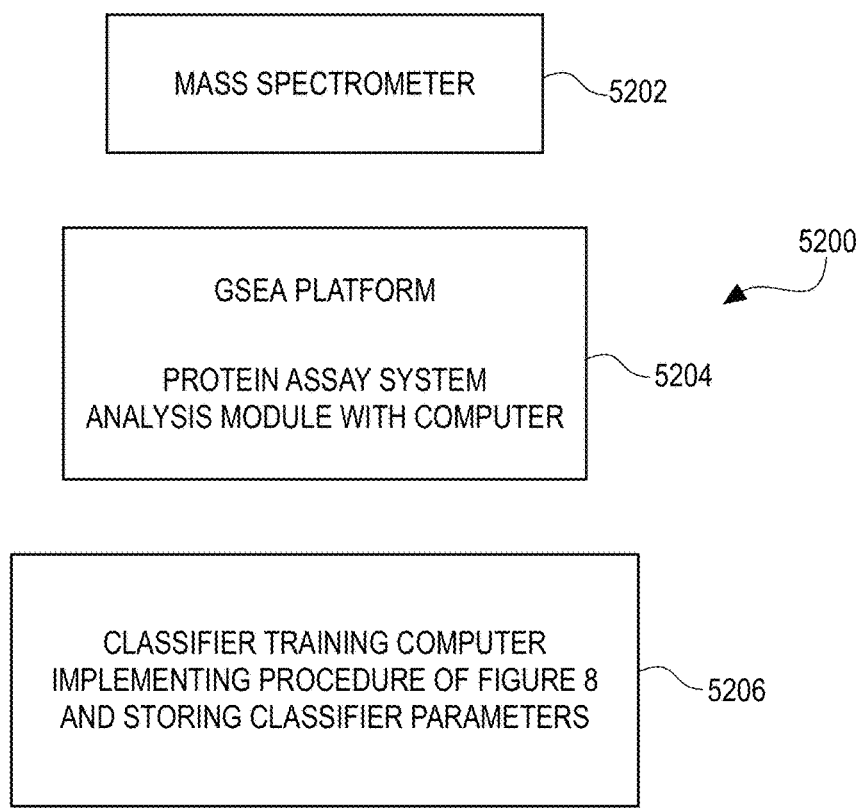
FIG. 52 is a block diagram of a classifier training system including a mass spectrometer for conducting mass spectrometry on a development set of samples (not shown, e.g., serum or blood samples), a GSEA platform, including protein assay system and computer with GSEA analysis module, and a computer programmed to conduct a classifier training procedure using sets of mass spectral peaks associated with a particular protein function group of a biological process of interest in the development set of samples.
Figure 53A:
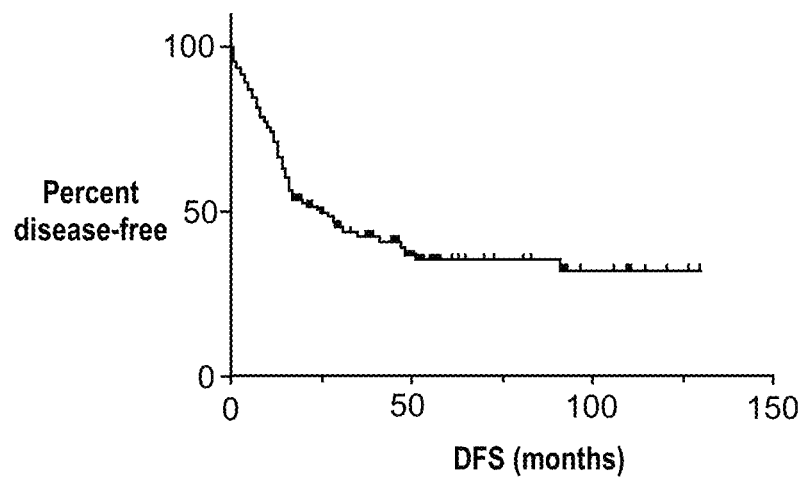
FIGS. 53A and 53B are Kaplan-Meier plots of time to event data for disease free survival (DFS, FIG. 53A) and overall survival (OS, FIG. 53B) for a cohort of 138 ovarian cancer patients with available clinical data and mass spectral data, which were used to develop the ovarian classifiers of Example 9.
Figure 53B:
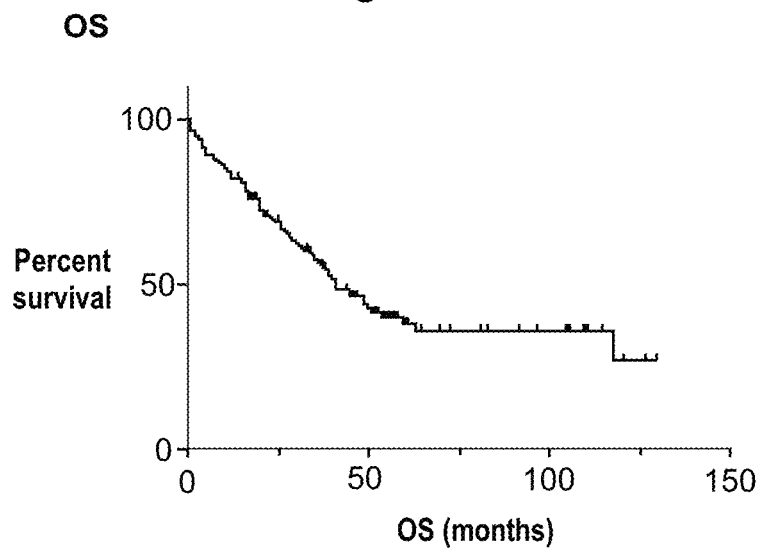

With reference to FIG. 52, it will be further appreciated that a classifier development system 5200 has been disclosed which includes a mass spectrometer 5202 for conducting mass spectrometry on a development set of samples, or, alternatively and more typically, another independent set of samples, to generate mass spectral data. The data includes intensity data for a multitude of mass spectral features. The system includes a platform 5204 for conducting a gene set enrichment analysis on the development set of samples, or, more typically, the other independent sample set, including a protein assay system such as the SOMAscan system of SomaLogic or the equivalent, and a computer for identifying statistically significant associations of one or more of the mass spectral features with sets of proteins grouped by their biological function. The system further includes a computer 5206 programmed to train a classifier on the development set of samples using the one or more mass spectral features identified by the GSEA platform, e.g., using the procedure of FIG. 8. The classifier is in the form of a set of parameters and programmed instructions which assign a class label to a sample of the same type as the development set of samples in accordance with the programmed instructions.

In this document we use the terms classifier training and classifier development interchangeably, to mean a process of constructing a classifier in a computer (i.e., specifying the parameters for such a classifier) and testing its ability to classify a set of samples (the development set of samples or some subset thereof). Typically, this process occurs in an iterative manner to tweak the parameters to optimize classifier performance, such as by refining class labels assigned to members of the development set, refining filtering parameters, feature deselection, varying the parameter k, etc. It will also be noted that while the present example describes the use of k-nearest neighbor with majority vote as a classification algorithm, in principle the invention can use other supervised learning classification algorithms, such as margin-based classifiers, support vector machine, decision trees, etc., or a classifier configured as a multitude of filtered mini-classifiers combined using a regularization procedure, for example as generated using the procedure of FIG. 8.

The following clauses are offered as further descriptions of the invention disclosed in Example 6.

1. A classifier for use in guiding immune checkpoint inhibitor treatment for a cancer patient, comprising:

a memory storing a reference set of class-labelled mass spectral data obtained from blood-based samples of melanoma patients treated with an immune checkpoint inhibitor agent, the mass spectral data in the form of feature values for at least 50 mass spectral features, wherein the mass spectral features are identified with proteins circulating in serum associated with at least the following biological processes: (1) acute phase, (2) acute response, (3) complement system, and (4) acute inflammatory response; and a programmed computer implementing a classification algorithm on a set of mass spectral data including feature values for the multitude of mass spectral features obtained from a test blood-based sample and the reference set and generating a class label for the test blood-based sample.

2. The classifier of clause 1, wherein the mass spectral features include the features listed in one of Appendix A, Appendix B, Appendix C, or Appendix D.

3. The classifier of clause 1, wherein the mass spectral features further include features associated with the following additional biological processes: immune response type 2 and interleukin-10.

4. The classifier of clause 1, wherein the mass spectral data of the test blood-based sample and the reference set samples is acquired from at least 100,000 laser shots performed on the samples using MALDI-TOF mass spectrometry.

5. The classifier of clause 1, wherein the test blood-based sample is obtained from a melanoma patient.

6. The classifier of clause 1, wherein the immunotherapy comprises an antibody drug targeting programmed cell death 1 (PD-1).

7. The classifier of clause 1, wherein the immunotherapy comprises an antibody drug targeting CLTA4.

8. A method of training a classifier, comprising the steps of:

a) obtaining a development set of samples from a population of subjects and optionally a second independent set of samples from a similar, but not necessarily identical population of subjects;

b) conducting mass spectrometry on the development set of samples, and optionally on the second set of samples, and identifying mass spectral features present in the mass spectra of the set(s) of samples;

c) obtaining protein expression data from a large panel of proteins spanning biological functions of interest for each of the samples in the development set of samples or each of the samples in the second set of samples;

d) identifying statistically significant associations of one or more of the mass spectral features with sets of proteins grouped by their biological function; and e) with the aid of a computer, training a classifier on the development set of samples using the one or more mass spectral features identified in step d), the classifier in the form of a set of parameters which assigns a class label to a sample of the same type as the development set of samples in accordance with programmed instructions.

9. The method of clause 8, wherein step d) further comprises the step of performing a gene set enrichment analysis.

10. The method of clause 8 or clause 9, wherein the classifier is in the form of a filtered combination of mini-classifiers which have been subject to a regularization procedure.

11. The method of any one of clauses 8-10, wherein the samples in the development set, and optional second sample set, are blood-based samples.

12. The method of any one of clauses 8-11, wherein step b) comprises subjecting each of the samples in the sample set(s) to at least 100,000 laser shots in MALDI-TOF mass spectrometry.

13. The method of clause 8, wherein the classifier trained in step e) is deemed a first classifier, and the method further comprising repeating step e) for a second set of one or more mass spectral features associated with a different group of proteins associated with a different biological function, thereby training a second classifier.

14. The method of clause 13, further comprising the step of defining a final classifier from a combination of the first and second classifiers.

15. The method of clause 13, wherein the second classifier is used to further stratify members of a classification group assigned by the first classifier.

16. A computer configured as a classifier trained in accordance with any of clauses 8-15.

17. A method of testing a sample, comprising steps of:
a) training a classifier in accordance with any of clauses 8-11;
b) storing the parameters of the classifier including a feature table of the set of mass spectral features in a memory;
c) conducting mass spectrometry on a test sample; and
d) classifying the test sample with the trained classifier with the aid of the computer.

18. A method of testing a sample, comprising the steps of:
a) training a first classifier and a second classifier in accordance with clause 13;
b) storing the parameters of the first and second classifiers including a feature table of the sets of mass spectral features in a memory, and logical instructions for combining the first and second classifiers into a final classifier;
c) conducting mass spectrometry on a test sample; and
d) classifying the test sample with the final classifier defined in step b) with the aid of the computer.

19. A computer configured as a classifier comprising:
a memory storing a feature table in the form of intensity data for a set of mass spectral features obtained from a development set of biological samples, wherein the set of mass spectra features have been determined to have statistically significant associations with sets of proteins grouped by their biological function present in the biological sample;
a set of parameters defining a classifier including a classification algorithm operating on mass spectral data from a test sample and the feature table.

20. A classifier development system, comprising:
a mass spectrometer for conducting mass spectrometry on a development set of samples, and optionally a second independent set of samples, to generate mass spectral data, said data including a multitude of mass spectral features;
a platform for conducting a gene set enrichment analysis on the development set of samples, or optionally the second independent set of samples, and identifying statistically significant associations of one or more of the mass spectral features with sets of proteins grouped by their biological function; and
a computer programmed to train a classifier on the development set of samples using the one or more mass spectral features identified by the platform, the classifier in the form of a set of parameters which assigns a class label to a sample of the same type as the development set of samples in accordance with programmed instructions.

21. The system of clause 20, wherein the development set of samples, and optional second independent set of samples, are blood-based samples from humans.

22. The system of clause 21, wherein the blood-based samples for the development sample set are obtained from melanoma patients treated with an immunotherapy drug.

23. A classifier training method, comprising the steps of:
a) obtaining a development set of samples, and optionally a second independent sample set, from a population of subjects;

b) conducting mass spectrometry on the development set of samples and optional second set of samples, and identifying mass spectral features present in the mass spectra of the sets of samples;

c) obtaining protein expression data from a large panel of proteins spanning biological functions of interest for each of the samples in the development set of samples or each of the samples in the optional second independent sample set;

d) identifying statistically significant associations of one or more of the mass spectral features with sets of proteins grouped by their biological function;

e) with the aid of a computer, training a first classifier on samples from the development sample set using the one or more mass spectral features identified in step d), the classifier in the form of a set of parameters which assigns a class label to a sample of the same type as the development set of samples in accordance with programmed instructions, the classifier generating at least a first class label and a second class label, and f) with the aid of the computer, training a second classifier using a different set of one or more mass spectral features identified in step d) associated with a different set of proteins grouped by a different biological function, and g) classifying a sample with the first classifier wherein if the first classifier generates the first class label reporting the class label and if the first classifier generates the second class label using the second classifier to further stratify the sample.

24. A classifier training method comprising the steps of:

(a) performing both mass spectrometry and gene set enrichment analysis on a development set of blood-based samples or alternatively performing mass spectrometry on a development set of blood-based samples and a second independent set of blood-based samples and gene set enrichment analysis on the second set of samples;

(b) identifying a plurality of sets of mass spectral peaks which have statistically significant associations with sets of proteins grouped by their biological function;

(c) executing in a computer a classifier training procedure using one of the sets of peaks identified in step b) associated with a first protein functional group, the classifier training procedure classifying the mass spectral data of the development set of samples or a subset thereof.

25. The method of clause 24, further comprising repeating step c) for a second set of peaks identified in step b) associated with a second protein functional group different from the first protein functional group.

26. The method of clause 25, further comprising repeating step c) for a third set of peaks identified in step b) for a third protein functional group different from the first and second protein functional groups.

27. A method of testing a subject, comprising:

training a classifier in accordance with clause 24;

classifying a sample from the subject at a first point in time with the classifier;

classifying a second sample obtained from the subject at a later point in time with the classifier.

28. The method of clause 27, wherein the sample is provided by a patient enrolled in a clinical trial of a drug, wherein the first point in time is in advance of treatment by the drug, and wherein the later point of time is after treatment is commenced and the patient is still enrolled in the clinical trial.

29. A method of evaluation of a biological process within a human, comprising the steps of:

a) training a classifier in accordance with clause 24;

b) conducting mass spectrometry on a blood-based sample from the human;

c) classifying the sample using data obtained from step b) and the classifier trained in step a) and thereby obtaining a first class label for the sample;

d) conducting mass spectrometry on a second blood-based sample from the human taken at a later point in time from the time the sample of step b) was obtained;

e) classifying the second blood-based sample using data obtained from step 3) and the classifier trained in step a) and thereby obtaining a second class label;

f) comparing the first and second class labels, wherein the comparison provides information regarding a biological process occurring within the human.

30. A method of evaluation of a biological process within a human, comprising the steps of:

a) obtaining a development set of blood-based samples from a population of subjects and optionally a second independent set of blood-based samples from a similar, but not necessarily identical population of subjects;

b) conducting mass spectrometry on the development set of blood-based samples, and optionally on the second set of blood-based samples, and identifying mass spectral features present in the mass spectra of the set(s) of blood-based samples;

c) obtaining protein expression data from a large panel of proteins spanning biological functions of interest for each of the blood-based samples in the development set of samples or each of the samples in the second set of blood-based samples;

d) identifying statistically significant associations of one or more of the mass spectral features with sets of proteins grouped by their biological function;

e) conducting mass spectrometry on a blood-based sample from the human including obtaining values of features in the mass spectrum of one or more of the mass spectral features which were identified in step d).

31. The method of clause 30, further comprising the steps of obtaining a second blood-based sample from the human, and conducting mass spectrometry on the second blood-based sample from the human including obtaining values of features in the mass spectrum of one or more of the mass spectral features which were identified in step d).

32. The method of clause 31, wherein the human is enrolled in a clinical trial of a drug or combination of drugs.

33. The method of clause 30, wherein the human is enrolled in a clinical trial of a drug or combination of drugs, and wherein the method further comprises the steps of repeatedly obtaining blood-based samples from the human over the course of the human's enrollment in the clinical trial, and conducting mass spectrometry on the blood-based samples including obtaining values of features in the mass spectrum of one or more of the mass spectral features which were identified in step d) as with sets of proteins grouped by their biological function.

33. A method of monitoring a set of patients enrolled in a clinical trial, comprising performing the method of clause 30 on each of patients enrolled in the clinical trial.

34. The method of clause 33, further comprising repeatedly obtaining blood-based samples from the patients enrolled in the clinical trial over the course of the trial, and conducting mass spectrometry on the blood-based samples including obtaining values of features in the mass spectrum of one or more of the mass spectral features which were identified in step d) of clause 30 as being associated with sets of proteins grouped by their biological function.

Example 7

Longitudinal Studies

We conducted an analysis of samples collected during treatment of the nivolumab study (described in Example 1), and specifically at weeks 7 ("WK7") and weeks 13 ("WK13") of the trial. We explored how the classifications for a given patient changed over time, using the full-set classifier of Example 1 and the classifier of Example 2. We found that in some patients the labels changed e.g., an initial class label of Late at the commencement of treatment, followed by Late at week 7 and Early at week 13. As another example, some patients had the class label of Early at commencement of treatment, followed by Early at week 7 and Late at week 13.

Figure 30A:
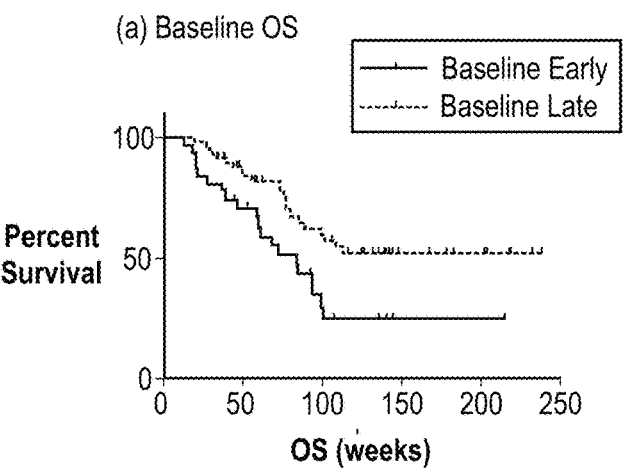
FIGS. 30A-30F are Kaplan-Meier plots of classifications by early and late groups produced by the full set classifier of Example 1 initially (advance of treatment, "baseline" herein) shown in FIGS. 30A and 30B, after 7 weeks of treatment (WK7) shown in FIGS. 30C and 30D, and after 13 weeks (WK13), shown in FIGS. 30E and 30F.
Figure 30B:
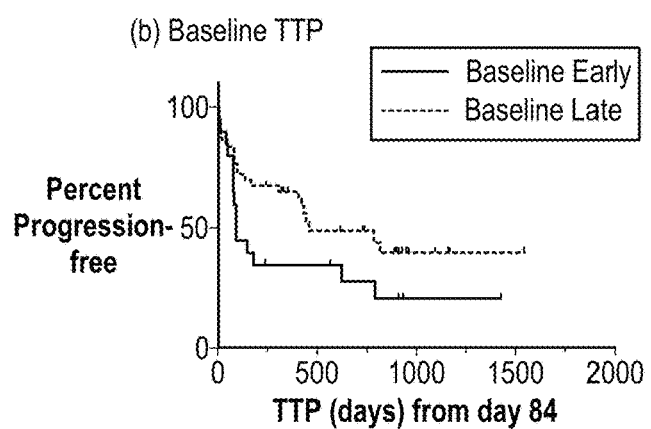
Figure 30C:
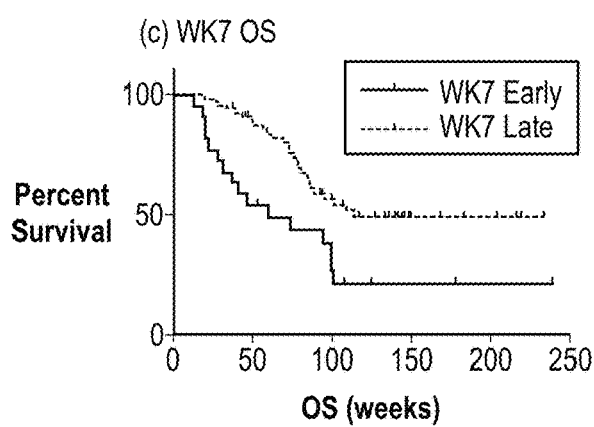
Figure 30D:
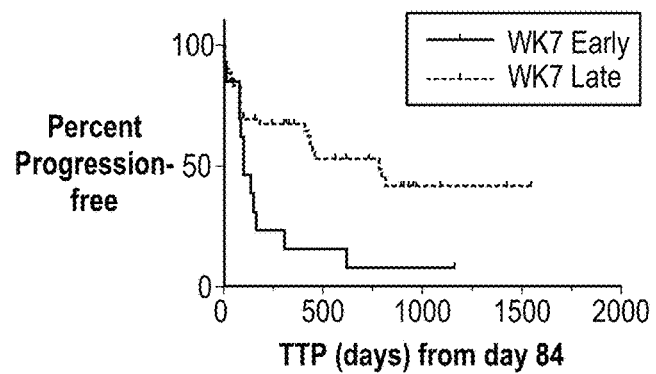
Figure 30E:
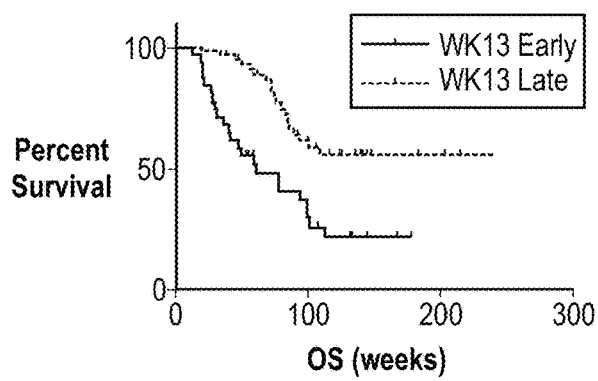
Figure 30F:
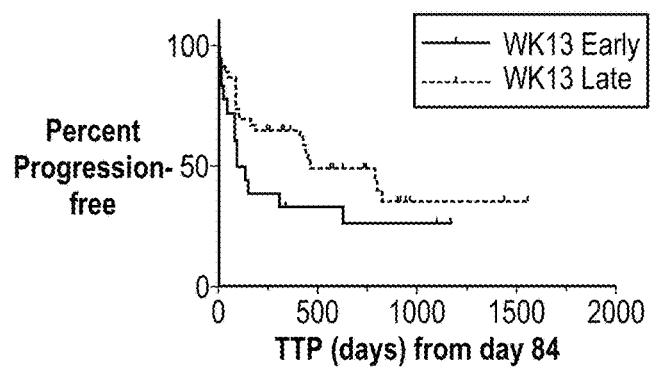

The results for the longitudinal studies using the Example 1 full-set classifier are shown in FIGS. 30A-30F. FIGS. 30A and 30B are Kaplan-Meier plots for overall survival (FIG. 30A) and time to progression (TTP)(FIG. 30B) for Early and Late groups as defined by the baseline classifications. FIGS. 30C and 30D are Kaplan-Meier plots for overall survival and TTP, respectively for Early and Late groups as defined by the week 7 classifications. FIGS. 30E and 30F are Kaplan-Meier plots for overall survival and TTP, respectively for Early and Late groups as defined by the week 13 classifications, for the 90 patients for which we had class labels at all three time points. Table 54 is a table of the survival analysis for the plots of FIG. 30A-30F.

TABLE 54

| | HR (95% CI) | log-rank p value | Medians |
|---|---|---|---|
| Baseline OS | 0.45 (0.21-0.78) | 0.008 | Early: 84 weeks, Late: Not reached |
| WK7 OS | 0.39 (0.14-0.64) | 0.002 | Early: 60 weeks, Late: 113 weeks |
| WK13 OS | 0.33 (0.14-0.54) | <0.001 | Early: 61 weeks, Late: Not reached |
| Baseline TTP | 0.53 (0.24-1.01) | 0.055 | Early: 91 days, Late: 457 days |
| WK7 TTP | 0.37 (0.10-0.61) | 0.003 | Early: 91 days, Late: 782 days |
| WK13 TTP | 0.58 (0.25-1.15) | 0.112 | Early: 112 days, Late: 457 days |

Table 55 shows the distribution of the classifications across the three time points for all samples.

TABLE 55

Distribution of classifications across the three time points: Baseline, WK 7, WK 13.

| Classifications | n |
|---|---|
| Early Early Early | 15 |
| Early Early — | 8 |
| Early — — | 8 |
| Early Early Late | 1 |
| Early Late Early | 1 |
| Early Late Late | 14 |
| Late Early Early | 3 |
| Late Early Late | 3 |
| Late Early — | 3 |
| Late Late Early | 12 |
| Late Late Late | 41 |
| Late Late — | 6 |
| Late — — | 4 |

Missing classifications are denoted by "—".

The majority of classifications remain the same across the available time points (82/119=69%). There are proportionately more changes from Early to Late than from Late to Early and most of the changes from Early to Late occurred at WK7 and remained Late at WK13. It is possible that this is due to the onset of the immunotherapy treatment. Half of the patients with a change from Late to Early at WK7 reverted back to Late at WK13, when the sample was available. Twelve (16%) of the patients classified as Late at WK7 changed to Early at WK13 and half of these progressed between 70 and 93 days, although three of the others experienced progression-free intervals in excess of 1000 days.

Figure 31A:
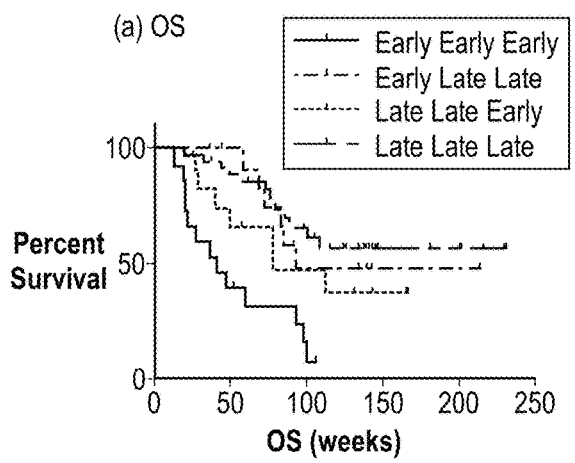
FIGS. 31A and 31B are Kaplan-Meier plots of overall survival and time to progression (TTP), respectively, grouped by the triplet of baseline, WK7, and WK13 classifications produced by the Example 1 full set classifier. There were too few patients with other label combinations for a meaningful analysis.
Figure 31B:
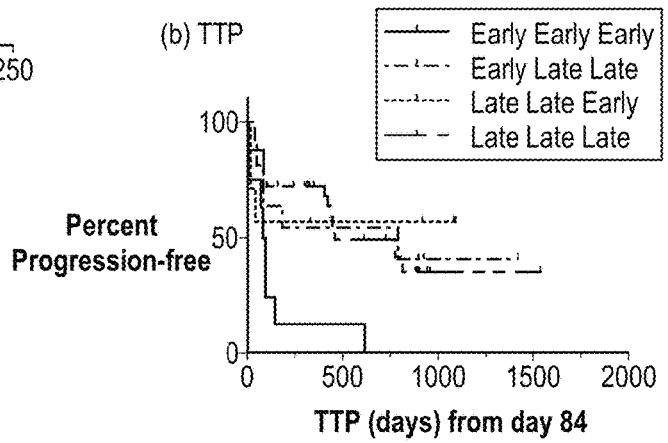

FIGS. 31A and 31B show Kaplan-Meier curves that plot the outcomes when the patients are grouped according to their triplet of baseline, WK7, and WK13 classifications. FIG. 31A is a plot of overall survival; FIG. 31B is a plot of time to progression. In these figures, the groups are labeled by the baseline classification first, the WK7 classification second, and the WK13 classification last (i.e. "Early Late Early" indicates baseline classification of Early, WK7 classification of Late, and WK13 classification of Early). Repeated Early classifications mark particularly poor OS and TTP and, at least in OS, having an Early label at WK 13 indicates poorer prognosis, even when the previous two classifications were Late. However, a Late label at WK13 and WK7 corresponded to better outcomes, even if the baseline classification had been Early. Note: there were too few patients with other label sequences for a meaningful analysis.

Table 56 shows the medians for the plots of FIGS. 31A and 31B.

TABLE 56

| | Median OS (weeks) | Median TTP (days) from day 84 |
|---|---|---|
| Early Early Early(N = 15) | 41 | 84 |
| Early Late Late (N = 14) | 94 | 789 |
| Late Late Early (N = 12) | 78 | Not reached |
| Late Late Late (N = 41) | Not reached | 457 |

We repeated this analysis for the classifications produced by the Example 2 classifier over time. The results are generally similar to those presented here for the Example 1 full set classifier. The majority of classifications remain the same across the available time points (59/90=66% across all three time points, 83/107=78% across the first two time points). There are proportionately more changes from Early to Late than from Late to Early and most of the changes from Early to Late occurred at WK7 and remained Late at WK13. It is possible that this is due to the onset of the immunotherapy treatment. Most of the patients with a change from Late to Early at WK7 reverted back to Late at WK13, when the sample was available.

Figure 32A:
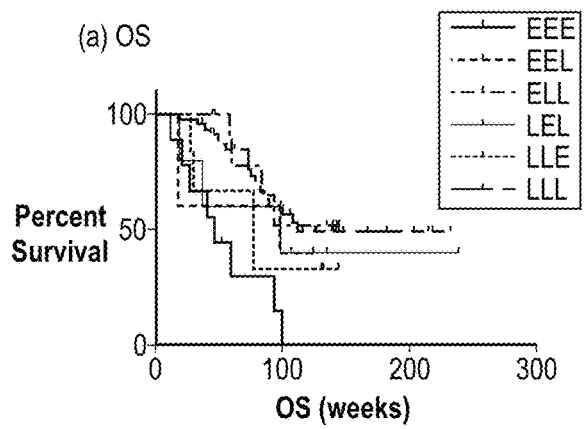
FIGS. 32A and 32B are Kaplan-Meier plots of overall survival and time to progression (TTP), respectively, which show the outcomes when the patients are grouped according to their triplet of baseline, WK7, and WK13 classifications produced by the Example 2 classifier. (E=Early, L=Late)
Figure 32B:
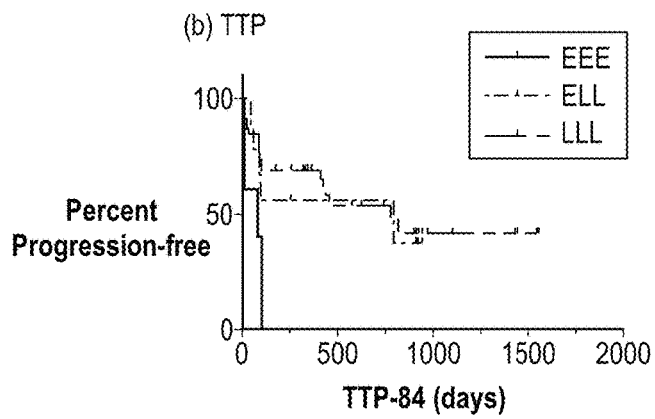

FIG. 32A and FIG. 32B are Kaplan-Meier plots which show the outcomes when the patients are grouped according to their triplet of baseline, WK7, and WK13 classifications produced by the Example 2 classifier. FIG. 32A is a plot of overall survival; FIG. 32B is a plot of time to progression. The groups are labeled by the baseline classification first, the WK7 classification second, and the WK13 classification last. Repeated Early classifications mark particularly poor OS and TTP, while repeated Late classifications indicate particularly good OS and TTP. Changing from Early to Late at WK7 and staying Late at WK13 leads to similar outcomes to having a Late classification at all three time points.

The statistics for FIG. 32A are set forth in table 57.

TABLE 57

Medians for the OS plots of FIG. 32A

| | Median OS (weeks) |
|---|---|
| Early Early Early(N = 9) | 47 |
| Early Early Late (N = 5) | 99 |
| Early Late Late (N = 11) | Not reached |
| Late Early Late (N = 5) | 99 |
| Late Late Early (N = 6) | 78 |
| Late Late Late (N = 50) | 113 |

The statistics for FIG. 32B are set forth in table 58.

TABLE 58

Medians for the TTP plots of FIG. 32B

| | Median TTP (days) from day 84 |
|---|---|
| Early Early Early(N = 5) | 78 |
| Early Late Late (N = 9) | 789 |
| Late Late Late (N = 38) | 782 |

We have some theories for why the class labels changed over time. It is possible that the class label changes were induced by biological changes in the patients caused by the commencement of the nivolumab therapy. It is possible that the changes were due to the influence on tumor size on classification labels (see the discussion below), and large tumor shrinkage that some patients achieve. Whatever the origin of the changes, we do observe that most patients keep their baseline label. Of those patients whose class label changes over time, we observe that when the label changes from Early at baseline to Late later on (week 7 or 13) these patients have relatively good outcome, similar to those patients having a Late baseline class label. Accordingly, in one embodiment, the test of Example 1 or 2 can be conducted periodically over the course of treatment, e.g. every 4, 6 or 8 weeks. By comparing the results and the progression of class labels over time during treatment it may be possible to monitor the therapeutic effect of the nivolumab treatment, or predict the patient's prognosis or overall survival. This treatment monitoring can be direct, i.e., direct changing of some immune status measured by the class label, or indirect, i.e., the change in class label is a proxy or approximation of measurement of tumor shrinkage/expansion. How often one would want to conduct the test and determine the patient's class label during the course of treatment might also depend on whether the change in class label is due to direct action of the drug on the patient's immune system or whether one has to wait for an indirect effect of the treatment on shrinkage (or lack thereof) of the tumor.

A change of the patient's label over time from Late to Early may be an early indication of lack of efficacy of the drug. This lack of efficacy could be optionally confirmed by conducting radiological studies of the patient, e.g., CT scan to determine tumor size and change as compared to baseline. Potentially, if the changes from Late to Early are due to the drug changing the immune state of the patient directly and if this happens in a relatively short space of time (say 4 weeks or so) the baseline Late label could be an indication to commence treatment with nivolumab and the subsequent Early label could be used to either stop treatment, change treatment to a different treatment (such as combination nivolumab and ipilimumab) or take other action. Another possibility would be to conduct a monitoring test periodically during the first few weeks of treatment and use the class labels to indicate how long the patient needs to take the nivolumab. Currently, patients take the drug until disease progression. This can be a long time and the drug is very expensive. So, if there is a way to tell within the first few months whether a patient could stop nivolumab treatment without detriment to outcome it could result in some savings to health care costs. In any event, in one possible embodiment, the tests of Examples 1 and 2 are conducted periodically over the course of treatment. The class labels are compared over the course of treatment. The status of the class label over the course of treatment can be used to guide treatment or predict the patient's prognosis, either maintain the treatment, stop the treatment, or change the treatment in some fashion such as by combining nivolumab with another drug in a combination treatment regime.

In one specific example of how the monitoring tests can be done, the initial class label is determined in accordance with Example 1 or Example 2 using the system of FIG. 15 (described above), at least once again within the first four weeks of treatment, and at least once again after the first four weeks of treatment.

The following clauses are offered as further descriptions of the inventions described in Example 7.

1. Classifying a patient sample initially in accordance with the methodology of Example 1, 2, 3, 4, or 6 and repeatedly over the course of treatment or over the course of the patient enrollment in a clinical trial obtaining a sample from the patient, conducting mass spectrometry of the sample, and classifying the sample with the classifier and thus generating a class label repeatedly.

2. The method of clause 1, further comprising the step of determining if the class label changes over the course of treatment and using the change in class label to guide treatment of the patient.

3. The method of clause 1, further comprising the step of determining if the class label does not change over the course of treatment and using the absence of change in the class label to guide treatment of the patient.

4. The method of clause 1, wherein the repeatedly conducting step is performed initially in advance of treatment, at least once again within the first four weeks of treatment, and at least once again after the first four weeks of treatment.

5. As indicated in Example 6, a method of determining the association between a biological function and mass spectral features obtained from a blood-based sample (e.g., using GSEA), by repeatedly obtaining blood-based samples from a patient and performing mass spectrometry on the samples, and analyzing the mass spectral data from the samples over the course of time to observe or understand changes in the biological function over time, for example up regulation or down regulation of particular proteins associated with the biological functions, e.g., over the course of treatment or over the course of a patient participation in a clinical trial.

6. The invention of clause 5, further including the step of performing a classification of each of the blood-based samples using a computer-implemented classifier trained from a development set of samples and a set of mass spectrometry features associated with the biological function.

Example 8

Classifiers Trained from Tumor Size Information

We have discovered a method for generating a classifier that takes into account tumor size at baseline which improves the classifier performance. This method and how it is used in practice will be explained in this section. Note that the studies described below used the same 119 samples of Example 1, tumor size data was provided for all patients, and we used the same sample feature table data (mass spectral data for features in Appendix A) as we did for Example 1. The only difference was that feature m/z 9109 was dropped from the feature table as it has possible reproducibility issues and little value for classification.

Initial attempts at taking account of tumor size in the assignment of a prognostic label for melanoma patients treated with nivolumab indicated that for patients who had available tumor size follow data on treatment, there was a definite influence of tumor size at baseline on the classification we should assign to the samples in the development set. We noticed this by taking the data of the 104 patients for whom we initially had baseline and follow up tumor size data and splitting the set into two: one half with smaller tumors at baseline and the other half with larger tumors at baseline. We then used the classifier development method of FIG. 8 as we had done to make the classifier of Example 1, and made separate classifiers, one for patients with smaller tumors and one for patients with larger tumors. We then proceeded to classify the samples in the development set using either the large or small tumor classifiers, depending in the size of the tumor at baseline.

Figure 33A:
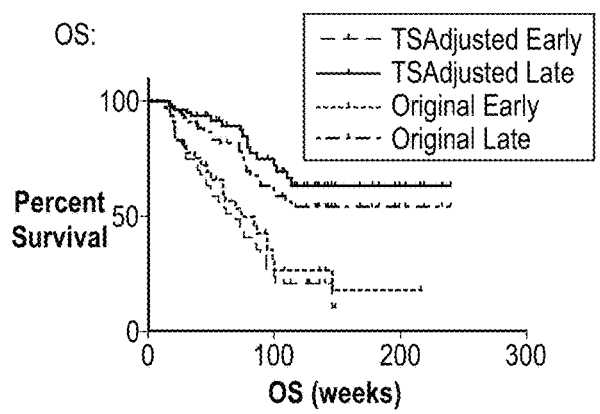
FIGS. 33A and 33B are Kaplan-Meier plots of a subset of 104 patients of the development sample set of Example 1, showing the Early and Late labeled patients from the original classifications produced by the Example 1 full set classifier ("Original") and the classifications produced by new "large" and "small" tumor classifiers ("TSAdjusted").
Figure 33B:
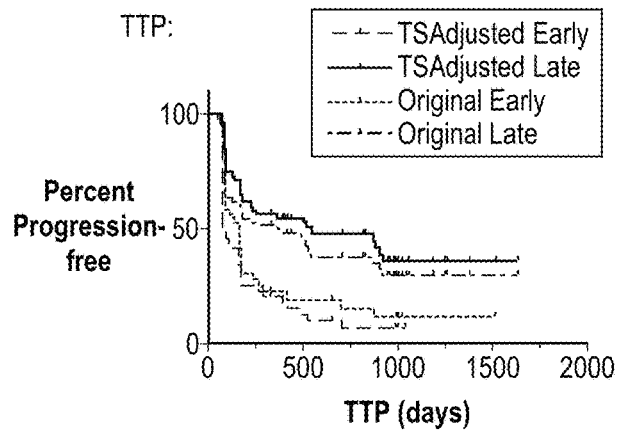

We noticed that some of the smaller tumors classified by the Example 1 full-set classifier as Late now got an Early classification and some of the larger tumors that had been classified by the Example 1 full set classifier as Early were now classified as Late. In particular, some of the small tumors that previously were classified as Late and which had demonstrated huge tumor growth on treatment were now classified as Early and some of the large tumors that previously had been classified as Early and which had shrunk considerably in the first 26 weeks of treatment were now classified as Late. Plotting the Kaplan-Meier plots for this subset of 104 patients, taking the classifications from the two separate classifiers, as defined by pretreatment tumor size, increased the hazard ratio between the new Early and Late groups, as shown in FIGS. 33A and 33B. In these figures, "Original Early/Late" are the classification groups defined for the 104 patient subset using Example 1 full-set classifier, approach 1, and "TSAdjusted Early/Late" are the classifications generated by the new classifiers for the smaller and larger tumors, each applied to the samples with smaller and larger tumors, respectively.

The results of the survival analysis comparison between the Early and Late groups adjusted for tumor size are given in table 58.

improve by taking tumor size into account when designing and generating the classifier of Example 1.

We then obtained baseline tumor size data for the remaining 15 samples. When we applied the new classifiers to these samples (depending on whether they were in the small tumor size group or large tumor size group), and added these patients into the Kaplan-Meier analysis, we noticed that the improved separation almost disappeared. Apparently, we were doing a worse job of classifying these 15 samples than we had done before. We also tried to carry out the same approach as above training on all 119 samples, but again the result was more or less no improvement from our initial classification. These observations led us to the conclusion that these 15 patients whom we had initially omitted were essentially different—indeed they were omitted because they did not reach a follow up tumor size assessment, having very early progression (all 15 patients progressed before 78 days). We hypothesized that for patients who progress very quickly, tumor size plays a much weaker role than it does for the patients who remain progression free for a longer period of time. To try to keep the improvement noted above for the 104 patients reaching the 26 week assessment and classify the other 15 samples correctly, we decided to first find a classifier to remove the patients progressing the fastest, and then repeat classifier development by tumor size for the remaining samples. That is, we wanted to remove from classifier development those samples with the patients progressing fastest, and then conduct a new classifier development taking into account tumor size, and generate a "small tumor" classifier and a "large tumor" classifier. These new classifiers are designed for later use in testing a patient for immune checkpoint inhibitor benefit, with the additional input at the time of testing data on whether the patient has a "large" or "small" tumor and then using the appropriate large or small tumor classifier. It will be apparent from the following discussion that the methodology we describe below may be useful generally in generating "small tumor" and "large tumor" classifiers in the oncology setting.

In order to remove the patients progressing the fastest, we returned to the full set Example 1 classifier. Using this classifier, we divided the samples in the development set into Early (N=47) and Late (N=72) groups. We took the Early group of 47 samples and used the same methodology of FIG. 8 as detailed above, using the Early group of 47 samples as the input development sample set. In performing the new classifier development we performed label flips for misclassified samples in an iterative manner until convergence to make a classifier that splits these 47 samples into two sub-groups, which we called "Earlier" and "Later". The initial class definitions (FIG. 8, step 102) were based on

TABLE 58

Performance of classifications obtained for the subset of 104 patients when adjusted for tumor size

|  | # Early/# Late | HR OS (95% CI) | Log-rank p | Median OS Earlier/Later (weeks) | HR TTP (95% CI) | Log-rank p | Median TTP Earlier/Later (days) |
|---|---|---|---|---|---|---|---|
| TS Adjusted | 44/60 | 0.24 (0.11-0.37) | <0.001 | 69/not reached | 0.36 (0.18-0.49) | <0.001 | 88/541 |
| Original | 36/68 | 0.42 (0.20-0.68) | 0.002 | 73/not reached | 0.57 (0.32-0.88) | 0.015 | 157/362 |

These results indicated to us that we were not making optimal decisions on classification for some of the samples with the smallest and largest tumors, and that we could shorter and longer OS and we used filtering (FIG. 8 step 126) based on hazard ratio for OS between the classification groups of the training set. This produced a classifier that split the 47 Early patients into two groups with better ("Later") and worse ("Earlier") outcomes.

Figure 34A:
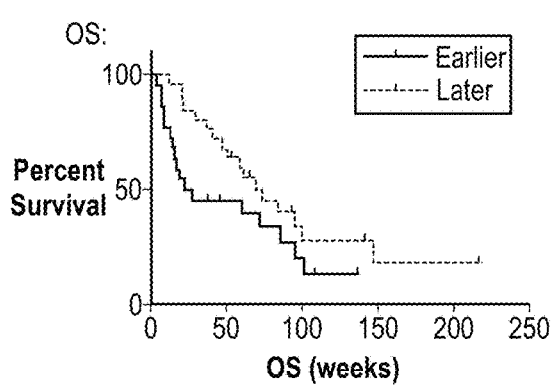
FIGS. 34A and 34B are Kaplan-Meier plots of overall survival and time to progression (TTP), respectively, of 47 Early patients (classified according to the Example 1 full-set Approach 1 classifier) classified into Earlier and Later groups by a classifier using these 47 samples as its development set. The patients in the Earlier classification group are removed from the development sample set in generating classifiers which take into account tumor size.
Figure 34B:
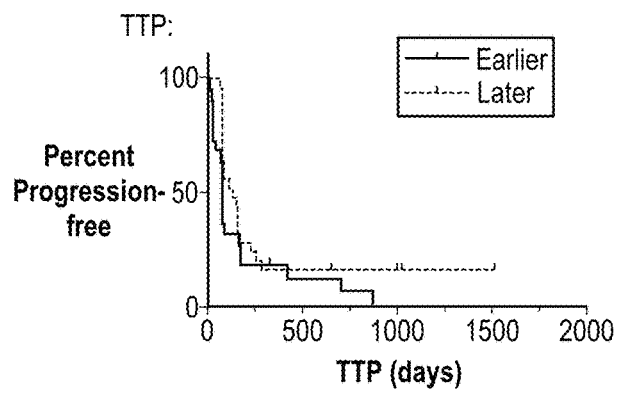

The Kaplan-Meier plots for OS and TTP for the groups generated by this classifier are shown in FIGS. 34A and 34B. Twenty two patients were assigned to the Earlier group and 25 to the Later group. The results of the survival analysis comparison between the Earlier and Later groups are given in table 59.

TABLE 59

Performance of classifier developed on only full-set classifier "Early" samples

| # Earlier/# Later | HR OS (95% CI) | Log-rank p | Median OS Earlier/Later (weeks) | HR TTP (95% CI) | Log-rank p | Median TTP Earlier/Later (days) |
|---|---|---|---|---|---|---|
| 22/25 | 0.57 (0.27-1.10) | 0.094 | 26/73 | 0.60 (0.31-1.07) | 0.085 | 77/132 |

It is apparent that the Earlier group has particularly poor outcomes in terms of TTP and OS. We decided to remove these 22 samples from further analysis and leave them their already assigned "Early" classification. We then conducted two new classifier developments, again using the procedure of FIG. 8, one for large tumors and one for small tumors, using the remaining 97 samples of the initial development sample set. This set of 97 samples was split into two groups depending on tumor size: the smallest 49 samples were used to generate one classifier (small tumor classifier) and the largest 48 samples were used to generate another classifier (large tumor classifier). Both classifiers were trained as before using the procedure of FIG. 8 in an iterative manner, with label flips for misclassified samples until convergence, with the initial class assignments of "Early" and "Late" (FIG. 8, step 102) defined based on duration of OS.

Figure 35A:
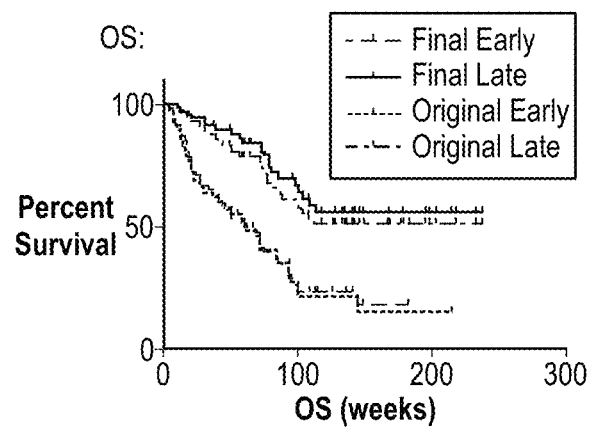
FIGS. 35A and 35B are Kaplan-Meier plots of all 119 samples in the original development set of Example 1, with the large tumors classified by a classifier developed using only large tumors, the small tumors classified by a classifier developed using only small tumors and early progressing patients (the Early/Earlier patients of FIG. 34) classified as Early (their original Example 1 full-set Approach 1 classifications). These groups are labeled as "Final" and compared with the groups produced by the Example 1 full-set classifier ("Original").
Figure 35B:
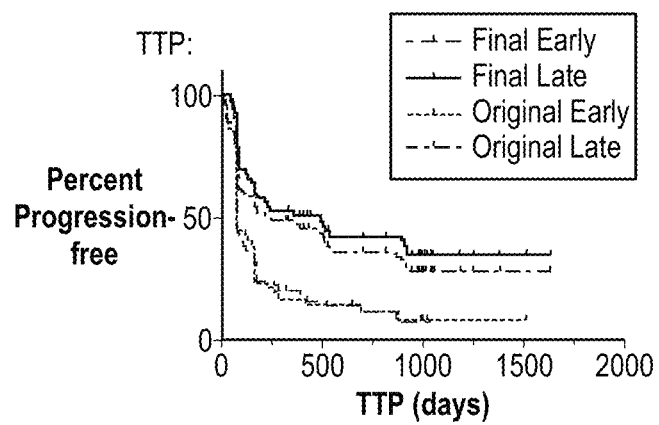
Figure 36A:
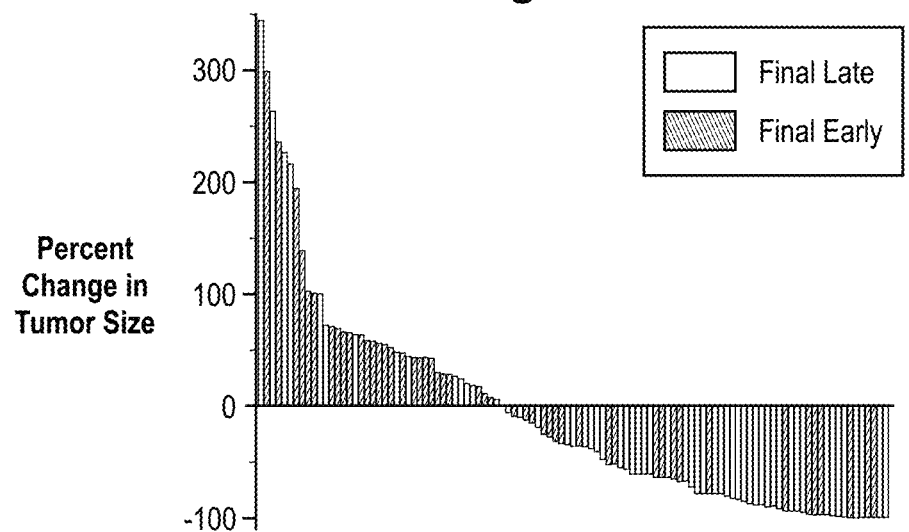
FIGS. 36A and 36B are waterfall plots showing the class identifications for melanoma patients who had either increasing or decreasing tumor size over the course of treatment with nivolumab.
Figure 36B:
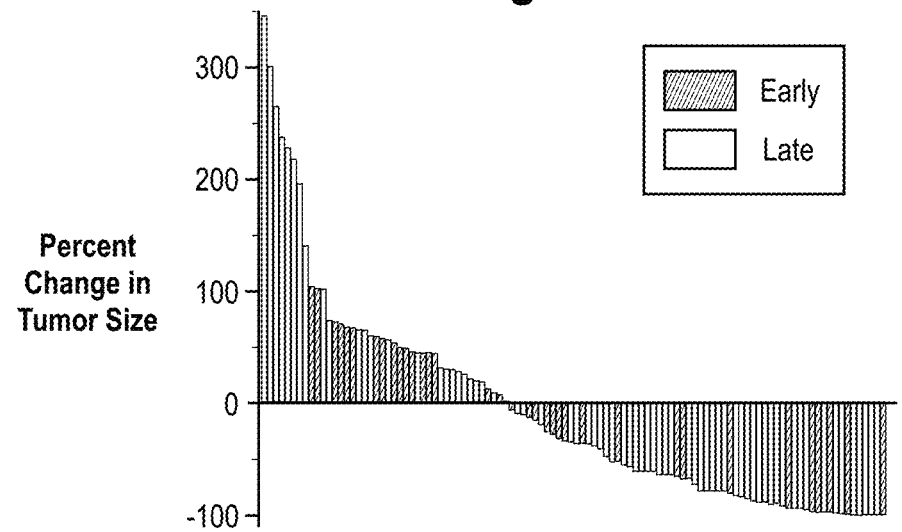

When the data for the patients with larger tumors, patients with smaller tumors and quickly progressing patients (Early/Earlier classification) were combined, the Kaplan-Meier plots of FIGS. 35A and 35B were obtained. The results of the survival analysis comparison between the Early and Late groups are given in table 60.

known as "waterfall plots," are shown in FIGS. 36A and 36B. The waterfall plots show the percentage reduction in tumor size for the 104 patients assessable at the 26 week evaluation. FIG. 36A is the plot for the "final" classifiers (i.e., taking into account tumor size and using either the large or small tumor classifier). FIG. 36B is the plot for the original Example 1 full-set classifier.

What is noticeable from comparing the plots of FIGS. 36A and 36B is that the new final classifications using tumor size classifiers is considerably better at classifying the patients with tumor growth as Early. That is, the majority of patients having significant tumor growth over the course of treatment were classified as Early when the tumor size classifiers were used, as would be expected given the clinical meaning the Early class label. Moreover, the majority of the patients with significantly diminished tumor size over the course of treatment were classified as Late, which is also expected. However, comparing the right hand side of FIGS. 36A and 36B, the new classifiers using tumor size data performed slightly worse in identifying the patients with tumor shrinkage as Late as compared to the Example 1 full set classifier.

Figure 37:
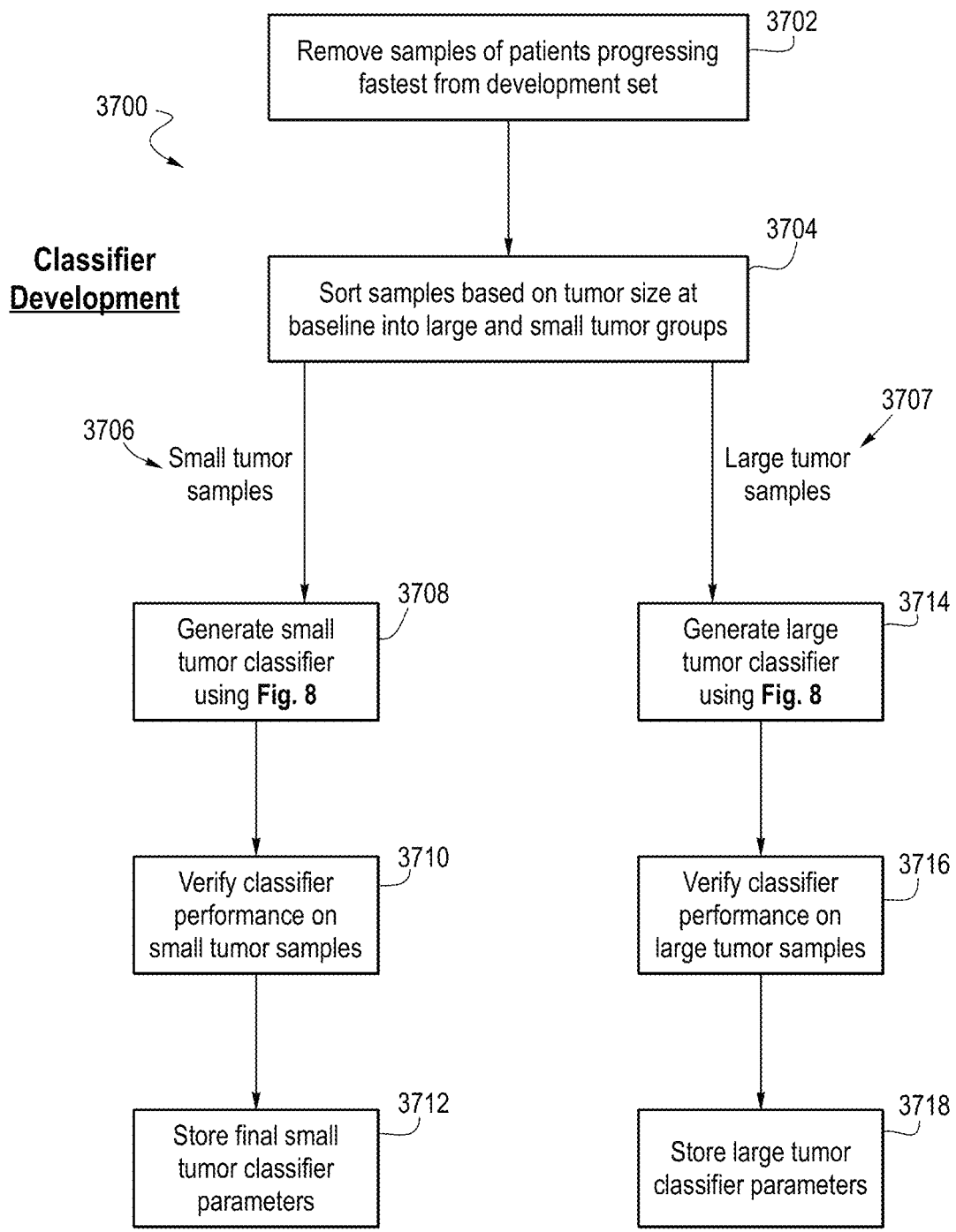
FIG. 37 is a flow-chart showing the process of development of small and large tumor classifiers from a development sample set.

A preferred method for generating classifiers using tumor size data in a development sample set can be summarized and explained in flow chart form. Referring now to FIG. 37, the classifier development process is shown at 3700 and includes a first step 3702 of removing the samples of patients from the development sample set who progressed fastest

TABLE 60

Performance of classifications obtained for all 119 patients when adjusted for tumor size, first removing the 22 patients classified as having especially poor outcomes

| | # Early/# Late | HR OS (95% CI) | Log-rank p | Median OS Earlier/Later (weeks) | HR TTP (95% CI) | Log-rank p | Median TTP Earlier/Later (days) |
|---|---|---|---|---|---|---|---|
| Final | 60/59 | 0.32 (0.19-0.51) | <0.001 | 61/not reached | 0.40 (0.24-0.57) | <0.001 | 83/490 |
| Original | 47/72 | 0.38 (0.19-0.55) | 0.002 | 61/not reached | 0.50 (0.29-0.71) | 0.001 | 84/230 |

The final Late group has slightly better outcomes than the original Late group and is composed of significantly fewer patients. Outcomes in the final Early group are quite similar to those of the original Early group, although its size has increased by 28%. The hazard ratios between the groups are slightly better for both endpoints than they were for the original Example 1 classifications.

Investigation of classifier performance in this context can also be made by plotting the percent change in tumor size from baseline to a later point in time (e.g., 26 weeks after commencement of treatment) for each member of the development set, and indicating in such a plot whether the data points represent Early or Late classified patients. Such plots, after commencement of treatment. This step 3702 is shown in detail in FIG. 39 and will be explained in detail below.

At step 3704, once these samples are removed from the development set, the samples remaining in the development set are sorted based on tumor size at baseline into small tumor and large tumor groups, 3706 and 3707, respectively.

At step 3708, the small tumor samples (associated mass spectral data, feature values of features listed in Appendix A) are used as the development set for generating a small tumor classifier using the procedure of FIG. 8.

At step 3710, the performance of the classifier developed at step 3708 is then verified by using the classifier to classify the small tumor samples 3706.

At step 3712, the parameters of the small tumor classifier generated at step 3708 are then stored for later use in classifying test samples for patients with small tumors. These parameters include, inter alia, the data identifying the small tumor sample mass spectra data sets forming the reference set for classification; the feature values at pre-defined mass spectral features for the reference set; identification and kNN parameters of the mini-classifiers passing filtering; logistic regression weights derived from the combination of mini-classifiers with drop-out regularization; and the definition of the final classifier from the master classifiers generated during the performance of FIG. 8 on the small tumor development sample set (FIG. 8B, step 150).

The steps 3714, 3716 and 3718 are performed on the large tumor samples 3707, exactly the same as for steps 3708, 3710 and 3712 described above.

Figure 38:
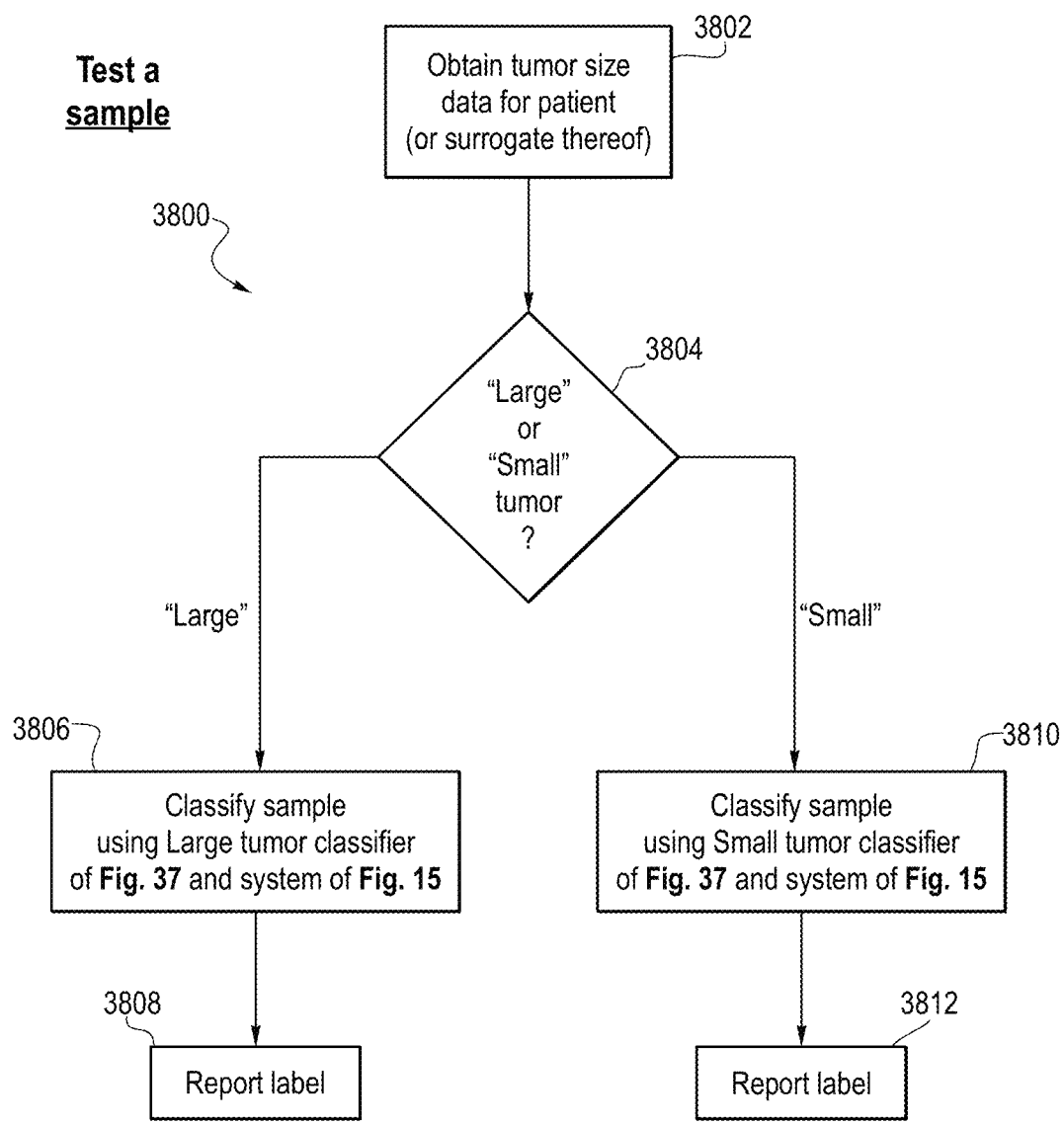
FIG. 38 is a flow-chart showing how either the large and small tumor classifier generated in accordance with FIG. 37 is used to test a sample of a cancer patient, depending on whether the patient has a large or small tumor.

The manner of use of the classifiers generated in accordance with FIG. 37 is shown in FIG. 38. The classifiers are used for conducting a test of blood-based sample of a melanoma or other cancer patient to determine whether they are likely or not to obtain benefit from an immune checkpoint inhibitor in treatment of cancer, such as anti-PD-1 antibody or anti-CTLA4 antibody. This process is shown at 3800. At step 3802, tumor size data for the patient is obtained. Such data could be obtained from CT or PET scan data of the patient. The tumor size data ideally will accompany a blood-based sample provided for testing. Alternatively, some surrogate or proxy for tumor size data could be used (for example, some combination of mass spectral features alone or combined with other serum proteins measured by alternative methods, such as ELISA). At step 3804, the determination is made as to whether the tumor is "large" or "small", again using this data. The criteria for this determination could take the form of criteria used to sort samples in step 3704 of FIG. 37.

If the tumor size is "small", then at step 3806 the sample is classified using the small tumor classifier generated and stored at step 3712 of FIG. 37, using the system of FIG. 15. That is, the blood-based sample is subject to mass spectrometry, and the mass spectrometry data is subject to the steps shown in FIG. 15 with the classifier used for classification being the small tumor classifier generated in FIG. 37. At step 3808 the class label Early or Late is assigned to the sample. If the patient is identified as Late, the patient is predicted to obtain benefit from the immune checkpoint inhibitor and have improved overall survival as compared to a class label of Early.

If at step 3804 the tumor size is "large", the large tumor classifier of FIG. 37 is then used to classify the blood-based sample of the patient using the system of FIG. 15. At step 3812 the class label Early or Late from the classifier is reported. The Early and Late labels have the same meaning as explained in the previous paragraph.

Figure 39:
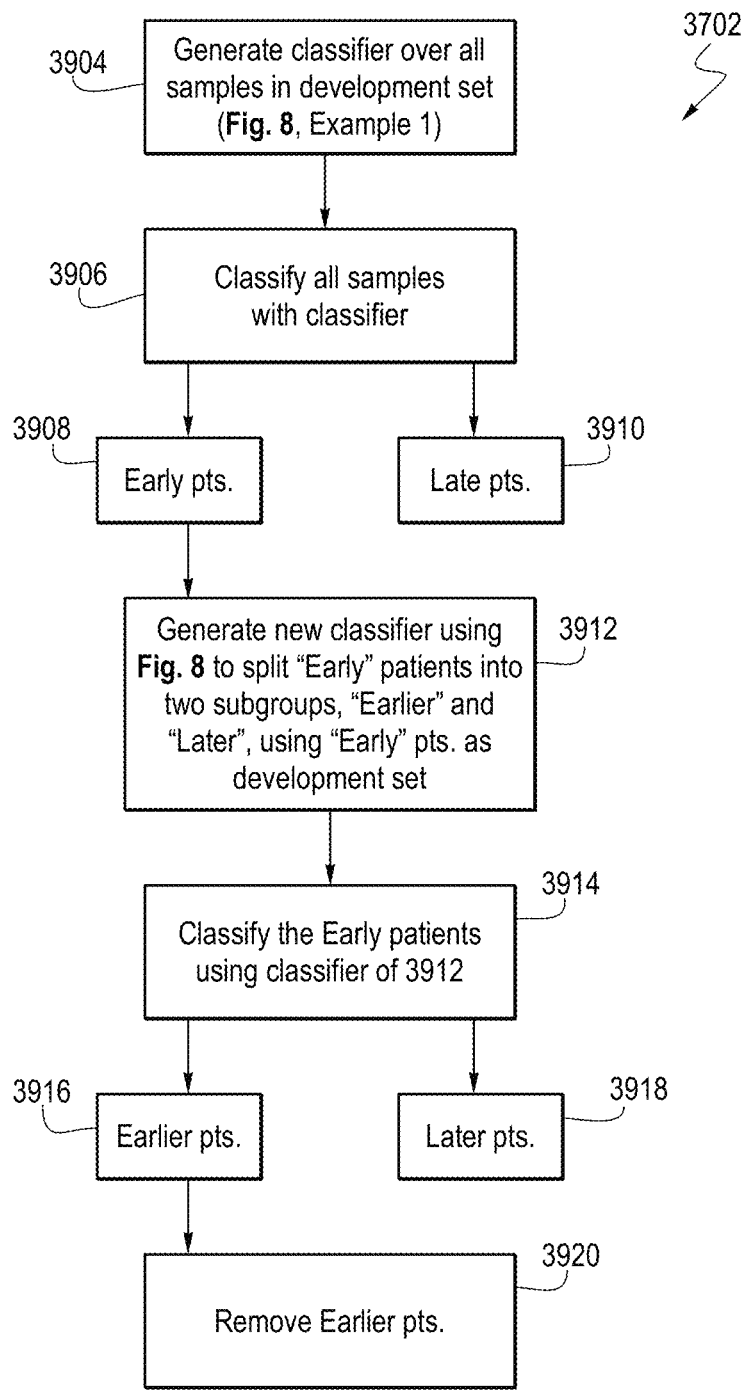
FIG. 39 is a flow-chart showing one method for removing from the development set the fast progressing samples, step 3702 of FIG. 37.

FIG. 39 is a flow chart showing a procedure 3702 of removing the fastest progressing samples from a development set as a preliminary step in generating the large and small tumor classifiers of FIG. 37. At step 3904, a classifier is generated over all the samples in a development sample set using the procedure of FIG. 8. An example of this is the full set classifier of Example 1, described above.

At step 3906, this classifier is then used to classify all the samples in the development sample set. Each member of the development sample set is then classified as either Early or Late. The Early and Late patients are grouped into two groups shown at 3908 and 3910.

At step 3912, a new classifier is generated using the process of FIG. 8, with the Early patient group 3908 forming the development sample set of FIG. 8. The process FIG. 8 is performed in an effort to split the Early patients into Earlier and Later sub-groups. An example of this was described at the beginning of this section of the document and the results shown in FIGS. 34A and 34B. At step 3914, after the classifier of 3912 has been generated it is applied to all the Early samples (3908) and the resulting classifications of the Early patients into "Earlier" and "Later" sub-groups 3916 and 3918 is performed. The Earlier patients 3916 are then identified and removed from the development sample set. The process of FIG. 37 then proceeds at step 3704 with the development sample set minus this "Earlier" sub-group of patients to produce the small tumor and large tumor classifiers.

From the above discussion, it will be apparent that one aspect of the disclosed inventions is a machine (e.g., FIG. 15, 1510) programmed as a classifier for classifying a cancer patient as likely or not likely to benefit from an immune checkpoint inhibitor. The machine 1510 includes a memory 1514 storing parameters of a small tumor classifier and a large tumor classifier, and a reference set of class-labeled mass spectral data for each of the small tumor classifier and the large tumor classifier. The reference sets are obtained from blood-based samples of other cancer patients treated with the immune checkpoint inhibitor, as explained above. The machine further includes a processing unit (FIG. 15, 1512) executing a classifier defined by the parameters stored in the memory. In a preferred embodiment, the parameters defining the classifier for each of the small tumor classifier and large tumor classifier include parameters defining a classifier configured as a combination of filtered mini-classifiers with drop out regularization, e.g., resulting from the procedure of FIG. 8 steps 102-150. In one possible embodiment the mass spectral data is obtained from performing MALDI-TOF mass spectrometry on the blood-based samples and wherein each of the samples is subject to at least 100,000 laser shots, e.g. using the so-called Deep MALDI methods described in Example 1.

In another aspect, a method of generating a classifier for classifying cancer patients as likely or not likely to benefit from a drug has been described, comprising the steps of: 1) obtaining a development sample set (FIG. 8, 100) in the form of a multitude of blood-based samples; 2) conducting mass spectrometry on the development sample set (see Example 1); 3) removing from the development sample set samples from patients with a relatively fast progression of disease after commencement of treatment by the drug; (step 3702, FIG. 37) 4) sorting the remaining samples based on tumor size at baseline (commencement of treatment) into large and small tumor groups; (FIG. 37 step 3704); 5) for the small tumor group: a) generating a small tumor classifier using the small tumor group as an input development sample set in a classifier development exercise; (FIG. 37, step 3708) b) verifying the performance of the small tumor classifier in classification of the members of the small tumor sample group; (FIG. 37, step 3710) and c) storing the parameters of the small tumor classifier; (FIG. 37, step 3712); and 6) for the large tumor group: a) generating a large tumor classifier using the large tumor group as an input development sample set in a classifier development exercise; (FIG. 37 step 3714) b) verifying the performance of the large tumor classifier in classification of the members of the large tumor sample group; (FIG. 37 step 3716) and c) storing the parameters of the large tumor classifier (FIG. 37, 3718).

Preferably, as explained above in this section, the classifier development exercise of step 5a) and step 6a) takes the form of implementing the procedure of FIG. 8 steps 102-150.

In still another aspect, a method of classifying a cancer patient as likely or not likely to benefit from a drug is contemplated. The method includes the steps of a) determining whether the patient has a large or small tumor; (FIG. 38, 3802); b) if the patient has a large tumor, using the large tumor classifier generated in the method described above to classify a blood-based sample of the patient as likely or not likely to benefit from the drug, (FIG. 38, 3806) and c) if the patient has a small tumor, using the small tumor classifier generated as described above to classify a blood-based sample of the patient as likely or not likely to benefit from the drug.

In still another aspect, a method of classifying a cancer patient as likely or not likely to benefit from a drug is contemplated. The method includes the step of a) conducting two classifier generation exercises on a development set of samples which are sorted into small tumor and large tumor groups, resulting in the generation of a large tumor classifier and a small tumor classifier and storing the large tumor and small tumor classifiers in a programmed computer (FIG. 37). The development set of samples are blood-based samples which have been subject to mass spectrometry. The method includes a step b) of determining whether the patient has a large or small tumor, either directly from tumor measurement data or indirectly using a surrogate for tumor measurement data (FIG. 38 step 3084). The method further includes a step c) of conducting mass spectrometry on the blood-based sample of the cancer patient (FIG. 15, 1506, 1508). If the patient has a large tumor, the method includes a step of using the large tumor classifier generated in step a) and the mass spectrometry data obtained in step c) with the programmed computer to classify the patient as likely or not likely to benefit from the drug, and if the patient has a small tumor, using the small tumor classifier generated in step a) and the mass spectrometry data obtained in step c) with the programmed computer to classify the patient as likely or not likely to benefit from the drug.

In one example, the cancer patient is a melanoma patient, and the drug is an antibody drug targeting programmed cell death 1 (PD-1). However the methods described in FIGS. 37-39 are applicable to other types of cancer patients and drugs.

The following clauses are offered as further descriptions of the disclosed inventions of Example 8.

1. A machine programmed as a classifier for classifying a cancer patient as likely or not likely to benefit from an immune checkpoint inhibitor comprising;
a memory storing parameters of a small tumor classifier and a large tumor classifier, a reference set of class-labeled mass spectral data for each of the small tumor classifier and the large tumor classifier, the reference sets obtained from blood-based samples of other cancer patients treated with the immune checkpoint inhibitor; and
a processing unit executing either the large tumor classifier or the small tumor classifier defined by the parameters stored in the memory to classify mass spectral data of a blood-based sample of the cancer patient and assign a class label to the sample, the class label indicating whether or not the patient is likely to benefit from the immune checkpoint inhibitor.

2. The machine of clause 1, wherein the parameters defining the classifier for each of the small tumor classifier and large tumor classifier include parameters defining a classifier configured as a combination of mini-classifiers with drop out regularization.

3. The machine of clause 1 or clause 2, wherein the mass spectral data is obtained from performing MALDI-TOF mass spectrometry on the blood-based samples and wherein each of the samples is subject to at least 100,000 laser shots.

4. A method of generating a classifier for classifying cancer patients as likely or not likely to benefit from a drug, comprising the steps of:
1) obtaining a development sample set in the form of a multitude of blood-based samples;
2) conducting mass spectrometry on the development sample set;
3) removing from the development sample set samples from patients with a relatively fast progression of disease after commencement of treatment by the drug; and with a computer:
4) sorting the remaining samples based on tumor size at baseline (commencement of treatment) into large and small tumor groups;
5) for the small tumor group:
a) generating a small tumor classifier using the small tumor group as an input development sample set in a classifier development exercise;
b) verifying the performance of the small tumor classifier in classification of the members of the small tumor sample group; and
c) storing the parameters of the small tumor classifier; and
6) for the large tumor group:
a) generating a large tumor classifier using the large tumor group as an input development sample set in a classifier development exercise;
b) verifying the performance of the large tumor classifier in classification of the members of the large tumor sample group; and
c) storing the parameters of the large tumor classifier.

5. The method of clause 4, wherein the classifier development exercise of step 5a) and step 6a) comprises the procedure of FIG. 8 steps 102-150.

6. A method of classifying a cancer patient as likely or not likely to benefit from a drug, comprising the steps of
a) making an assignment of whether the patient has a large or small tumor, either directly by tumor measurement data or indirectly using a surrogate for tumor size data;
b) if the patient has a large tumor, using the large tumor classifier generated in accordance with clause 4 to classify a blood-based sample of the patient as likely or not likely to benefit from the drug, and
c) if the patient has a small tumor, using the small tumor classifier generated in accordance with clause 4 to classify a blood-based sample of the patient as likely or not likely to benefit from the drug.

7. A method of classifying a cancer patient as likely or not likely to benefit from a drug, comprising the steps of
a) conducting two classifier generation exercises on a development set of samples which are sorted into small tumor and large tumor groups, resulting in the generation of a large tumor classifier and a small tumor classifier and storing the large tumor and small tumor classifiers in a programmed computer; wherein the development set of samples are blood-based samples which have been subject to mass spectrometry;
b) making an assignment of whether the patient has a large or small tumor, either directly from tumor measurement data or indirectly using a surrogate for tumor measurement data;

c) conducting mass spectrometry on the blood-based sample of the cancer patient;

d) if the patient has a large tumor, using the large tumor classifier generated in step a) and the mass spectrometry data obtained in step c) with the programmed computer to classify the patient as likely or not likely to benefit from the drug, and e) if the patient has a small tumor, using the small tumor classifier generated in step a) and the mass spectrometry data obtained in step c) with the programmed computer to classify the patient as likely or not likely to benefit from the drug.

8. The method of clause 7, wherein the classifier generation exercises of step a) comprise the procedure of FIG. 8 steps 102-150.

9. The method of clause 7 or clause 8, wherein the cancer patient is a melanoma patient, and wherein the drug is an antibody drug targeting programmed cell death 1 (PD-1).

Example 9

Development of an Ensemble of Classifiers from Clinically Different Classifier Development Sets and Use Thereof to Guide Treatment Our work described in Example 8 made use of the development of different classifiers using clinically different development sets, i.e., with one set from "small tumor" patients and another set from "large tumor" patients. In this Example, we extend this method of developing classifiers more generally and describe an ensemble of different classifiers, each derived from clinically different development sets. In one implementation of this Example, each development set represents different tumor sizes or different proportions of tumor sizes in a population of melanoma patients. From this approach, we have discovered a reproducible ternary classification method and system which is better able to identify patients who do so badly on the immune checkpoint inhibitor anti-PD-1 that they might be better not taking it at all and, perhaps more importantly, others that do so well on anti-PD-1 monotherapy that they might be just as well off taking anti-PD-1 monotherapy rather than undergoing anti-PD1/anti-CTLA4 combination therapies, which incur tremendous addition expense and can have severe toxicity side effects. Later in this Example, we describe the development and implementation of an ensemble of classifiers to predict survival of ovarian cancer patients on chemotherapy.

Accordingly, in this section we describe a different approach to classifier development that we have not considered before, namely designing the development sets of a set of classifiers to explore different clinical groups, and using an ensemble of classifiers obtained from such development sets to result in a, for example, ternary (three-level) classification scheme. We further describe how a class label produced from this ensemble of classifiers can be used to guide treatment of a cancer patient or predict survival of a cancer patient. Those skilled in the art will appreciate that the present example of designing the development set of a set of classifiers with different clinical groups is offered by way of example and not limitation, and that this methodology can be extended to other classifier development scenarios generally, including in particular other classifier developments to predict patient benefit or survival from treatment with drugs.

A. Ensemble of Classifiers for Melanoma Patient Benefit from Nivolumab

In the melanoma/nivolumab portion of this Example, the deep MALDI feature table for the pretreatment serum samples from patients treated with nivolumab at the Moffitt Cancer Center (see Example 1 and Appendix A) was used for classifier development. For classifier development, the 104 samples for the patients who had tumor size follow up data were used. These 104 samples were split into two groups according to baseline tumor size: the 50 patients with smallest tumors and the 54 patients with largest tumors. Each of these subsets was used as the development set to develop a classifier using the process of FIG. 8, with bagged feature deselection and filtering of mini-classifiers on overall survival. These aspects have been described previously in this document in Example 8 and Appendix F of our prior provisional application Ser. No. 62/289,587.

In addition, five other subsets of the 104 sample classifier development set were defined as additional or alternative development sets. The first of these took the set of 50 patients with smallest tumors, dropped 10 of them, and replaced these with 10 patients from the set of 54 with the larger tumors. The second of these took the set of 50 patients with smallest tumors, dropped 20 of them, and replaced these with 20 patients from the set of 54. Three other development sets were defined extending this approach further. The fifth classifier was accordingly a subset of the original 54 large tumor size set. In this way, 5 development sets of 50 patient samples were generated that contained different proportions of patients with smaller and larger tumor sizes (80%-20%, 60%-40%, 40%-60%, 20%-80%, and 0%-100%, respectively). For each of these 5 development sets, classifiers were generated using the same procedure of FIG. 8 described in detail above, i.e., each classifier was defined as a final classifier (FIG. 8, step 150) as an ensemble average over 625 master classifiers generated from 625 test/training splits of the development set used for that classifier, and each master classifier is a logistic regression combination of a multitude of mini-classifiers that pass overall survival performance filtering criteria, and regularized by extreme drop out. Each classifier produces a binary class label for a sample, either Early or Late, and Early and Late have the same clinical meaning as explained in Example 1. Hence, we obtained an ensemble of 7 different classifiers (the 5 developed as described here, plus the "large" and "small" tumor classifiers described in the "Classifiers incorporating tumor size information" section, Example 8), each of which was developed on a clinically different classifier development set. It will be noted that the "large" tumor classifier described in the "Classifiers incorporating tumor size information" section and the fifth of the new classifiers generated from 50 "large" tumor patients are similar, but distinct in that they were formed from different sets of patients. This ensemble of seven classifiers is referred to herein as "IS6" or "the IS6 classifier."

An alternative method for defining the classifier development sets with different clinical groupings is as follows:

1. Order the 104 samples by tumor size.
2. Take the 50 samples with the smallest tumor size for one classifier development and the remaining 54 samples with the largest tumor for another, just as here.
3. Define 5 other classifier development sets by
   a. Dropping the 10 samples with the smallest tumor size and taking the next 50 samples for a classifier development set.
   b. Dropping the 20 samples with the smallest tumor size and taking the next 50 samples for a second classifier development set.

c. Dropping the 30 samples with the smallest tumor size and taking the next 50 samples for a third classifier development set.
d. Dropping the 40 samples with the smallest tumor size and taking the next 50 samples for a forth classifier development set.
e. Dropping the 50 samples with the smallest tumor size and taking the next 50 samples for a fifth classifier development set.

Classifiers are then developed from each of these seven classifier development sets using the procedure of FIG. 8 steps 102-150. One then establishes rules to combine the classification results from these seven classifiers, e.g., as explained below. This method of designing classifier development sets may have similar performance as the classifiers produced from the development sets described in the previous paragraphs, but may be more reproducible, for example in a rerunning of the samples or have better performance in identifying patients with particularly good or poor outcomes.

To conduct a test on a patient's blood-based sample, the sample is subject to mass spectrometry as described above in the description of FIG. 15. The resulting mass spectral data (integrated intensity values at the classification features used in the classifier development exercise, such as Appendix A or Appendix B) is then subject to classification by each of the 7 classifiers in the ensemble, using the general procedure of FIG. 15. Each of the 7 classifiers generates a class label (Early/Late or similar). The set of 7 class labels is used to define an overall classification for a test sample in accordance with a set of rules. In one particular example, samples where all classifiers in the ensemble return a good prognosis "Late" label are classified as "Good", samples where all classifiers return a poor prognosis "Early" label are classified as "Bad", and all other samples with mixed labels are classified as "Other". Of course, other monikers for this ternary class label scheme could be used and the particular choice of moniker is not particularly important. The results for classifications obtained using this rule for combining the labels of the 7 classifiers are presented below. Other rules for combining the 7 labels could, of course, be used.

Figure 40A:
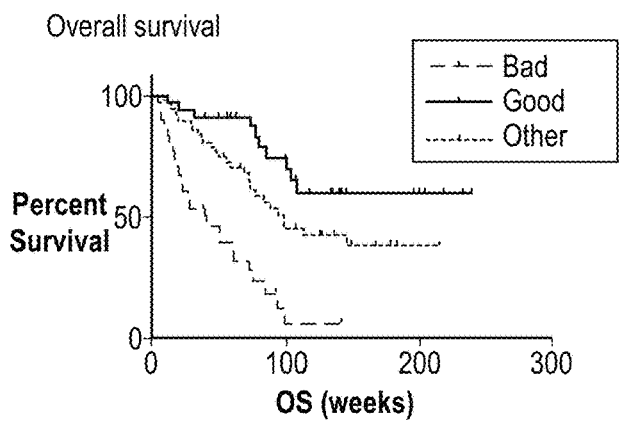
FIGS. 40A and 40B are Kaplan-Meier plots of overall survival and time to progression, respectively, for classifications generated by an ensemble of seven classifiers, each of which are based on different classifier development sets having different clinical groupings (based on tumor size in this example) and generated in accordance with FIG. 8. The ensemble of classifiers is generated from the 119 patient samples described in Example 1. A set of rules define a class label from labels produced by the ensemble of classifiers, such as "Bad", "Good" and "Other," which can be used to guide melanoma patient treatment as explained in Example 9 below.
Figure 40B:
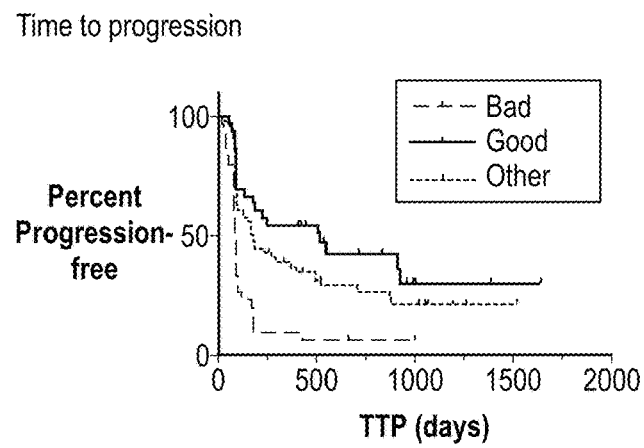

FIGS. 40A and 40B shows Kaplan-Meier plots of the results of applying these 7 classifiers to all 119 samples in the Moffitt Cancer Center sample set and using the rule above to generate a ternary classification. FIG. 40A depicts the Kaplan-Meier plot for overall survival, and FIG. 40B depicts the Kaplan-Meier plot for time to progression. Samples used in the development of each classifier in the ensemble are classified according to a final classifier defined from a modified majority vote (out of bag estimate) and other samples are classified according to a final classifier defined as the average over all 625 master classifiers. Thirty samples (25%) classified as Bad and 33 (28%) as Good. Patients classified as Good show very good outcomes: overall survival plateaus at 60% and time to progression at 30%. In contrast, the patients classified as Bad demonstrate very poor outcomes, with 36% survival at one year and only 6% at two years, and 10% progression-free at 6 months and 7% at one year.

Figure 41:
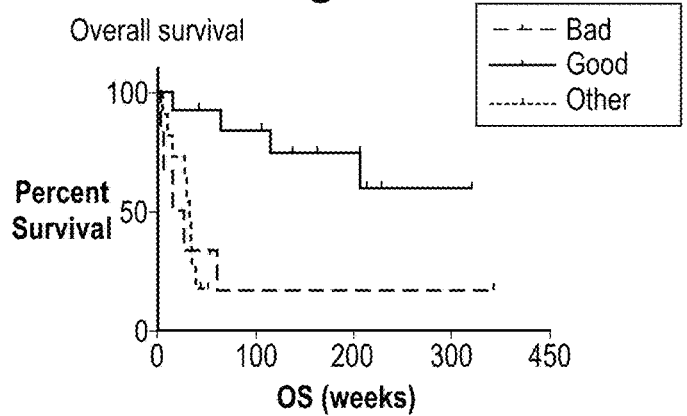
FIG. 41 is a Kaplan-Meier plot of overall survival for the classifications obtained by a test composed of the ensemble of seven classifiers of Example 9 for 30 samples in an anti-PD-1 treated validation cohort.

When the ensemble of classifiers was applied to a validation set of mass spectral data from blood-based samples obtained from 30 patients also treated with anti-PD1 antibodies, the test showed similar performance. This is shown in FIG. 41, which is a Kaplan-Meier plot for overall survival by the classifications obtained by the ensemble of 7 classifiers for the 30 samples in the anti-PD1 treated validation cohort. Thirteen patients (43%) were classified as Good and six patients (20%) as Bad.

The high proportion of patients with durable long term responses to therapy and long overall survival in the Good group is similar to the efficacy reached for patients treated with the combination of nivolumab and ipilimumab, a newly approved therapy for melanoma. This combination therapy, however, is not only extremely expensive (list price for a year of treatment being greater than $250,000, see also Leonard Saltz, M D, at ASCO 2015 plenary session: "The Opdivo+Yervoy combo is priced at approximately 4000× the price of gold ($158/mg)"), but also has significant toxicities associated with it. The excellent performance of patients in the Good group indicates that within this group patients may not need to be treated with the combination of an anti-PD-1 agent and an anti-CTLA4 agent, but may in fact be likely to achieve similar outcomes with reduced risks of severe toxicities with the anti-PD-1 agent, such as nivolumab, alone.

In addition, the very poor outcomes of the Bad group, indicate that the likelihood of these patients receiving durable benefit from nivolumab or other anti-PD-1 agents is extremely low. Such patients may be directed towards less costly therapies of similar efficacy, therapies of better efficacy in this population, if they can be found, or to a clinical trial or palliative care.

The classification label of "Other" produced by the ensemble of classifiers in this Example is also useful, and in this particular application a ternary classifier is quite appropriate and even desirable in terms of guiding treatment decisions in melanoma: The Goods should get nivolumab monotherapy, the Others would be good candidates for nivolumab plus ipilimumab (as, at least in the Moffitt set, they appear to get some benefit from nivolumab, but could probably do better on the combination therapy, as combination therapy demonstrates better outcome in an unselected population), and the Bads do not seem to benefit at all from nivolumab and probably would not be saved by addition of ipilimumab (anti-CTLA4 antibody, Yervoy TM), and so should be directed to some other kind of therapy, or possibly clinical trials or palliative care.

As noted above, the rules defined for the ensemble of classifiers can vary and in one possible embodiment a majority vote over the 7 classifiers in the ensemble could be used to assign a class label to a test sample. In this particular Example, the majority vote gives a class label, either Early or Late. The classification produced by the majority vote are very close to the class labels produced by the full-set approach 1 classifier of Example 1 ("IS2" herein), which is perhaps not surprising since both are generated over development sets covering a wide range of tumor sizes.

The ensemble of seven tumor size classifiers created from development subsets drawn with different distributions of baseline tumor size (referred to herein as "IS6")) was also applied to pretreatment serum samples collected from two patient cohorts: 30 patients treated with anti-PD-1 therapies in an observational study (the validation set used for IS6 and shown in FIG. 41 and used as the independent validation set for classifiers 1 and 2 of our provisional application Ser. No. 62/191,895 filed Jul. 13, 2015) and 21 patients treated with the combination of the anti-PD-1 agent, nivolumab, with the anti-CTLA4 agent, ipilimumab. Both cohorts were collected at a single institution as part of an observational study.

It had been noted that IS6 identifies a group of patients with especially good outcome when treated with anti-PD-1 agents. As identifying this group of very good performing patients was the aim here, instead of plotting the three outcome groups of IS6, we look at the best outcome group, the "Good" group and we combine the other two classification groups, intermediate prognosis group ("Other") and poor outcome group ("Bad"), into a single group which we call "Not Good" (i.e., "Not Good"="Other"+"Bad"). When the Kaplan-Meier curves for overall survival for these two cohorts of patients are plotted by "Good" versus "Not Good" on the same plot, one obtains results shown in FIG. 42.

Figure 42:
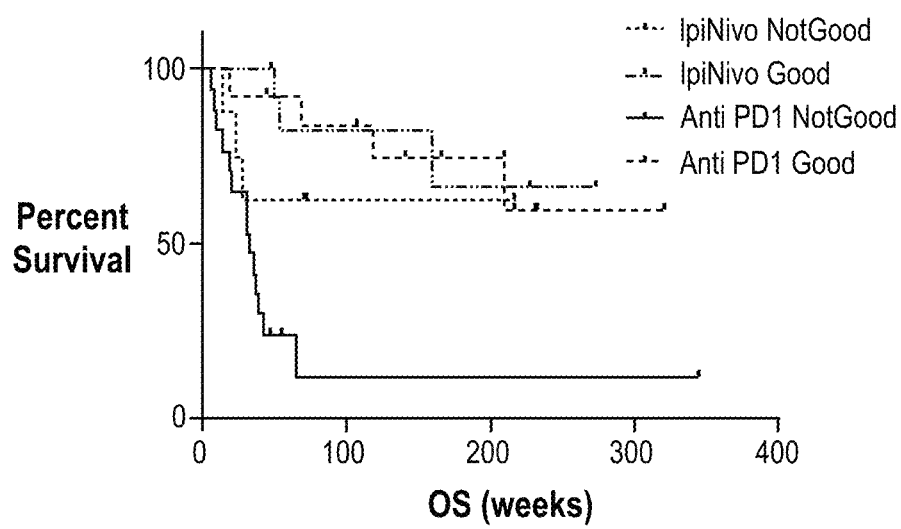
FIG. 42 is a Kaplan-Meier plot of overall survival by Good and NotGood class labels produced by an ensemble of seven classifiers of Example 8 for melanoma patients treated with anti-PD1 monotherapy (nivolumab) as well as melanoma patients treated with both ipilimumab and nivolumab combination therapy. The plot shows that nivolumab patients having the class label Good have very similar survival as compared to patients with the nivolumab+ipilimumab combination therapy.

It can be seen from FIG. 42 that the difference in outcomes between "Good" and "Not Good" is smaller for patients treated with the combination therapy (ipilimumab+nivolumab) than for patients treated with nivolumab alone. More importantly, there is no evidence that patients classified as "Good" receive benefit from the addition of ipilimumab to nivolumab therapy. Although this comparison should be made with some caution as these two cohorts are not two arms of a randomized trial, both cohorts were collected from patients treated at the same institution, and, as significant toxicities can be experienced with the combination therapy, it might be expected that any bias between the populations would be in favor of better prognostic factors for patients treated with combination therapy. These results would indicate that it may be possible to identify, using the IS6 classifier or other similar performing classifiers (for example the classifiers of Example 6 constructed from mass spectral feature subsets associated with specific protein functions), a group of patients identified with the class label "Good" or the equivalent who would achieve similar outcomes with nivolumab as with the combination of nivolumab and ipilimumab. Hence these patients would receive no significant benefit from receiving ipilimumab in addition to nivolumab, while combination therapy for these patients would still incur considerable extra cost and expose patients to significantly higher risk of severe toxicities and side-effects. On the other hand those patients whose serum is classified as Not Good by the IS6 classifier (i.e., where any one of the ensemble of classifiers returns the Early class label), such patient would likely benefit from the addition of ipilimumab to nivolumab as compared to nivolumab monotherapy. As noted above, the IS6 classifier of Example 9 provides similar classification results to the classifier developed using features selected according to their association with their biological function of acute response and wound healing in Example 6.

Figure 50A:
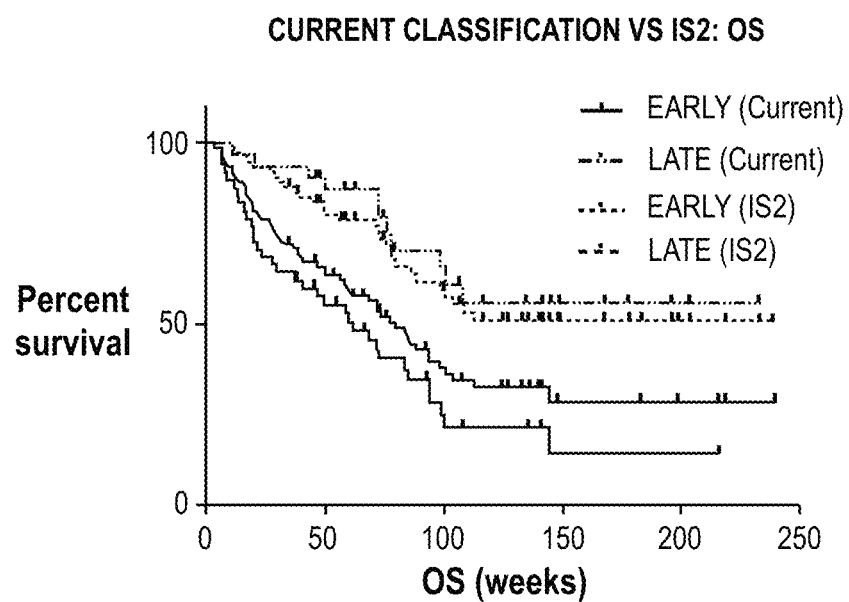
FIGS. 50A-50D illustrates Kaplan-Meier plots comparing the performance of the classifier developed in Example 6 ("Current") with those developed in Example 1 (FIGS. 50A and 50B, OS and TTP, respectively)("IS2") and Example 8 (FIGS. 50C and 50D, OS and TTP, respectively)("IS6").
Figure 50B:
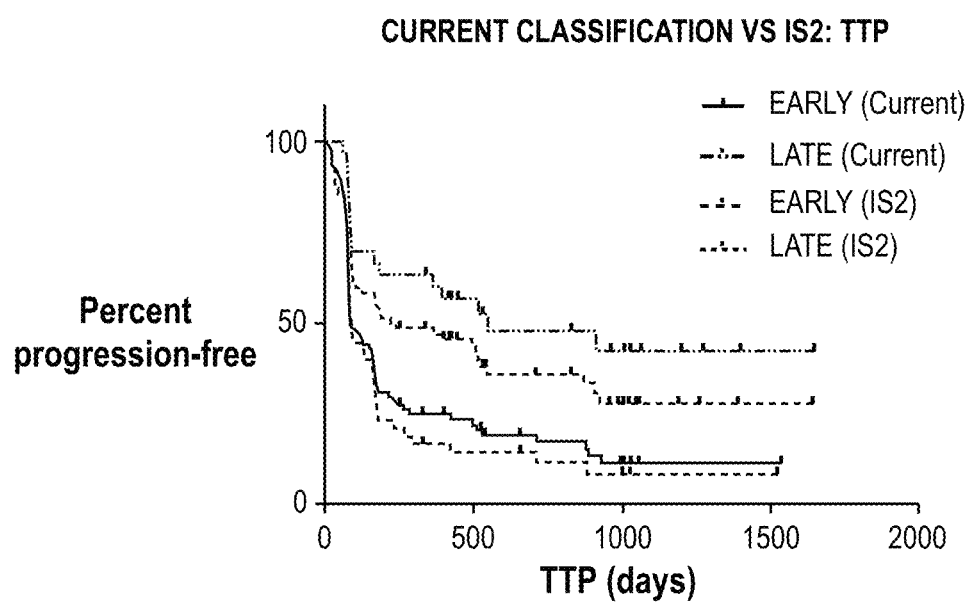
Figure 50C:
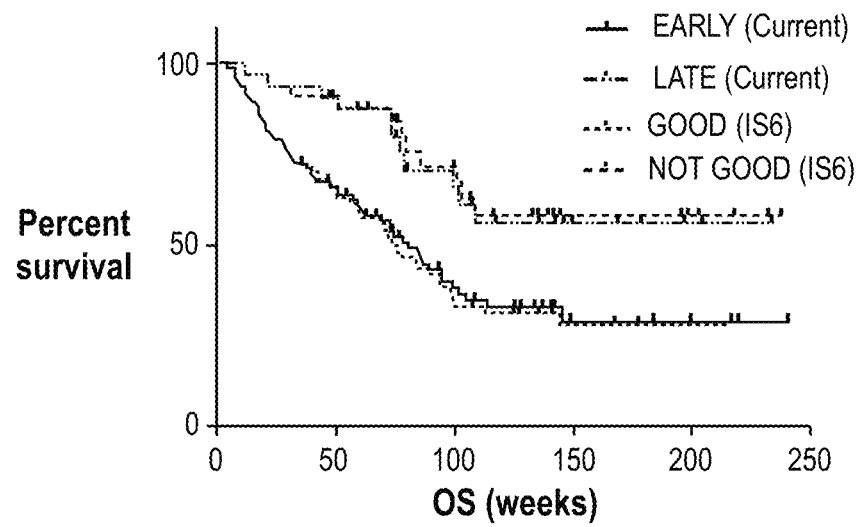
Figure 50D:
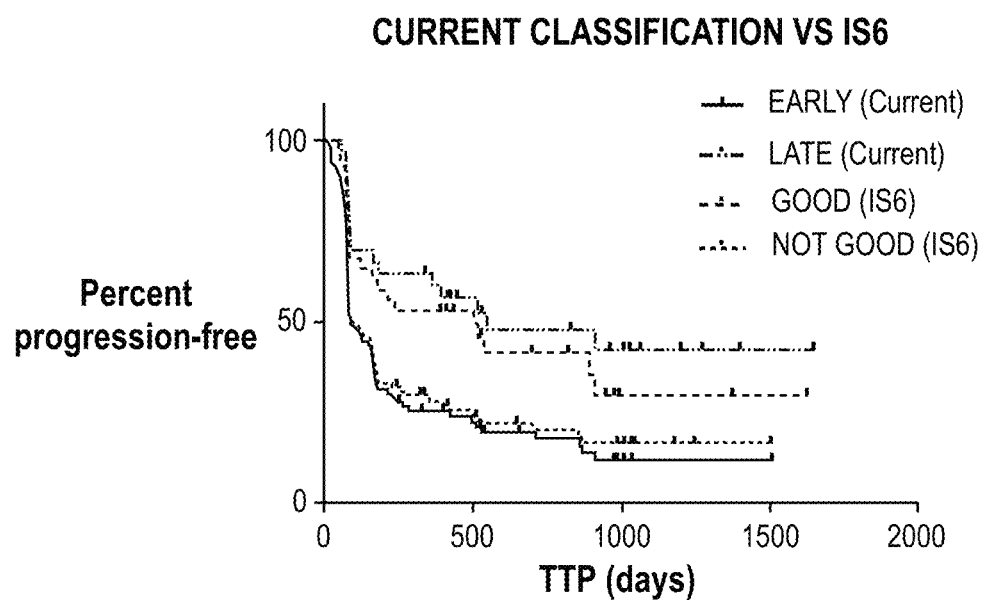

Generalizing this discovery (and considering the content of Example 10 below, especially the discussion of FIGS. 50C and 50D, wherein we disclose that classifiers developed from mass spectral features associated with biological functions have similar classifier performance to IS6), we can say that we described a method of guiding melanoma patient treatment with immunotherapy drugs, comprising the steps of a) conducting mass spectrometry on a blood-based sample of the patient and obtaining mass spectrometry data; (b) obtaining integrated intensity values in the mass spectrometry data of a multitude of mass-spectral features; and (c) operating on the mass spectral data with a programmed computer implementing a classifier; wherein in the operating step the classifier compares the integrated intensity values with feature values of a reference set of class-labeled mass spectral data obtained from blood-based samples obtained from a multitude of other melanoma patients treated with an antibody drug blocking ligand activation of programmed cell death 1 (PD-1) with a classification algorithm and generates a class label for the sample. The class label "Good" or the equivalent (e.g., Late in the description of Example 10) predicts the patient is likely to obtain similar benefit from a combination therapy comprising an antibody drug blocking ligand activation of PD-1 and an antibody drug targeting CTLA4 and is therefore guided to a monotherapy of an antibody drug blocking ligand activation of PD-1 (e.g., nivolumab), whereas a class label of "Not Good" or the equivalent (e.g., Early in the description of Example 10) indicates the patient is likely to obtain greater benefit from the combination therapy as compared to the monotherapy of an antibody drug blocking ligand activation of programmed cell death 1 (PD-1) and is therefore guided to the combination therapy.

In one embodiment the mass spectral features include a multitude of features listed in Appendix A, Appendix B or Appendix C, or features associated with biological functions Acute Response and Wound Healing. In preferred embodiments the classifier is obtained from filtered mini-classifiers combined using a regularized combination method, e.g., using the procedure of FIG. 8 or FIG. 54. The regularized combination method can take the form of repeatedly conducting logistic regression with extreme dropout on the filtered mini-classifiers. In one example the mini-classifiers are filtered in accordance with criteria listed in Table 10. As disclosed in this example, the classifier may take the form of an ensemble of tumor classifiers combined in a hierarchical manner. In the illustrated embodiment if any one of the tumor classifiers returns an Early or the equivalent label the Not Good or equivalent class label is reported, whereas if all the tumor classifiers return a Late class label the Good or equivalent class label is reported.

In this method the relatively greater benefit from the combination therapy label means significantly greater (longer) overall survival as compared to monotherapy.

In another aspect the reference set takes the form of a set of class-labeled mass spectral data of a development set of samples having either the class label Early or the equivalent or Late or the equivalent, wherein the samples having the class label Early are comprised of samples having relatively shorter overall survival on treatment with nivolumab as compared to samples having the class label Late.

In preferred embodiments the mass spectral data is acquired from at least 100,000 laser shots performed on the sample using MALDI-TOF mass spectrometry.

In one embodiment, as indicated in Examples 6 and 10 the mass-spectral features are selected according to their association with at least one biological function, for example sets of features which are associated with biological functions Acute Response and Wound Healing.

B. Ensemble of Classifiers for Predicting Ovarian Cancer Patient Benefit from Platinum-Based Chemotherapy This Example also discloses the development of classifiers which predict in advance whether an ovarian cancer patient is likely to be platinum-refractory or platinum-resistant in treatment of the ovarian cancer with platinum-based chemotherapy. In one embodiment, the classifier includes: a) a machine-readable memory storing a reference set of class-labeled mass spectral data obtained from blood-based samples of other ovarian cancer patients treated with the platinum-based chemotherapy. The mass spectral data is in the form of a feature table of intensity values of a multitude of mass spectral features. The class labels are of the form Early or the equivalent, indicating that the sample was from a patient who did relatively poorly on platinum-based chemotherapy, or Late or the equivalent, indicating that the sample was from a patient that did relatively well on platinum-based chemotherapy. The classifier also includes b) a programmed computer implementing a classification algorithm comparing mass spectral data of a sample to be tested with the reference set and generating a class label for the sample to be tested.

In particular, the classification algorithm implements a hierarchical multi-level classification in series including classification at at least a first level ("Classifier A" in the following description) and a second level ("Classifier B" in the following description). The classification algorithm at the first level produces a class label of Early or Late or the equivalent. The class label Late or the equivalent identifies patients as being likely to not be platinum-refractory or platinum-resistant in treatment of the ovarian cancer with platinum-based chemotherapy. If the class label assigned at the first level is Early or the equivalent, the classification algorithm proceeds to the second level. The classifier at the second level uses a subset of the reference set in the form of patients identified with the class label Early or the equivalent and further stratifies into Early and Late class labels (or Earlier or Later labels, or the equivalent). The classification algorithm at the second level generates a class label of Bad or the equivalent identifying patients as likely to perform very poorly on platinum-based chemotherapy, i.e., be platinum-refractory or platinum-resistant.

In one embodiment, the hierarchical multi-level classification includes a third classification level ("Classifier C" in the following description), wherein a class label assigned at the third classification level is used to identify patients as being likely to have particularly good outcomes on the platinum-based chemotherapy, and is applied to those samples which are assigned the Late (or equivalent) class label by the first level classifier.

We have found that is desirable to develop classifiers from different clinical sub-groups within a classifier development set used to generate the first level classifier. For example, the classifiers at the first classification level can be developed from one or more different clinical subgroups, for example four different classifiers C1, C2, C3, and C4, each developed from the different clinical sub-groups. In the ovarian cancer scenario, these clinical subgroups can take the form of: C1: a subset of patients with non-serous histology or serous histology together with unknown FIGO (a cancer scoring system) score; C2: a subset of patients not used to develop Classifier C1 (e.g., patients with serous histology and known FIGO score); C3: a subset of patients with residual tumor after surgery; C4: a subset of patients with no residual tumor after surgery.

A further example of this methodology will be described below in conjunction with a set of ovarian cancer patient samples.

Samples

A set of 165 blood-based (serum) samples from an observational trial of patients with ovarian cancer were available. Patients underwent surgery followed by platinum-based chemotherapy. Samples were taken at the time of surgery (in advance of treatment with platinum-based chemotherapy). This cohort has already been described in Example 4 and the baseline characteristics of the cohort were shown in Table 37 above.

Kaplan-Meier plots for disease-free-survival (DFS) and overall survival (OS) for the cohort of 138 patients with baseline samples and acquired spectra were shown in FIGS. 27A and 27B.

Sample preparation, spectral acquisition and spectral data processing were similar to the description in Example 1 and so a detailed description here is omitted.

Turning now to FIG. 54A, the classifier development process will be described in further detail in the context of the ovarian/platinum chemotherapy classifier.

The subset of 129 patients with available DFS data and DFS known to be in excess of 1 month were selected from the whole cohort of 138 patients. This subset was then split in half stratified on outcome and taking account of how features were related to outcome within each half, as explained in Appendix B of our prior provisional application 62/319,958, to produce a matched development and internal validation set. The resulting development set of 65 samples was used to develop and initial or first level classifier, referred to as Classifier A, in the following discussion. It will be appreciated that it would also be possible to develop a classifier from the whole cohort, e.g., where there is another cohort of samples available for a validation exercise.

Figure 54B:
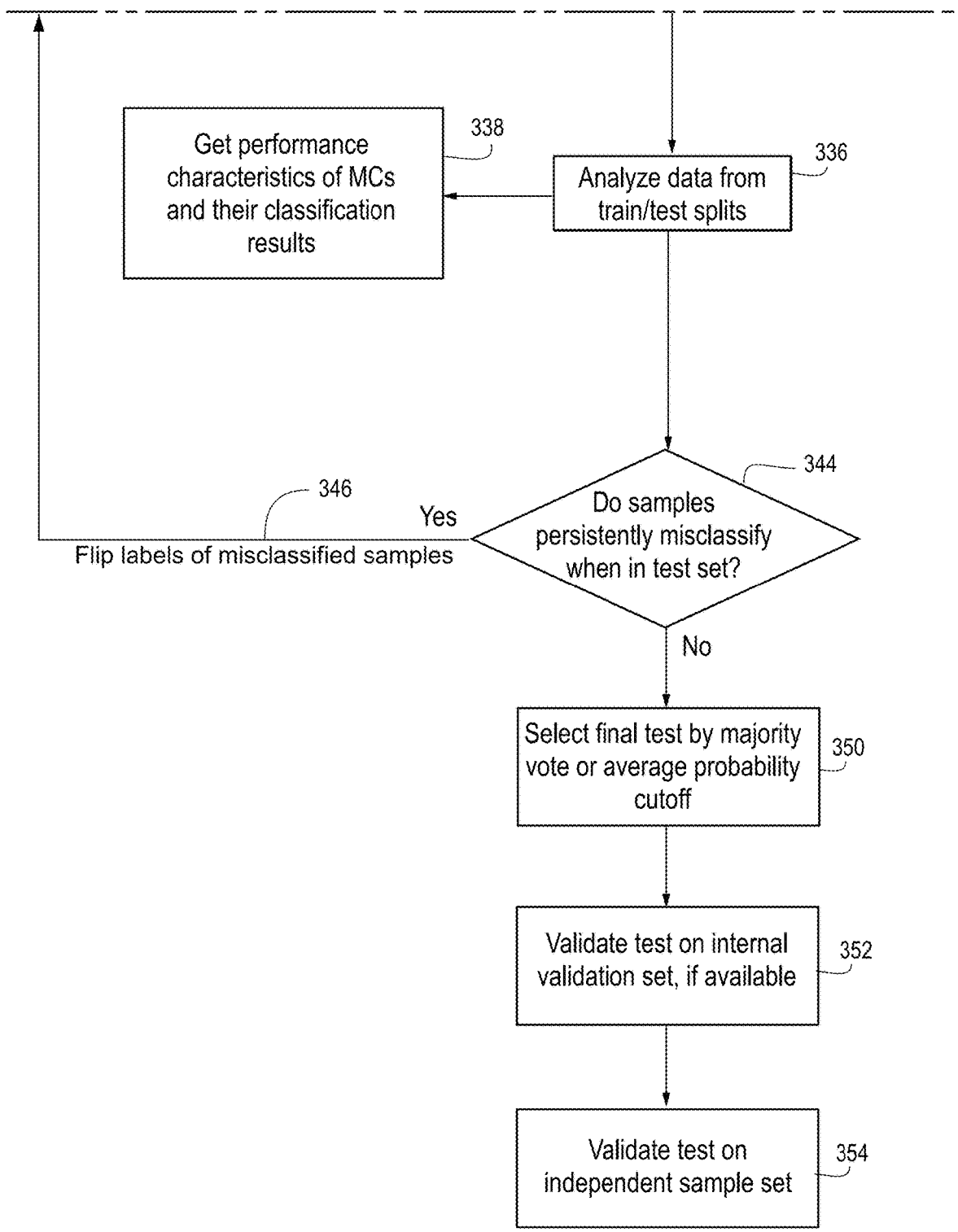

At step 302, a definition of the two class labels (or groups) for the samples in the development set 300 was performed. While some preliminary approaches used for classifier development employed well-defined class labels, such as response categories or chemo-resistance (yes/no), these proved to be unsuccessful. All approaches discussed in this section of the Example 9 make use of time-to-event data for classifier training. In this situation class labels are not obvious and, as shown in FIGS. 54A and 54B, the methodology uses an iterative method to refine class labels (loop 346) at the same time as creating the classifier. At step 302, an initial guess is made for the class labels. Typically the samples are sorted on either DFS or OS and half of the samples with the lowest time-to-event outcome are assigned the "Early" class label (early death or progression, i.e. poor outcome) while the other half are assigned the "Late" class label (late death or progression, i.e. good outcome). Classifiers (step 330) are then constructed using the outcome data and these class labels for many different training sets (312) drawn from the development set and the associated test sets (310) classified. The class labels of samples which persistently misclassify when in the test set across the multiple training/test set splits (loop 335) are flipped (344 and loop 346) and the resulting new set of class labels are then used for a second iteration of the classifier construction step. This process is iterated until convergence. The Early and Late groups are shown at 304 and 306.

At step 308, the Early and Late samples of the development set (300) are then divided randomly into training (312) and test sets (310). The training set (312) is then subject to steps 320, 326 and 330. In step 320, many k-nearest neighbor (kNN) mini-classifiers (mCs) that use the training set as their reference set are constructed (defined) using subsets of features from the reduced set of spectral features identified. For these investigations, all possible single features and pairs of features were examined (s=2); however, one could choose to explore the reduced feature space more deeply using triplets (s=3) or even higher order combinations of features. All approaches described in this section of Example 9 all use k=9, but other values of k such as 7 or 11 could be considered.

In step 326 a filtering process was used to select only those mini-classifiers (mC) that had useful or good performance characteristics. This can be understood in FIG. 54A by the spectra 324 containing many individual features (shown by the hatched regions) and the features alone and in pairs are indicated in the reduced feature space 322. For some of the kNN mini-classifiers, the features (singly or in pairs) perform well for classification of the samples and such mini-classifiers are retained (indicated by the "+" sign in FIG. 54A at 328) whereas others indicated by the "−" sign are not retained.

To target a final classifier that has certain performance characteristics, these mCs were filtered as follows. Each mC is applied to its training set and performance metrics are calculated from the resulting classifications of the training set. Only mCs that satisfy thresholds on these performance metrics pass filtering to be used further in the process. The mCs that fail filtering are discarded. For this project hazard ratio filtering was used. For hazard ratio filtering, the classifier was applied to the training set. The hazard ratio for OS was then calculated between the group classified as Early and the rest classified as Late. The hazard ratio had to lie within specified bounds for the mC to pass filtering.

At step 330, we generated a master classifier (MC) for each realization of the separation of the development set into training and test sets at step 308. Once the filtering of the mCs was complete, at step 332 the mCs were combined in one master classifier (MC) using a logistic regression trained using the training set class labels, step 332. To help avoid overfitting the regression is regularized using extreme drop out with only a small number of the mCs chosen randomly for inclusion in each of the logistic regression iterations. The number of dropout iterations was selected based on the typical number of mCs passing filtering to ensure that each mC was likely to be included within the drop out process multiple times. All approaches outlined in this section of Example 9 left in 10 randomly selected mCs per drop out iteration and used 10,000 drop out iterations.

At step 334, we evaluated the performance of the MC arrived at in step 332 and its ability to classify the test set of samples (310). With each iteration of step 320, 326, 330, 334 via loop 335 we evaluate the performance of the resulting MC on its ability to classify the members of the test set 310. In particular, after the evaluation step 334, the process looped back via loop 335 to step 308 and the generation of a different realization of the separation of the development set into training and test sets. The process of steps 308, 320, 326, 330, 332, 334 and looping back at 335 to a new separation of the development set into training and test sets (step 308) was performed many times. The use of multiple training/test splits avoids selection of a single, particularly advantageous or difficult, training set for classifier creation and avoids bias in performance assessment from testing on a test set that could be especially easy or difficult to classify.

At step 336, there is an optional procedure of analyzing the data from the training and test splits, and as shown by block 338 obtaining the performance characteristics of the MCs from each training/test set split and their classification results. Optional steps 336 and 338 were not performed in this project.

At step 344, we determine if there are samples which are persistently misclassified when they are present in the test set 310 during the many iterations of loop 335. If so, we flip the class label of such misclassified samples and loop back in step 346 to the beginning of the process at step 302 and repeat the methodology shown in FIGS. 54A and 54B.

If at step 344 we do not have samples that persistently misclassify, we then proceed to step 350 and define a final classifier in one of several ways, including (i) a majority vote of each master classifier (MC) for each of the realizations of the separation of the development set into training and test sets, or (ii) an average probability cutoff.

The output of the logistic regression (332) that defines each MC is a probability of being in one of the two training classes (Early or Late). These MC probabilities can be averaged to yield one average probability for a sample. When working with the development set 300, this approach is adjusted to average over MCs for which a given sample is not included in the training set ("out-of-bag" estimate). These average probabilities can be converted into a binary classification by applying a threshold (cutoff). During the iterative classifier construction and label refinement process, classifications were assigned by majority vote of the individual MC labels obtained with a cutoff of 0.5. This process was modified to incorporate only MCs where the sample was not in the training set for samples in the development set (modified, or "out-of-bag" majority vote). This procedure gives very similar classifications to using a cutoff of 0.5 on the average probabilities across MCs.

Figure 55A:
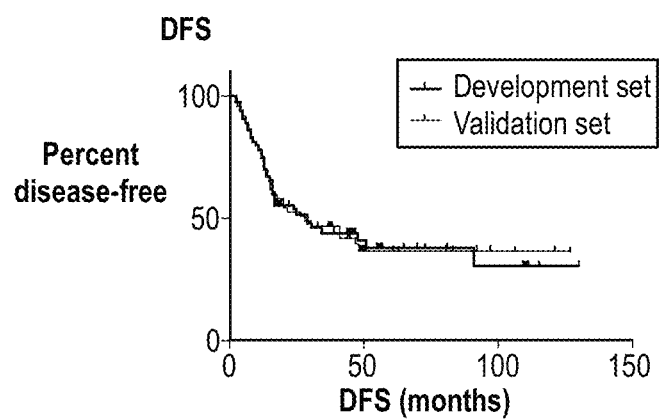
FIGS. 55A and 55B are Kaplan-Meier plots of time to event data for the 129 patients in the ovarian development sample set of Example 9 with available clinical data, DFS >1 month, and mass spectral data from pretreatment samples, showing the plots for a split of the sample set into development (N=65) and validation (N=64) sets.
Figure 55B:
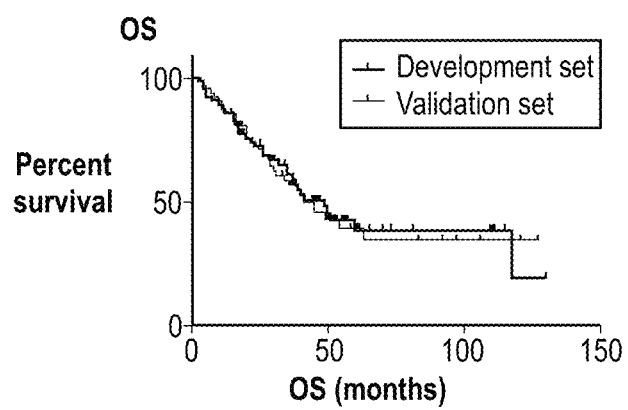
Figure 56A:
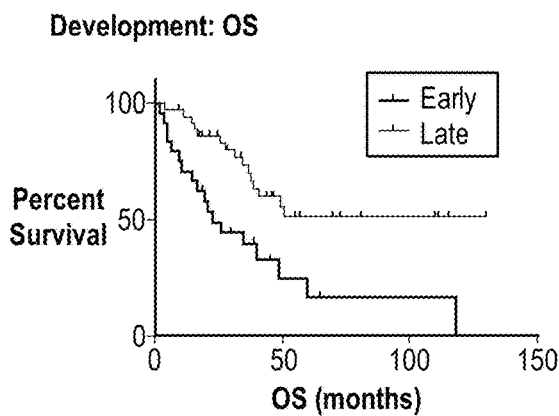
FIGS. 56A-56D are Kaplan-Meier plots of OS and DFS by Early and Late classification groups produced by the first tier or "Classifier A" classifier of Example 9, for the 129 patients split into development and validation sets.
Figure 56B:
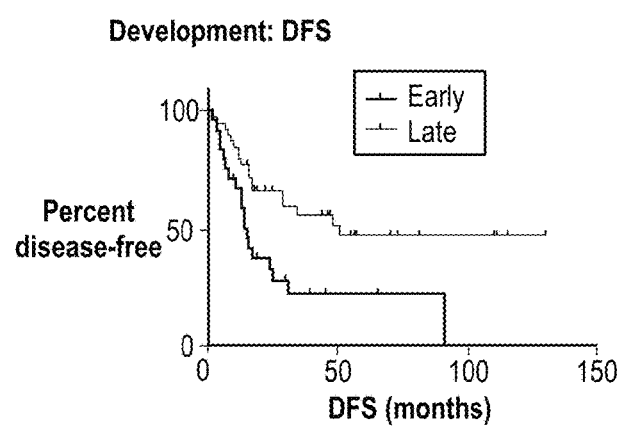
Figure 56C:
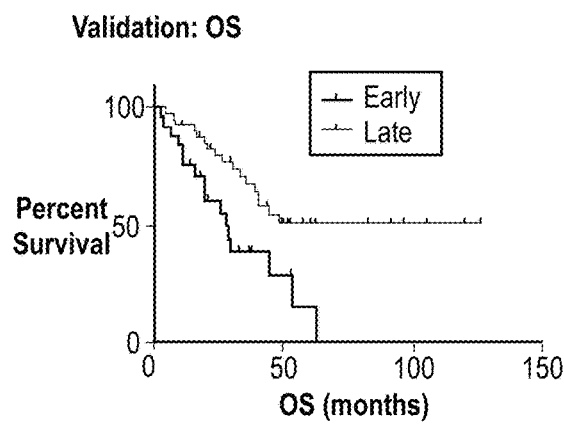
Figure 56D:
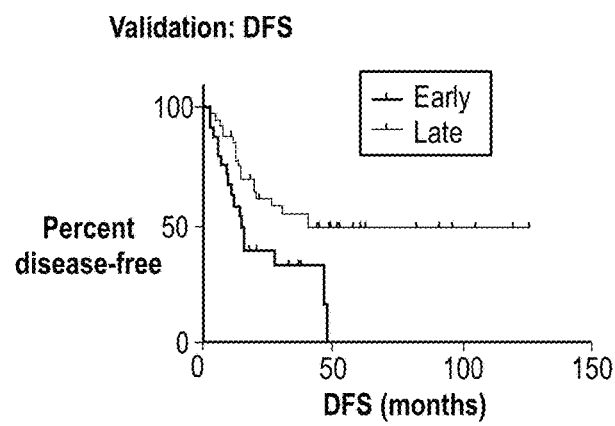

After the final classifier is defined at step 350, the process optionally continues with a validation step 352 in which the final classifier defined at step 350 is tested on an internal validation set of samples, if it is available. In the present example, the initial set of samples was divided into a development set (300) and a separate internal validation set, and so this validation set existed and was subject to the validation step 352. See FIGS. 55A and 55B for the Kaplan-Meier plots for DFS and OS for the development and validation sets. Ideally, in step 354 this final classifier as defined at step 350 is also validated on an independent sample set.

FIG. 54A shows a step 52 of deselection of features from an initial feature space to a reduced feature space. This was done using a bagged feature deselection procedure which is described in our prior provisional application Ser. No. 62/319,958, see FIGS. 3 and 4 thereof, the details of which are omitted for the sake of brevity.

Classifier A development

Initial new classifier development was performed using the process of FIGS. 54A and 54B described in detail above, using 129 samples. This was a reduced set including only patients with DFS greater than 1 month. The sample number allowed for a split into a development set and an internal validation set for classifier development. The split into development and validation sets was stratified by censoring of DFS and OS. The assignment of individual samples to validation or development sets is shown and described in detail in Appendix A and Appendix B, respectively, of our prior provisional application Ser. No. 62/319,958. The development set had 65 patients and validation set had 64 patients. The clinical characteristics are listed for the development and validation split in table 61.

TABLE 61

Baseline characteristics of patients with available spectra split into development (n = 65) and internal validation (n = 64) sets

| | | Development set n (%) | Validation set n (%) |
|---|---|---|---|
| Histology | serous | 47 (72) | 47 (73) |
| | non-serous | 18 (28) | 17 (27) |
| VeriStrat Label | Good | 50 (77) | 53 (83) |
| | Poor | 15 (23) | 11 (17) |
| FIGO | NA | 16 (25) | 21 (33) |
| | 1 | 6 (9) | 7 (11) |
| | 2 | 1 (2) | 2 (3) |
| | 3 | 30 (46) | 21 (33) |
| | 4 | 12 (18) | 13 (20) |
| Histologic Grade | NA | 1 (2) | 1 (2) |
| | 1 | 2 (3) | 5 (8) |
| | 2 | 25 (38) | 23 (36) |
| | 3 | 37 (57) | 35 (55) |

TABLE 61-continued

Baseline characteristics of patients with available spectra split into development (n = 65) and internal validation (n = 64) sets

| | | Development set n (%) | Validation set n (%) |
|---|---|---|---|
| Metastatic | yes | 9 (14) | 7 (11) |
| Disease | no | 56 (86) | 57 (89) |
| Residual | yes | 27 (42) | 20 (31) |
| Tumor | no | 38 (58) | 44 (69) |
| Age | Median (range) | 57 (18-88) | 59 (20-83) |

This development set of samples was used with its associated clinical data in the procedure of FIGS. 54A and 54B, as described above, to generate a classifier (Classifier A) able to stratify patients into two groups with better ("Late"=late progression) and worse ("Early"=early progression) outcomes. The features used in Classifier A (the reduced feature space created by feature deselection in the final iteration of loop 346 FIG. 54A) are listed in Appendix E of our prior provisional application Ser. No. 62/319,958. Performance of the classifier was assessed within the development set using out-of-bag estimates as previously described. The classifier was then applied to the validation set to assess its performance in an internal validation set not used at all in the development of the classifier (352 in FIG. 54B).

Performance of Classifier A

The performance of the Classifier A was assessed using Kaplan-Meier plots of DFS and OS between samples classified as Early and Late, together with corresponding hazard ratios (HRs) and log-rank p values. The results are summarized in tables 62 and 63.

Figure 57A:
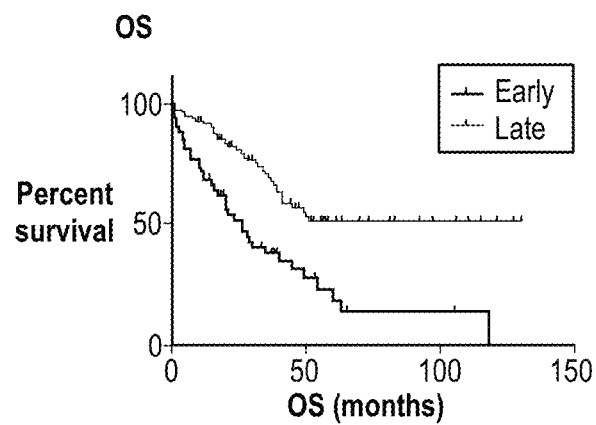
FIGS. 57A and 57B are Kaplan-Meier plots of OS and DFS by Early and Late classification groups, for the "Classifier A" of Example 9 run on all 138 samples.
Figure 57B:
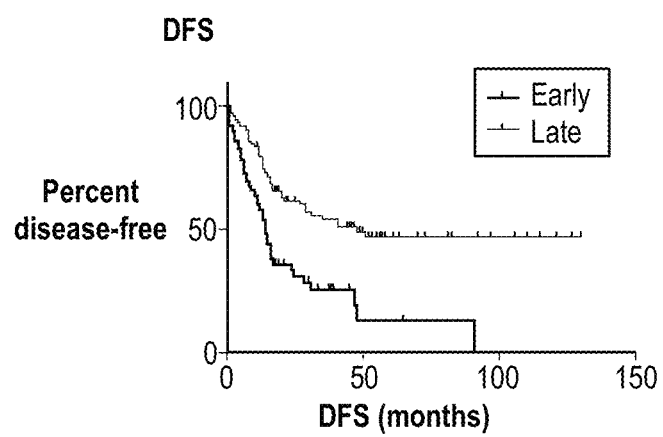

Kaplan-Meier plots corresponding to the data in table 62 are shown in FIGS. 56A-56D and data in table 63 are shown in FIGS. 57A and 57B. The classifications per sample are listed in Appendix C of our prior provisional application Ser. No. 62/319,958.

Of note for prediction of chemo-resistance: DFS is 74% at 6 months in the Early group, compared with 93% in the Late group and at 12 months DFS is 58% in the Early group compared with 80% in the Late group. Of 14 patients with DFS of 4 months or less 9 (64%) are classified as Early and of the 20 patients with DFS of 6 months or less 14 (70%) are classified as Early, see table 64.

TABLE 64

| DFS before 4 months, 6 months, 10 and 12 months | | | |
|---|---|---|---|
| | Early | Late | P value |
| DFS ≤ 4 months | 9 | 5 | 0.079 |
| No DFS ≤ 4 months | 44 | 77 | |
| DFS ≤ 6 months | 14 | 6 | 0.005 |
| No DFS ≤ 6 months | 39 | 76 | |
| DFS ≤ 10 months | 19 | 13 | 0.007 |
| No DFS ≤ 10 months | 32 | 68 | |
| DFS ≤ 12 months | 22 | 16 | 0.006 |
| No DFS ≤ 12 months | 29 | 63 | |

Baseline clinical characteristics are summarized by classification group in table 65.

TABLE 65

| Clinical characteristic by classification group when run on 138 samples | | | | |
|---|---|---|---|---|
| | | Early set (N = 54) n (%) | Late set (N = 84) n (%) | P value |
| Histology | serous | 45 (83) | 55 (65) | 0.031 |
| | non-serous | 9 (17) | 29 (35) | |

TABLE 62

| Performance summary for Classifier A | | | | | | | |
|---|---|---|---|---|---|---|---|
| | #Early/#Late | OS HR (95% CI) | OS log-rank p | OS Median (Early, Late) | DFS HR (95% CI) | DFS log-rank p | DFS Median (Early, Late) |
| Development | 25/40 | 2.76 (1.54-6.82) | 0.002 | 23, not reached (Months) | 2.44 (1.42-5.77) | 0.004 | 15, 51 (Months) |
| Validation | 24/40 | 2.54 (1.44-6.67) | 0.005 | 28, not reached (Months) | 2.31 (1.33-5.69) | 0.008 | 15, 41 (Months) |

TABLE 63

| Performance summary for classifier run on all the 138* samples | | | | | | | |
|---|---|---|---|---|---|---|---|
| | #Early/#Late | OS HR (95% CI) | OS log-rank p | OS Median (Early, Late) | DFS HR (95% CI) | DFS log-rank p | DFS Median (Early, Late) |
| Whole set | 54/84 | 2.65 (1.89-5.21) | <0.001 | 26, not reached (Months) | 2.44 (1.80-4.72) | <0.001 | 14, 48 (Months) |

*Note:
2 samples of the 138 samples did not have DFS time-to-event data.

TABLE 65-continued

Clinical characteristic by classification group when run on 138 samples

|  |  | Early set (N = 54) n (%) | Late set (N = 84) n (%) | P value |
|---|---|---|---|---|
| VeriStrat Label | Good | 27 (50) | 83 (99) | <0.001 |
|  | Poor | 26 (48) | 1 (1) |  |
|  | Indeterminate | 1 (2) | 0 (0) |  |
| FIGO | 1 | 0 (0) | 13 (15) | <0.001‡ |
|  | 2 | 1 (2) | 2 (2) |  |
|  | 3 | 21 (39) | 33 (39) |  |
|  | 4 | 20 (37) | 9 (11) |  |
|  | NA | 12 (22) | 27 (32) |  |
| Histologic Grade | NA | 0 (0) | 2 (2) | 0.379* |
|  | 1 | 1 (2) | 6 (7) |  |
|  | 2 | 20 (37) | 33 (39) |  |
|  | 3 | 33 (61) | 43 (51) |  |
| Metastatic Disease | yes | 14 (26) | 6 (7) | 0.003 |
|  | no | 40 (74) | 78 (93) |  |
| Residual Tumor | yes | 38 (70) | 15 (18) | <0.001 |
|  | no | 16 (30) | 69 (82) |  |
| Age | Median (range) | 60 (35-88) | 57.5 (18-83) |  |

*1 + 2 vs 3,
‡1 − 3 vs 4

Test classification is significantly associated with histology, FIGO score and presence of metastatic disease. Table 66 shows the results of multivariate analysis of OS and DFS for the whole cohort.

TABLE 66

Multivariate analysis of the whole cohort

|  | OS |  | DFS |  |
|---|---|---|---|---|
| Covariate | HR (95% CI) | P value | HR (95% CI) | P value |
| Early vs Late | 1.68 (0.99-2.84) | 0.054 | 1.63 (0.97-2.72) | 0.064 |
| FIGO 1-3 vs 4 | 0.33 (0.18-0.59) | <0.001 | 0.46 (0.26-0.82) | 0.009 |
| FIGO NA vs 4 | 0.46 (0.24-0.87) | 0.018 | 0.67 (0.35-1.28) | 0.220 |
| Non-Serous vs Serous | 0.88 (0.47-1.64) | 0.681 | 0.86 (0.47-1.57) | 0.621 |
| Tumor Residual (yes vs no) | 2.40 (1.38-4.16) | 0.002 | 2.07 (1.23-3.49) | 0.006 |

Test classification retains a trend to significance as a predictor of OS and DFS when adjusted for known prognostic factors.

Second Classifier Development ("Classifier B")

While the performance of Classifier A was quite promising, we hoped to be able to improve performance. In particular we have been successful in isolating subgroups of patients who exhibit particularly poor outcomes by taking the subgroup of patients who are classified as Early by an initial classification and further stratifying within this population by using this subgroup to train a second, follow-up classifier. This approach was used to create Classifier B.

Figure 58A:
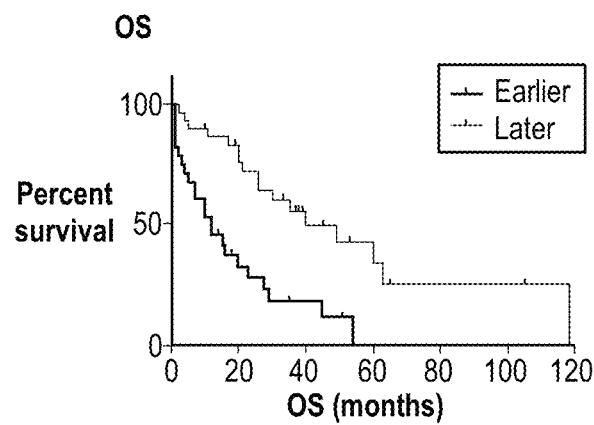
FIGS. 58A and 58B are Kaplan-Meier plots of OS and DFS, respectively, by classification group produced by the Classifier B classifier of Example 9, for the subset of the development set of samples which were used to develop the Classifier B.
Figure 58B:
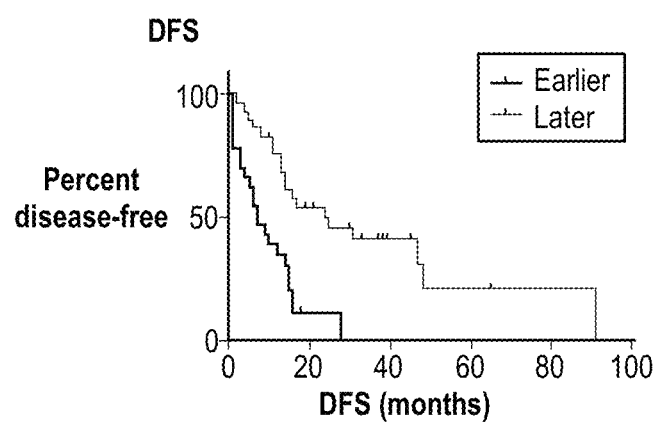

This classifier was developed using the samples that had been classified as "Early" from either the development set (n=25) or the validation set (n=24) by Classifier A, with the addition of the 9 samples from patients with exceptionally poor outcomes (DFS less than 2 months) that were not used in the development of Classifier A. This subset of samples with associated clinical data was used in the classifier development procedure of FIGS. 5A and 5B as explained above to create a new classifier, Classifier B, again assigning each sample in the reduced development set one of two classifications, "Early" or "Late". To avoid confusion with the Early and Late classification labels assigned by the Classifier A, we can refer to these labels as "Earlier" or "Later". The particular choice of moniker is not particularly important. What is important is that these Early, poor performing patients identified by Classifier A, are further stratified by Classifier B into two groups, one performing relatively better (Late or Later) and another group that performs particularly poorly (Early or Earlier). The features used in Classifier B (the reduced feature space created by feature deselection in the final iteration of loop 346 FIG. 54) are listed in Appendix E of our prior provisional application Ser. No. 62/319,958. In particular, this classifier was able to split the patients in its development set into two groups with better and worse DFS and OS, as shown in the Kaplan-Meier plots of FIGS. 58A and 58B. Twenty eight of the 58 samples used in development were classified as Early. Note in FIGS. 58A and 58B that those samples classified by Classifier B as Earlier have much poorer OS and DFS than those patients classified as Later.

Figure 59:
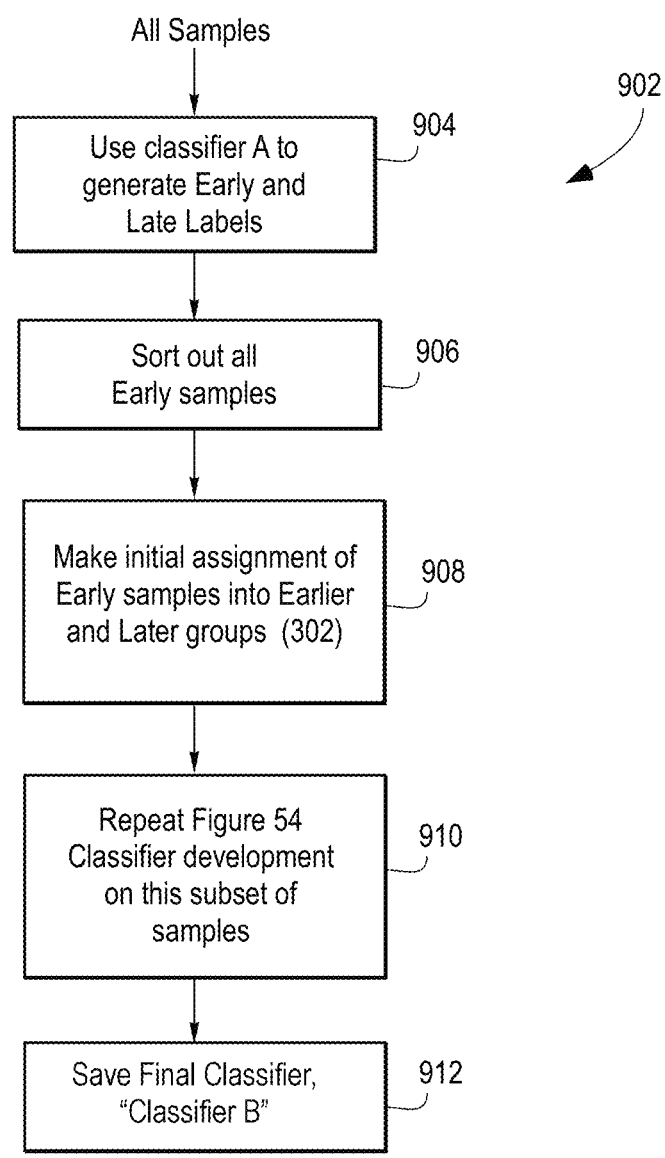
FIG. 59 is a flow chart showing a process for generating a second tier classifier ("Classifier B") from those development set samples that were classified as "Early" by the first tier "Classifier A" classifier of Example 9.

The procedure we used for generating Classifier B is illustrated in flow chart form in FIG. 59 as process 902. At step 904, we used Classifier A to generate Early or Late labels for all the samples in the entire development set. At step 906 we sorted out all the Early samples. At step 908 we made an initial label assignment of either Earlier or Later for this subset of samples based on DFS and OS data in performing step 302 of the classifier development process of FIG. 54. At step 910 we then repeated the classifier generation method of FIG. 54A-54B on this subset of samples as the development set (augmented by 9 samples that we had decided not to use in development or validation sets for classifier A as their DFS was one month or less). The process generated a new final classifier (step 350), the parameters of which were saved at step 912. These parameters include the identification of the set of samples used for classifier development, the features passing filtering in the miniClassifiers, the miniClassifiers definitions, the logistic regression weights computed in step 332, the value of k in the miniClassifiers, and the definition of the final classifier at step 350.

Third Classifier Development "Classifier C"

We have been successful in isolating subgroups of patients who demonstrate particularly good outcomes by identifying clinically distinct subgroups of the patient cohort and developing a classifier, as described above in FIGS. 54A and 54B, for each distinct subgroup. We apply these multiple classifiers to a test sample and if the sample always classifies as "Late" with each of the multiple classifiers we assign an overall classification of "Good" to indicate a likelihood of a particularly good prognosis. This approach was used to create Classifier C (which is composed of the multiple classifiers C1, C2, C3, and C4).

Classifier C was created using all 138 available samples. Four different classifiers (C1, C2, C3, and C4) were generated using the same procedure of FIGS. 54A and 54B as was used for Classifier A and Classifier B, with development sets chosen to be clinically distinct subsets of the total cohort of 138 patients. Given the available clinical data, histology and presence/absence of residual tumor after surgery were chosen to determine the clinically distinct subsets.

Classifier C1 was developed on the subset of 60 patients with non-serous histology or serous histology together with unknown FIGO score.

Classifier C2 was developed on the subset of 78 patients not used to develop Classifier C1. These patients all had serous histology, and a known FIGO score.

Classifier C3 was developed on the subset of 53 patients with residual tumor after surgery.

Classifier C4 was developed on the subset of 85 patients with no residual tumor after surgery.

Note: when ovarian cancer is diagnosed it is staged (usually using FIGO score) and given a histological type and grade by a pathologist from tumor tissue taken at surgery (biopsy is generally avoided in ovarian cancer as it is better to remove the tumor(s) whole). The predominant histological subtype for ovarian cancer is serous. Other less common types include mucinous, endometriod, and clear cell. These last 3 are combined into the "non-serous" histology type. Non-serous histology compared with serous histology is a positive prognostic factor.

As the goal of Classifier C was to be able to identify ovarian cancer patients that would likely do particularly well on platinum chemotherapy, the selection of the clinical subgroups for individual generation of classifiers was done with the idea of selecting clinically different subgroups known to have different prognosis and seeing which patients always do well. In particularly, for a patient to perform really well, ideally you they should be classified as performing well in comparison with all possible clinically distinct population. Hence, it doesn't really matter how one selects the clinical subgroups, but they need to be clinically different and should ideally be clearly different in terms of patient prognosis. It would be possible in some situations that one could select clinical subgroups based on tumor size. Here, we looked at the clinical characteristics that we had available which we knew were prognostic factors (FIGO score, histology, residual tumor). We split the cohort into two for each of these factors, and made 2 classifiers, one on each subset. Then we looked to see whether the resulting classifications were very different depending on the two classifiers for each factor. It turned out that histology and residual tumor worked best and complemented each other and adding in the FIGO score based classifiers didn't change the classifier performance much. The original plan was to then make more subgroups using one or more of these factors. But, we discovered that just using the two classifiers for each of histology and residual tumor already worked very well, so we didn't pursue further clinical subgroups, but in theory it would certainly be possible to do so. One might get the most advantage from this method by looking at the two most different subgroups e.g. all no residual tumor vs all residual tumor. Adding in further subgroups with admixtures of the two extreme groups, does not add so much in terms of principle refinement of the groups, but it does protect against the possibility of getting results in one of the two extreme subgroup classifiers that are just due to the particularities of the development set and not really due to the clinically different subsets. This is always a danger when, as usual, we have relatively low numbers of patient samples to work with, and having more than two subgroups per clinical characteristic might help to avoid this.

All four classifiers were created to split samples into two classes, Early and Late. Each classifier was then applied to all 138 samples. Classifications of samples within the development set of each classifier were generated using out-of-bag estimates. This provided four classifications for each sample, one from each of the four classifiers, C1, C2, C3, and C4. Samples receiving a "Late" classification from all four classifiers were assigned a "Good" classification label.

Figure 60:
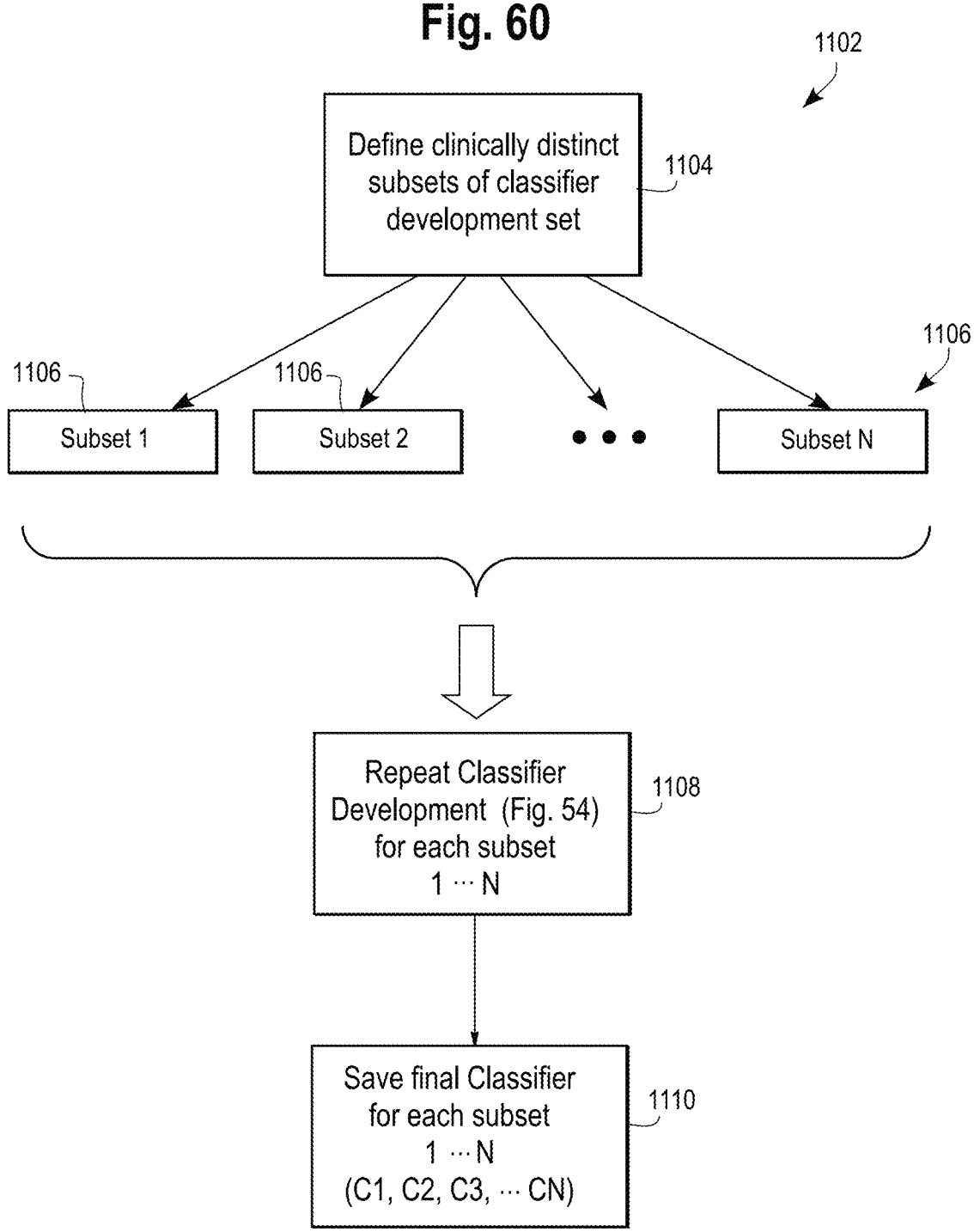
FIG. 60 is a flow chart showing a process for generating a third tier classifier C of Example 9; in this particular example the third tier consists of a several different classifiers each based on a different and clinically distinct subset of the development sample set.

The above method for generating Classifier C is illustrated in flow chart form in FIG. 60 as procedure 1102. At step 1104, one defines up to N clinically distinct subgroups of patients from the classifier development set, e.g., by inspection of the clinical data that is associated with each of the samples. The development set is then divided into subsets 1, 2, 3, . . . N, where N is typically an integer of 2 or more. At step 1108, we repeat the classifier development process (FIGS. 54A and 54B) for each of the subsets 1 . . . N. In the present ovarian context, N=4 and the subgroups are as identified above. At step 1110, the final classifier resulting at step 350 from procedure of FIGS. 54A and 54B is saved for each of the subsets, resulting in classifiers C1, C2, . . . CN. The features used in Classifiers C1, C2, C3, and C4 (the reduced feature space created by feature deselection in the final iteration of loop 346, FIG. 54A, for each of the four classifiers) are listed in Appendix E of our prior provisional application Ser. No. 62/319,958.

Figure 61:
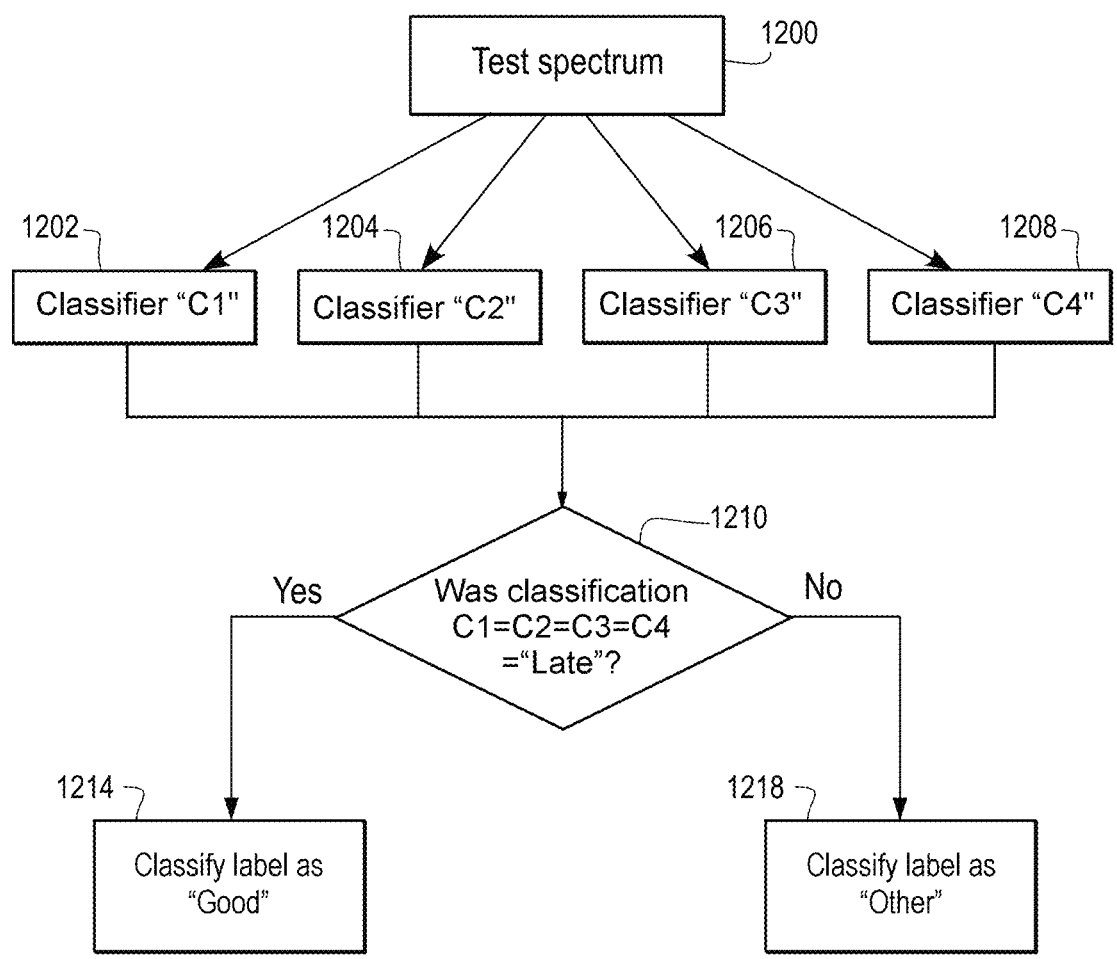
FIG. 61 is a diagram showing the construction of a third tier Classifier C, and how it could be used to generate a "Good" class label based on the results of classification by each of the members of the third tier.

The schema or composition of Classifier C is shown in FIG. 61. A test spectrum 1200 (feature values for the features used for classification of a test sample) is supplied to each of the classifiers 1202, 1204, 1206 and 1208. Each classifier generates a label, either Early or Late in this example. At step 1210, a check is made to determine whether each classifier C1 . . . C4 produced the Late class label. If so, the class label Good is reported at step 1214. In the present context, this class label indicates that the ovarian cancer patient is predicted to have a particularly good outcome on platinum chemotherapy. Conversely, if at step 1210 the classifiers are not unanimous in producing the Late class label, the class label Other (or the equivalent) is reported at step 1218. It will be noted that the Classifier C of FIG. 61 (strictly speaking, the set of parameters stored in memory including reference set, logistic regression weights, identification of features for miniClassifiers, etc.) includes not only the underlying classifiers C1 . . . . C4 defined per FIG. 54A but also the logic for comparing the results of each of the classifiers C1 . . . C4 and generating a final a class label depending on the results of the classifiers C1 . . . C4.

Hierarchical Combination of Classifiers

Classifiers A, B and C can be used in a hierarchical or ordered combination. For example, Classifier A can be used to initially classify a test sample, and if the Classifier A produces an Early class label then Classifier B is employed to generate a class label. If Classifier B produces an Early or Earlier label, the patient providing the samples is expected to perform particularly poorly on the platinum chemotherapy (platinum refractory or platinum resistant). If Classifier A produces the Late class label, the patient is predicted to perform well on platinum chemotherapy.

As another example, Classifier A and C can be used in combination. Classifier A can be used to initially classify a test sample, and if the Classifier A produces an Early class label the patient is predicted perform particularly poorly on the platinum chemotherapy (platinum refractory or platinum resistant). If Classifier A produces the Late class label, the patient sample is then subject to classification by Classifier C. If Classifier C produces a Late class the patient providing the samples is expected to perform very well on platinum chemotherapy and the Good class label is returned. If Classifier C produces an Early class label, the Other class label can be returned. The meaning and usage of the Other class label is explained below.

Figure 62:
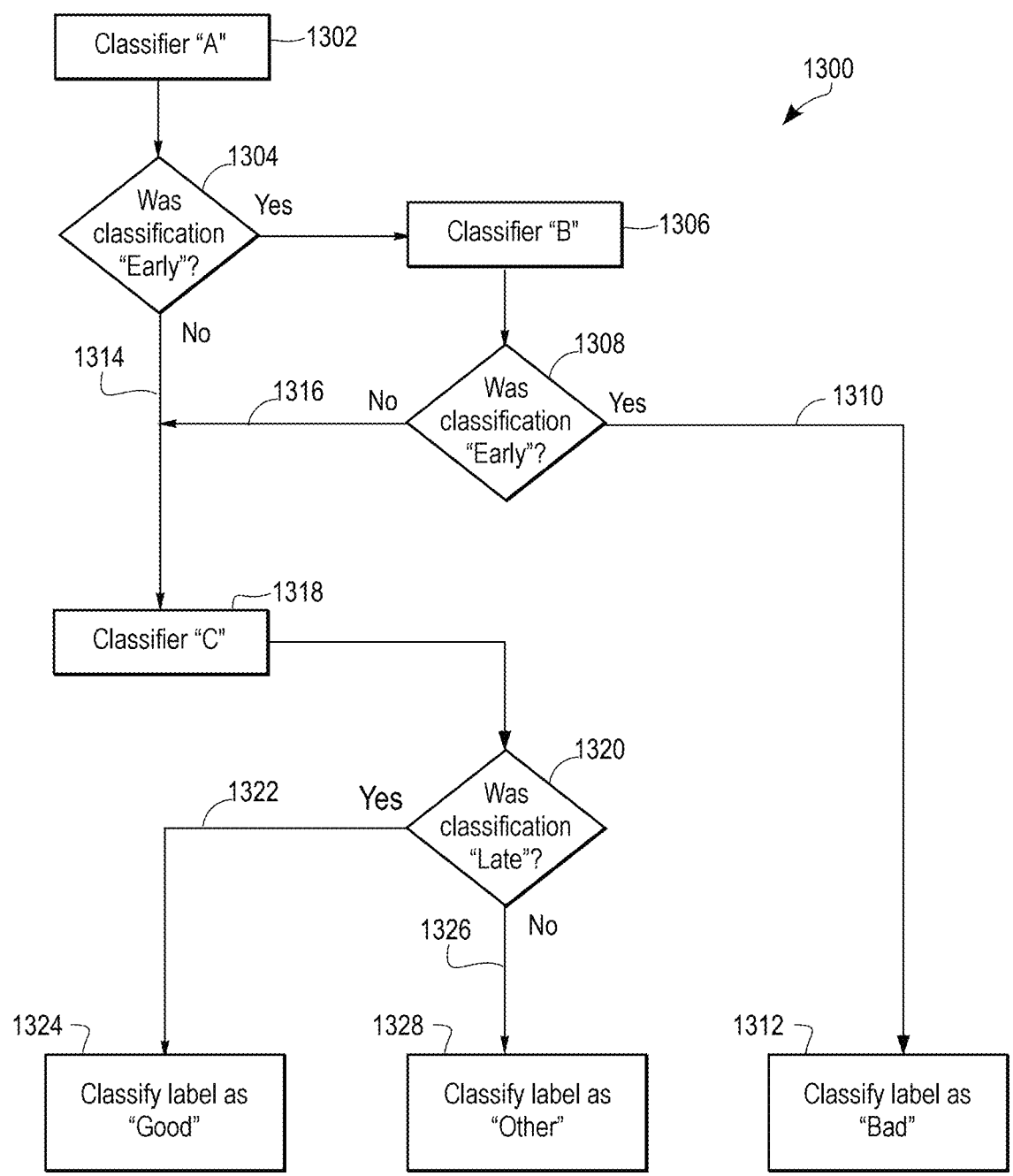
FIG. 62 is a diagram or schema showing the construction of a final classifier composed of a three-stage hierarchical classifier.

Furthermore, Classifiers A, B and C can also be used in a hierarchical or ordered manner as shown in FIG. 62. A test sample is first classified by Classifier A, step 1302. If it classifies as Early (step 1304), it is then classified by Classifier B (1306). At step 1308 the class label produced by Classifier B is inspected. If Classifier B also returns an Early classification (branch 1310) an overall label of "Bad" is returned (poor prognosis, platinum refractory or platinum resistant). If Classifier B returns a Late classification (branch 1316) or Classifier A returns a Late classification (branch 1314) the sample is classified by Classifier C (1318). Classifier C is trained to identify patients performing particularly well on the therapy. At step 1320 a check is made of the classification label produced by Classifier C. If Classifier C returns a "Late" classification (branch 1322), an overall "Good" classification is assigned to the sample (1324). If Classifier C does not return a "Late" classification (branch 1326), the sample receives an overall "Other" classification (1328).

Figure 63:
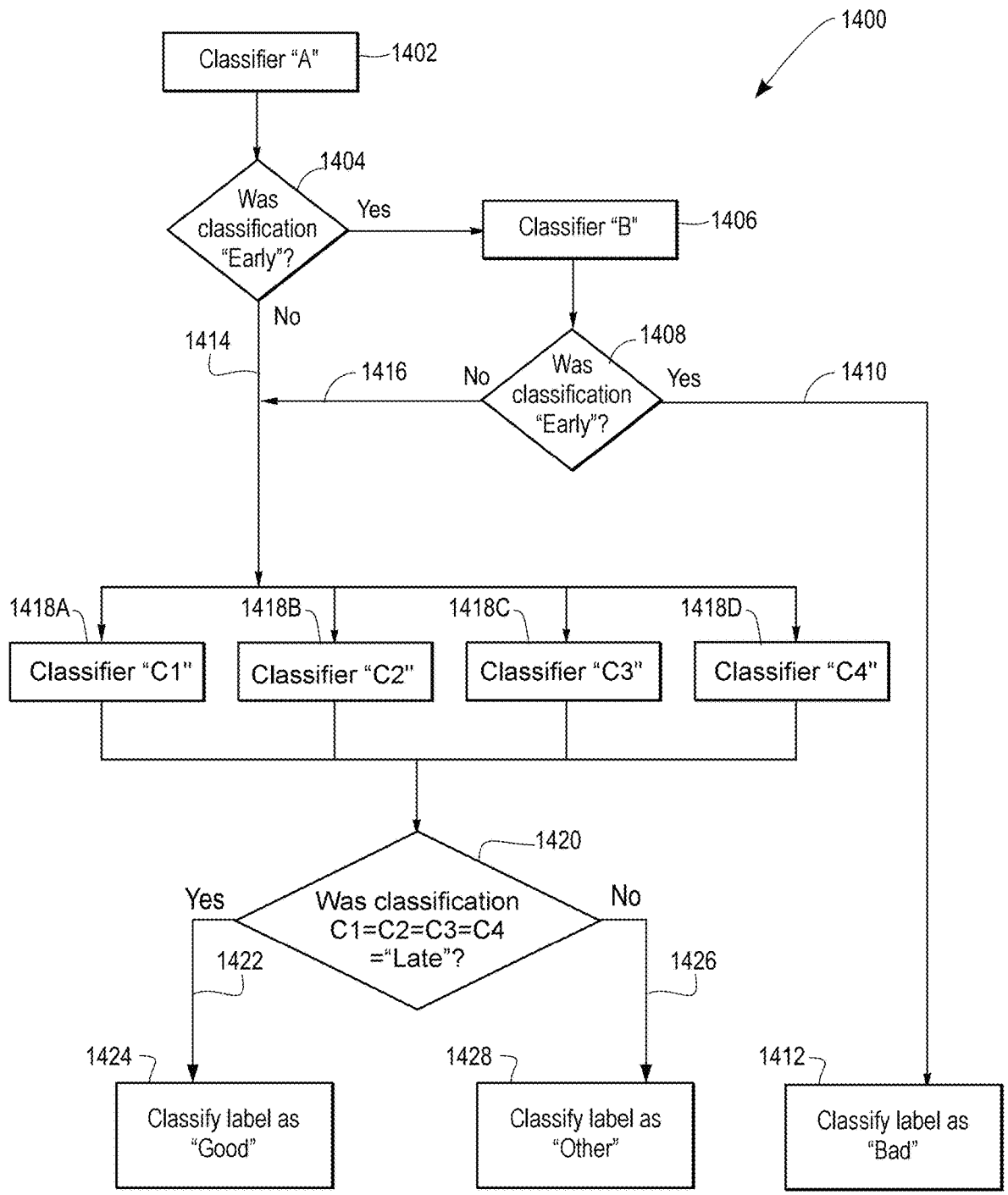
FIG. 63 is a diagram or schema showing the construction of an alternative final classifier in which the third stage of the three-stage hierarchical classifiers is made up of four individual classifiers developed from clinically distinct subgroups.

A variation of the construction of the final classifier of FIG. 62 is shown in FIG. 63. The sample is classified initially by Classifier A (1402). At step 1404, a check is made of the classification label. If the label is Early, the sample is classified by Classifier B. At step 1408 a check is made of the class label assigned by Classifier B. If Classifier B also produces a class of Early (branch 1410) the class label of Bad is assigned 1412. If at step 1404 the Classifier A produced the Late class label (1414), or if Classifier B produced the Late class label, the sample is classified by the four third-level classifiers 1418A, 1418B, 1418C and 1418D, in this example corresponding to the C1 . . . C4 classifiers explained above. At step 1420, a check is made to see if each of the four classifiers produced a Late class label. If so, branch 1422 is taken and the Good class label is reported. If at step 1420 the four classifiers do not all produce the Late class label, branch 1426 is taken and the Other class label is reported.

As was the case with the classifier construction of FIG. 61, the "final classifier" shown in FIGS. 62 and 63 is a combination of the individual classifiers A, B and C (or C1 . . . C4 in FIG. 63), plus a set of logical instructions to inspect the class labels produced by the classifiers (including subgroup classifiers) and assign the final class labels as shown in the figures.

Results for Final Classifier Constructed in Accordance with FIG. 63.

After the "final classifier" of FIG. 63 was defined and constructed, we subjected the set of samples in the development set to the classification procedure shown in FIG. 63. Twenty eight samples (20%) were classified as Bad, 61 (44%) as Other and 49 (36%) as Good. The patients' clinical characteristics by classification are shown in table 67.

TABLE 67

Patient characteristics by test classification for classifier run on all the 138 samples

|  |  | Bad (N = 28) n (%) | Other (N = 61) n (%) | Good (N = 49) n (%) | $\chi^2$ p value |
|---|---|---|---|---|---|
| Age | Median | 60 | 60 | 56 | |
|  | (Range) | (41-78) | (18-88) | (18-83) | |
| FIGO | 1 | 0 (0) | 1 (2) | 12 (24) | <0.001 |
|  | 2 | 0 (0) | 2 (3) | 1 (2) | (1 + 2 vs 3 vs |
|  | 3 | 11 (39) | 26 (43) | 17 (35) | 4) |
|  | 4 | 13 (46) | 13 (21) | 3 (6) | |
|  | N/A | 4 (14) | 19 (31) | 16 (33) | |
| Histology Grade | 1 | 0 (0) | 2 (3) | 5 (10) | 0.113 |
|  | 2 | 12 (43) | 20 (33) | 21 (43) | |
|  | 3 | 16 (57) | 39 (64) | 21 (43) | |
| Histology | Non-Serous | 6 (21) | 10 (16) | 22 (45) | 0.003 |
|  | Serous | 22 (79) | 51 (84) | 27 (55) | |
| Residual Tumor | No | 6 (21) | 36 (59) | 43 (88) | <0.001 |
|  | Yes | 22 (79) | 25 (41) | 6 (12) | |
| Metastatic Disease | No | 19 (68) | 52 (85) | 47 (96) | 0.004 |
|  | Yes | 9 (32) | 9 (15) | 2 (4) | |
| "Platinum Resistant" as assigned by investigator | No | 7 (25) | 39 (64) | 42 (86) | <0.001 |
|  | Yes | 11 (39) | 14 (23) | 6 (12) | (No vs Yes) |
|  | N/A | 10 (36) | 8 (13) | 1 (2) | |

As a test for platinum resistance as assigned by the investigator, classification Bad compared with Other or Good has 35% sensitivity and 92% specificity.

Classification is strongly associated with the known prognostic factors of FIGO score, histology, presence of metastatic disease and presence of residual tumor post-surgery.

Figure 64A:
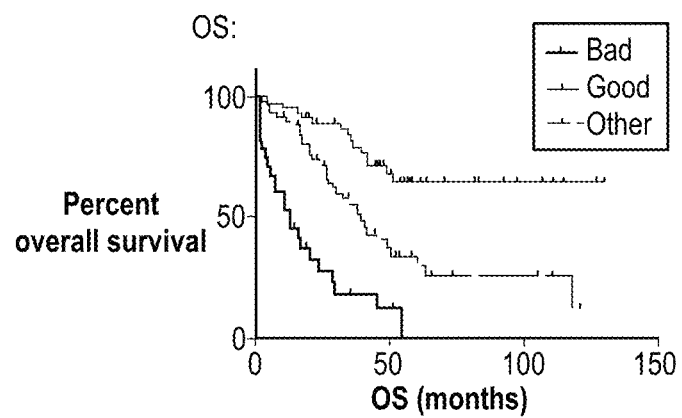
FIGS. 64A and 64B are Kaplan-Meier plots of OS and DFS, respectively by classification group produced on the development sample set using the final classifier construction of FIG. 63 and Example 9.
Figure 64B:
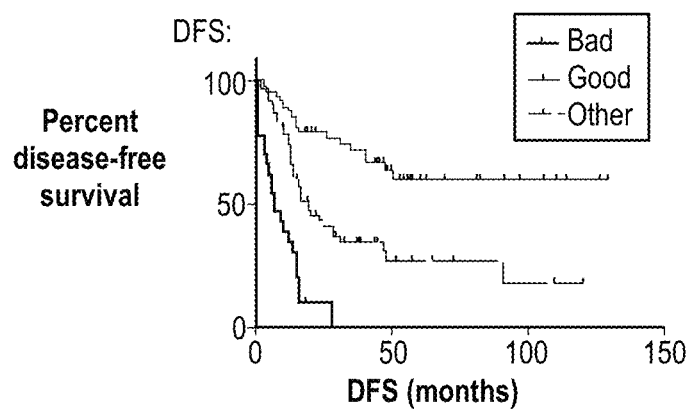
Figure 66A:
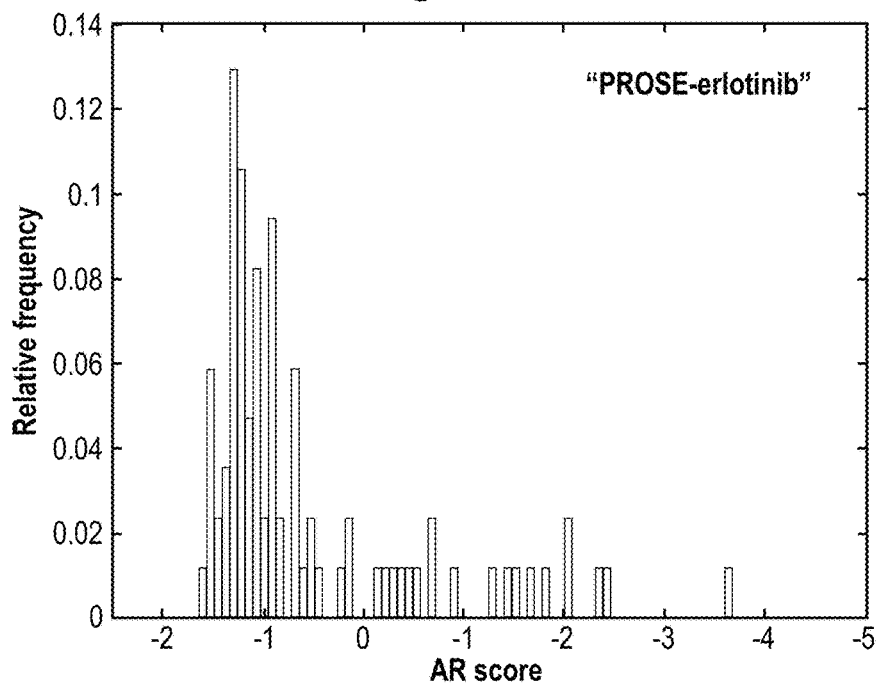
FIGS. 66A-66D are distributions of the Acute Response Score in four sample sets described in Example 10. In the results shown in FIG. 66A-66D, twenty nine mass spectrometry features were determined to be correlated with the AR biological function and were used in calculation of the corresponding Score.
Figure 66B:
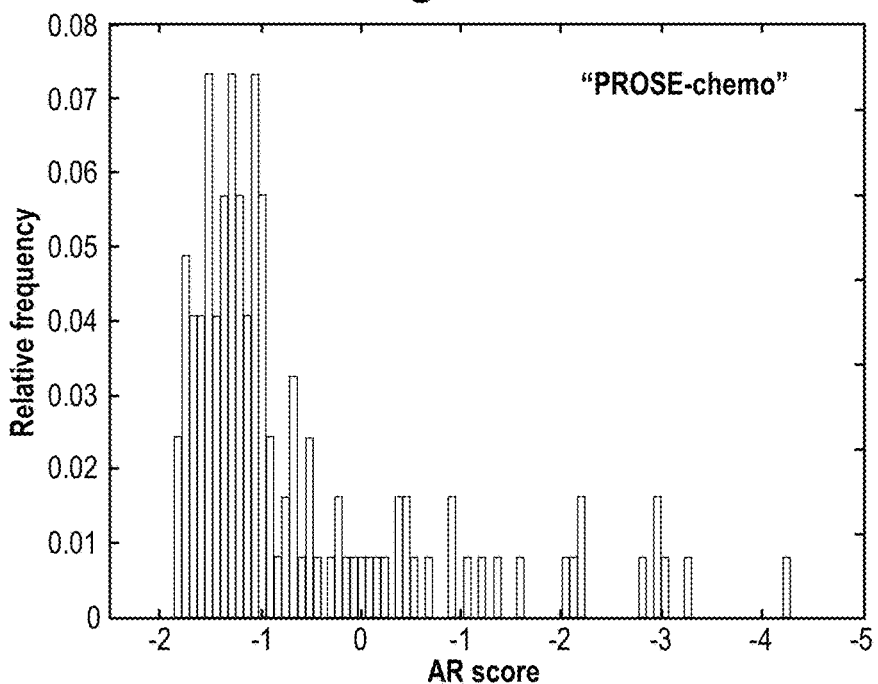
Figure 66C:
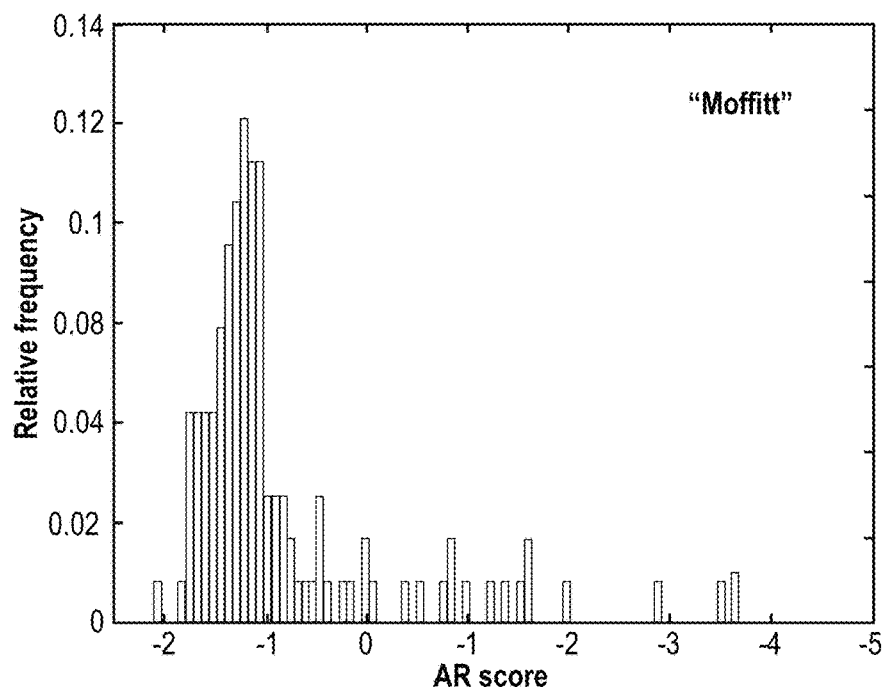
Figure 66D:
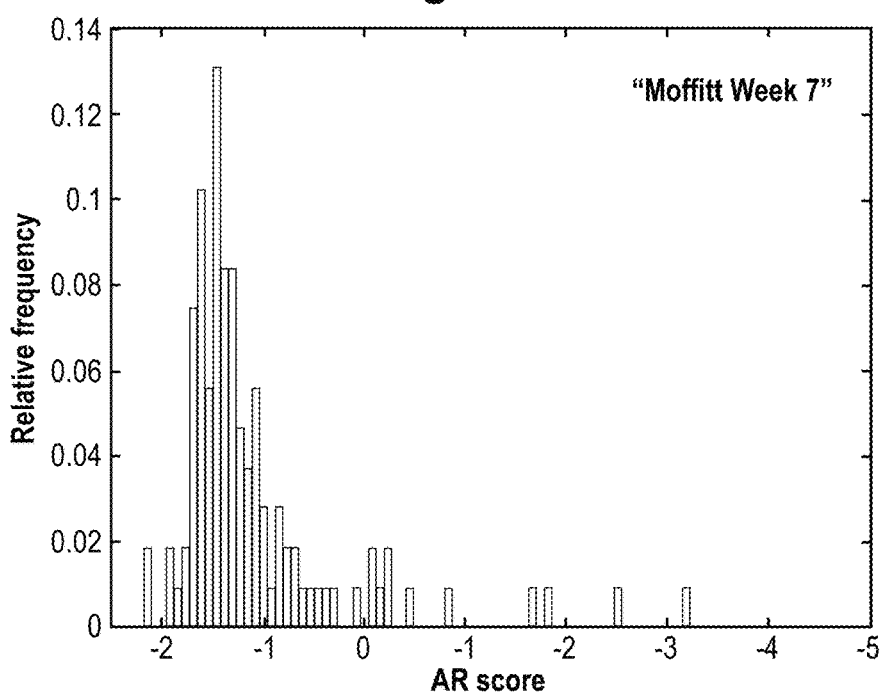
Figure 67A:
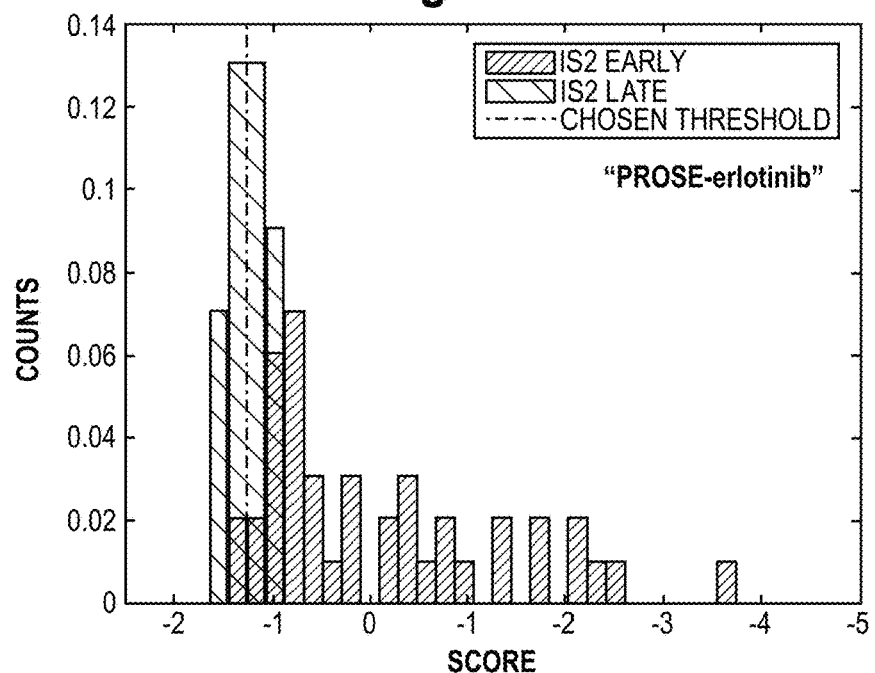
FIGS. 67A-67D are distributions of the Acute Response Score in four sample sets: "PROSE-erlotinib" (85 samples with available IS2 labels), FIG. 67A; "PROSE-chemo" (122 samples with available IS2 labels), FIG. 67B; "Moffitt", FIG. 67C; and "Moffitt-Week7", FIG. 67D. Figures FIGS. 67A-67D also shows the Scores split by IS2 classification label for the samples from the Example 1 classifier.
Figure 67B:
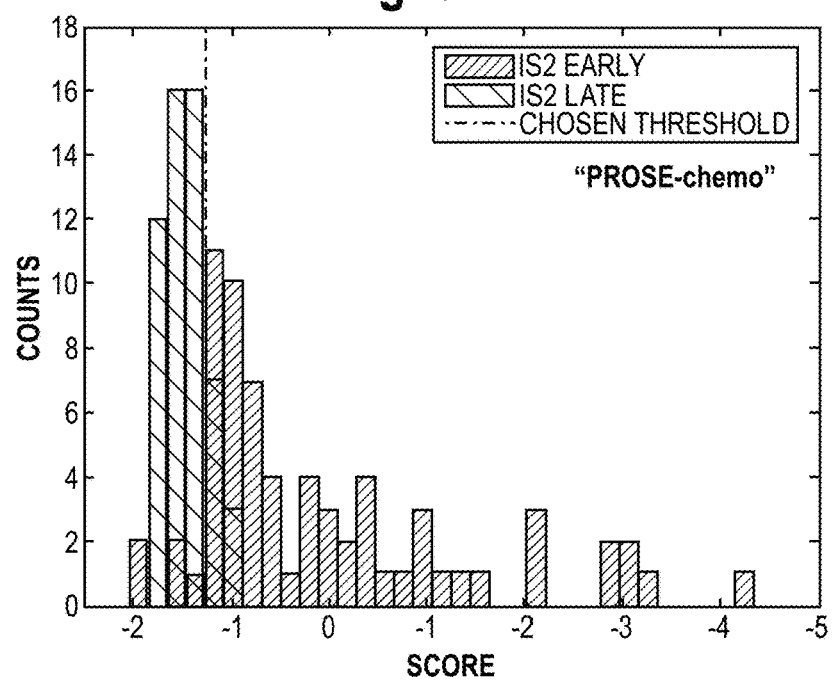
Figure 67C:
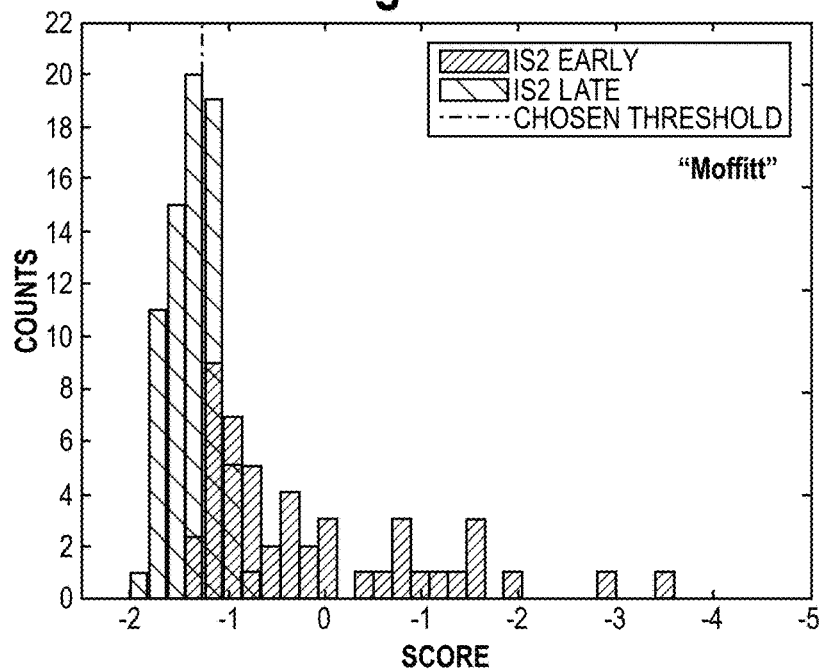
Figure 67D:
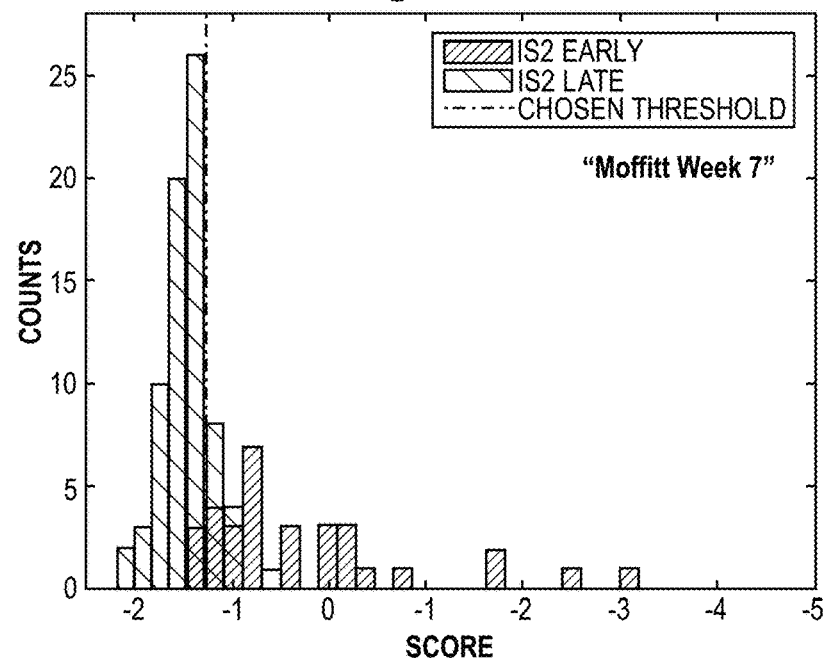
Figure 68A:
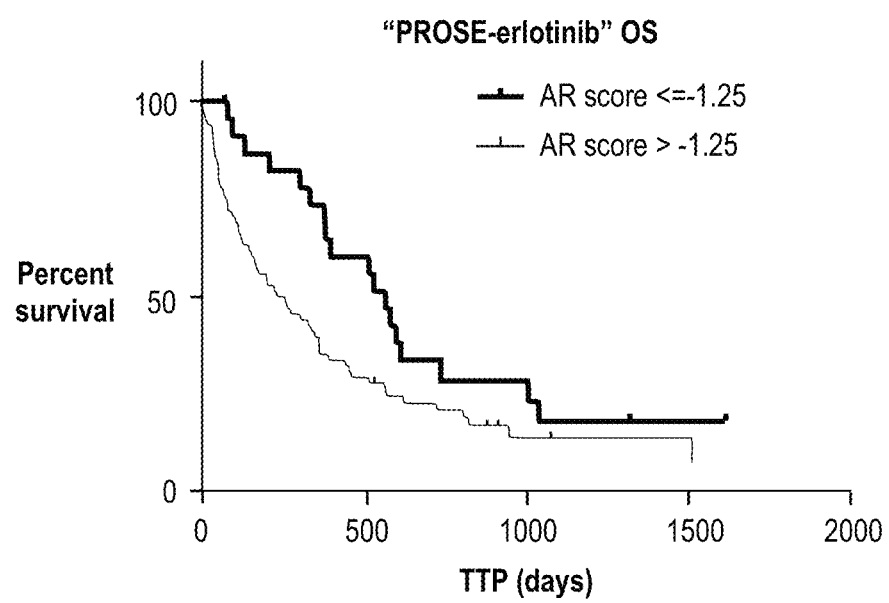
FIGS. 68A-68B are Kaplan-Meier plots for OS, PFS for "PROSE-erlotinib" sample set.
Figure 68B:
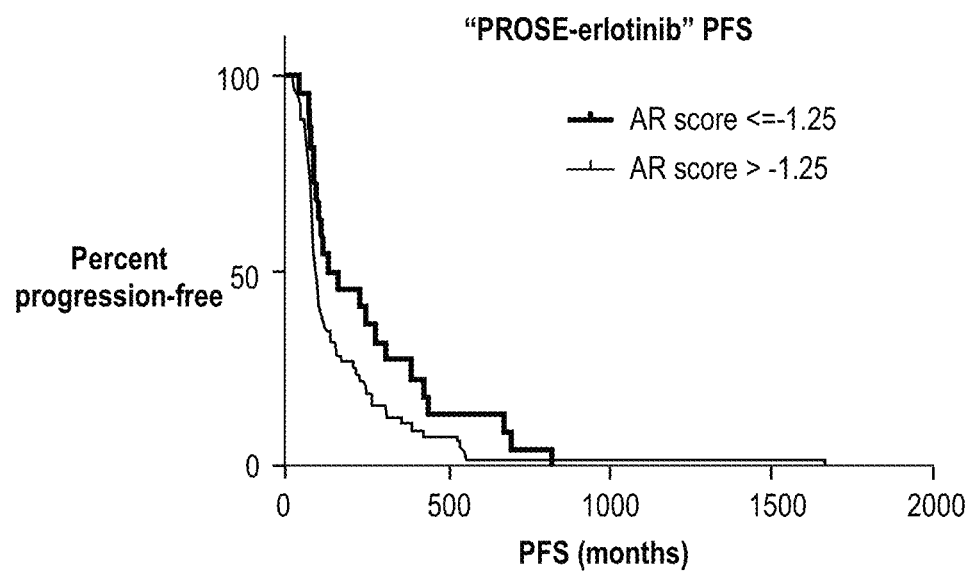
Figure 68C:
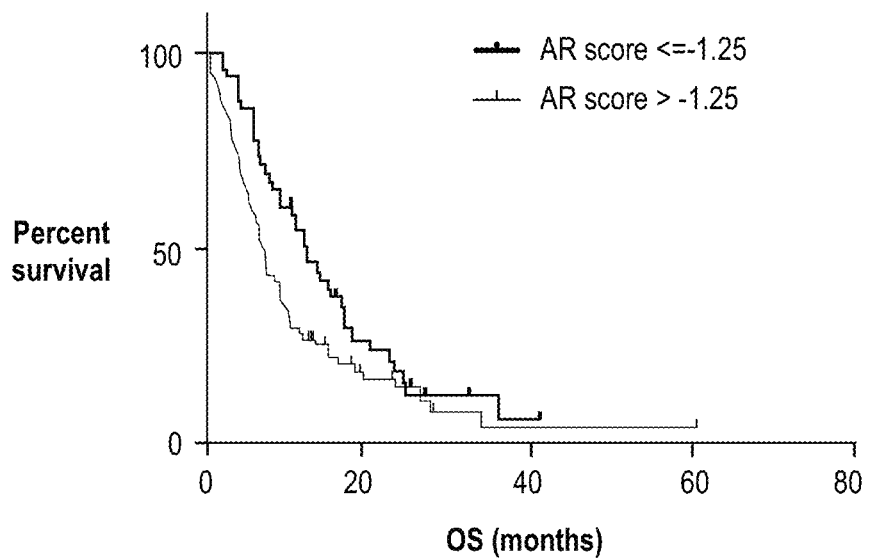
FIGS. 68C-68D are Kaplan-Meier plots for OS and PFS in a "PROSE-chemo" set.
Figure 68D:
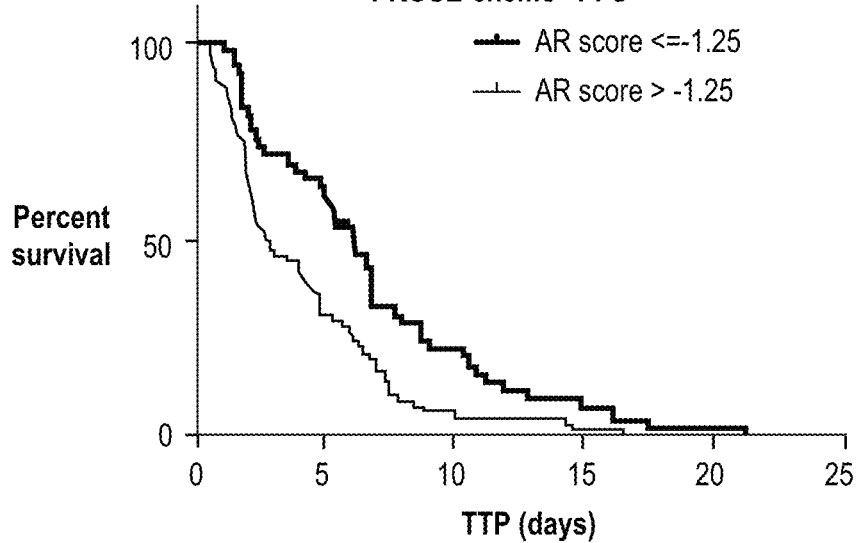
Figure 68E:
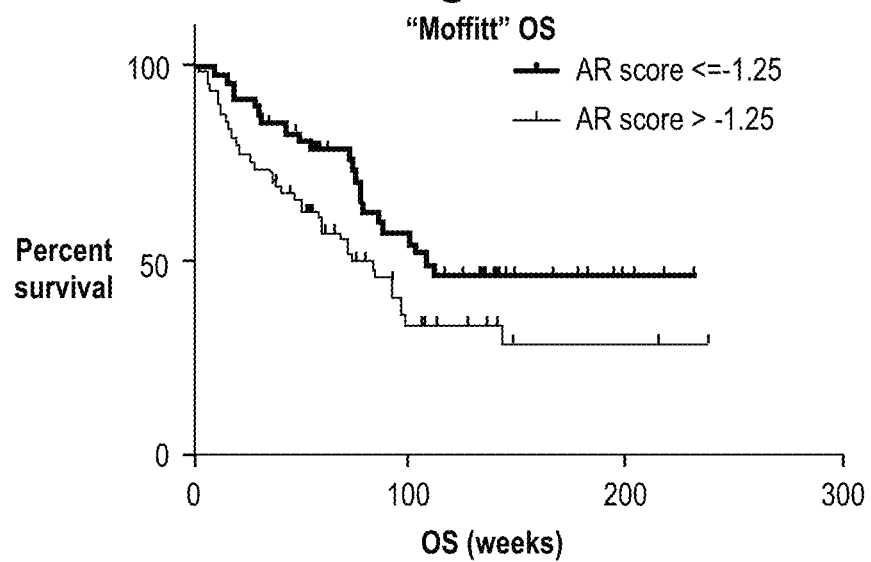
FIG. 68E-68F are Kaplan-Meier plots for OS and TTP in a "Moffitt" set, by group defined according to the AR Score threshold defined as illustrated in the FIGS. The corresponding numbers of samples in each group, hazard ratios (HRs), log-rank p-values and medians are shown below each plot.
Figure 68F:
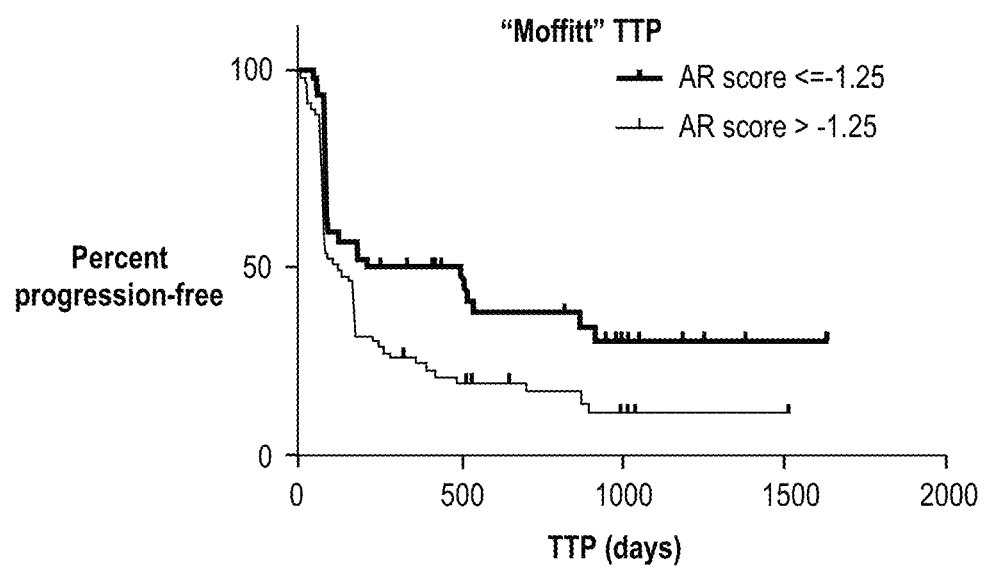
Figures 69A, 69B:
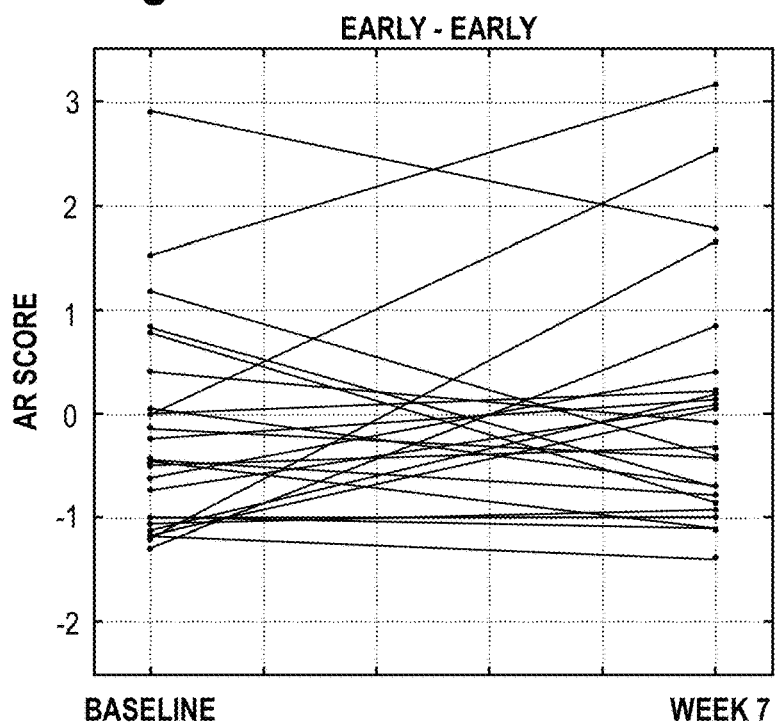
FIGS. 69A-69D are illustrations of the evolution of the Acute Response Score over time for 107 patients in both the Moffitt and Moffitt-Week7 sets, grouped by combination of IS2 label at baseline (before treatment) and week 7 (after treatment). Each line in the plots represent the score of an individual patient.
Figure 69C:
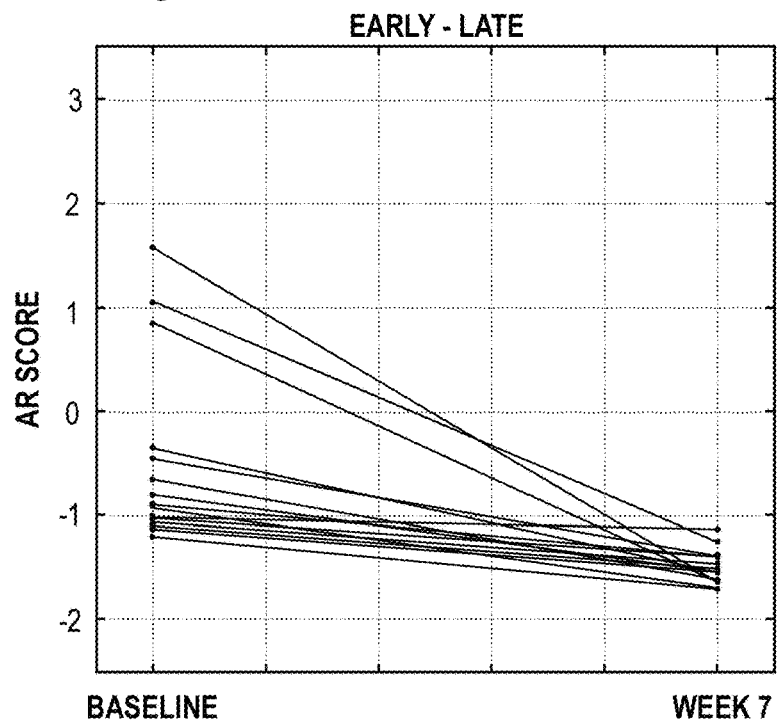
Figure 69D:
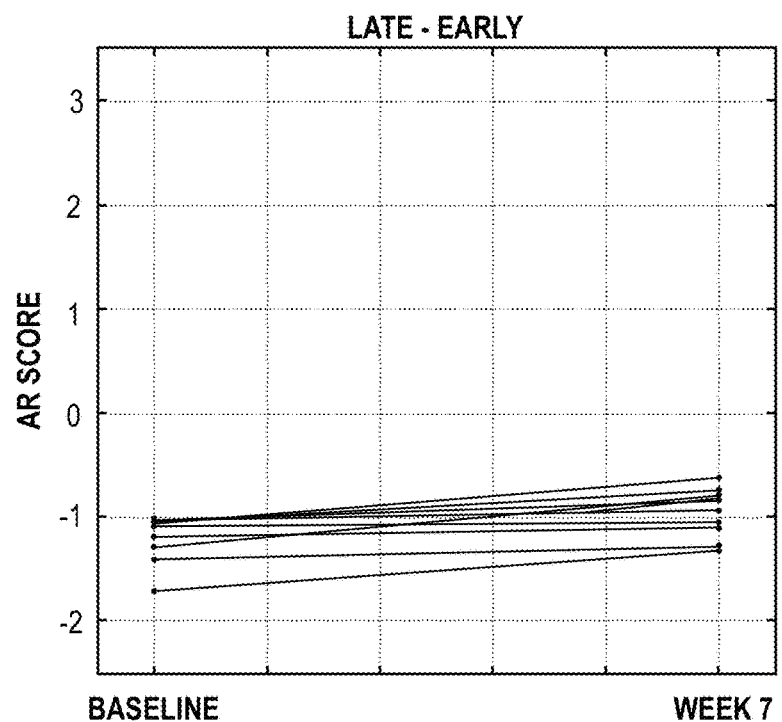

FIGS. 64A and 64B show the Kaplan-Meier plots by classification group for OS and DFS for the classifications produced by the classifier of FIG. 63. The associated survival analysis statistics are given in tables 68 and 69. Note the extremely poor outcomes, particularly DFS, for the group assigned the label Bad, and the particularly good outcomes for the group assigned the label Good.

TABLE 68

Medians for time-to-event endpoints by classification group

|  | Median OS (95% CI) in months | Median DFS (95% CI) in months |
|---|---|---|
| Bad | 12 (5-23) | 7 (3-14) |
| Other | 39 (28-50) | 20 (14-29) |
| Good | Not reached (51-undefined) | Not reached (48-undefined) |

TABLE 69

Survival analysis statistics between classification groups

| | OS | | | DFS | | |
|---|---|---|---|---|---|---|
| | log-rank p | CPH p | HR (95% CI) | log-rank p | CPH p | HR (95% CI) |
| Bad vs Good | <0.001 | <0.001 | 0.13 (0.06-0.26) | <0.001 | <0.001 | 0.10 (0.05-0.22) |
| Bad vs Other | <0.001 | <0.001 | 0.31 (0.18-0.53) | <0.001 | <0.001 | 0.28 (0.16-0.49) |
| Other vs Good | <0.001 | <0.001 | 0.34 (0.18-0.64) | <0.001 | <0.001 | 0.35 (0.19-0.62) |

These results indicate that our hierarchical classifier shown in FIG. 63 is able to stratify the patients into three groups with better, worse, and intermediate outcomes. As can be seen from the data in tables 70 and 71, patients with samples classified as Good are likely to have good long term outcomes on platinum-based chemotherapy, while patients with samples classified as Bad are very unlikely to have good long term outcomes on platinum-based chemotherapy.

TABLE 70

Proportions still alive and disease-free at key timepoints

| | Bad | Other | Good |
|---|---|---|---|
| % alive at 1 year | 46 | 88 | 96 |
| % alive at 2 years | 28 | 72 | 89 |
| % disease-free at 6 months | 54 | 90 | 96 |
| % disease-free at 1 year | 35 | 75 | 88 |

TABLE 71

Number of patients disease-free at key timepoints

| | Bad | Other | Good |
|---|---|---|---|
| # DFS ≤ 4 months (N = 14) | 9 (64%) | 3 (21%) | 2 (14%) |
| # DFS > 4 months (N = 121) | 17 (14%) | 57 (47%) | 47 (39%) |
| # DFS ≤ 6 months (N = 20) | 12 (60%) | 6 (30%) | 2 (10%) |
| # DFS > 6 months (N = 115) | 14 (12%) | 54 (47%) | 47 (41%) |
| # DFS ≤ 10 months (N = 32) | 16 (50%) | 11 (34%) | 5 (16%) |
| # DFS > 10 months (N = 100) | 9 (9%) | 48 (48%) | 43 (43%) |
| # DFS ≤ 1 year (N = 38) | 17 (45%) | 15 (39%) | 6 (16%) |
| # DFS > 1 year (N = 92) | 8 (9%) | 42 (46%) | 42 (46%) |

In terms of predicting 6 months disease free survival status, a classification of Bad compared with Other or Good has a sensitivity of 60% and specificity of 88% (odds ratio=0.09 Wald 95% CI: 0.03-0.27). For prediction of 12 months disease free survival status, a classification of Bad compared with Other or Good has a sensitivity of 45% and specificity of 91%.

Table 72 shows the multivariate analysis of classification Bad vs Not Bad (i.e., Other or Good). This shows that while the classification is strongly correlated with other prognostic factors (see table 67), it remains a clearly statistically significant predictor of both OS and DFS when adjusted for other known prognostic factors. This indicates that the classification can provide additional information to other prognostic factors available to physicians.

TABLE 72

Multivariate analysis of OS and DFS

| | OS | | DFS | |
|---|---|---|---|---|
| Covariate | HR (95% CI) | P value | HR (95% CI) | P value |
| NotBad (Other or Good) vs Bad | 0.35 (0.20-0.62) | <0.001 | 0.30 (0.17-0.55) | <0.001 |
| FIGO 1-3 vs 4 | 0.35 (0.19-0.63) | <0.001 | 0.52 (0.29-0.93) | 0.027 |
| FIGO NA vs 4 | 0.47 (0.24-0.88) | 0.019 | 0.80 (0.41-1.55) | 0.509 |
| Non-Serous vs Serous | 0.85 (0.46-1.58) | 0.615 | 0.77 (0.43-1.39) | 0.386 |
| Tumor Residual (yes vs no) | 2.25 (1.30-3.90) | 0.004 | 1.81 (1.06-3.08) | 0.031 |

In terms of predicting disease free survival status at six months, the analysis can be adjusted for possible confounding factors using logistic regression. The results are shown in table 73.

TABLE 73

Adjustment of odds ratio for prediction of DFS at 6 months for potential confounding factors

| Covariate | Odds Ratio (95% CI) | P value |
|---|---|---|
| (Other or Good) vs Bad | 0.18 (0.05-0.65) | 0.009 |
| FIGO 1-3 vs 4 | 0.31 (0.08-1.20) | 0.089 |
| FIGO NA vs 4 | 0.26 (0.05-1.40) | 0.118 |
| Serous vs Non-Serous | 4.36 (1.17-16.17) | 0.028 |
| Tumor Residual (yes vs no) | 3.05 (0.83-11.25) | 0.094 |

Classification (Bad vs Other or Good) remains a significant predictor of DFS status at 6 months even when adjusted for potential confounding factors.

Conclusions from the Ovarian Cancer/Platinum Chemotherapy Classifiers

We were able to construct classifiers that could separate ovarian cancer patients treated with surgery and platinum based chemotherapy into groups with better and worse outcomes from mass spectra of pretreatment serum samples. The classifier constructed using half of the reduced set of 129 sample set for development (Classifier A) validated well on the remainder of the samples held for internal validation, and the results for the cohort as a whole indicated promising performance. While the test classification was associated with baseline clinical factors known to have prognostic significance, it still showed a trend to statistical significance for providing additional information for prediction of outcomes.

By selecting clinically distinct patient subgroups from the whole cohort to use for classifier development it was possible to construct a classification system composed of multiple hierarchical classifiers that could stratify the ovarian cancer patients into three classes: one with very good outcomes ("Good"), one with very poor outcomes ("Bad") and a third with intermediate outcomes ("Other"). This classification was also strongly correlated with other prognostic factors, but Bad versus Other or Good classifications retained its ability to predict outcome with clear statistical significance even when adjusted for other prognostic factors in multivariate analysis. This indicates that the classification could be of direct clinical utility for physicians advising or making treatment decisions for patients in this indication, providing information supplementary to that available to them from their patients' clinical characteristics.

Interpreted in terms of a test to identify patients who are platinum resistant or platinum refractory, a classification of Bad vs Other or Good showed 60% sensitivity and 88% specificity for identification of patients progressing within 6 months of surgery (odds ratio 0.09). It remained a strong statistically significant predictor of DFS status at six months when adjusted for potential confounding factors, indicating that it again provides physicians with additional information to inform patient care.

To summarize, in this Example we have described a method of generating an ensemble of classifiers. The method includes the steps of:

a. from a set of patient samples, defining a plurality of classifier development sample sets, each of which have different clinical characteristics (in this example, different proportions of tumor sizes, but in practice this could be different proportions of any clinical characteristic which might be relevant to classifier performance, such as age or age group, smoker status, disease stage, level of a serum or tissue protein or gene expression, mutation status, performance status, surgical resection status, menopausal status, number of lines or kinds of prior therapy received, response to prior lines of therapy, histology class or grade, etc., tumor size, or other types of groupings of the development sample set into different clinical groups)

b. conducting mass spectrometry on the set of patient samples and storing mass spectrometry data (for example using Deep MALDI and generating a feature table for the mass spectral features listed in Appendix A; it will be appreciated that Deep MALDI and Appendix A features are not necessary and are offered by way of example and not limitation)

c. using a programmed computer, conducting a classifier development exercise using the mass spectral data for each of the development sets defined in step a. and storing in a memory associated with the computer the parameters of the classifiers thus generated (it being understood that the procedure of FIG. 8 steps 102-150 is offered by way of example and not limitation), thereby generating an ensemble of classifiers; and d. defining a rule or set of rules for generating a class label for a test sample subject to classification by the ensemble of classifiers generated in step c. For example, the rules could be if all classifiers generate the same class label, assigning to the test sample that class label, or some new class label such as "Bad" (with all classifiers in the ensemble assigned the Early class label) or Good (with all classifiers in the ensemble assigning a Late class label). As another example the rules could be assigning a label to the test sample based on a majority vote of the ensemble of classifiers. As another example, assigning to the test sample a label in accordance with a ternary classification scheme, in which a class label of "other" or the equivalent is assigned if the class labels produced by the ensemble of classifiers for the test sample are not all the same, and if all classifiers in the ensemble generate the same class label assigning the sample a class label indicative of such unanimity of classifications, such as Good or Bad as in Example 5.

As another example, a method of testing a sample using an ensemble of classifiers is contemplated, wherein the ensemble of classifiers are generated using steps a., b., c., and d., mass spectral data of the test sample is classified by each of the members in the ensemble, and a class label is assigned to the test sample according to the rule or set of rules.

The following clauses are offered as further descriptions of the invention disclosed in Example 9:

1. A method of generating an ensemble of classifiers from a set of patient samples, comprising the steps of:

a. defining a plurality of classifier development sample sets from the set of patient samples, each of which have different clinical characteristics;

b. conducting mass spectrometry on the set of patient samples and storing mass spectrometry data;

c. using a programmed computer, conducting a classifier development exercise using the mass spectral data for each of the development sets defined in step a. and storing in a memory associated with the computer parameters defining the classifiers thus generated, thereby generating an ensemble of classifiers, one for each classifier development sample set; and d. defining a rule or set of rules for generating a class label for a test sample subject to classification by the ensemble of classifiers generated in step c.

2. The method of clause 1, wherein the patient samples are samples from cancer patients, and wherein each of the development sets have different proportions of patients having a given clinical characteristic.

3. The method of clause 2, wherein the clinical characteristic is tumor size.

4. The method of clause 3, wherein step c. comprises performing the procedure of FIG. 8 steps 102-150.

5. The method of clause 1, wherein the clinical characteristic is at least one of age or age group, smoker status, disease stage, level of a serum or tissue protein or gene expression, mutation status, performance status, surgical resection status, menopausal status, number of lines or kinds of prior therapy received, response to prior lines of therapy, tumor size, and histology class or grade.

6. A method of testing a blood-based sample, comprising the steps of:

generating an ensemble of classifiers by performing the method of clause 1 on a development set of blood-based samples;

conducting mass spectrometry on the blood-based sample and obtaining mass spectral data, and classifying the mass spectral data of the blood-based sample with each of the members of the ensemble and assigning a class label to the test sample according to the rule or set of rules.

7. A multi-stage classifier comprising:

a programmed computer implementing a hierarchical classification procedure operating on mass spectral data of a test sample stored in memory and making use of a reference set of class-labeled mass spectral data stored in the memory;

wherein the classification procedure further comprises:

a first stage classifier for stratifying the test mass spectral data into either an Early or Late group or the equivalent;

a second stage classifier for further stratifying the Early group of the first stage classifier into Early and Late groups (or Earlier and Later groups, or the equivalent), the second stage classifier operating on the mass spectral data of the test sample if the first stage classifier classifies the test mass spectral data into the Early group and wherein the Early or Earlier class label, or the equivalent, produced by the second stage classifier is associated with an exceptionally poor prognosis; and a third stage classifier for further stratifying the Late group of the first stage classifier into Early and Late groups (or Earlier and Later groups, or the equivalent), the third stage classifier operating on the mass spectral data of the test sample if the first stage classifier classifies the test mass spectral data into the Late group, wherein a Late or Later class label, or the equivalent, produced by the third stage classifier is associated with an exceptionally good prognosis.

8. The multi-stage classifier of clause 7, wherein the third stage classifier comprises one or more classifiers developed from one or more different clinical sub-groups of a classifier development set used to generate the first level classifier.

9. A method of generating a classifier for classifying a test sample, comprising the steps of:

(a) generating a first classifier from measurement data of a development set of samples using a classifier development process;

(b) performing a classification of the measurement data of the development set of samples using the first classifier, thereby assigning each member of the development set of samples with a class label in a binary classification scheme (Early/Late, or the equivalent);

(c) generating a second classifier using the classifier development process with an input classifier development set being the members of the development set assigned one of the two class labels in the binary classification scheme by the first classifier, the second classifier thereby stratifying the members of the input classifier development set with the first class label into two further sub-groups.

10. The method of clause 9, further comprising the steps of:

(d) dividing the development set of samples into different clinical subgroups 1 . . . N where N is an integer of at least 2;

(e) repeating the classifier development process for each of the different clinical subgroups 1 . . . N, thereby generating different third classifiers C1 . . . CN; and (f) defining a hierarchical classification process whereby:

i. a patient sample is classified first by the first classifier generated in step a);

ii. if the class label assigned by the first classifier is the class label used to generate the second classifiers, then classifying the patient sample with the second classifier; and iii. if the class label assigned by the first classifier is not the class label used to generate the second classifier, then classifying the patient sample with the third classifiers C1 . . . CN; and iv. generating a final label as a result of classification steps ii or step iii.

11. A classifier generation method, comprising:

a) obtaining physical measurement data from a development set of samples and supplying the measurement data to a general purpose computer, each of the samples further associated with clinical data;

b) generating a first classifier (Classifier A) from the measurement data of the development set of samples;

c) identifying a plurality of different clinical sub-groups C1 . . . CN within the development set based on the clinical data;

d) for each of the different clinical sub-groups, conducting a classifier generation process from the measurement data for each of the members of the development set that is associated with such clinical sub-groups thereby generating clinical subgroup classifiers C1 . . . CN;

e) storing in memory of a computer a classification procedure involving the Classifier A and the classifiers C1 . . . CN generated in step d).

12. The method of clause 11, wherein the classifier development of steps b) and d) is in accordance with the procedure of FIG. 8 steps 102-150.

13. The method of clause 11 or clause 12, wherein the method further comprises a step of conducting a bagged filtering operation to filter the measurement data obtained from the samples to either deselect junky features in the measurement data or select a subset of the features in the measurement data which have significant classification performance.

14. The method of clause 13, wherein the classifier generation process is performed iteratively with the bagged filtering operation to deselect junky features or select a subset of features which have significant classification performance.

15. The method of any of clauses 11-14, wherein the measurement data comprises MALDI-TOF mass spectrometry data.

16. The method of any of clause 15, wherein the MALDI-TOF mass spectrometry data is acquired from a process in which each of the samples in the development set is subject to at least 100,000 laser shots.

17. A method comprising generating an ensemble of classifiers each based on different proportions of patients with large and small tumors and generated in a computer from mass spectrometry data of blood-based samples from a development set of samples, and defining a classification procedure using the ensemble of classifiers.

18. The method of clause 17, wherein the ensemble of classifiers comprises the ensemble of classifiers identified as IS6 in this document.

19. A method of guiding treatment of a melanoma patient comprising performing mass spectrometry on a blood-based sample from the patient and generating a class label of a blood-based sample using an ensemble of classifiers generated in accordance with clause 17, and using the class label to guide the patient in treatment of the melanoma.

20. The method of clause 19, wherein the treatment comprises administration of nivolumab.

21. The method of clause 19, wherein the guiding of treatment comprises not administering the combination of nivolumab and ipilimumab.

Example 10

Method and System for Measurement of Biological Function Scores Using Mass Spectrometry Data and Uses Thereof, Including Guiding Treatment, Predicting Survival, and Developing Classifiers This Example details the methodology and systems which are used in order to obtain a novel and useful score (e.g., a numerical value) that measures a particular biological function, e.g. acute response, wound healing, complement system, or other, for a given patient. Such a biological function score is calculated from mass spectral data from a serum sample. By way of example and not limitation, in this Example we obtain mass spectral data using the Deep MALDI technique as described previously in this document from Example 1.

Data used in Example 10 In order to obtain the results presented in Example 10, the following five sample sets were used:

"Analysis" set—composed of 49 patients, most with non-small cell lung cancer (NSCLC), but a few with chronic obstructive pulmonary disease (COPD) but no cancer. Matched mass spectral data (298 features) and protein expression of 1129 proteins/peptides obtained from running the SomaLogic 1129 panel (see Example 6) were available for these samples.

"PROSE-erlotinib" set—85 patients from the PROSE trial treated with erlotinib. All patients had advanced, previously treated NSCLC. Mass spectral data (298 features) and the corresponding classification labels produced by the Example 1 "IS2" classifier were available from pre-treatment samples.

"PROSE-chemo" set—123 patients from the PROSE trial treated with single agent chemotherapy. All patients had advanced, previously treated NSCLC. Mass spectral data (298 features) and the corresponding class labels produced by the Example 1 "IS2" classifier were available from pre-treatment samples.

"Moffitt" set—119 melanoma patients treated with nivolumab (anti-PD1 agent) at Moffitt Cancer Center, see Example 1. The samples were collected before treatment. Mass spectral data (298 features) and the corresponding classification labels produced by the Example 1 "IS2" classifier were available.

"Moffitt-Week7" set—a subset of 107 patients from the "Moffitt" cohort, collected 7 weeks after beginning of treatment. See Example 7. Mass spectral data (298 features) and the corresponding classification labels produced by the Example 1 "IS2" classifier were available.

Sample preparation and pre-processing Samples were prepared and mass spectra acquired using standard Deep MALDI acquisition procedures explained in Example 1. We improved a few of the processing parameters, but the details are not particularly important and do not make any principal difference to the present results. For example, we used slightly different feature definitions than were used in Example 6 and excluded a few features that have shown some reproducibility issues. Consequently, the number of features associated with a particular protein set or functional group for a fixed p value may vary from what was specified in Example 6 and used for classifier development in Example 6.

PSEA Protein Set Enrichment Analysis

The correlation of each mass spectral (MS) feature with the biological functions described in this Example was calculated by running Protein Set Enrichment Analysis—PSEA (a variant of the Gene Set Enrichment Analysis method, applied to protein expression data) on the "Analysis" set. The PSEA correlates MS features with expression of multiple proteins, rather than expression of single proteins, providing some protection against identifying randomly correlated and not generalizable associated features. This method also allows for the identification of a significant effect that is smaller in magnitude (per protein) than that which could be identified in a univariate analysis. The protein sets were created based on the intersection of the list of SomaLogic 1129 panel targets and results of queries from GeneOntology/AmiGO2 and UniProt databases. The PSEA returns, for each MS feature and protein set pair, an enrichment score, ES, which reflects the degree of correlation, and a p-value that reflects the significance of the ES when compared with the null distribution of no correlation. For further details, see Example 6 and the Mootha et al. and Subramanian et al. papers cited in Example 6.

Biological Function Score—Methodology

Figure 81:
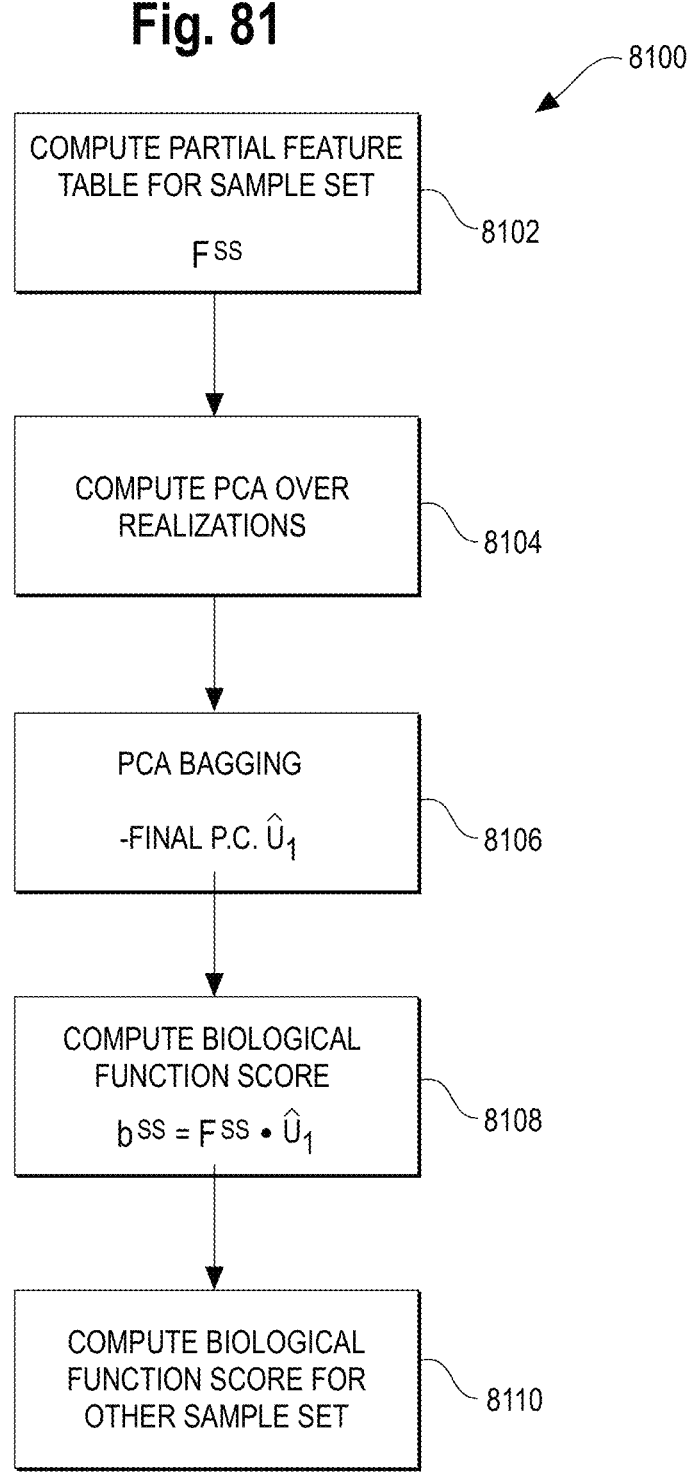
FIG. 81 is a flow chart showing the steps for calculating the biological function scores of Example 10 from mass spectrometry data.

Given a biological function, e.g., Wound Healing or Acute Response, we determined which MS features were correlated with the corresponding protein set at the $\alpha=0.05$ significance level (unadjusted for multiple comparisons) using the PSEA results of the "Analysis" set. A Principal Component Analysis (PCA) is then performed using the $N_S=85$ samples from the "PROSE-erlotinib" set. PCA is a known methodology in statistics and data analysis to reduce a complex data set to lower dimensions and reveal hidden, simplified dynamics underlying it. As shown in FIG. 81, the procedure for calculation of a biological function score is shown at 8100 in a flow-chart form. It will be appreciated that the flow chart of FIG. 81 and the description below can be reduced to a set of programmed instructions by those skilled in the art. At step 8102, a particular feature table for a sample set (ss) is computed set, $F^{ss}$. At step 8104, we perform a PCA over many realizations of subsets of the development sample set. At step 8106 we compute a PCA bagging procedure and arrive at a first principal component $\hat{u}_1$. At step 8108 $\hat{u}_1$ we compute a biological function score $b^{ss}=F^{ss}\cdot\hat{u}_1$ for each member of the sample set. At step 8110 we calculate the biological function score of other sample sets, if present. Since the number of samples available for the calculations was small and thus prone to leading to a randomly biased PCA solution, we implemented a bagged version of PCA step 8106. The procedure in more detail is as follows:

1. Step 8102 Construct partial feature table for a sample set, here the "PROSE-erlotinib" set
   a. For each sample in the "PROSE-erlotinib" set, the subset of MS features significantly correlated with the biological function (as determined using the PSEA of the "Analysis" set), was extracted from the total of 298 available features. This resulted in a "partial feature table": $F^{erlotinib}=f_{si}$ with $1\leq i\leq N_f$ ($N_f$ is the number of significantly correlated MS features) and $1\leq s\leq N_S$ ($N_S=85$ samples) runs over the sample indices. FIG. 82 is an illustration of the partial feature table matrix $F^{ss}$ for a given sample set (ss), such as the PROSE-erlotinib sample set.
2. Step 8104 Perform PCA over many subset realizations of the sample set
   a. A subset of $N_{S'}=56$ samples was randomly chosen (using Matlab® R2015a randperm function) out of the 85 available. (Note that the choice of a subset of 56 of the 85 samples is arbitrary. It was chosen to be approximately ⅔ of the cohort, which is a good trade-off between sufficient samples in the subset, and diversity of the subset realizations.)
   b. The PCA was implemented using the Matlab® R2015a pca function, which returns a matrix containing the principal component coefficients, C, of dimensions $N_f \times N_f$ if $N_f < N_{S'}$, or $N_f \times (N_{S'}-1)$ if $N_f \geq N_{S'}$. This matrix allows the transformation of a data point (sample) represented in the MS feature space into an hyper-space whose basis vectors (columns of $C=[u_1 \ldots u_{N_f}]$, or $C=[u_1 \ldots u_{N_{S'}-1}]$) define directions of decreasing variance in the data. The pca function also returns a list of percentages of the total data variance explained by each principal component. It was found that, for the studied protein sets (biological functions) presented here, the first principal component explained the majority (65% or more) while the second principal component explained less than 15%) of the variance (see FIGS. 65A-65C). Therefore, we considered only the first Principal Component (PC), $$u_1 = \begin{bmatrix} u_{11} \\ \dots \\ u_{1i} \\ \dots \\ u_{1N_f} \end{bmatrix},$$

for the calculation of the biological function score, corresponding to the first column of C. Note that $u_1$ is a vector with scalar values of the first PC for each of the $N_f$ features.

c. Steps 1a. and 1b. were repeated $N_r=2^{17}=131,072$ times, drawing a different subset of 56 samples from the "PROSE-erlotinib" set at each iteration.

3. Step 8106 PCA bagging
   a. A total of $2^{17}$ first principal components had been calculated at this point. Subsets of 2 first principal components were taken, each pair was then averaged and the resulting average normalized according to the following calculation:

$$u_{1i}^k \leftarrow \frac{u_{1i}^k + u_{1i}^{k+N_r/2}}{\sqrt{\sum_{l=1}^{l=N_f}(u_{1l}^k + u_{1l}^{k+N_r/2})^2}} \text{ with } 1 \le k \le 2^{16} \quad \text{Equation (2)}$$

b. Step a. was repeated 16 more times, obtaining in each iteration half as many averaged and normalized first principal components as the previous iteration, until one final bagged first principal component, $\hat{u}_1$, was obtained. $\hat{u}_1$ (first principal component) is a vector with entries for each of the mass spectral features. More particularly, $\hat{u}_1$ is just the average of $u_1$ over the sample set realizations. We bag the PCA to give a more robust estimator of the first principal component vector. FIG. 83 is an illustration of the final bagged (or average) first principal component $\hat{u}_1$.

4. Step 8108 Biological function score calculation
   a. A vector of the biological function scores for the "PROSE-erlotinib" samples, $b^{erlotinib}$, was then calculated, which consisted of the projection of the sample MS feature vectors onto the direction of the first principal component $\hat{u}_1$:

$$b^{erlotinib} = \begin{bmatrix} b_1 \\ \dots \\ b_s \\ \dots \\ b_{N_S} \end{bmatrix} = F^{erlotinib} \cdot \hat{u}_1 \quad \text{Equation (3)}$$

The scalar numbers $b_1, b_2, \dots b_s, \dots b_{N_S}$ are the biological function scores for samples $1, 2, \dots s, \dots N_S$, respectively, in the sample set. In Equation (3) the first element of $\hat{u}_1$ gets multiplied by the first feature to give its contribution to the score, the second element of $\hat{u}_1$ gets multiplied by the second feature to give its contribution to the score, etc. for all features and these are summed up to give the final score. Or put another way, the score for a given sample is the projection of the vector of feature values for that sample onto the first principal component vector $\hat{u}_1$. As will be shown in the following Results section, the biological function score is a number typically between −5 and +50. While the magnitude of the number is important and can give insight to a given biological function associated with the score, especially if it is obtained over a period of time from a series of samples, of perhaps greater importance is its value relative to samples from other patients in a suitable population of patients, e.g., melanoma or NSCLC patients. The meaning and use of the scores will be explained in later sections of Example 10.

The process of FIG. 81 can be performed many times, e.g., when one wishes to obtain biological functions scores for different biological functions in the development set of samples.

5. Step 8110 Calculation of the biological score for the other sample sets
   a. Similarly to step 4, the biological function scores were calculated for the other four sample sets of this example using the averaged first principal component $\hat{u}_1$ determined in the "PROSE-erlotinib" set (step 3)

$$b^{sample-set} = \begin{bmatrix} b_1 \\ \dots \\ b_s \\ \dots \\ b_{N_S^{sample-set}} \end{bmatrix} = F^{sample-set} \cdot \hat{u}_1$$

Example 10 Results
Acute Response Score

Twenty-nine MS features were determined to be correlated by PSEA with the protein set corresponding to acute response (AR) and were used in the calculations of the corresponding Acute Response Score. FIG. 66A-66D shows the distributions of the Acute Response Score (AR score) in the "PROSE-erlotinib", "PROSE-chemo", "Moffitt" and "Moffitt-Week7" sample sets, respectively. Notably, the distributions of the Acute Response Scores between values of −2 and +4 are quite similar across all sample sets, even between NSCLC and melanoma sample sets.

Kaplan-Meier plots of the Overall Survival (OS) and Time to Progression (TTP) for all the 119 patients of the "Moffitt" set were already shown in FIGS. 1A and 1B. A Cox model applied to these time-to-event data using the AR Score as the single explanatory variable yields the statistics presented in Table 74. Table 75 shows the same statistics when a multivariate analysis is considered including known baseline prognostic factors.

Table 74: Statistics obtained by applying a Cox model to the time-to-event data of the "Moffitt" set using AR score as the single explanatory variable

TABLE 74

Statistics obtained by applying a Cox model to the time-to-event data of the "Moffitt" set using AR score as the single explanatory variable

| | OS | | TTP | |
|---|---|---|---|---|
| | HR (95% CI) | p-value | HR (95% CI) | p-value |
| AR score | 1.58 (1.27-1.97) | <0.001 | 1.51 (1.24-1.85) | <0.001 |

TABLE 75

Statistics obtained from a multivariate analysis of the "Moffitt" set

|  | OS | | TTP | |
|---|---|---|---|---|
|  | HR (95% CI) | p-value | HR (95% CI) | p-value |
| AR score | 1.59 (1.23-2.04) | <0.001 | 1.57 (1.24-2.00) | <0.001 |
| Female vs Male | 0.55 (0.31-0.97) | 0.038 | 0.56 (0.35-0.90) | 0.017 |
| PD-L1 (5%) − vs + | 0.53 (0.18-1.62) | 0.267 | 0.75 (0.29-1.92) | 0.542 |
| PD-L1 (5%) − vs NA | 0.78 (0.42-1.42) | 0.415 | 1.00 (0.58-1.74) | 0.988 |
| Prior Ipi (no vs yes) | 0.67 (0.38-1.19) | 0.169 | 0.74 (0.45-1.22) | 0.242 |
| LDH/1000 | 1.58 (1.11-2.26) | 0.011 | 1.47 (1.07-2.04) | 0.019 |

The AR score was defined without use of outcome data. On an independent sample set it is a significant predictor of both OS and TTP, and it remains a significant independent predictor of OS and TTP when adjusted for other known prognostic factors.

FIGS. 67A-67D show the distributions of the AR score in the "PROSE-erlotinib", "PROSE-chemo", "Moffitt" and "Moffitt-Week7" sample sets, split by IS2 classification label. (Recall that "IS2" refers to the "full set" classifier developed in Example 1 on the Moffitt nivolumab sample set). We performed a t-test as well as Mann-Whitney test to investigate the association of the AR scores with the IS2 classification groups and obtained p-values <0.001 for all the sample sets. Based on the distributions of the score for IS2 Early and IS2 Late samples in the "PROSE-chemo" data set we chose a tentative threshold (AR score) of −1.25 in order to define samples that had higher and lower AR function, according to their score being higher or smaller than the threshold, respectively. FIGS. 68A-68F show the Kaplan-Meier plots for time-to-event outcomes (OS and progression-free survival (PFS) or TTP) of the "PROSE-chemo", "PROSE-erlotinib" and "Moffitt" sets by groups as defined by the chosen threshold. Note that there is a separation in the survival plots of FIG. 68A-68F, namely the group of patients with a score of >−1.25 had a relatively worse OS and PFS as compared to the group of patients with a score of <−1.25. The statistics of the survival plots are shown in the legends for FIGS. 68A-68F.

FIGS. 68A-69F thus shows that it is possible to use the AR Score together with a cutoff to stratify patients with both melanoma and NSCLC into two groups with better and worse time-to-event outcomes.

Figures 70A, 70B:
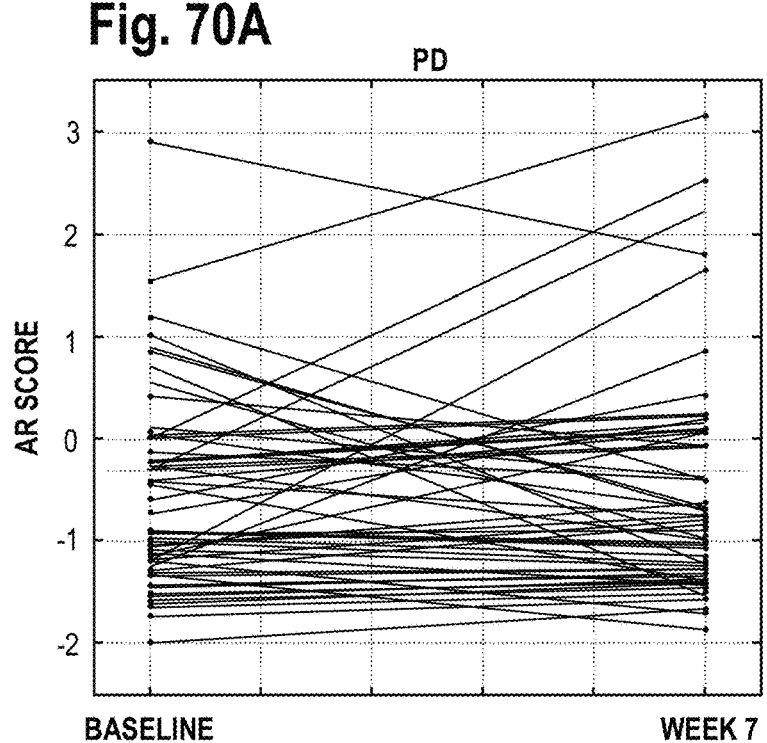
FIG. 70A-70C are plots of evolution of the Acute Response Score for the 107 patients with samples both in the "Moffitt" and the "Moffitt-Week7" sets, grouped by treatment response. Each line represents one single patient.
Figure 70C:
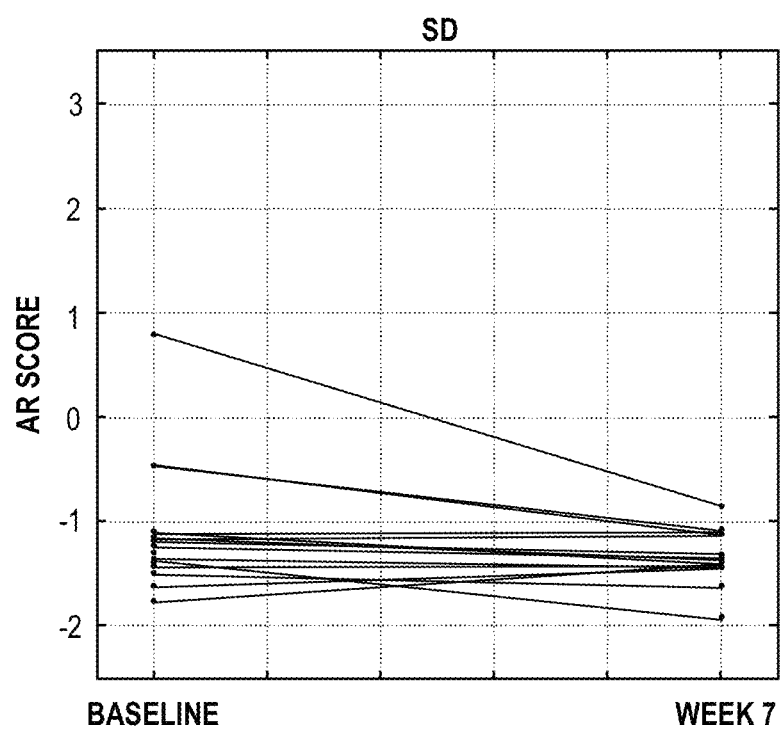

FIGS. 69A-69D shows the evolution of the Acute Response Score for the 107 patients with samples both in the "Moffitt" and the "Moffitt-Week7" sets, grouped by combination of IS2 label at baseline (before treatment) and week 7 (during treatment). FIGS. 70A-70C shows the evolution of the acute response score for the 107 patients with samples both in the "Moffitt" and the "Moffitt-Week7" sets, grouped by treatment response. As expected from the plots of FIG. 69A-69D, patients with an "Early" IS2 classification generally have higher AR scores. Changes of IS2 label from "Early" to "Late" are associated with a lowering of the AR score and vice versa for changes from "Late" to "Early". Recall from Example 1 that class label "Late" indicates that the patient is a member of a class of patients that are likely to obtain relatively greater benefit from nivolumab in treatment of melanoma as compared to patients that are a member of the class of patients having the class label "Early." These longitudinal assessments show that a patient's AR score can change during the course of therapy. Hence, it is possible, by collecting a series of serum samples and evaluating the AR score, to monitor the level of acute response in a cancer patient.

To explore the value of monitoring of AR score further we investigated the prognostic impact of changes in the score. Change in AR score between week 7 and baseline was an independent significant predictor of OS and TTP for the "Moffitt" set in addition to baseline AR score (Table 76). So, monitoring the AR score of melanoma patients treated with nivolumab provides additional information to a baseline assessment of AR score.

TABLE 76

Statistics obtained by applying a Cox model to the time-to-event data of the "Moffitt" set using AR score and change in AR score between baseline and week 7 as explanatory variables

|  | OS | | | TTP | | |
|---|---|---|---|---|---|---|
|  | P-value | HR | 95% CI | P-value | HR | 95% CI |
| Baseline AR score | 0.007 | 1.50 | 1.12-2.00 | <0.001 | 1.77 | 1.36-2.30 |
| Change in AR score | 0.013 | 0.69 | 10.52-0.93 | <0.001 | 0.58 | 0.45-0.75 |

Figure 71A:
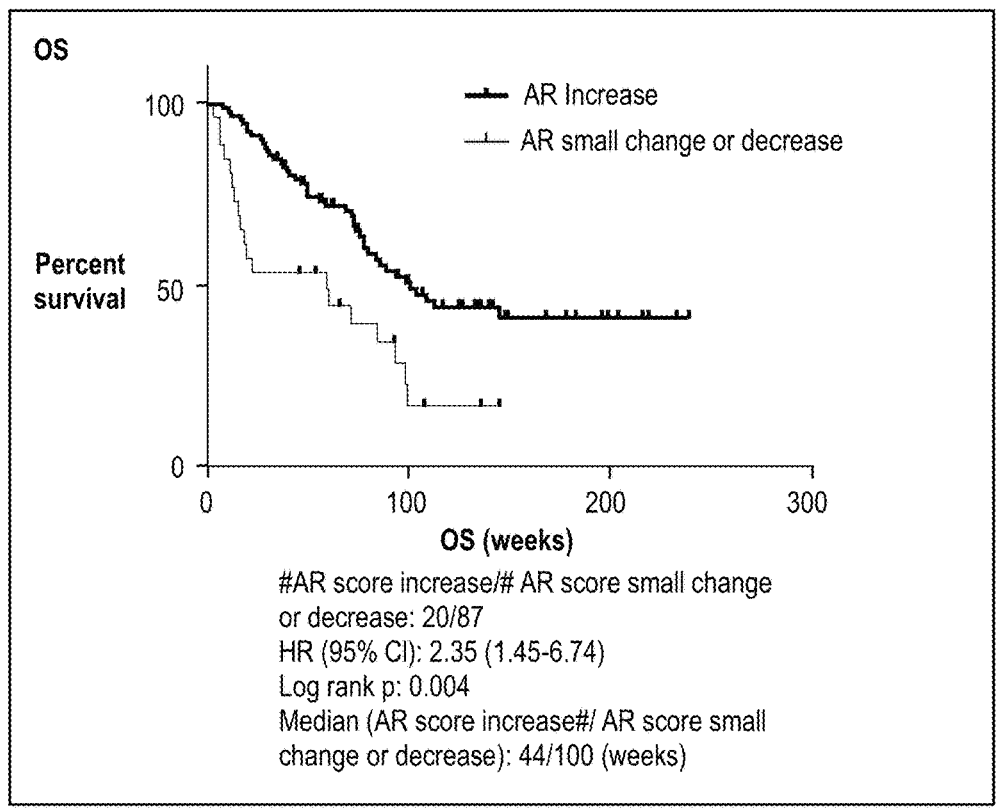
FIGS. 71A and 71B are Kaplan-Meier plots of OS and TTP, respectively for the samples both in the "Moffitt" and the "Moffitt-Week7" sets grouped by whether the AR score increased or had a small change or decrease. The plots show the change in AR score has prognostic significance.
Figure 71B:
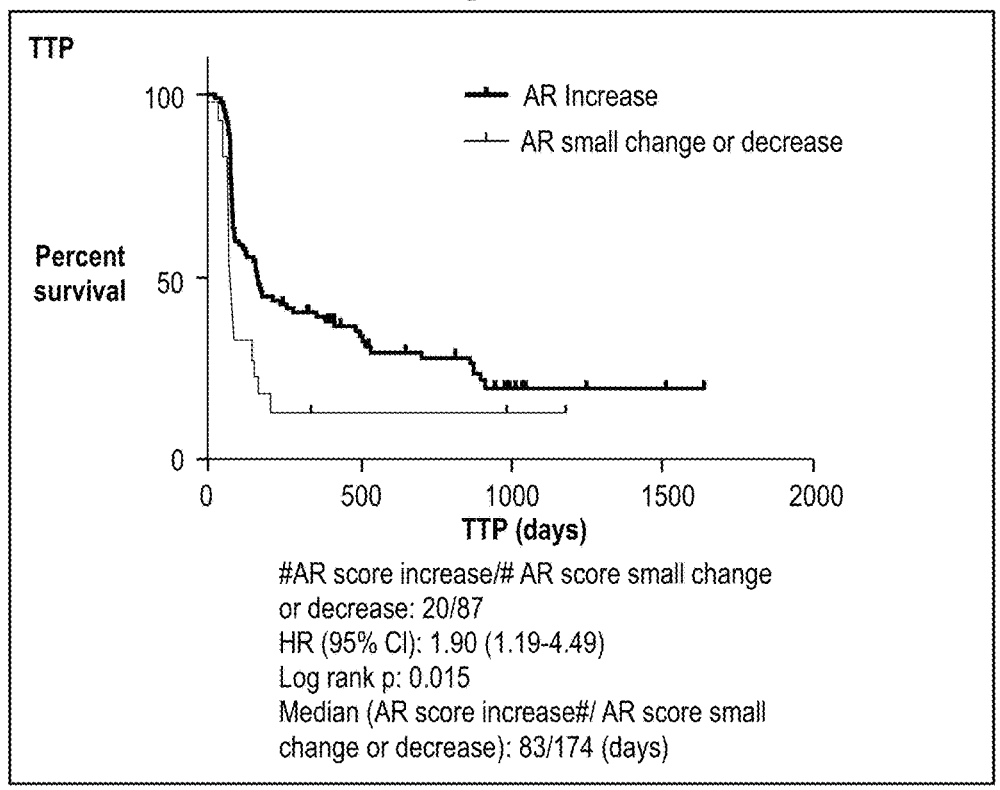
Figure 72A:
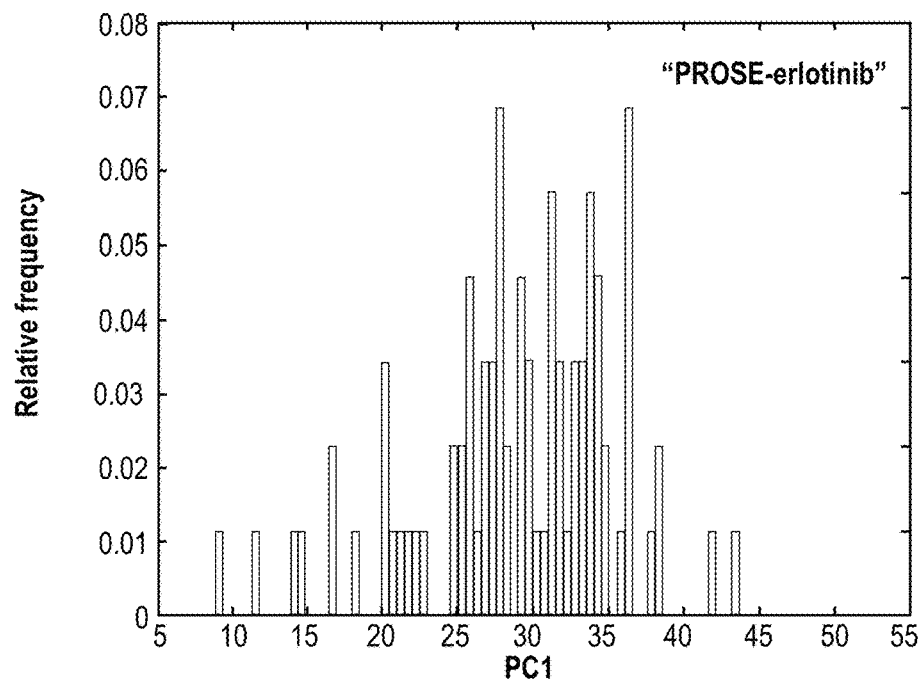
FIG. 72A-72D are the plots of distribution of the Wound Healing Score across four sample sets described in Example 10.
Figure 72B:
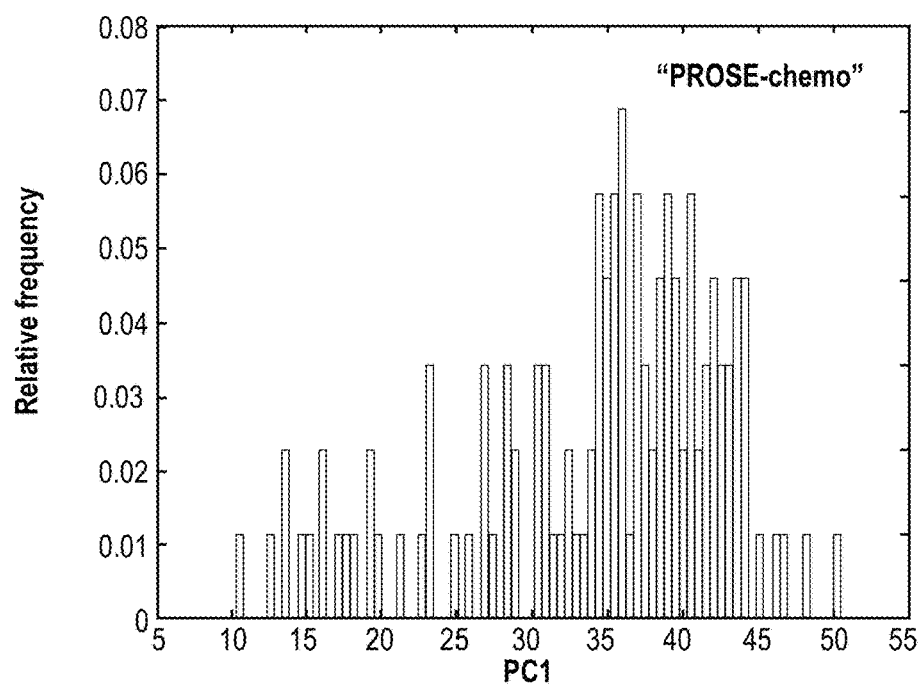
Figure 72C:
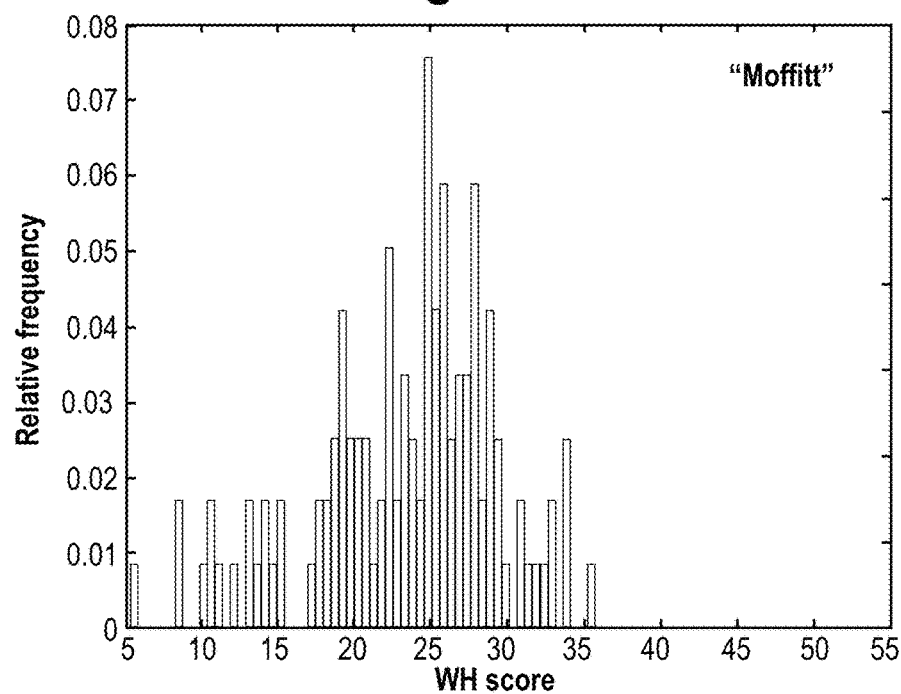
Figure 72D:
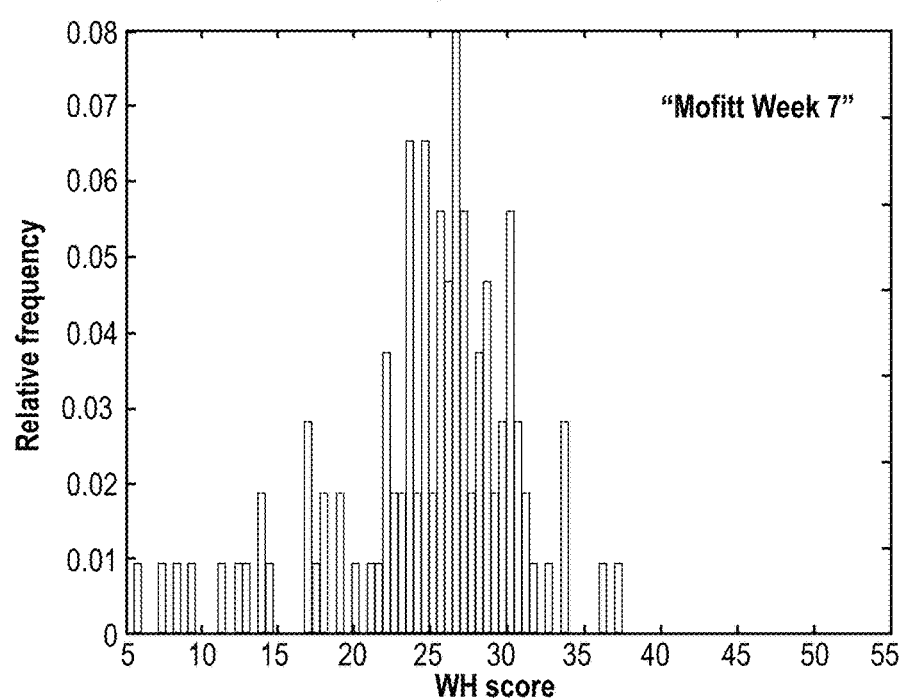
Figure 73A:
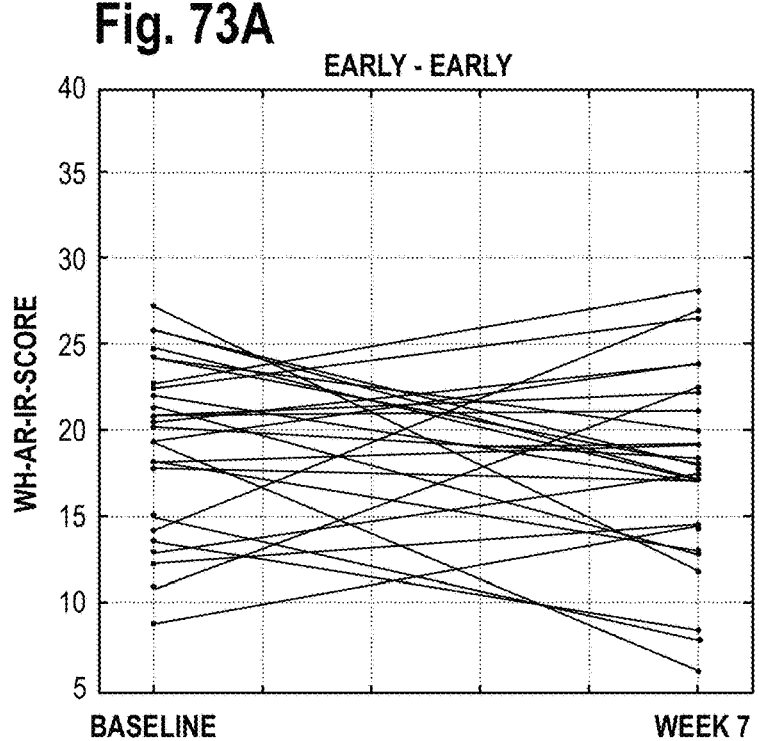
FIG. 73A-73D are illustrations of the evolution of the Wound Healing Score over time for 107 patients in both the Moffitt and Moffitt-Week7 sets, grouped by combination of IS2 label at baseline (before treatment) and week 7 (after treatment). Each line in the plots represents the score of an individual patient.
Figure 73B:
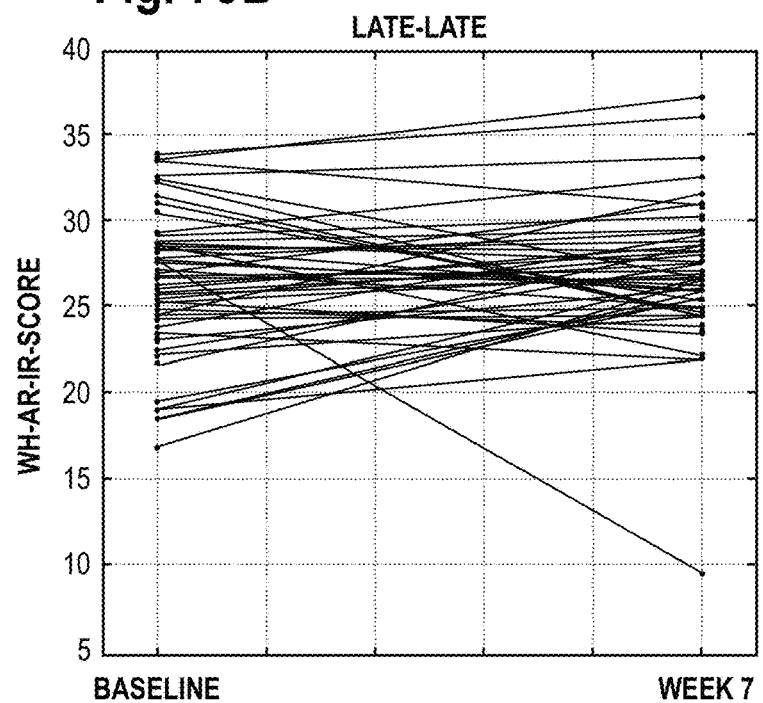
Figure 73C:
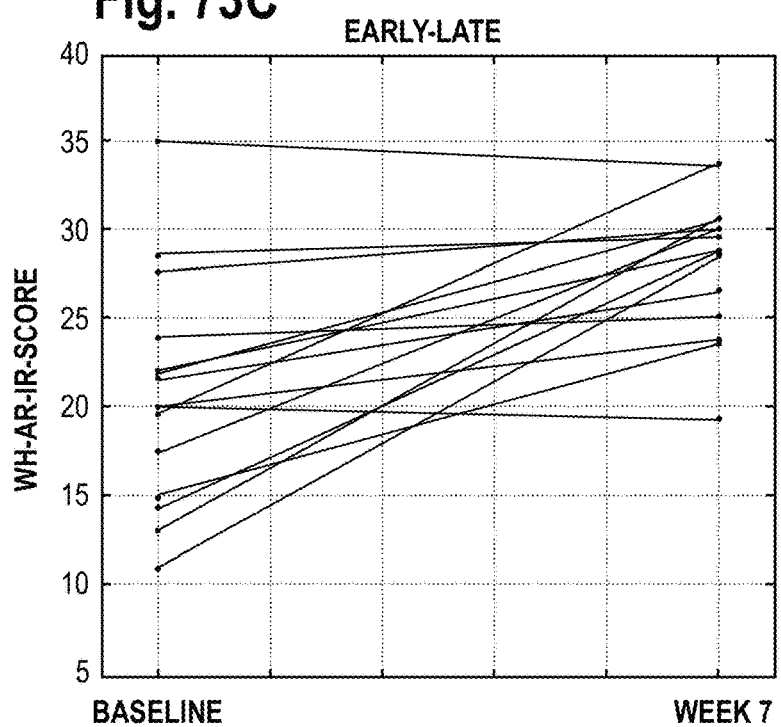
Figure 73D:
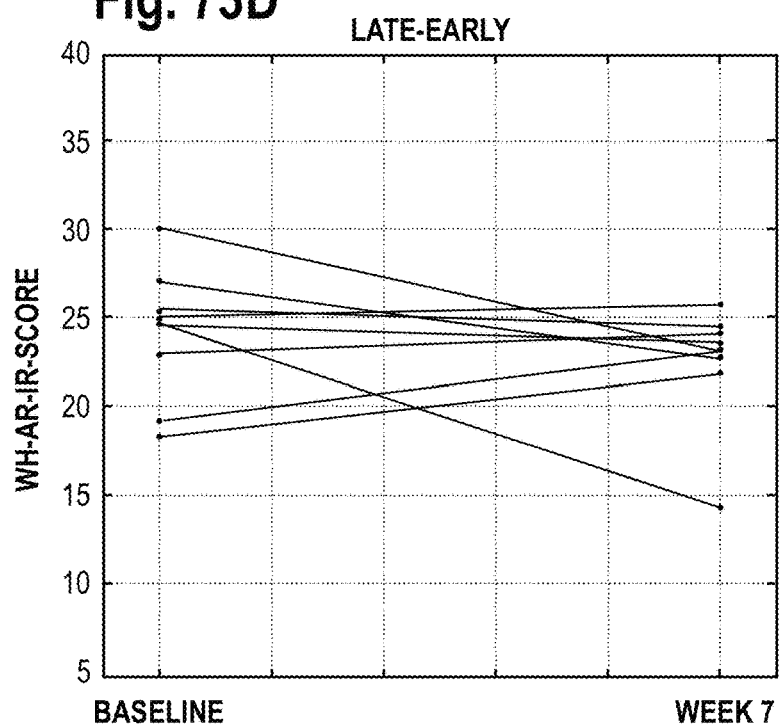

To illustrate the prognostic value of monitoring of AR score further, the Kaplan-Meier plots for the 107 patients in the "Moffitt" set with samples at both baseline and week 7 are shown in FIGS. 71A and 71B with the patients grouped according to change in AR score from baseline to week 7. Patients with an increase of the AR score in the course of treatment have significantly shorter TTP and OS than the rest of the patients, which is in agreement with the poor prognostic value of the high baseline AR score.

Wound Healing Score

Twenty-five MS features were determined to be correlated with the protein set corresponding to wound healing (WH) but not correlated with either acute response or immune response. Those features were used in the calculations of a Wound Healing Score in accordance with the biological function score calculation procedure explained above. FIGS. 72A-72D show the distributions of the scores in the "PROSE-erlotinib", "PROSE-chemo", "Moffitt" and "Moffitt-Week7" sample sets, respectively. Note in the plots the legend for Wound Healing uses the abbreviation WH-AR-IR, meaning that the feature set contains features associated with wound healing but not correlated to either acute response (AR) or immune response (IR). To arrive at this reduced set of features we did not just to look at all MS features associated with wound healing with p<0.05, but rather we identified those features associated with wound healing at p<0.05, excluding those that are associated with acute response or immune response with p<0.05, hence the terminology WH-AR-IR. If we do not exclude the features associated with AR and IR (which also overlap), we would (likely) get similar behavior for the AR and WH scores, because the AR features tend to dominate the behavior. What would be ideal would be to have a bigger, i.e., more complete, protein panel run on a much larger set of samples; then we could use much more refined, less broad biological functions to start with and still have enough measured proteins in each set for a meaningful analysis. As it stands the protein groups we have are broad and tend to overlap. In the following discussion, the term Wound Healing and Wound Healing Score means the set of mass spectral features (and associated Score) which is associated with the wound healing biological function but not significantly correlated with either AR or IR.

Figure 74A:
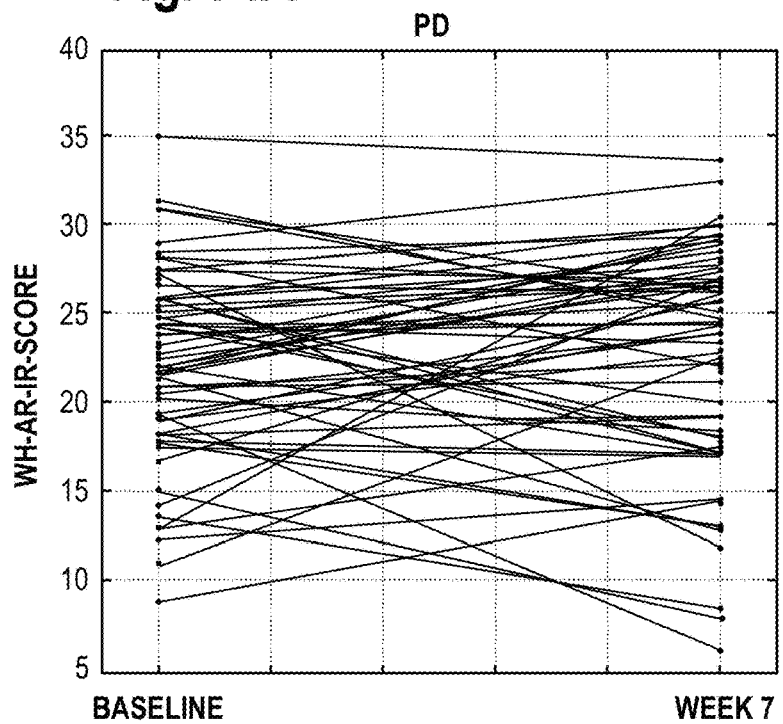
FIG. 74A-74C are plots of evolution of the Wound Healing Score for the 107 patients with samples both in the "Moffitt" and the "Moffitt-Week7" sets, grouped by treatment response. Each line represents one single patient.
Figure 74B:
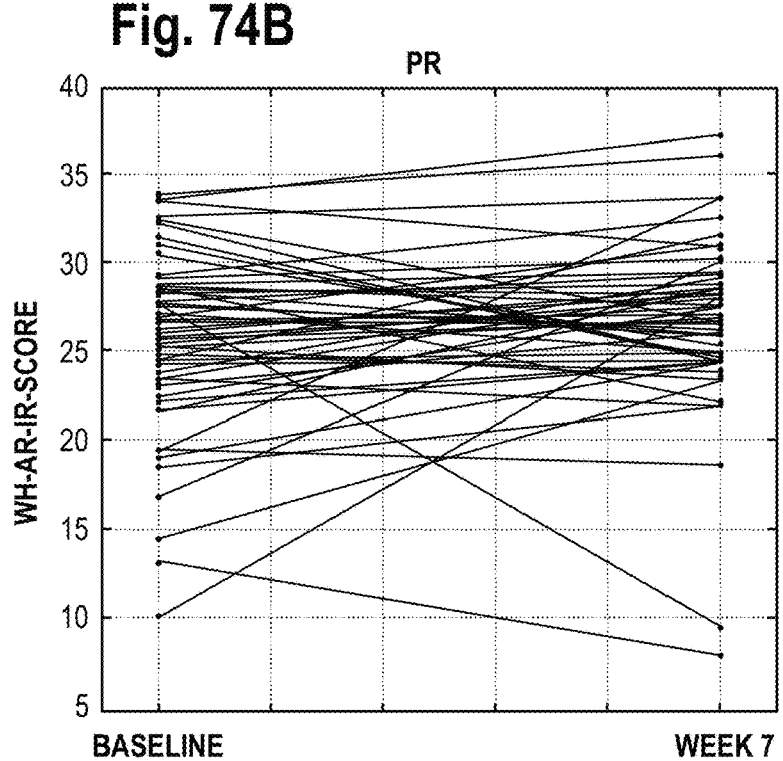
Figure 74C:
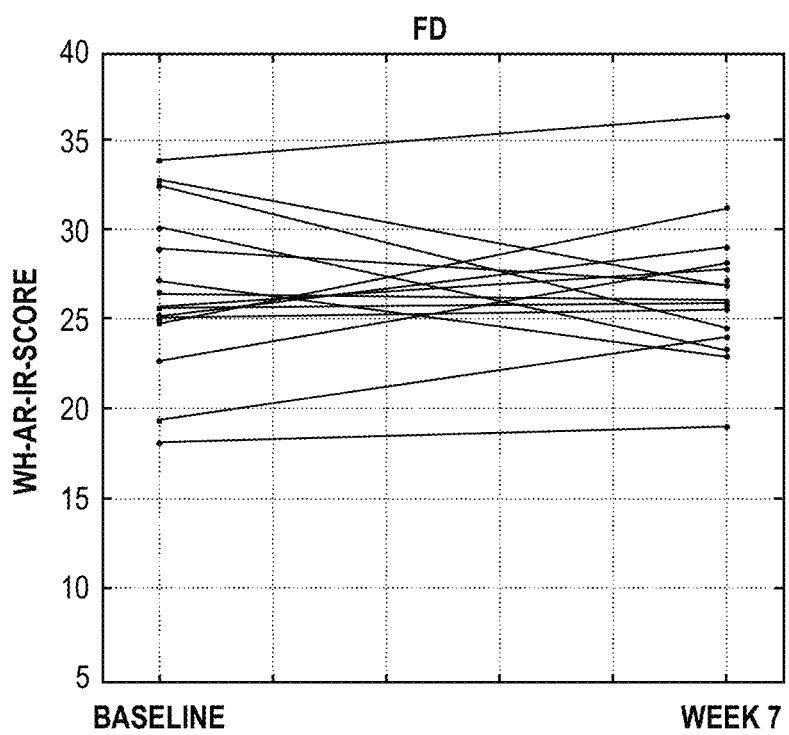
Figure 75A:
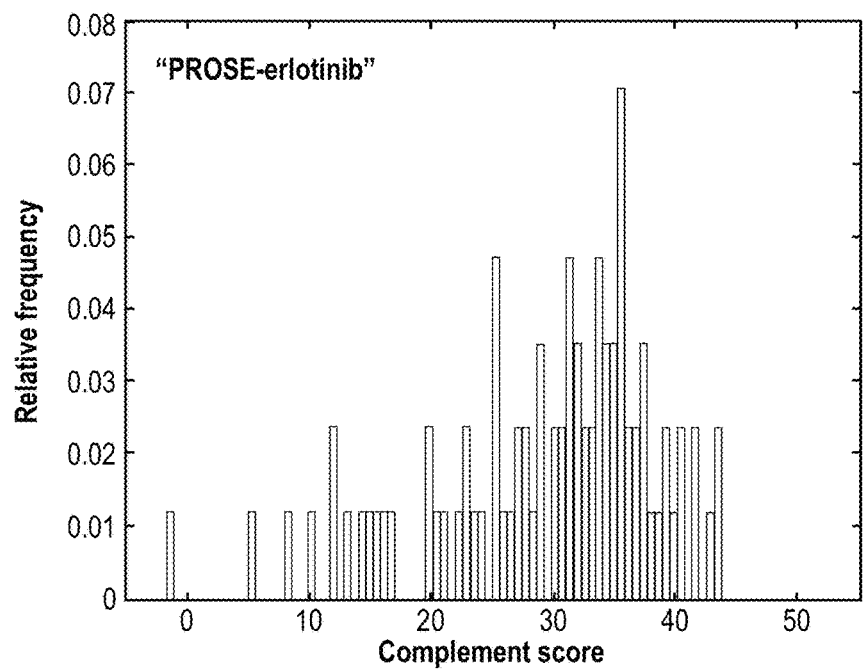
FIGS. 75A-75D are the plots of distribution of the Complement System Score across four sample sets described in Example 10.
Figure 75B:
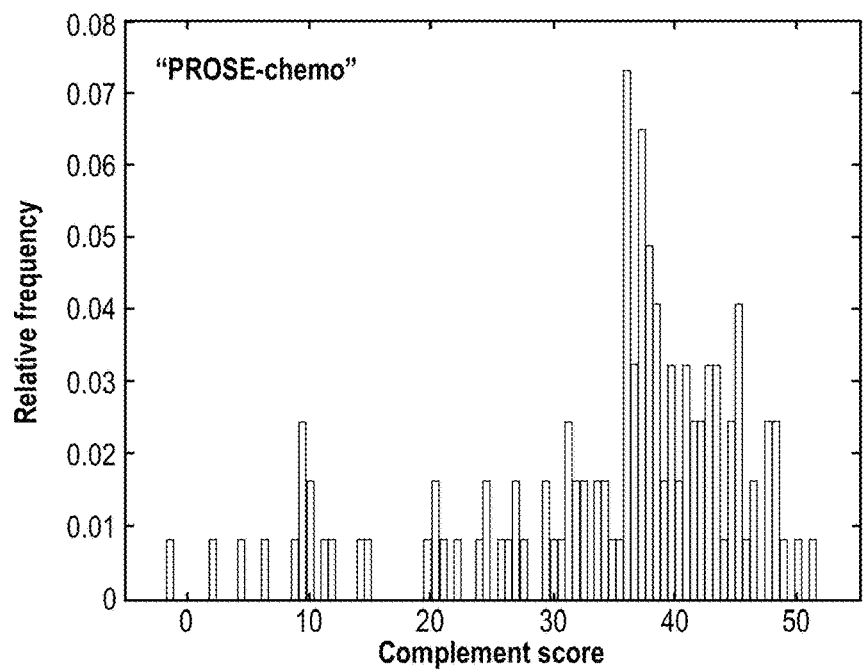
Figure 75C:
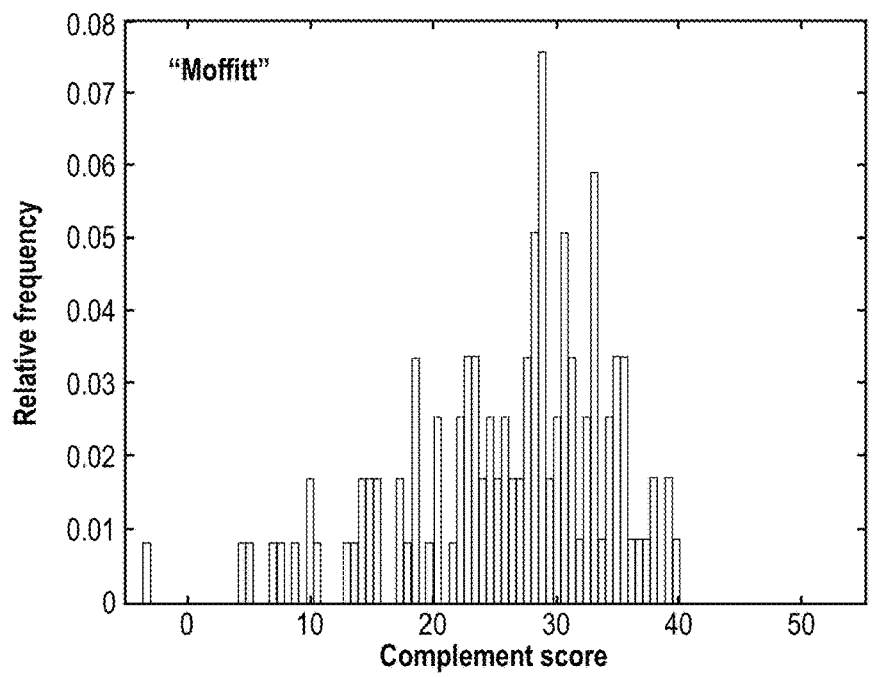
Figure 75D:
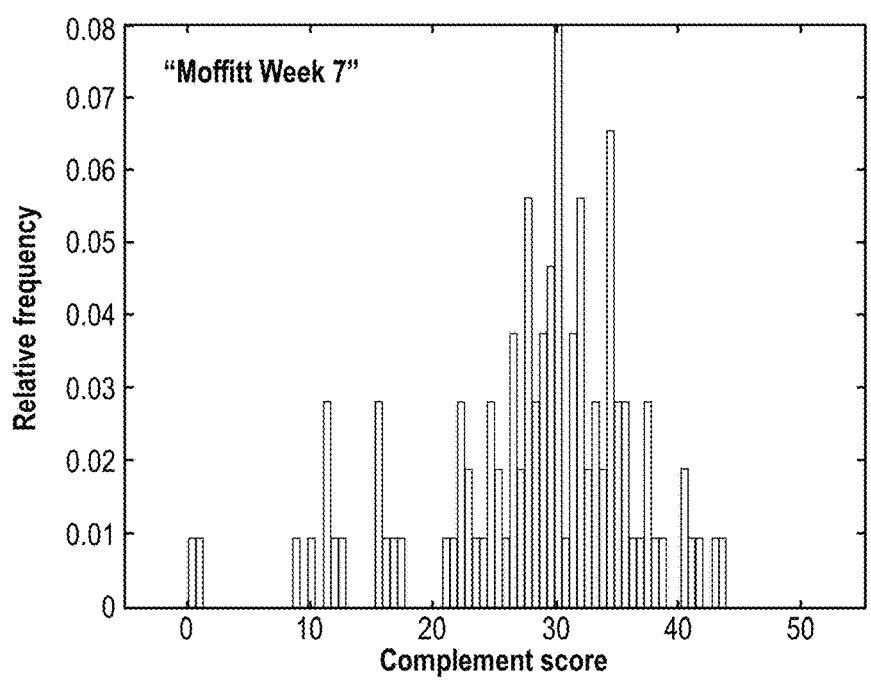
Figure 76C:
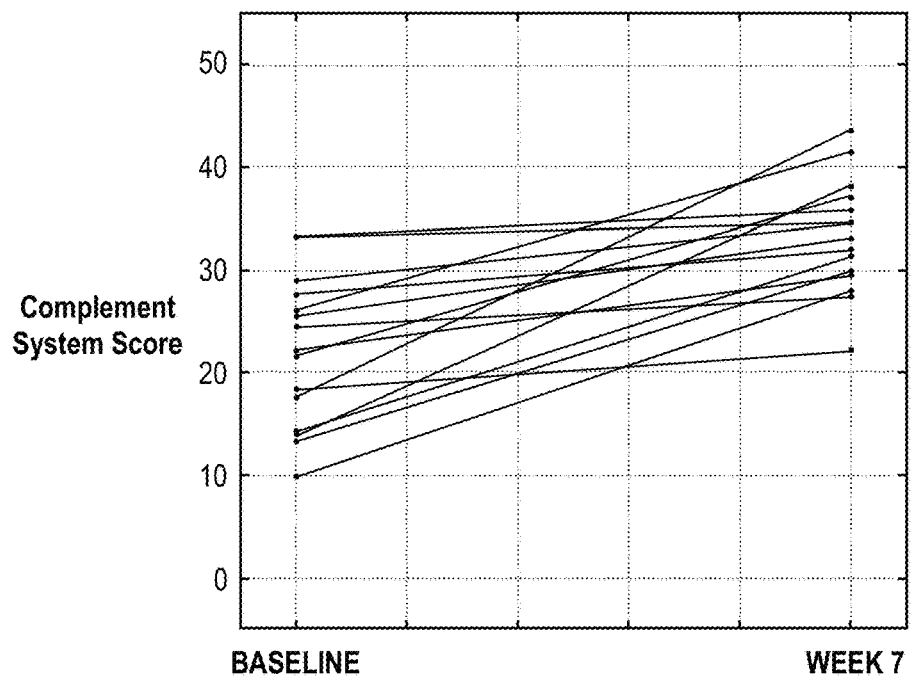
Figure 76D:
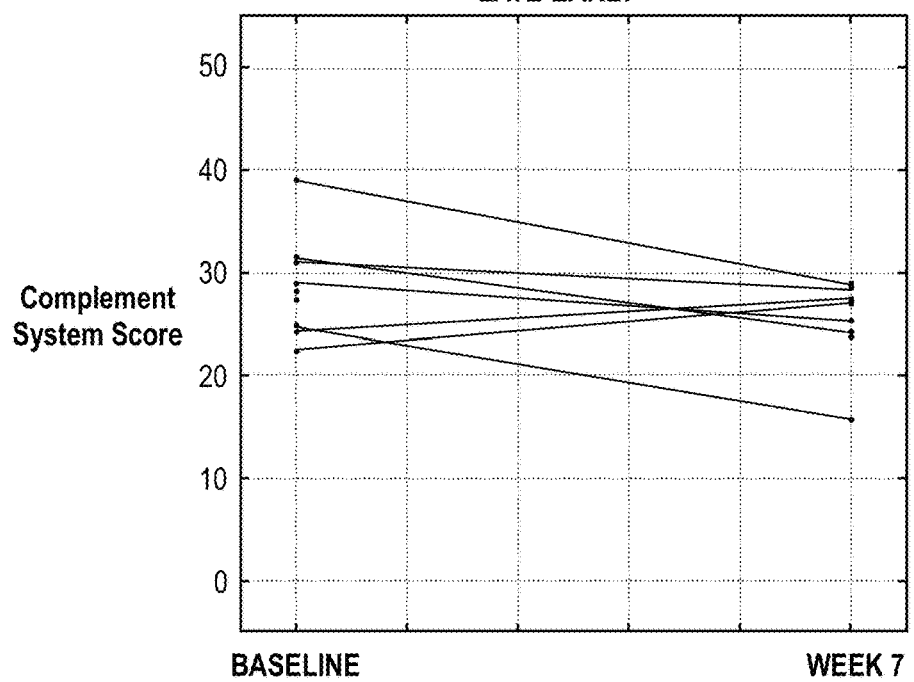

FIGS. 73A-73D show the evolution of the Wound Healing Score plotted on the Y axis ("WH-AR-IR" in the figures) for the 107 patients with samples both in the "Moffitt" and the "Moffitt-Week7" sets, grouped by combination of IS2 label at baseline (before treatment) and week 7 (during treatment). FIGS. 74A-74C show the evolution of the wound healing score for the same 107 patients, grouped by treatment response, namely progressive disease (FIG. 74A), partial response (FIG. 74B) and stable disease (FIG. 74C).

As illustrated in FIGS. 72A-72D, the Wound Healing Score appears to have a somewhat different distribution depending on tumor type, with the distributions for melanoma (Moffitt plots FIGS. 72C and 72D) centered at a lower WH score than those for NSCLC (PROSE plots 72A and 72B). The association of IS2 classification with WH score is markedly less strong than it is with AR score. However, Cox proportional hazard models of OS and TTP for the "Moffitt" set show that WH score is a highly significant predictor of outcome (Table 77). In addition, inclusion in the Cox models of change of WH score from baseline to week 7 as an additional explanatory variable show that this is independently significant, so that monitoring of WH score during treatment provides additional prognostic information.

Note that as the first principal component is defined only up a factor of multiplication by −1, and generally protein sets associated with a given biological function will contain proteins that have both higher levels and lower levels when this biological function is more relevant or more active, it is not obvious from inspecting the score whether a high score or a low score corresponds to more relevant or active biological function. In our PSEA analysis of our IS2 classifications (Example 6), we observed that complement and acute response were both elevated in the IS2 Early classification group compared with IS2 Late classification group. This observation is consistent with the results presented here in Example 10, in that the complement score should be interpreted so that the elevated levels of features (and tentatively identified corresponding proteins (Example 1 Protein Identification) correspond to lower levels of this complement score.

Uses of the Biological Function Scores for Treatment and Monitoring

Summarizing the results presented above, we envision several applications of biological function scores, both in relation to the existing classification labels or in the absence of classification results. For further discussion, we will use scores associated with Acute Response (AR) function, but

TABLE 77

Cox proportional hazard analysis of OS and TTP for the "Moffitt" set with WH score as the single explanatory variable (Model 1) and with baseline WH score and change in WH score from baseline to week 7 as simultaneous explanatory variables (Model 2)

| | | OS | | | TTP | | |
|---|---|---|---|---|---|---|---|
| | | P-value | HR | 95% CI | P-value | HR | 95% CI |
| Model 1 | WH alone | <.001 | 0.92 | 0.88-0.96 | <.001 | 0.93 | 0.90-0.96 |
| Model 2 | Baseline WH score | 0.001 | 0.91 | 0.87-0.96 | <0.001 | 0.91 | 0.87-0.96 |
| | Change in WH score | 0.037 | 1.05 | 1.00-1.09 | 0.003 | 1.06 | 1.02-1.10 |

Complement System Score

Figure 77A:
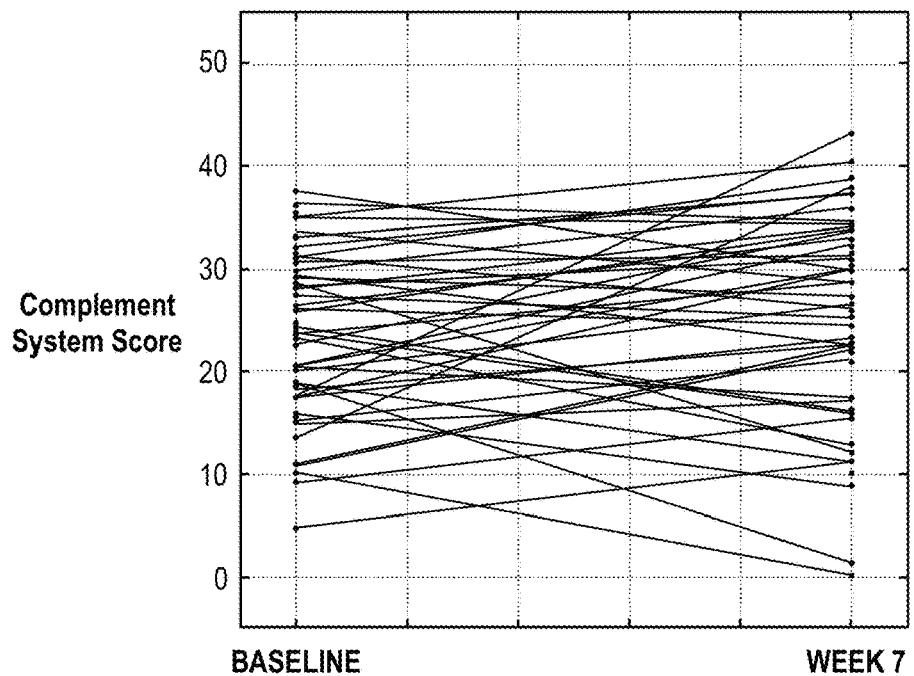
FIG. 77A-77C are plots of evolution of the Wound Healing Score for the 107 patients with samples both in the "Moffitt" and the "Moffitt-Week7" sets, grouped by treatment response. Each line represents one single patient.
Figure 77B:
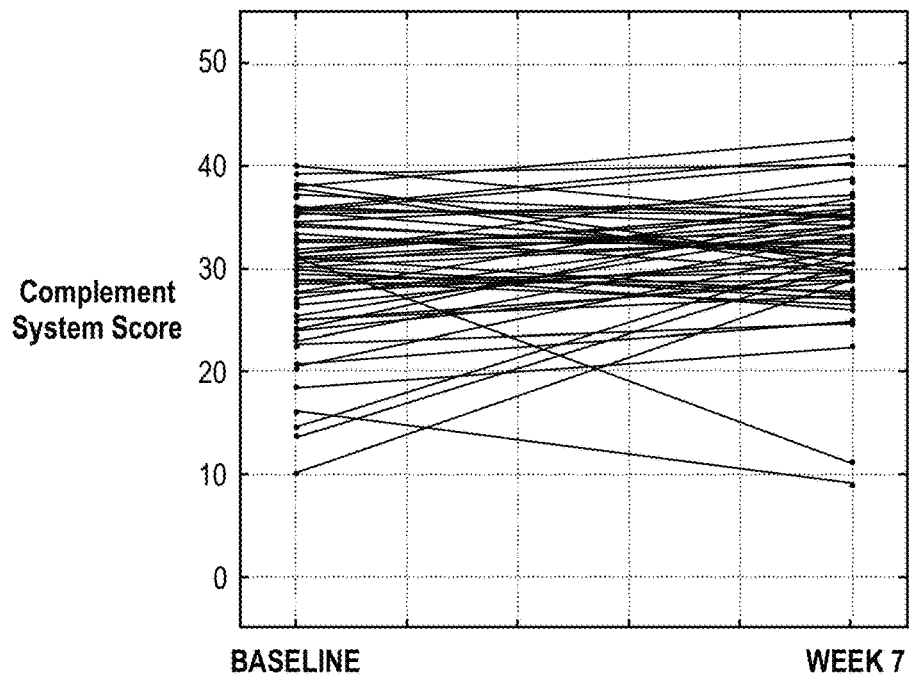
Figure 77C:
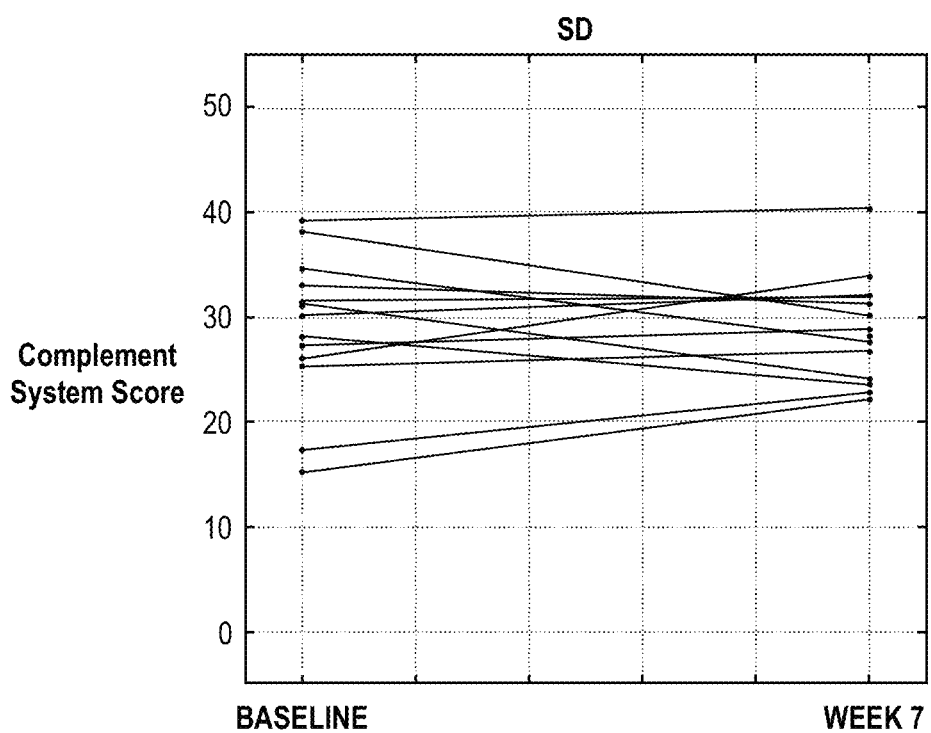

One hundred fifty-seven (157) MS features were determined to be correlated with the protein set corresponding to the complement system (see Example 6). Those features were used in the calculations of the complement system score using the procedure explained above including Equations (2) and (3). FIGS. 75A-75D show the distributions of the score in the "PRO SE-erlotinib", "PRO SE-chemo", "Moffitt" and "Moffitt-Week7" sample sets. FIGS. 76A-76D show the evolution of the complement system score for the 107 patients with samples both in the "Moffitt" and the "Moffitt-Week7" sets, grouped by combination of IS2 label at baseline (before treatment) and week 7 (during treatment). FIGS. 77A-77D show the evolution of the complement system score for the same 107 patients, grouped by treatment response, namely progressive disease (FIG. 77A), partial response (FIG. 77B) and stable disease (FIG. 77C).

FIGS. 75A-75D indicate again that there is some difference in the location of the distributions of the complement system score depending on tumor type, with NSCLC being centered at higher levels of complement score as compared to melanoma. IS2 classification (Example 1) of Late is generally associated with somewhat higher levels of complement score compared with IS2 classification of Early, and changes of classification from Early to Late show a general decrease in complement score, and vice versa for changes from Late to Early.

the suggestions are applicable to any biological function that can be associated with mass spectral features.

1. Biological Function Scores in Relation to Existing Classifications

In the first case, using the classification labels, e.g. Early and Late, obtained by IS2 (Example 1 full set classifier), we can evaluate whether there is a significant difference between the distributions of score values in the two groups (FIG. 68A-68D). In all our studied examples the distribution of AR scores were highly significantly different (p<0.001), as assessed both by t-test and Mann-Whitney test, between IS2 classifications.

Evidence for this difference may serve as an additional support of the effect of the biological function associated with the score, on the classification.

Analyzing the distribution of the score in the groups defined by classification, we could choose cut-offs that can be used to assign a patient to a specific sub-group, e.g. "high", "medium", and "low", which can be correlated with outcome, or prognosis, or some other clinically relevant measure.

For example, a cut-off chosen based on the AR scores of the PROSE chemotherapy NSCLC set (−1.25), based on IS2 classification, separates patients in this set, as well as in the Moffitt set (which consists of the melanoma patients treated with nivolumab) in two groups with significantly different OS and PFS (or TTP, in case of Moffitt) (see FIG. 69). In other words, by assigning a patient sample a biological function score using the procedure described in this Example and comparing the score to a cutoff (e.g., defined from scores obtained from a development set of samples) we can assign a class label to the sample and make a prediction on their response or survival by comparison of the score to the scores of the group of patients with similar scores relative to the threshold and their survival or response characteristics.

2. Biological Function Scores Independent of Other Classifications

Importantly, biological function scores can be used and analyzed independently of any classification labels.

Thus, the significance of the score, used as an explanatory variable, for outcomes can be evaluated using Cox Proportional Hazards models, either in a univariate or in a multivariate analysis, taking into account additional clinical information (see Tables 74 and 75 previously). When used for the Moffitt set, the AR score was a highly significant predictor of OS and TTP both in univariate and multivariate analyses.

Additionally, in the multivariate approach, the effect of several biological functions, based on their scores, can be assessed for significance of their simultaneous impact on outcomes, which potentially can be hypothesis generating for the relative roles of different biological functions on outcomes.

The scores associated with a biological function can be used to classify patients, e.g. using cut-offs that can be defined based on quantiles of scores in the training set, and then applied to new samples. In the following example we defined the cut-off based on grouping the lower two tertiles of scores associated with the PROSE chemotherapy subset (defined as AR score Low, ≤−0.744), and comparing with the upper tertile >−0.744 (defined as AR score High), and applied these thresholds to the Moffitt data. The results can be seen in FIG. 78A-78D. These figures are Kaplan-Meier plots for OS, PFS ("PROSE-chemo") and TTP ("Moffitt" set) by group defined according to the AR score threshold defined by tertiles in the PROSE set. The corresponding number of samples in each group, hazard ratios (HRs), log-rank p-values and medians are shown below each plot. Note that the patients with the AR Low score have greater OS and PFS as compared with those patients with the AR High score.

Figure 78A:
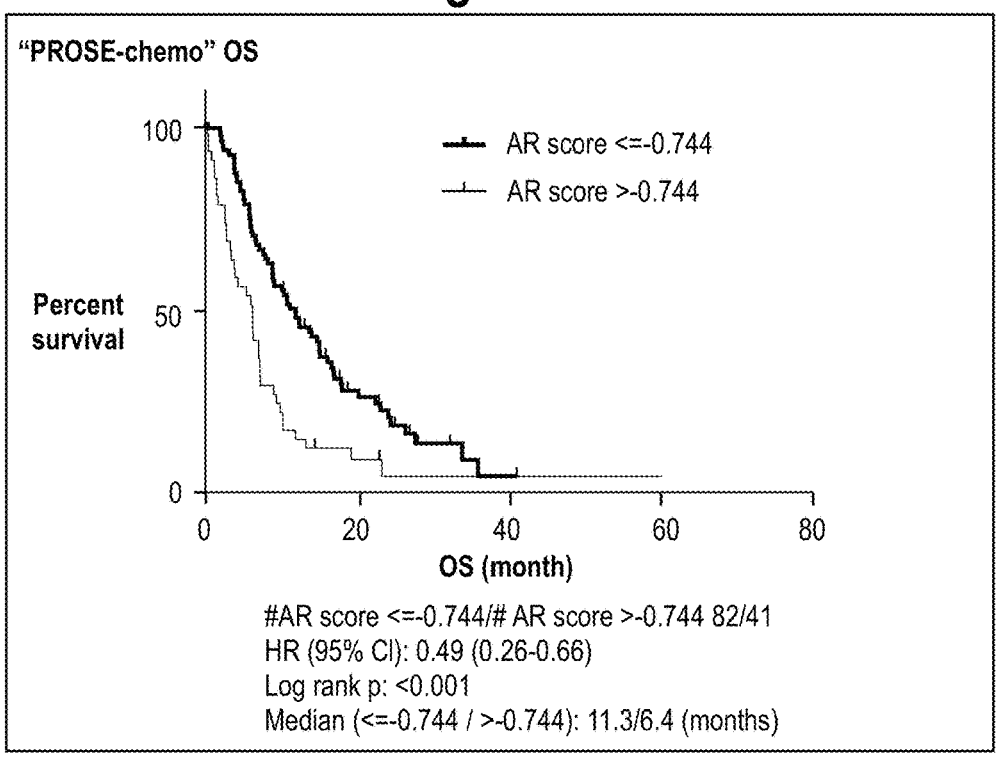
FIGS. 78A-78D are Kaplan-Meier plots for OS, PFS ("PROSE-chemo"), FIGS. 78A-78B, and OS and TTP ("Moffitt" set), FIGS. 78C and 78D, by group defined according to the AR score threshold defined by tertiles in the PROSE set. The corresponding number of samples in each group, hazard ratios (HRs), log-rank p-values and medians are shown below each plot.
Figure 78B:
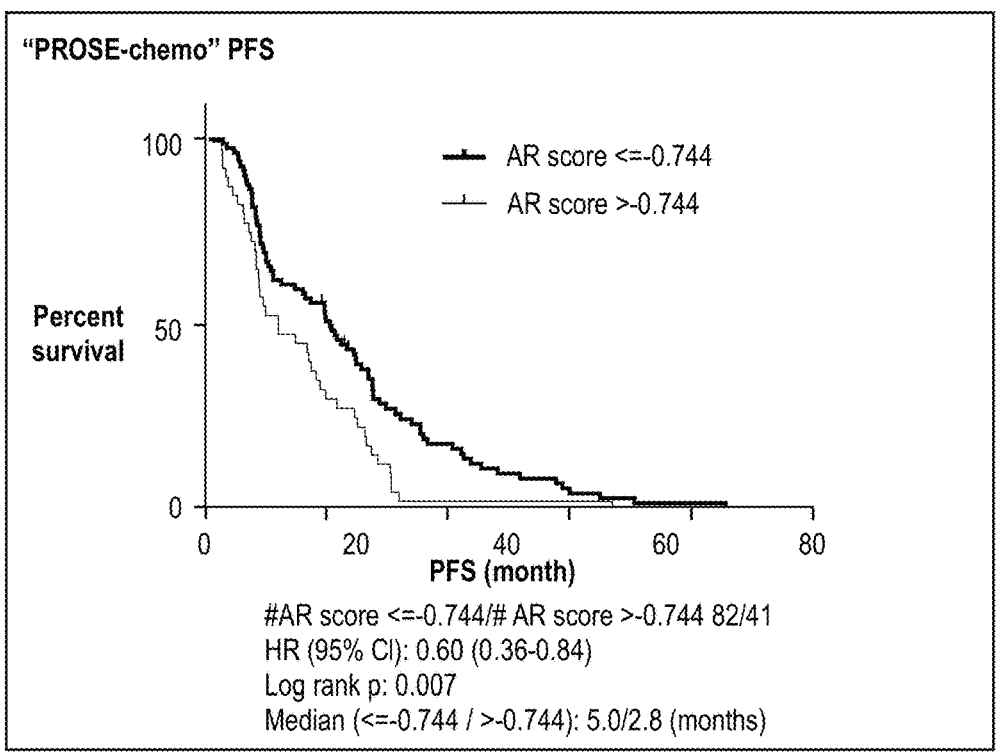
Figure 78C:
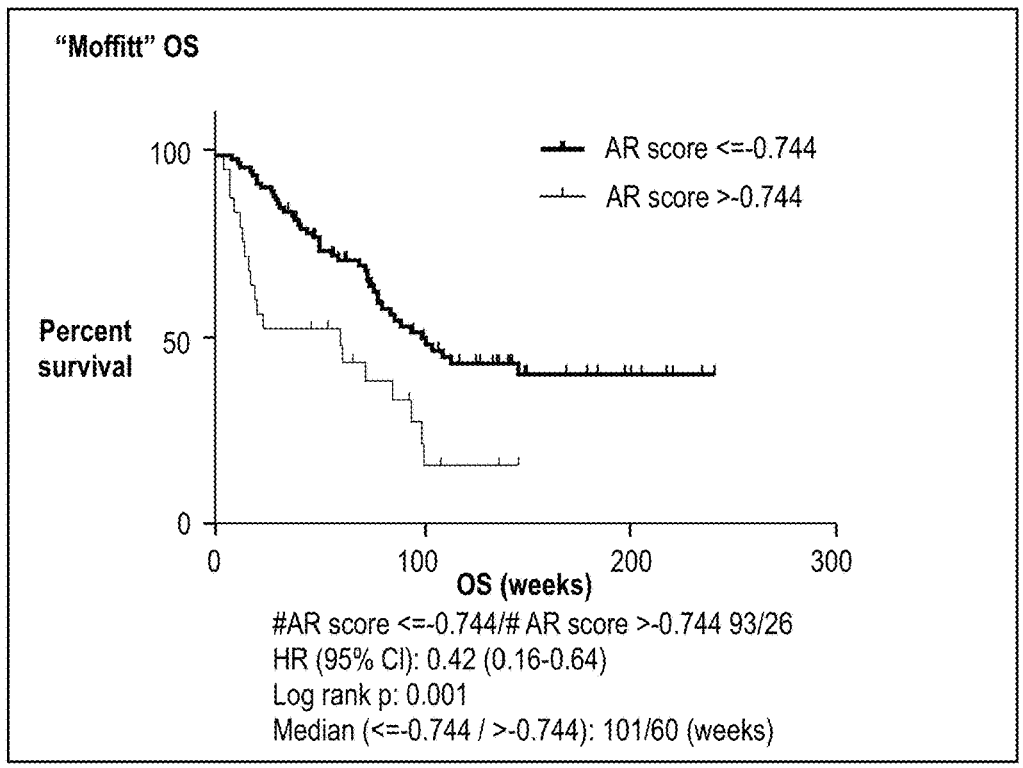
Figure 78D:
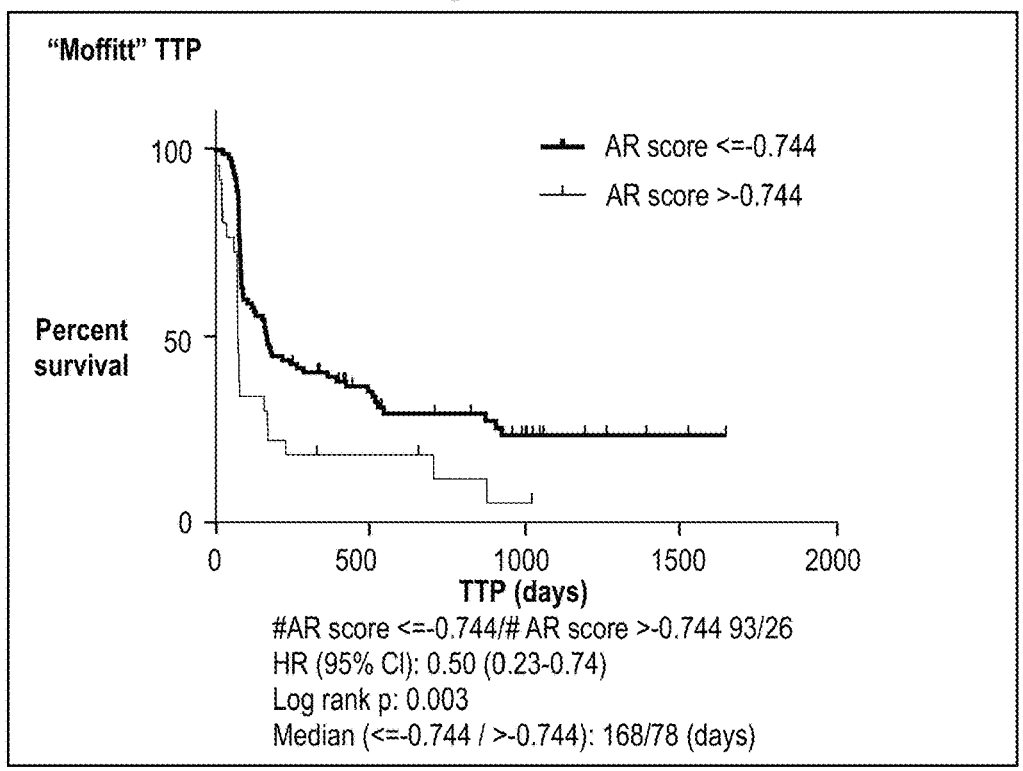

In this example the prognostic classifier defined using data from NSCLC patients by the AR biological score is shown to significantly separate patients by OS and TTP in the independent cohort of melanoma patients treated with nivolumab, see FIGS. 78C-78D.

Alternatively, scores for several biological functions can be used to create a more sophisticated classifier, e.g. using the Diagnostic Cortex approach described in FIG. 8. As an example, we used the three scores defined above (Acute Response, Wound Healing and Complement System) as features for classifier development using the Moffitt set with the Diagnostic Cortex, instead of mass spectral features as in previous examples of FIG. 8. For creation of the mini-classifiers, we used all possible combinations of one, two, and three features (Scores) to give 7 possible mini-classifiers (FIG. 8A, step 120). We used mini-classifier filtering (of the 7 possible mini-classifiers, FIG. 8A step 126), but we did not do any feature deselection in further iterations of the loop 135 as we did in the similar procedure of FIG. 54A, step 52. So, all 7 mini-classifiers were considered for filtering, but not all passed in each teration of loop 335 and so we did not use all 7 mini-classifiers in the logistic regression forming each master classifier. In fact, for a few test/training split realizations none of the 7 possible mini-classifiers passed filtering and then this realization was dropped and not used at all.

Figure 79A:
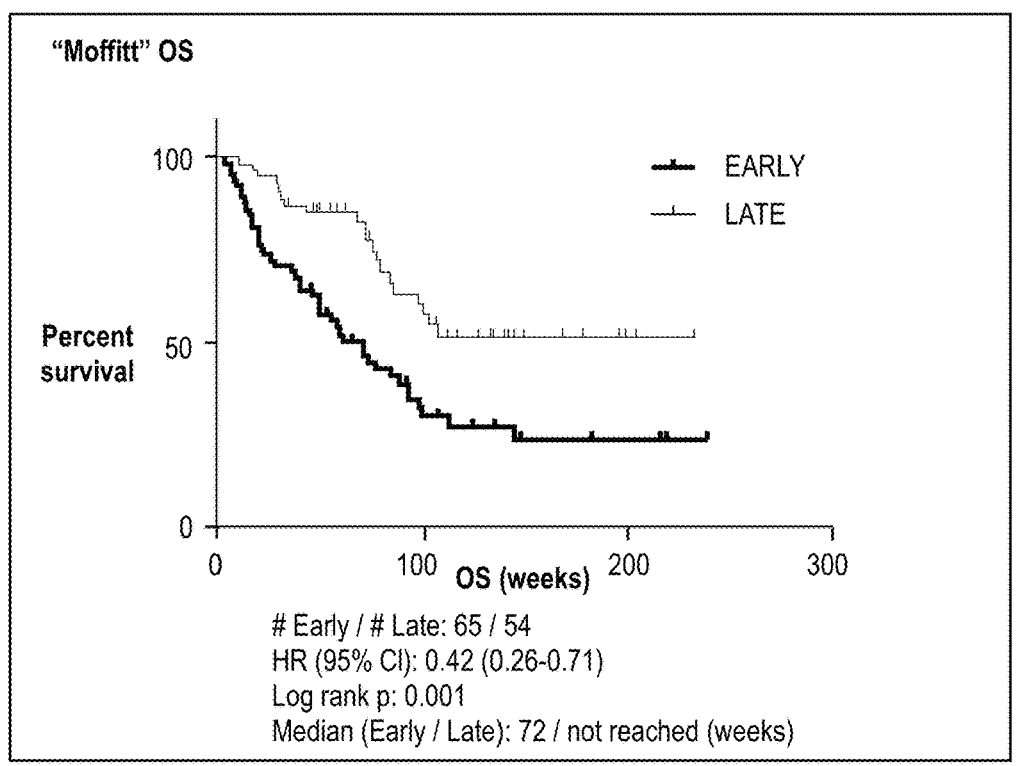
FIGS. 79A and 79B are Kaplan-Meier plots for classification groups Early and Late, obtained from a classifier developed in accordance with the procedure of FIG. 8 but instead of using mass spectral features, the features used for classification are the Biological Function Scores of Example 10, in this example the Acute Response Score, the Wound Healing Score and the Complement Score.
Figure 79B:
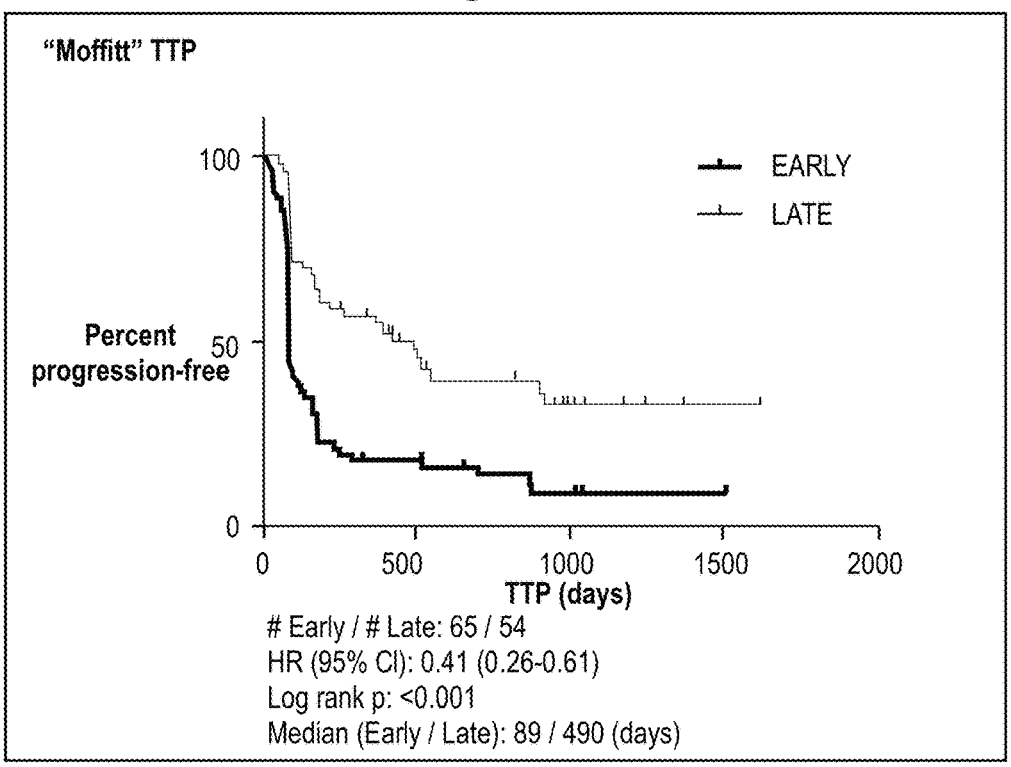

When the classifier was developed in accordance with FIG. 8 and applied to the Moffitt set the approach produced two classification groups, "Early" (poor outcomes, Early progression) and "Late" (good outcomes, Late progression). The Kaplan-Meier plots for these classification groups are shown in FIGS. 79A and 79B, FIG. 79A showing the overall survival by classification group and FIG. 79B showing the time to progression by classification group. There is excellent stratification of the patients into groups with better and worse outcomes from the classifier developed using the three biological functions scores as the only features.

It would also be possible to relate an individual patient's score to the distribution of scores obtained for the population of patients in the same indication, to get an indication of whether the individual patient has a particularly high or low level of activation of the biological function being considered. For example, patients with melanoma with an AR score of greater than 1 lie above the 90th percentile of AR score in their indication, indicating exceptionally high levels of acute response. This could potentially be used to select patients for or indicate against certain therapies. See G Simpson, S D Heys, P H Whiting, et al., Acute phase proteins and recombinant IL-2 therapy: prediction of response and survival in patients with colorectal cancer. Clin Exp Immunol 1995; 99: 143-147.

Accordingly, in one aspect of this disclosure we develop/train a classifier from a set of biological function scores on a development set of samples, and can use such a classifier and associated reference set (class labels and scores) to classify a new sample. The new sample is subject to mass spectrometry, the feature values are obtained for the features in the set associated with the PCA first principal component vector for each of the biological functions, and a set of biological function scores are assigned to the sample using the same procedures to generate the biological function scores in the development sample set. Then the sample is classified with the classifier and a label is generated, e.g., Early or Late or the equivalent. The class label is then useful for guiding treatment or predicting patient response or survival.

3. Using Biological Scores for Patient Monitoring

As shown for example in FIGS. 70A-70D, numerical changes in the score of a patient in the course of treatment in some cases can be associated with the change of classification: thus, decrease of the AR score seems to be associated with changes of classification from Early to Late by week 7, while changes from Late to Early seem to correspond with the increase of the score.

It would be possible to observe changes over time in score, or the change in percentile of the observed score in the distribution of scores for the particular indication to monitor changes in levels of a particular biological function. This could be used to investigate the effectiveness of a therapy or to test whether a patient's status has changed to allow initiation of a therapy. For example, if a therapy is known to be ineffective when acute response levels are high, a patient may need to wait until his AR score is reduced, either naturally or by some intervention, until he should commence that particular therapy. This approach could also be used to monitor chronic diseases to try to predict disease flares or progression.

In addition we have demonstrated (see for example FIGS. 71A-B and Table 76) that as well as baseline evaluation of scores, changes in score can be significant prognostic factors, providing additional information to physicians to inform patient prognosis.

4. Identifying Differences in Relative Importance of Biological Functions Across Tumor Types The results of Example 10 show that, while the distribution of AR scores is quite similar between melanoma patients and patients with NSCLC, the distributions of WH-AR-IR score and complement score are different. Hence, examination of the score distributions across different indications may reveal differences in the relative importance of different biological functions and related pathways across different tumor types and could be used, for example, to investigate why some therapies are more effective in some tumor types than in others.

In summary, biological function scores can be used to characterize the role of a biological function in an existing classifier, as well as to classify patients independently, with the potential to define groups with different outcomes and prognoses. It can also be used to monitor changes in level of biological function that may be useful for assessing course of disease, effectiveness of therapy, or when a patient can optimally commence a treatment.

While the examples here are specific, the methodology used in quite general and can be extended in several ways.

1. Choice of What Features to Use within PCA

In these examples, in the PSEA we used features associated with the protein sets linked to a particular biological function with a p value of 0.05. This choice of cutoff in level of association is arbitrary and can be taken to be larger or smaller, thereby bringing in larger or smaller sets of features associated with a particular biological function.

2. Use of Only One Principal Component of PCA

In the examples explored here, the first principal component dominated the variance within the datasets. See FIGS. 65A-65C and the previous discussion. This might not always be the case and it might be necessary to extend the approach to characterize the level of a particular biological function by a set of several scores, rather than a single score. Alternatively, it might be necessary to combine the projections onto several principal components or their locations in the population distributions of these projections to create a single score that more precisely reflects the biological function.

3. Alternatives to PCA

Here we used simple PCA on the set of features associated with the biological function to reduce the feature values to one score. It would be possible to use other methods to do this dimensional reduction, for example, the technique known as kernel PCA. See for example the description of this technique on wikipedia.org and the references therein.

Figure 80:
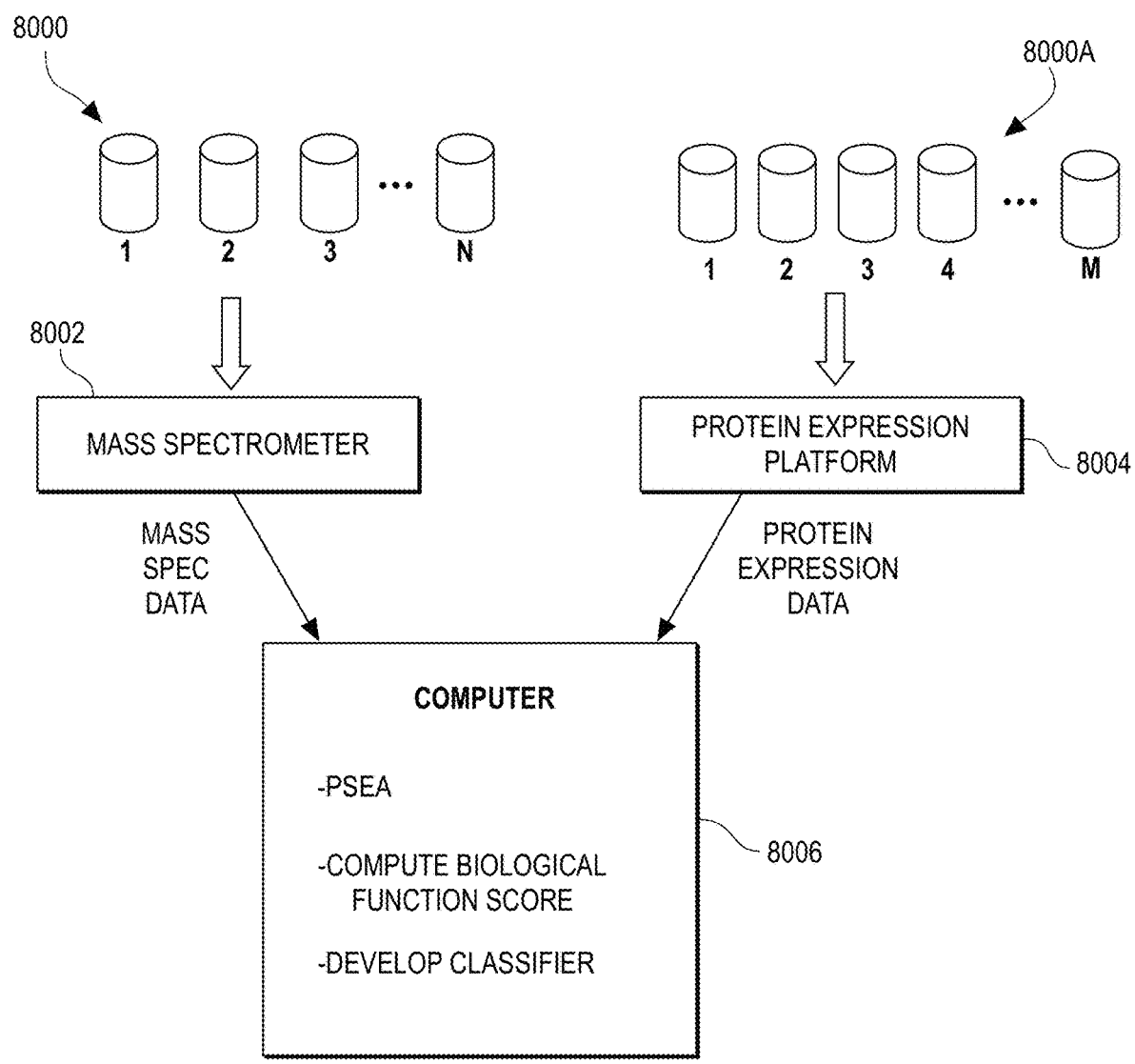
FIG. 80 is a schematic illustration of system for generating the biological function scores of Example 10 for a sample set.

FIG. 80 summarizes in block diagram form a system and method for creation of a biological function score. As indicated at 8000, we have a development set of N samples 1, 2, 3, . . . N e.g., from a population of patients enrolled in a clinical trial of a drug or all having a disease, e.g., cancer. The samples in this example are blood based samples, e.g., serum, obtained for example in advance of treatment. The samples are subject to mass spectrometry as indicated at 8002. Additionally, the samples are subject to a protein expression assay in a platform 8004 (such as the SOMAscan system of SomaLogic, Inc., Boulder Colo. or the equivalent). Protein expression data of a large set of proteins, ideally at least 1000 such proteins and mass spectrometry data is provided to a computer 8006. The computer 8006 performs a protein set enrichment analysis (PSEA), including derivation of ES scores and p values which correlate sets of proteins associated with particular biological functions with mass spectrometry features, using the methodology explained in Example 6. From this data, the computer generates a biological function score for the biological function(s) identified from the PSEA analysis using the procedure explained above. This can be an array of scores for each member of the development sample set 8000. Additionally and alternatively, a classifier can be developed using FIG. 8 using the scores in the development set as features for classification as explained above, if clinical data or class labels for the samples are also available for classifier training. The scores for the set of samples, along with class labels for the members of the development set, are stored in memory of the computer 80006, for example in later use in classification of a sample.

As another example, a sample from a new patient with similar characteristics as the development sample set is obtained, mass spectrometry is performed on the sample and feature values for the features associated with the biological function(s) are obtained, and a score is assigned to the sample. The score is then compared with the scores in the sample set 8000, or a threshold derived from the scores in the development sample set, and the score for the new sample is used to guide treatment or predict patient outcome or prognosis.

As shown in FIG. 80, in one alternative a second set of M samples 1, 2, 3 . . . . M 8000A could be obtained and the protein expression assay in the platform 8004 could be performed on this second set of samples. The PSEA analysis could be done on this set of protein expression data instead of the first set of samples. This second set of samples could also be subject to mass spectrometry and the processes in the computer 8006.

The following clauses are offered as further descriptions of the inventions disclosed in Example 10.

1. A system for characterizing a biological function in a human, comprising:

a mass spectrometer conducting mass spectrometry on a blood-based sample from the human; and a computer operating with programmed instructions for generating a biological function score from a feature table of mass spectral features obtained from the mass spectrometry of the blood-based samples which are associated with the biological function projected onto the direction of a first principal component vector obtained from the mass spectral features and a sample set in the form of a multitude of other blood-based samples.

2. The system of clause 1, further comprising a protein expression assay system obtaining protein expression data from a large panel of proteins spanning biological functions of interest for each of the samples in the development set of samples or alternatively each of the samples in the second set of samples; and wherein the computer is operable to perform a protein set enrichment analysis associating proteins or sets of proteins from the large panel of proteins with the biological function.

3. A method of evaluating a set of blood-based samples obtained from a population of humans, comprising the steps of:

a) obtaining the set of samples;

b) conducting mass spectrometry on the set of samples and obtaining mass spectrometry data including feature values of a set of mass spectrometry features;

c) identifying associations of sets of the mass spectrometry features with a biological function; and d) computing a biological function score for each member in the set of samples by projecting a feature table containing feature values of the mass spectral features which are associated with the biological function onto the direction of a first principal component vector obtained from the mass spectral features and a sample set of blood-based samples.

4. The method of clause 3, comprising repeating step c) to identify a second set of features which are associated with a second biological function and repeating step d) by computing a biological function score for the second biological function.

5. The method of clause 3 or 4, wherein the biological function comprises acute response, wound healing, or complement system.

6. The method of clause 3, wherein steps a), b), and d) are performed for a second set of blood-based samples.

7. A method of evaluation of a biological process of a human, comprising the steps of:
a) performing the process of clause 4 on a development set of samples and obtaining biological function scores for each of the members of the development set of samples for at least two different biological functions;
b) developing a classifier from the biological function scores for the development set of samples; and
c) performing mass spectrometry of a blood-based sample from the human and obtaining feature values for sets of mass spectral features associated with the at least two different biological functions, and
d) computing a biological function score for each of the at least two biological functions for the blood-based sample from the human, and
e) classifying the sample with the classifier developed in step b) on the biological function scores computed in step d).

8. The method of clause 7, further comprising generating a class label for the sample with a classifier trained from mass spectrometry data of the development set of samples and class labels associated with the development set of samples.

9. The method of clause 7, wherein the classifier developed in step b) is organized to classify a sample based on a threshold in the biological function score.

10. The method of clause 7, wherein the development set of samples comprises a set of samples from melanoma patients treated with an immune checkpoint inhibitor.

11. A method of classifier development, comprising the steps of:
   a) obtaining a development set of blood-based samples from a plurality of humans;
   b) conducting mass spectrometry on the development set of samples and obtaining mass spectrometry data including feature values of a set of mass spectrometry features;
   c) identifying associations of sets of the mass spectrometry features with at least one biological function;
   d) computing a biological function score for each member in the development sample set by projecting a feature table containing feature values of the mass spectral features which are associated with the biological function onto the direction of a first principal component vector obtained from the mass spectral features and a development sample set or alternatively on a second sample set; and
   e) training a classifier with the biological function score for the at least one biological function.

12. The method of clause 11, wherein steps c) and d) are performed to identify at least two sets of mass spectrometry features with at least two biological functions and computing at least two biological function scores for each member in the development sample set; and wherein step e) comprises training the classifier with the at least two biological function scores.

13. The method of clause 12, wherein the training step e) comprises the procedure of FIG. 8.

14. The method of clause 3, further comprising computing a projection of the feature table containing feature values of the mass spectral features which are associated with the biological function onto the direction of a second principal component vector obtained from the mass spectral features and the sample set.

15. The method of clause 3, wherein the first principal component vector is computed from a principal component analysis procedure over many different realizations of subsets of the sample set.

16. The method of clause 15, further comprising the step of iteratively averaging and normalizing first principal components until a bagged first principal component vector $\hat{u}_1$ is obtained.

The appended claims are provided as further descriptions of the disclosed inventions.

APPENDICES

APPENDIX A

Feature Definitions

| Left | Center | Right |
|---|---|---|
| 3073.625 | 3085.665 | 3097.705 |
| 3098.586 | 3109.891 | 3121.197 |
| 3123.546 | 3138.669 | 3153.793 |
| 3190.793 | 3210.615 | 3230.436 |
| 3230.73 | 3242.623 | 3254.516 |
| 3255.103 | 3264.647 | 3274.191 |
| 3296.802 | 3316.77 | 3336.739 |
| 3349.072 | 3363.608 | 3378.144 |
| 3380.2 | 3391.946 | 3403.692 |
| 3405.16 | 3420.283 | 3435.407 |
| 3435.7 | 3445.097 | 3454.494 |
| 3454.788 | 3465.359 | 3475.931 |
| 3531.431 | 3553.896 | 3576.36 |
| 3581.059 | 3593.099 | 3605.138 |
| 3665.631 | 3679.286 | 3692.941 |
| 3693.235 | 3702.631 | 3712.028 |
| 3712.616 | 3723.334 | 3734.052 |
| 3745.211 | 3754.755 | 3764.299 |
| 3764.592 | 3775.604 | 3786.616 |
| 3804.529 | 3817.744 | 3830.958 |
| 3831.545 | 3841.53 | 3851.514 |
| 3876.474 | 3887.486 | 3898.499 |
| 3914.356 | 3928.158 | 3941.959 |
| 3942.253 | 3953.412 | 3964.571 |
| 3994.23 | 4008.619 | 4023.008 |
| 4024.182 | 4031.67 | 4039.159 |
| 4039.452 | 4050.464 | 4061.476 |
| 4086.437 | 4098.77 | 4111.104 |
| 4111.308 | 4118.525 | 4125.742 |
| 4126.043 | 4133.109 | 4140.176 |
| 4198.812 | 4209.788 | 4220.764 |
| 4255.194 | 4264.44 | 4273.687 |
| 4273.837 | 4286.166 | 4298.495 |
| 4328.264 | 4340.217 | 4352.17 |
| 4352.32 | 4360.815 | 4369.31 |
| 4369.611 | 4380.962 | 4392.314 |
| 4393.817 | 4408.627 | 4423.436 |
| 4424.789 | 4431.179 | 4437.569 |
| 4437.87 | 4459.22 | 4480.57 |
| 4496.507 | 4506.58 | 4516.654 |
| 4538.304 | 4545.07 | 4551.836 |
| 4552.738 | 4564.991 | 4577.245 |
| 4577.997 | 4590.1 | 4602.203 |
| 4616.938 | 4625.282 | 4633.627 |
| 4633.927 | 4643.324 | 4652.721 |
| 4664.148 | 4675.274 | 4686.4 |
| 4690.609 | 4717.673 | 4744.736 |
| 4746.54 | 4756.162 | 4765.785 |

APPENDIX A-continued

Feature Definitions

| Left | Center | Right |
|---|---|---|
| 4766.386 | 4773.152 | 4779.918 |
| 4780.218 | 4791.194 | 4802.17 |
| 4802.621 | 4817.881 | 4833.142 |
| 4836.299 | 4855.995 | 4875.691 |
| 4880.953 | 4891.177 | 4901.401 |
| 4909.52 | 4918.316 | 4927.111 |
| 4927.261 | 4937.636 | 4948.01 |
| 4948.16 | 4963.045 | 4977.93 |
| 4987.552 | 4998.979 | 5010.405 |
| 5011.007 | 5020.103 | 5029.199 |
| 5029.65 | 5041.077 | 5052.504 |
| 5053.556 | 5067.839 | 5082.123 |
| 5087.535 | 5104.074 | 5120.613 |
| 5120.913 | 5129.182 | 5137.452 |
| 5137.602 | 5144.819 | 5152.036 |
| 5152.487 | 5157.824 | 5163.162 |
| 5163.312 | 5168.123 | 5172.935 |
| 5173.085 | 5179.776 | 5186.466 |
| 5187.218 | 5197.818 | 5208.417 |
| 5209.77 | 5223.753 | 5237.736 |
| 5238.036 | 5247.734 | 5257.432 |
| 5275.624 | 5289.757 | 5303.89 |
| 5347.191 | 5358.543 | 5369.894 |
| 5370.646 | 5377.186 | 5383.726 |
| 5383.877 | 5389.815 | 5395.754 |
| 5395.905 | 5403.422 | 5410.94 |
| 5411.09 | 5416.277 | 5421.464 |
| 5421.615 | 5429.809 | 5438.003 |
| 5439.807 | 5449.204 | 5458.601 |
| 5463.713 | 5472.057 | 5480.402 |
| 5481.454 | 5495.813 | 5510.171 |
| 5510.472 | 5521.222 | 5531.972 |
| 5538.738 | 5549.939 | 5561.14 |
| 5561.29 | 5570.011 | 5578.731 |
| 5666.235 | 5673.903 | 5681.571 |
| 5685.017 | 5691.464 | 5697.911 |
| 5698.296 | 5705.753 | 5713.211 |
| 5713.499 | 5720.428 | 5727.356 |
| 5727.548 | 5733.899 | 5740.25 |
| 5740.923 | 5748.044 | 5755.165 |
| 5756.127 | 5762.381 | 5768.636 |
| 5769.502 | 5776.671 | 5783.84 |
| 5787.496 | 5795.483 | 5803.469 |
| 5803.95 | 5815.979 | 5828.007 |
| 5828.68 | 5842.055 | 5855.431 |
| 5856.297 | 5867.218 | 5878.14 |
| 5879.39 | 5889.157 | 5898.924 |
| 5899.02 | 5910.808 | 5922.595 |
| 5930.871 | 5950.212 | 5969.553 |
| 5978.694 | 5997.458 | 6016.222 |
| 6016.895 | 6026.806 | 6036.717 |
| 6082.713 | 6090.94 | 6099.167 |
| 6099.552 | 6108.597 | 6117.642 |
| 6117.738 | 6122.213 | 6126.687 |
| 6145.74 | 6153.101 | 6160.462 |
| 6161.136 | 6170.373 | 6179.611 |
| 6184.807 | 6192.938 | 6201.069 |
| 6201.261 | 6209.585 | 6217.908 |
| 6218.004 | 6226.039 | 6234.074 |
| 6244.081 | 6252.693 | 6261.305 |
| 6262.46 | 6267.993 | 6273.526 |
| 6273.718 | 6283.244 | 6292.771 |
| 6292.867 | 6301.238 | 6309.61 |
| 6309.706 | 6315.48 | 6321.253 |
| 6321.927 | 6331.742 | 6341.556 |
| 6349.736 | 6357.77 | 6365.805 |
| 6379.18 | 6386.108 | 6393.037 |
| 6393.229 | 6399.965 | 6406.7 |
| 6408.625 | 6437.829 | 6467.033 |
| 6467.129 | 6485.171 | 6503.214 |
| 6519.476 | 6534.342 | 6549.209 |
| 6560.275 | 6567.684 | 6575.093 |
| 6577.691 | 6589.431 | 6601.17 |
| 6603.961 | 6611.61 | 6619.26 |
| 6620.319 | 6634.319 | 6648.32 |
| 6648.512 | 6657.076 | 6665.64 |
| 6668.623 | 6680.651 | 6692.68 |
| 6719.237 | 6731.65 | 6744.063 |
| 6754.648 | 6761.047 | 6767.446 |
| 6767.638 | 6773.171 | 6778.704 |
| 6778.8 | 6788.952 | 6799.104 |
| 6799.97 | 6808.919 | 6817.868 |
| 6824.892 | 6836.679 | 6848.467 |
| 6848.948 | 6859.629 | 6870.31 |
| 6873.797 | 6881.433 | 6889.07 |
| 6890.609 | 6897.599 | 6904.589 |
| 6914.565 | 6921.586 | 6928.606 |
| 6933.102 | 6941.477 | 6949.853 |
| 6950.469 | 6956.75 | 6963.032 |
| 6963.34 | 6970.545 | 6977.75 |
| 6978.92 | 6992.222 | 7005.524 |
| 7014.269 | 7022.06 | 7029.85 |
| 7029.912 | 7034.592 | 7039.272 |
| 7039.395 | 7045.154 | 7050.912 |
| 7067.293 | 7073.79 | 7080.287 |
| 7119.824 | 7147.228 | 7174.633 |
| 7177.589 | 7188.951 | 7200.314 |
| 7235.047 | 7244.438 | 7253.83 |
| 7254.384 | 7260.204 | 7266.023 |
| 7266.085 | 7273.598 | 7281.111 |
| 7281.173 | 7286.839 | 7292.504 |
| 7292.812 | 7300.633 | 7308.454 |
| 7310.117 | 7318.369 | 7326.622 |
| 7326.991 | 7333.581 | 7340.17 |
| 7352.179 | 7359.261 | 7366.343 |
| 7379.768 | 7393.009 | 7406.249 |
| 7406.742 | 7419.613 | 7432.484 |
| 7432.607 | 7441.075 | 7449.543 |
| 7449.604 | 7456.44 | 7463.276 |
| 7463.584 | 7474.361 | 7485.138 |
| 7497.824 | 7510.356 | 7522.889 |
| 7523.751 | 7535.975 | 7548.2 |
| 7731.041 | 7738.801 | 7746.561 |
| 7761.341 | 7779.077 | 7796.813 |
| 7874.347 | 7882.876 | 7891.405 |
| 7904.954 | 7912.836 | 7920.719 |
| 8007.424 | 8015.07 | 8022.717 |
| 8134.845 | 8146.885 | 8158.925 |
| 8173.99 | 8183.91 | 8193.83 |
| 8195.752 | 8206.991 | 8218.23 |
| 8238.737 | 8253.917 | 8269.098 |
| 8308.327 | 8315.347 | 8322.368 |
| 8322.784 | 8330.844 | 8338.904 |
| 8353.406 | 8363.536 | 8373.667 |
| 8380.133 | 8391.495 | 8402.857 |
| 8404.767 | 8413.388 | 8422.01 |
| 8422.133 | 8430.231 | 8438.33 |
| 8457.421 | 8464.072 | 8470.723 |
| 8470.846 | 8477.558 | 8484.271 |
| 8485.195 | 8492.061 | 8498.928 |
| 8506.934 | 8513.585 | 8520.236 |
| 8520.544 | 8531.198 | 8541.852 |
| 8554.723 | 8564.761 | 8574.799 |
| 8575.476 | 8585.268 | 8595.06 |
| 8618.77 | 8631.702 | 8644.635 |
| 8649.87 | 8660.554 | 8671.239 |
| 8671.855 | 8696.119 | 8720.383 |
| 8720.568 | 8728.512 | 8736.456 |
| 8736.518 | 8745.817 | 8755.116 |
| 8756.348 | 8770.604 | 8784.861 |
| 8791.574 | 8796.962 | 8802.351 |
| 8802.474 | 8822.181 | 8841.887 |
| 8861.964 | 8871.848 | 8881.732 |
| 8883.826 | 8890.538 | 8897.251 |
| 8897.436 | 8901.654 | 8905.873 |
| 8905.934 | 8928.258 | 8950.582 |
| 8967.272 | 8974.415 | 8981.559 |
| 8988.149 | 8997.971 | 9007.794 |
| 9010.011 | 9020.295 | 9030.58 |
| 9030.764 | 9038.216 | 9045.668 |
| 9067.961 | 9077.198 | 9086.436 |
| 9091.547 | 9097.798 | 9104.049 |

APPENDIX A-continued

Feature Definitions

| Left | Center | Right |
| --- | --- | --- |
| 9105.613 | 9109.456 | 9113.299 |
| 9115.171 | 9134.336 | 9153.501 |
| 9175.08 | 9187.076 | 9199.073 |
| 9199.122 | 9208.31 | 9217.498 |
| 9217.991 | 9226.317 | 9234.643 |
| 9234.742 | 9244.546 | 9254.35 |
| 9254.941 | 9263.932 | 9272.924 |
| 9273.899 | 9284.974 | 9296.05 |
| 9310.761 | 9318.865 | 9326.969 |
| 9344.962 | 9359.289 | 9373.615 |
| 9387.662 | 9395.293 | 9402.923 |
| 9410.817 | 9430.014 | 9449.211 |
| 9475.524 | 9484.41 | 9493.296 |
| 9494.536 | 9504.042 | 9513.549 |
| 9520.898 | 9534.803 | 9548.707 |
| 9559.484 | 9576.179 | 9592.874 |
| 9615.006 | 9641.179 | 9667.352 |
| 9689.387 | 9720.901 | 9752.414 |
| 9784.265 | 9793.021 | 9801.777 |
| 9840.895 | 9862.594 | 9884.294 |
| 9908.49 | 9918.931 | 9929.371 |
| 9929.66 | 9941.495 | 9953.331 |
| 10002.41 | 10012.36 | 10022.32 |
| 10066.88 | 10079.24 | 10091.61 |
| 10091.7 | 10102.24 | 10112.77 |
| 10120.09 | 10135.29 | 10150.49 |
| 10150.78 | 10162.62 | 10174.45 |
| 10174.65 | 10185.23 | 10195.82 |
| 10195.91 | 10210.35 | 10224.78 |
| 10225.16 | 10236.04 | 10246.91 |
| 10250.09 | 10263.03 | 10275.97 |
| 10276.55 | 10285.11 | 10293.68 |
| 10294.45 | 10304.31 | 10314.17 |
| 10314.27 | 10321.34 | 10328.41 |
| 10333.03 | 10346.26 | 10359.49 |
| 10359.69 | 10365.85 | 10372 |
| 10409.53 | 10418.53 | 10427.52 |
| 10436.76 | 10448.55 | 10460.34 |
| 10465.73 | 10476.5 | 10487.28 |
| 10487.47 | 10493.58 | 10499.69 |
| 10500.46 | 10508.4 | 10516.34 |
| 10517.4 | 10533.61 | 10549.83 |
| 10568.97 | 10588.56 | 10608.14 |
| 10615.84 | 10636.81 | 10657.79 |
| 10705.55 | 10734.07 | 10762.59 |
| 10773.07 | 10782.59 | 10792.12 |
| 10792.22 | 10801.79 | 10811.36 |
| 10827.72 | 10846.77 | 10865.83 |
| 10912.98 | 10923.56 | 10934.15 |
| 10934.82 | 10944.01 | 10953.2 |
| 10953.3 | 10961.23 | 10969.17 |
| 11032.68 | 11044.95 | 11057.22 |
| 11057.51 | 11067.08 | 11076.66 |
| 11091.28 | 11103.93 | 11116.59 |
| 11137.08 | 11149.06 | 11161.04 |
| 11187.6 | 11197.22 | 11206.85 |
| 11217.43 | 11228.06 | 11238.7 |
| 11288.09 | 11306.44 | 11324.78 |
| 11357.26 | 11375.9 | 11394.54 |
| 11426.18 | 11445.9 | 11465.63 |
| 11465.99 | 11480.52 | 11495.05 |
| 11498.47 | 11526.91 | 11555.36 |
| 11560.53 | 11576.4 | 11592.27 |
| 11602.51 | 11632.22 | 11661.93 |
| 11662.77 | 11686.28 | 11709.8 |
| 11712.08 | 11733.43 | 11754.78 |
| 11756.23 | 11786.66 | 11817.09 |
| 11817.93 | 11834.77 | 11851.61 |
| 11868.93 | 11898.52 | 11928.11 |
| 11928.7 | 11952.25 | 11975.8 |
| 11976.8 | 12002.53 | 12028.25 |
| 12219.68 | 12232.71 | 12245.74 |
| 12271.47 | 12290.85 | 12310.22 |
| 12310.89 | 12321.25 | 12331.6 |
| 12340.29 | 12351.31 | 12362.34 |
| 12400.43 | 12412.62 | 12424.81 |
| 12433.83 | 12457.39 | 12480.94 |
| 12536.4 | 12565.8 | 12595.2 |
| 12597.2 | 12613.41 | 12629.61 |
| 12647.98 | 12674.21 | 12700.44 |
| 12716.47 | 12738.02 | 12759.57 |
| 12761.24 | 12785.79 | 12810.35 |
| 12829.73 | 12873.16 | 12916.59 |
| 12935.63 | 12967.54 | 12999.44 |
| 13051.23 | 13080.96 | 13110.69 |
| 13117.71 | 13134.41 | 13151.12 |
| 13258.69 | 13274.73 | 13290.77 |
| 13304.46 | 13323.17 | 13341.88 |
| 13347.56 | 13364.6 | 13381.64 |
| 13510.26 | 13524.96 | 13539.66 |
| 13551.35 | 13567.72 | 13584.09 |
| 13595.12 | 13614.66 | 13634.21 |
| 13703.7 | 13721.07 | 13738.44 |
| 13740.45 | 13762.16 | 13783.88 |
| 13784.55 | 13798.24 | 13811.94 |
| 13826.64 | 13842.84 | 13859.05 |
| 13864.06 | 13882.93 | 13901.81 |
| 13903.15 | 13916.01 | 13928.87 |
| 13929.87 | 13943.07 | 13956.27 |
| 13958.61 | 13983.66 | 14008.72 |
| 14015.73 | 14042.8 | 14069.86 |
| 14076.2 | 14097.59 | 14118.97 |
| 14124.31 | 14149.03 | 14173.76 |
| 14178.77 | 14198.98 | 14219.19 |
| 14231.55 | 14254.61 | 14277.66 |
| 14281.33 | 14306.56 | 14331.78 |
| 14405.61 | 14433.68 | 14461.74 |
| 14462.41 | 14488.47 | 14514.53 |
| 14515.19 | 14540.58 | 14565.97 |
| 14567.31 | 14594.54 | 14621.77 |
| 14751.73 | 14784.47 | 14817.21 |
| 14857.63 | 14884.53 | 14911.42 |
| 15002.96 | 15026.68 | 15050.4 |
| 15527.48 | 15563.22 | 15598.97 |
| 15613 | 15629.04 | 15645.07 |
| 15719.58 | 15751.48 | 15783.39 |
| 16465.93 | 16502.17 | 16538.42 |
| 16610.92 | 16630.13 | 16649.34 |
| 16999.46 | 17032.54 | 17065.61 |
| 17104.03 | 17148.13 | 17192.23 |
| 17225.64 | 17270.91 | 17316.18 |
| 17344.57 | 17394.52 | 17444.47 |
| 17445.13 | 17476.37 | 17507.61 |
| 17569.08 | 17604.33 | 17639.57 |
| 17774.54 | 17815.47 | 17856.39 |
| 17982.34 | 18031.12 | 18079.9 |
| 18232.58 | 18275.34 | 18318.1 |
| 18593.72 | 18636.99 | 18680.25 |
| 18704.31 | 18728.69 | 18753.08 |
| 18816.22 | 18850.13 | 18884.04 |
| 19339.07 | 19373.15 | 19407.22 |
| 19407.56 | 19463.85 | 19520.15 |
| 19522.82 | 19575.27 | 19627.72 |
| 19843.56 | 19992.15 | 20140.74 |
| 20482.31 | 20562.33 | 20642.34 |
| 20886.89 | 20945.69 | 21004.49 |
| 21005.16 | 21061.95 | 21118.75 |
| 21119.42 | 21170.37 | 21221.31 |
| 21221.98 | 21275.44 | 21328.89 |
| 21330.89 | 21377.17 | 21423.44 |
| 21436.13 | 21485.91 | 21535.69 |
| 21642.26 | 21687.7 | 21733.13 |
| 21733.47 | 21760.7 | 21787.93 |
| 21788.93 | 21816.49 | 21844.05 |
| 22967.23 | 23036.05 | 23104.87 |
| 23106.91 | 23146.16 | 23185.42 |
| 23187.46 | 23249.14 | 23310.82 |
| 23311.84 | 23356.7 | 23401.56 |
| 23407.68 | 23468.85 | 23530.03 |
| 27874.33 | 27944.17 | 28014.01 |
| 28015.03 | 28082.32 | 28149.61 |

APPENDIX B

Features included in the classifiers (Example 1)

| Approach 1 | Approach 2 | Approach 3 | Approach 4 | Whole Set Approach 1 | Whole Set Approach 2 |
|---|---|---|---|---|---|
| 3445 | 3265 | 3243 | 3110 | 3243 | 3110 |
| 3465 | 3554 | 3703 | 3364 | 3703 | 3703 |
| 3703 | 3703 | 3723 | 3593 | 3723 | 3723 |
| 3928 | 3723 | 3928 | 3703 | 3755 | 3755 |
| 4050 | 3755 | 4381 | 3723 | 3842 | 3776 |
| 4133 | 3776 | 4409 | 3776 | 3928 | 3928 |
| 4286 | 3928 | 5416 | 3928 | 3953 | 3953 |
| 4565 | 3953 | 5472 | 4133 | 4050 | 4050 |
| 4718 | 4050 | 5496 | 4264 | 4409 | 4133 |
| 4818 | 4133 | 5550 | 4381 | 4545 | 4756 |
| 5020 | 4264 | 5762 | 4409 | 4590 | 4791 |
| 5168 | 4381 | 5777 | 4431 | 5020 | 5020 |
| 5180 | 4409 | 5816 | 4545 | 5145 | 5068 |
| 5449 | 4590 | 5842 | 4590 | 5168 | 5104 |
| 5472 | 5020 | 5867 | 4756 | 5449 | 5145 |
| 5521 | 5068 | 5889 | 4791 | 5550 | 5550 |
| 5550 | 5104 | 5911 | 4999 | 5706 | 5570 |
| 5674 | 5129 | 5950 | 5020 | 5777 | 5734 |
| 5748 | 5168 | 5997 | 5068 | 5816 | 5762 |
| 5777 | 5390 | 6027 | 5104 | 5842 | 5842 |
| 5867 | 5449 | 7045 | 5145 | 5867 | 5867 |
| 5889 | 5472 | 7274 | 5472 | 5889 | 5889 |
| 5911 | 5550 | 7301 | 5521 | 5911 | 5911 |
| 5950 | 5570 | 7318 | 5550 | 5950 | 5950 |
| 5997 | 5762 | 7739 | 5570 | 5997 | 5997 |
| 6027 | 5777 | 7883 | 5706 | 6027 | 6091 |
| 6091 | 5816 | 8254 | 5734 | 6091 | 6109 |
| 6210 | 5842 | 8661 | 5762 | 6153 | 6170 |
| 6568 | 5867 | 8696 | 5777 | 6210 | 6210 |
| 6860 | 5889 | 8729 | 5795 | 6568 | 6568 |
| 6881 | 5911 | 8771 | 5816 | 6860 | 6860 |
| 6941 | 5950 | 8872 | 5842 | 6992 | 6881 |
| 6971 | 5997 | 8891 | 5867 | 7260 | 7318 |
| 7045 | 6091 | 8998 | 5889 | 7274 | 8391 |
| 7287 | 6170 | 9020 | 5911 | 7287 | 8531 |
| 7441 | 6210 | 9038 | 5950 | 7318 | 9109 |
| 7779 | 6789 | 9098 | 5997 | 8771 | 11446 |
| 8771 | 6860 | 9226 | 6091 | 9098 | 11481 |
| 9134 | 6941 | 10163 | 6210 | 9134 | 11527 |
| 9187 | 7045 | 10285 | 6634 | 9319 | 11686 |
| 9226 | 7318 | 10346 | 6681 | 9430 | 11733 |
| 9285 | 7883 | 10847 | 6732 | 10210 | 11787 |
| 9319 | 7913 | 11067 | 6761 | 11446 | 11835 |
| 9430 | 8391 | 11104 | 6837 | 11481 | 11899 |
| 9641 | 8413 | 11376 | 6881 | 11527 | 11952 |
| 9941 | 8492 | 11446 | 6898 | 11632 | 12003 |
| 10102 | 8771 | 11481 | 6957 | 11686 | 13134 |
| 10185 | 9020 | 11527 | 7074 | 11733 | 13323 |
| 10210 | 9109 | 11576 | 7318 | 11787 | 13721 |
| 10285 | 9187 | 11632 | 7334 | 11835 | 13762 |
| 10346 | 9226 | 11686 | 7739 | 11899 | 13843 |
| 10449 | 9535 | 11733 | 7883 | 11952 | 17033 |
| 10734 | 10135 | 11787 | 8391 | 12003 | 18275 |
| 11045 | 10285 | 11835 | 8413 | 12413 | 18637 |
| 11104 | 11045 | 11899 | 8565 | 12873 | 18729 |
| 11197 | 11067 | 11952 | 8661 | 13134 | 18850 |
| 11835 | 11197 | 12003 | 8696 | 13323 | 19992 |
| 11952 | 11446 | 13568 | 8729 | 13568 | 23357 |
| 12003 | 11481 | 13615 | 8771 | 13615 | 23469 |
| 12351 | 11527 | 13721 | 8797 | 13721 | |
| 12413 | 11576 | 13883 | 8872 | 14541 | |
| 12674 | 11632 | 13916 | 8891 | 14784 | |
| 13134 | 11686 | 18275 | 8998 | 17033 | |
| 13323 | 11733 | 23357 | 9098 | 17148 | |
| 13365 | 11787 | 23469 | 9109 | 18275 | |
| 13568 | 11835 | | 9226 | 18637 | |
| 13615 | 11899 | | 9504 | 18729 | |
| 13721 | 11952 | | 10102 | 21170 | |
| 13762 | 12003 | | 11067 | 21486 | |
| 14255 | 12351 | | 11104 | 23036 | |
| 15629 | 12968 | | 11376 | 23146 | |
| 17033 | 13134 | | 11446 | 23357 | |
| 17148 | 13323 | | 11481 | 23469 | |

APPENDIX B-continued

Features included in the classifiers (Example 1)

| Approach 1 | Approach 2 | Approach 3 | Approach 4 | Whole Set Approach 1 | Whole Set Approach 2 |
|---|---|---|---|---|---|
| 17271 | 13365 | | 11527 | | |
| 17476 | 13568 | | 11576 | | |
| 18275 | 13615 | | 11632 | | |
| 18637 | 13721 | | 11686 | | |
| 18729 | 13762 | | 11733 | | |
| 19992 | 13883 | | 11787 | | |
| 21062 | 15629 | | 11835 | | |
| 21170 | 17033 | | 11899 | | |
| 21486 | 17476 | | 11952 | | |
| 23036 | 18031 | | 12003 | | |
| 23146 | 18275 | | 12413 | | |
| | 18637 | | 13134 | | |
| | 18729 | | 13615 | | |
| | 18850 | | 13721 | | |
| | 19992 | | 13762 | | |
| | 20946 | | 13984 | | |
| | 21062 | | 18275 | | |
| | 21170 | | 18637 | | |
| | 21275 | | 18729 | | |
| | 23357 | | 18850 | | |
| | 23469 | | 19992 | | |
| | | | 21062 | | |
| | | | 23357 | | |
| | | | 23469 | | |

APPENDIX C

Subset of features used in the classifier of Example 2

3086
3317
3755
3776
3818
3928
3953
4264
4545
4675
4756
4773
5068
5104
5198
5403
5472
5674
5706
5795
6301
6400
6534
6612
6634
6681
6789
6837
6898
6941
6957
7420
8315
8464
8531
8565
8797
8891
8998
9098
9187

APPENDIX C-continued

Subset of features used in the classifier of Example 2

9226
9245
9319
9395
9504
9941
10079
10263
10346
10961
12457
13798
13883
13916
13984
14098
17033
17604
17815
23249

APPENDIX D

Mass spectral features used in Classifier 1 or Classifier 2 of Example 6

3465
3679
3703
3842
4032
4133
4545
4590
4718
4818
4891
4999
5068
5129
5158
5180
5290
5377
5430
5496
5550
6438
6681
6761
6809
6881
6898
6992
7022
7035
7274
7287
7334
7536
7883
7913
8331
8391
8902
8928
9430
9641
10012
10924
12291
12351
12413
13275
13762
13798

APPENDIX D-continued

Mass spectral features used in Classifier 1 or Classifier 2 of Example 6

14098
14541
14595
15751
16630
17033
18275
18637
23249

We claim:

1. A method of detecting a class label in a non-small cell lung cancer patient comprising:
   a) conducting mass spectrometry on a blood-based sample of the patient and obtaining mass spectral data;
   (b) obtaining integrated intensity values in the mass spectral data of a multitude of mass-spectral features, wherein the mass-spectral features include a multitude of features listed in Appendix A, Appendix B, or Appendix C; and
   (c) operating on the mass spectral data with a programmed computer implementing a classifier;
   wherein in the operating step the classifier compares the integrated intensity values with feature values of a reference set of class-labeled mass spectral data obtained from blood-based samples obtained from a multitude of cancer patients treated with an antibody drug blocking ligand activation of programmed cell death 1 (PD-1) with a classification algorithm and detects a class label for the sample.

2. The method of claim 1, wherein the classifier is obtained from filtered mini-classifiers combined using a regularized combination method.

3. The method of claim 2, wherein the regularized combination method comprises repeatedly conducting logistic regression with extreme dropout on the filtered mini-classifiers.

4. The method of claim 1, wherein the classifier comprises an ensemble of tumor classifiers combined in a hierarchical manner.

5. The method of claim 1, wherein the reference set comprise a set of class-labeled mass spectral data of a development set of samples having either the class label Early or the equivalent or Late or the equivalent, wherein the samples having the class label Early are comprised of samples having relatively shorter overall survival on treatment with nivolumab as compared to samples having the class label Late.

6. The method of claim 1, wherein the mass spectral data is acquired from at least 100,000 laser shots performed on the sample using MALDI-TOF mass spectrometry.

7. The method of claim 1, wherein the mass-spectral features are selected according to their association with the biological functions Acute Response and Wound Healing.

8. The method of claim 2, wherein the mini-classifiers are filtered in accordance with criteria listed in Table 10.

9. The method of claim 1, wherein the classifier is obtained from filtered mini-classifiers combined using a regularized combination method, and wherein the mini-classifiers are filtered in accordance with criteria listed in Table 10.

10. The method of claim 1, wherein if the class label for the sample is Late or the equivalent then the patient is treated with an antibody drug blocking ligand activation of PD-1, and wherein if the class label for the sample is Early or the equivalent then the patient is treated with an antibody drug blocking ligand activation of PD-1 and an antibody drug targeting CTLA4.

11. The method of claim 10, wherein the antibody drug blocking ligand activation of PD-1 is nivolumab, and the antibody drug targeting CTLA4 is ipilimumab.

\* \* \* \* \*